(12) United States Patent
Sandall et al.

(10) Patent No.: US 11,617,798 B2
(45) Date of Patent: Apr. 4, 2023

(54) ANTI-CD228 ANTIBODIES AND ANTIBODY-DRUG CONJUGATES

(71) Applicant: Seagen Inc., Bothell, WA (US)

(72) Inventors: Sharsti Sandall, Bothell, WA (US); Lori Westendorf, Bothell, WA (US); Timothy Lewis, Bothell, WA (US)

(73) Assignee: Seagen Inc., Bothell, WA (US)

( * ) Notice: Subject to any disclaimer, the term of this patent is extended or adjusted under 35 U.S.C. 154(b) by 356 days.

(21) Appl. No.: 16/780,711

(22) Filed: Feb. 3, 2020

(65) Prior Publication Data

US 2020/0246479 A1     Aug. 6, 2020

Related U.S. Application Data

(60) Provisional application No. 62/934,424, filed on Nov. 12, 2019, provisional application No. 62/882,016, filed on Aug. 2, 2019, provisional application No. 62/879,660, filed on Jul. 29, 2019, provisional application No. 62/824,923, filed on Mar. 27, 2019, provisional application No. 62/801,590, filed on Feb. 5, 2019.

(51) Int. Cl.
*A61K 47/68* (2017.01)
*A61P 35/00* (2006.01)
*C07K 16/28* (2006.01)

(52) U.S. Cl.
CPC ...... *A61K 47/6811* (2017.08); *A61K 47/6843* (2017.08); *A61P 35/00* (2018.01); *C07K 16/2896* (2013.01); *C07K 2317/24* (2013.01); *C07K 2317/52* (2013.01); *C07K 2317/565* (2013.01)

(58) Field of Classification Search
CPC ............ A61K 47/6811; A61K 47/6843; A61K 39/395; A61K 39/39566; A61K 47/6803; A61K 47/6849; A61K 47/6883; A61K 47/6889; A61K 2039/505; A61K 2039/545; A61P 35/00; C07K 16/2896; C07K 2317/24; C07K 2317/52; C07K 2317/565; C07K 16/18; C07K 16/28; C07K 2317/92; C07K 2317/567; C07K 2317/732; C07K 2317/76
See application file for complete search history.

(56) References Cited

U.S. PATENT DOCUMENTS

| | | |
|---|---|---|
| 4,474,893 A | 10/1984 | Reading |
| 4,714,681 A | 12/1987 | Reading |
| 4,880,935 A | 11/1989 | Thorpe |
| 4,925,648 A | 5/1990 | Hansen |
| 5,122,368 A | 6/1992 | Greenfield |
| 5,225,539 A | 7/1993 | Winter |
| 5,530,101 A | 6/1996 | Queen et al. |
| 5,573,920 A | 11/1996 | Randle |
| 5,585,089 A | 12/1996 | Queen et al. |
| 5,591,639 A | 1/1997 | Bebbington |
| 5,601,819 A | 2/1997 | Wong |
| 5,622,929 A | 4/1997 | Willner |
| 5,624,821 A | 4/1997 | Winter |
| 5,658,759 A | 8/1997 | Bebbington |
| 5,824,805 A | 10/1998 | King |
| 5,834,597 A | 11/1998 | Tso |
| 5,859,205 A | 1/1999 | Adair et al. |
| 5,879,936 A | 3/1999 | Bebbington |
| 5,891,693 A | 4/1999 | Bebbington |
| 5,981,216 A | 11/1999 | Kenten |
| 6,130,237 A | 10/2000 | Denny |
| 6,132,722 A | 10/2000 | Siemers |
| 6,214,345 B1 | 4/2001 | Firestone |
| 6,407,213 B1 | 6/2002 | Carter |
| 6,624,821 B1 | 9/2003 | Shin |
| 6,881,557 B2 | 4/2005 | Foote |
| 7,498,298 B2 | 3/2009 | Doronina |
| 7,659,241 B2 | 2/2010 | Senter |
| 7,968,687 B2 | 6/2011 | Mcdonagh |
| 2005/0238649 A1 | 10/2005 | Doronina |
| 2006/0074008 A1 | 4/2006 | Senter |
| 2006/0160174 A1 | 7/2006 | Mcdonagh |
| 2008/0241128 A1 | 10/2008 | Jeffrey |
| 2009/0018086 A1 | 1/2009 | Doronina |
| 2009/0111756 A1 | 4/2009 | Doronina |
| 2010/0158909 A1 | 6/2010 | Mcdonagh |
| 2017/0320960 A1* | 11/2017 | Williams ......... G01N 33/57492 |
| 2018/0092984 A1 | 4/2018 | Lewis |

FOREIGN PATENT DOCUMENTS

| | | |
|---|---|---|
| EP | 0216846 B1 | 4/1987 |
| EP | 0323997 B1 | 7/1989 |
| EP | 0629240 B1 | 12/1994 |
| EP | 0338841 B1 | 3/1995 |
| WO | WO198704462 A1 | 7/1987 |
| WO | WO198912624 A2 | 12/1989 |

(Continued)

OTHER PUBLICATIONS

Edwards et al, J Mol Biol 334:103-118 (2003) (Year: 2003).*
Marchalonis et al., Dev & Comp Immunol 30:223-247 (2006) (Year: 2006).*
Almagro & Fransson, Frontiers in Bioscience 2008; 13:1619-33 (Year: 2008).*
Lu, et al., 2019, vol. 11, Issue 1; Published online Dec. 10, 2018 (Year: 2018).*
Al-Lazikani, B. et al., (1997). "Standard Conformations for the Canonical Structures of Immunoglobulins," J. Mol. Biol. 273:927-948.

(Continued)

*Primary Examiner* — Julie Wu
*Assistant Examiner* — John L Van Druff
(74) *Attorney, Agent, or Firm* — Morrison & Foerster LLP

(57) ABSTRACT

Provided are novel anti-CD228 antibodies and antibody-drug conjugates and methods of using such anti-CD228 antibodies and antibody-drug conjugates to treat cancer.

114 Claims, 35 Drawing Sheets

Specification includes a Sequence Listing.

(56) References Cited

FOREIGN PATENT DOCUMENTS

| WO | WO198912624 A3 | 4/1990 | |
|---|---|---|---|
| WO | WO199100360 A1 | 1/1991 | |
| WO | WO199205793 A1 | 4/1992 | |
| WO | WO199208802 A1 | 5/1992 | |
| WO | WO199222653 A1 | 12/1992 | |
| WO | WO199317715 A1 | 9/1993 | |
| WO | 2004050867 A1 | 6/2004 | |
| WO | WO-2004050867 A1 * | 6/2004 | ......... C07K 16/2896 |
| WO | WO2006036291 A2 | 4/2006 | |
| WO | WO2006036291 A3 | 7/2006 | |

OTHER PUBLICATIONS

Arnon, R. et al. (1985). "Monoclonal Antibodies For Immunotargeting Of Drugs In Cancer Therapy," in Monoclonal Antibodies And Cancer Therapy, Reisfeidet al. (eds.), pp. 243-256.

Biolegend Cat. No. #363101 (Aug. 21, 2014). "Purified Anti-Human CD228 (MFI2, MTF1) Antibody," 2 pages.

Chari, R.V.J. et al. (Jan. 1, 1992). "Immunoconjugates Containing Noveal maytansinoids: Promissing Anticancer Drugs," Cancer Res. 52:127-131.

Chothia, C. et al. (1987). "Canonical Structures for the Hypervariabie Regions of Immunoglobulins," J. Mol. Biol. 196:901-917.

Clackson, T. et al. (Aug. 15, 1991). "Making Antibody Fragments Using Phage Display Libraries," Nature 352:624-628.

Co, M.S. et al. (Feb. 15, 1992). "Chimeric and Humanized Antibodies With Specificity for the CD33 Antigen," J. Immunol. 148(4):1149-1154.

Dako Cat #X0909 (Sep. 2009). "Protein Block Serum-Free," 2 pages.

Davies, J. et al. (Aug. 2001). "Expression of GnTIII in a Recombinant Anti-CD20 CHO Production Cell Line: Expression of Antibodies With Altered Glycoforms Leads to an Increase in ADCC Through Higher Affinity for FC gamma RIII," Biotechnol. Bioeng. 74(4):288-294.

De La Cruz, E.M.C. et al. (Oct. 2006). "Development Of Transfection And High-Producer Screening Protocols For The CHOK1SV Cell System," Molecular Biotechnology 34(2):179-190.

De Pascalis, R. et al. (2002). "Grafting Of 'Abbreviated' Complementarity-Determining Regions Containing Specificity-Determining Residues Essential For Ligand Contact To Engineer A Less Immunogenic Humanized Monoclonal Antibody," J. Immunol. 169(6):3076-3084.

Dubcwchik, G.M. et al. (Aug. 1999). "Receptor-Mediated and Enzyme-Dependent Targeting of Cytotoxic Anticancer Drugs," Pharm. Therapeutics 83(2):67-123.

EMD Millipore; Catalog No. 524653 (2020). "PBS_TWEEN™ Tablets—Calbiochem," 2 pages.

Ghetie, V. et al. (2000). "Multiple Roles For The Major Histocompatibility Complex Class I-Related Receptor FcRn," Annu. Rev. Immunol. 18:739-766.

Ghetie, V. et al. (2002). "Transcytosis and Catabolism Of Antibody," Immunol. Res. 25(2):97-113.

Gonzales_N.R. et al. (Jul. 2004, e-pub, Jun. 17, 2004). "SDR Grafting of a Murine Antibody Using Multiple Human Germline Templates to Minimize its Immunogenicity," Mol. Immunol. 41(9):863-872.

Hellstrom, K.E. et al. (1987). "Antibodies For Drug Delivery," in Controlled Drug Delivery pp. 623-653.

Hieter, P.A. et al. (Feb. 10, 1982). "Evolution Of Human Immunoglobulin Kappa J Region Genes," J. Biol. Chem. 257(3):1516-1522.

Hinton, P.R. et al. (Feb. 20, 2004). "Engineered Human IgG Antibodies with Longer Serum Half-lives in Primates," J. Biol. Chem. 279(8):6213-6216.

Honegger et al., "Yet another numbering scheme for immunoglobulin variable domains: an automatic modeling and analysis tool," J Mol Biol, (2001) 8;309(3):657-70.

Idusogie, E.E. et al. (2001). "Engineered Antibodies With Increased Activity to Recruit Complement," J.Immunol. 166:2571-2575.

Isidro-Liobet, A. et al. (Jun. 2009). "Amino Acid-Protecting Groups," 109(6):2455-2504.

Iwahashi, M. et al. (Oct.-Nov. 1999). "CDR Substitutions of a Humanized Monoclonal Antibody (CC49): Contributions of Individual CDRs to Antigen Binding and Immunogenicity," Mol. Immunol. 36(15-16):1079-1091.

Jackson ImmunoResearch Code # 109-035-098 (Date Unknown). "Peroxidase-Conjugated AffiniPure Goat Anti-Human IgG, Fcγ Fragment Specific (Minimal Cross-Reaction to Bovine, Horese, and Mouse Serum Proteins," 1 page.

Jefferis, R. et al. (Jul./Aug. 2009). "Human Immunoglobulin Allotypes," MABS 1(4):1-7.

Johnson, D.A. et al. (Jul.-Aug. 1995). "Anti-Tumor Activity of CC49-Doxorubicin Immunoconjugates," Anticancer Res. 15(4):1387-1394.

Kabat, E.A. et al. (1991). Sequences of Proteins of Immunological interest, 5th ed., Public Health Service, National Institutes of Health, Bethesda, MD. TOC, 21 pages.

Kohler, G. et al. (Aug. 7, 1975) "Continuous Cultures Of Fused Cells Secreting Antibody Of Predefined Specificity," Nature 256:495-497.

Kontermann, R.E. et al. (Jul. 1997). "Complement Recruitment Using Bispecific Diabodies," Nat. Biotech. 15(7):629-631.

Kostelny, S.A. et al. (Mar. 1, 1992). "Formation of a Bispecific Antibody By The Use of Leucine Zippers," J. Immunol. 148(5):1547-1553.

Lau, A. et al. (Oct. 1995). "Conjugation of Doxorubicin to Monoclonal Anti-Carcinoembryonic Antigen Antibody Via Novel Thiol-Directed Cross-Linking Reagents," Bioorganic & Medicinal Chemistry 3(10):1299-1304.

Lau, A. et al. (Oct. 1995). "Novel Doxorubicin-Monoclonal Anti-Carcinoembryonic Antigen Antibody Immunoconjugate Activity in vitro," Bioorganic & Medicinal Chemistry 3(10):1305-1312.

Lazar, G.A. et al. (Mar. 14, 2006)."Engineered Antibody Fc Variants with Enhanced Effector Function," PNAS 103(11):4005-4010.

Lefranc, M.P. et al., (Jan. 2003). "IMGT Unique Numbering For Immunoglobulin And T Cell Receptor Variable Domains And Ig Superfamily V-Like Domains," Dev. Comp. Immunol. 27(1):55-77.

Leica cat # AR9222 "Dewax Solution," retrieved from https:shop.leicabiosystems.com/us/ihc-ish/ancillaries-consumables/pid-dewax-solution, last visited Mar. 2, 2020, 2 pages.

Leica cat#AR9640 (2020). "BOND Epitope Retrieval Solution 2," retrieved from https://shop.leicabiosystems.com/us/ihc-ish-ancillaries-consumables/pid-epitope-retrieval-solution-s, last visited Mar. 2, 2020, 2 pages.

Leica cat# DS9305 (2020). "BOND Polymer Refine Red Detection," retrieved from https://shop.leicbiosystems.com/us/ihc-ish/detection-systems/pid-bond-polymer-refine-red-dection, last visited Mar. 2, 2020, 2 pages.

Lund, J. et al. (Dec. 1, 1996). "Multiple interactions of IgG With its Core Oligosaccharide Can Modulate Recognition By Complement and Human Fcγ Receptor I and Influence The Synthesis Of Its Oligosaccharide Chains," J. Jmmunol. 157(11):4963-4969.

Lyon, R.P. et al. (Oct. 2014, e-pub. Sep. 7, 2014). "Self-hydrolyzing Maleimides Improve the Stability and Pharmacological Properties of Antibody-Drug Conjugates," Nat Biotechnol 32(10):1059-1062.

MacCallum, R.M. et al. (1996). "Antibody-Antigen Interactions: Contact Analysis and Binding Site Topography," Journal of Molecular Biology 262:732-745.

Marks, J.D. et al. (1991). "By-Passing Immunization Human Antibodies from V-gene Libraries Displayed on Phage," J. Mol. Biol. 222:581-597.

Martin, A.C.R. et al. (Dec. 1989). "Modeling Antibody Hypervariable Loops: A Combined Algorithm," PNAS USA 86(23):9268-9272.

Mattila, P.S. et al. (Sep. 1995). "Extensive Allelic Sequence Variation In The J Region Of The Human Immunoglobulin Heavy Chain Gene Locus," Eur. J. Immunol. 25(9):2578-2582.

McDonagh, C.F. et al. (2003, e-pub. Jul. 25, 2003). "Improved Yield and Stability of L49-sFv-β-Lactamase_a Signle-Chain Antibody Fusion Protein for Anticancer Prodrug Activation, by Protein Engineering," Bioconjugate Chem. 14:860-869.

(56) References Cited

OTHER PUBLICATIONS

Neville, D.M. et al. (Sep. 5, 1989), "Enhancement of Immunotoxin Efficacy by Acid-cleavabie Crosslinking Agents Utilizing Diphtheria Toxin and Toxin Mutants," The Journal of Biological Chemistry 264(25):14653-14661.
Niwa, R. et al. (Mar. 15, 2004). "Defucosylated Chimeric Anti-CC Chemokine Receptor 4 IgG1 With Enhanced Antibody-Dependent Cellular Cytotoxicity Shows Potent Therapeutic Activity To T-Cell Leukemia and Lymphoma," Cancer Res. 64(6):2127-2133.
Okazaki, A. et al. (Mar. 5, 2004). "Fucose Depletion From Human IgG1 Oligosaccharide Enhances Binding Enthalpy And Association Rate Between IgG1 and FcγRIIIa," J. Mol. Biol. 336(5):1239-1249.
Order, S.E. (1985). "Analysis, Results, and Future Prospective of the Therapeutic Use of Radiolabeled Antibody In Cancer Therapy," in Monoclonal Antibodies For Cancer Detection And Therapy, pp. 303-316.
Paul, W.E. ed., Fundamental Immunology: Second Edition, Raven Press, New York at (1989) pp. 332-337.
Product Information (Date Unknown) (ADC-224LZY) "Anti-MTf/p97 (clone L49)-Vc-MMAF ADC," Creative Biolabs, 2 pages.
Queen, C. et al. (Feb. 1986). "Cell-Type Specific Regulation of a K Immunoglobulin Gene by Promoter and Enhancer Elements," Immunol. Rev. 89:49-68.
R&D Cat. #893416 (Oct. 12, 2015). "Human Melanotransferrin/CD228 PE-conjugated Antibody," 1 page.
Rolland, Y. et al. (Feb. 2009, e-pub. Dec. 1, 2008). "Inhibition of Melanoma Brain Metastasis by Targeting Melanotransferrin at the Cell Surface," Pigment Cell Melanoma Res. 22(1):86-98.
Sambrook, J. et al. (1989). Molecular Cloning: A Laboratory Manual, 3rd Ed. 29 pages.
Santa Cruz Cat. #271633 (Date Unknown) "Melanotransferrin (E-4): sc-271633," 1 page.
Shields, R.L. et al. (Jul. 26, 2002, e-pub. May 1, 2002). "Lack of Fucose on Human IgG N-Linked Oligosaccharide Improves Binding to Human FcγRIII and Antibody-dependent Cellular Toxicity," J. Biol. Chem. 277:26733-26740.
Shields, R.L. et al. (Mar. 2, 2001). "High Resolution Mapping of the Binding Site on Human IgG1 for FcγRI, FcγII, FcγIII, and FcRn and Design of IgG1 Variants With Improved Binding to the FcγR," J. Biol.Chem. 276(9):6591-6604.
Shin, E.K. et al. (Dec. 1991). "Physical Map Of The 3' Region Of The Human Immunoglobulin Heavy Chain Locus: Clustering Of Autoantibody-Related Variable Segments In One Haplotype," EMBO J. 10(12):3641-3645.
Shinkawa, T. et al. (Jan. 31, 2003). "The Absence Of Fucose But Not The Presence Of Galactose Or Bisecting N-Acetylglucosamine Of Human IgG1 Complex-Type Oligosaccharides Shows The Critical Role Of Enhancing Antibody-Dependent Cellular Cytotoxicity," Journal of Biological Chemistry, 278(5):3466-3473.
Shopes, B. et al. (May 1, 1992). "A Genetically Engineered Human IgG Mutant With Enhanced Cytolytic Activity," J. Imniunol. 148:2918-2922.

Siemers, N.O. et al. (Jul.-Aug. 1997). "Construction, Expression, and Activities of L49-sFv-β-Lactamase, a Single-Chain Antibody Fusion Protein for Anticancer Prodrug Activation," Bioconjug. Chem. 8:510-519.
Sigma Aldrich Cat # HPA004880 (2020). "Anti-MELTF Antibody Produced in Rabbit," Retrieved from http://www.sigmaaldrich.com/catalog/products/sigma/hpa004880?lang=en® ion=US, last visited Mar. 2, 2020,m 4 pages.
Sigma Aldrich Catalog No. A7030-100G (2020), "Bovine Serum Albumin," retrieved from http://www.sigmaaldrich.com/catalog/products/sigma/a7030?lang=en® ion=US, last visited Mar. 2, 2020, 4 pages.
Smith, R.I. et al. (Mar. 1, 1995). "Addition of a μ-tailpiece to IgG results in polymeric antibodies with enhanced effector functions including complement-mediated cytolysis by IgG4," J. Immunol. 154(5):2226-2236.
Tamura, M. et al. (Feb. 2000). "Structural Correlates of an Anticarcinoma Antibody: Identification of Specificity-Determining Residues (SDRs) and Development of a Minimally Immunogenic Antibody Variant by Retention of SDRs Only," J. Immunol. 164(3):1432-1441.
Thorpe, (1985). "Antibody Carriers Of Cytotoxic Agents In Cancer Therapy: A Review," in Monoclonal Antibodies '84 Biological And Clinical Applications, Pincheraet al. (eds.), pp. 475-506.
Thorpe, P.E. et al. (1982), "The Preparation And Cytotoxic Properties Of Antibody-Toxin Conjugates," Immunol. Rev. 62:119-158.
Thorpe, P.E. et al. (Nov. 15, 1987). "New Coupling Agents for the Synthesis of Immunotoxins Containing a Hindered Disulfide Bond with Improved Stability in Vivo," Cancer Research 47:5924-5931.
Tutt, A. et al. (Jul. 1, 1991) "Trispecific F(ab')3 Derivatives that use Cooperative Signaling Via the TCR/CD3 Complex and CD2 to Activate and Redirect Resting Cytotoxic T Cells," J. Immunol. 147(1):60-69.
Umaña, P. et al. (Feb. 1999). "Engineered Glycoforms of an Antineuro-Blastoma IgG 1 With Optimized Antibody-Dependent Cellular Cytotoxic Activity," Nat. Biotechnol. 17:176-180.
Vajdos, F. et al. (2002) "Comprehensive Functional Maps of the Antigen Binding Site of an Anti-ErbB2 Antibody Obtained with Shotgun Scanning Mutagenesis," J. Mol. Biol. 320:415-428.
Wawrzynczak et al. (1987). "Methods for Preparing Immunotoxins: Effect of the Linkage on Activity and Stability," in Immunoconjugates: Antibody Conjugates in Radioimagery and Therapy of Cancer, pp. 28-55.
Wright, A. et al. (Jan. 1997). "Effect of Glycosylation on Antibody Function: Implications for Genetics Engineering," Trends Biotechnol. 15:26-32.
International Preliminary Report on Patentabiltiy, dated Aug. 10, 2021, for PCT Application Nu. PCT/US2020/016381, filed Feb. 3, 2020, 5 pages.
International Search Report and Written Opinion, dated May 29, 2020, for PCT Application Nu. PCT/US2020/016381, filed Feb. 3, 2020, 14 pages.
Smith, L.M. (Jun. 1, 2006), "Potent Cytotoxicity of an Auristatin-Containing Antibody-Drug Conjugate Targeting Melanoma Cells Expressing Melanotransferrin/97," Molecular Cancer Therapeutics 5(6):1474-1482.

* cited by examiner

FIG. 8: Alignment of hL49 Heavy Chain Variants with Human Acceptor Sequence, IGHV4-59/HJ4.

```
                         10        20        30        40        50        60        70
                ....|....|....|....|....|....|....|....|....|....|....|....|....|....|
Mu L49 vH       E........S.....Q......S.T.D..T.G..N...KF..NK..YM...SD..I.Y.........IS.T
Hu IGHV4-59/HJ4 QVQLQESGPGLVKPSETLSLTCTVSGGSISSYYWSWIRQPPSKGLEWIGYIYYSGSTNYNPSLKSRVTIS
hvHA            .......................D..T.G..N............Y....SD..I.Y.............
hvHB            .......................D..T.G..N....F......YM...SD..I.Y..........I...
hvHC            .......................D..T.G..N....F......YM...SD..I.Y..........I...
Kabat CDRs                                     *****               ******************
IMGT CDRs                              ++++++++               +++++++

80        90       100       110
                ....|....|....|....|....|....|....|....|...
Mu L49 vH       R......TY.Q.NF...E...T.N...RTLATYYAM........S......
Hu IGHV4-59/HJ4 VDTSKNQFSLKLSSVTAADTAVYYCAR---------YFDYWGQGTLVTVSS
hvHA            R......Y...................RTLATYYAM...............
hvHB            R......Y...................RTLATYYAM...............
hvHC            R......Y.....F..........N..RTLATYYAM...............
Kabat CDRs                                  ************
IMGT CDRs                             +++++++++++++
```

FIG. 9: Alignment of hL49 Heavy Chain Variants

```
                         10        20        30        40        50        60        70
                ....|....|....|....|....|....|....|....|....|....|....|....|....|....|
hvHA            QVQLQESGPSLVKPSETLSLTCTVSGDSITSGYWNWIRQPPGKGLEYIGYISDSGITYYNPSLKSRVTIS
hvHB            ............................................F......M..............I....
hvHC            ............................................F......M..............I....
Kabat CDRs                                     *****               ******************
IMGT CDRs                              ++++++++               +++++++

80        90       100       110
                ....|....|....|....|....|....|....|....|...
hvHA            RDTSKNQYSLKLSSVTAADTAVYYCAPRTLATYYAMDYWGQGTLVTVSS
hvHB            ..................................................
hvHC            .............F..........N.........................
Kabat CDRs                                  ************
IMGT CDRs                             +++++++++++++
```

FIG. 10: Alignment of hL49 Light Chain Variants with Human Acceptor Sequence, IGKV2-30/KJ2.

```
                      10        20        30        40        50        60
                ....|....|....|....|....|....|....|....|....|....|....|....|
Mu L49 vL       .F....T.......S..DQ.......A......H.N.....H.YL.K.....KL...R....F..........
Hu IGKV2-30/KJ2 DVVMTQSPLSLPVTLGQPASISCRSSQSLVYSDGNTYLNWFQQRPGQSPRRLIYKVSNRDSGVPDRFSGS
hvLA            .F................A......H.N.....H...........R....F..........
hvLB            .F................A......H.N.....H.Y.........L...R....F..........
hvLC            .F................A......H.N.....H.Y.........L...R....F..........
Kabat CDRs                                **************      *******
IMGT CDRs                                   ++++++++++           +++

70        80        90       100
                ....|....|....|....|....|....|....|....|...
Mu L49 vL       ....................L...P.S..S..V.P....G........
Hu IGKV2-30/KJ2 GSGTDFTLKISRVEAEDVGVYYCMQGTHWPYTFGQGTKLEIKR
hvLA            .....................S.S..V.P.............
hvLB            .....................S.S..V.P.............
hvLC            .....................S.S..V.P.............
Kabat CDRs                            *********
IMGT CDRs                            ++++++++++
```

FIG. 11: Alignment of hL49 Light Chain Variants

```
                      10        20        30        40        50        60
                ....|....|....|....|....|....|....|....|....|....|....|....|
hvLA            DFVMTQSPLSLPVTLGQPASISCRASQSLVHSNGNTYLNWFQQRPGQSPRRLIYRVSNRFSGVPDRFSGS
hvLB            ..................................Y..........L.....................
hvLC            ...........................D.....Y..........L.....................
Kabat CDRs                                ***************      *******
IMGT CDRs                                   ++++++++++           +++

70        80        90       100
                ....|....|....|....|....|....|....|....|...
hvLA            GSGTDFTLKISRVEAEDVGVYYCSQSTHVPPTFGQGTKLEIKR
hvLB            ...........................................
hvLC            ...........................................
Kabat CDRs                             *********
IMGT CDRs                             ++++++++++
```

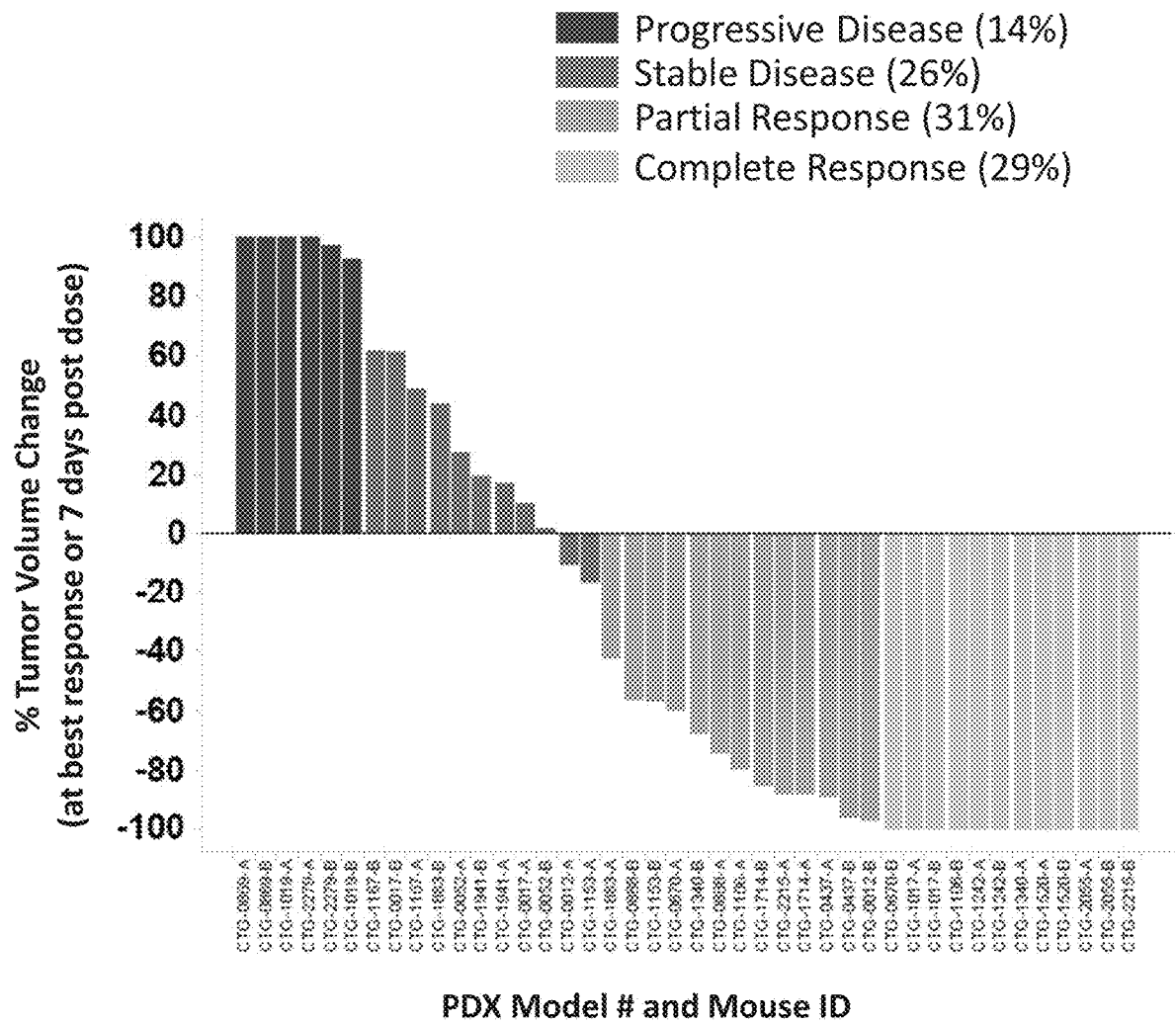

SEQUENCE LISTING

<160> NUMBER OF SEQ ID NOS: 35

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Ser Gly Tyr Trp Asn
1               5

<210> SEQ ID NO 2
<211> LENGTH: 16
<212> TYPE: PRT
<213> ORGANISM: Artificial Sequence

```
<220> FEATURE:
<223> OTHER INFORMATION: Synthetic Construct

<400> SEQUENCE: 2

Tyr Ile Ser Asp Ser Gly Ile Thr Tyr Tyr Asn Pro Ser Leu Lys Ser
1               5                   10                  15

<210> SEQ ID NO 3
<211> LENGTH: 11
<212> TYPE: PRT
<213> ORGANISM: Artificial Sequence
<220> FEATURE:
<223> OTHER INFORMATION: Synthetic Construct

<400> SEQUENCE: 3

Arg Thr Leu Ala Thr Tyr Tyr Ala Met Asp Tyr
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Synthetic Construct

<400> SEQUENCE: 4

Arg Ala Ser Gln Ser Leu Val His Ser Asp Gly Asn Thr Tyr Leu His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Arg Val Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Ser Gln Ser Thr His Val Pro Pro Thr
1               5

<210> SEQ ID NO 7
<211> LENGTH: 119
<212> TYPE: PRT
<213> ORGANISM: Artificial Sequence
<220> FEATURE:
<223> OTHER INFORMATION: Synthetic Construct

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Ser Gly
                20                  25                  30

Tyr Trp Asn Trp Ile Arg Gln Pro Pro Gly Lys Gly Leu Glu Tyr Ile
            35                  40                  45
```

Gly Tyr Ile Ser Asp Ser Gly Ile Thr Tyr Tyr Asn Pro Ser Leu Lys
            50                  55                  60

Ser Arg Val Thr Ile Ser Arg Asp Thr Ser Lys Asn Gln Tyr Ser Leu
 65                  70                  75                  80

Lys Leu Ser Ser Val Thr Ala Ala Asp Thr Ala Val Tyr Tyr Cys Ala
                 85                  90                  95

Arg Arg Thr Leu Ala Thr Tyr Tyr Ala Met Asp Tyr Trp Gly Gln Gly
                100                 105                 110

Thr Leu Val Thr Val Ser Ser
            115

<210> SEQ ID NO 8
<211> LENGTH: 112
<212> TYPE: PRT
<213> ORGANISM: Artificial Sequence
<220> FEATURE:
<223> OTHER INFORMATION: Synthetic Construct

<400> SEQUENCE: 8

Asp Phe Val Met Thr Gln Ser Pro Leu Ser Leu Pro Val Thr Leu Gly
 1               5                  10                  15

Gln Pro Ala Ser Ile Ser Cys Arg Ala Ser Gln Ser Leu Val His Ser
             20                  25                  30

Asp Gly Asn Thr Tyr Leu His Trp Tyr Gln Gln Arg Pro Gly Gln Ser
         35                  40                  45

Pro Arg Leu Leu Ile Tyr Arg Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Val Pro Pro Thr Phe Gly Gln Gly Thr Lys Leu Glu Ile Lys
                100                 105                 110

<210> SEQ ID NO 9
<211> LENGTH: 30
<212> TYPE: PRT
<213> ORGANISM: Artificial Sequence
<220> FEATURE:
<223> OTHER INFORMATION: Synthetic Construct

<400> SEQUENCE: 9

Gln Val Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Thr
             20                  25                  30

<210> SEQ ID NO 10
<211> LENGTH: 14
<212> TYPE: PRT
<213> ORGANISM: Artificial Sequence
<220> FEATURE:
<223> OTHER INFORMATION: Synthetic Construct

<400> SEQUENCE: 10

Trp Ile Arg Gln Pro Pro Gly Lys Gly Leu Glu Tyr Ile Gly
 1               5                  10

<210> SEQ ID NO 11
<211> LENGTH: 32
<212> TYPE: PRT

<213> ORGANISM: Artificial Sequence
<220> FEATURE:
<223> OTHER INFORMATION: Synthetic Construct

<400> SEQUENCE: 11

Arg Val Thr Ile Ser Arg Asp Thr Ser Lys Asn Gln Tyr Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 12
<211> LENGTH: 11
<212> TYPE: PRT
<213> ORGANISM: Artificial Sequence
<220> FEATURE:
<223> OTHER INFORMATION: Synthetic Construct

<400> SEQUENCE: 12

Trp Gly Gln Gly Thr Leu Val Thr Val Ser Ser
1               5                   10

<210> SEQ ID NO 13
<211> LENGTH: 23
<212> TYPE: PRT
<213> ORGANISM: Artificial Sequence
<220> FEATURE:
<223> OTHER INFORMATION: Synthetic Construct

<400> SEQUENCE: 13

Asp Phe Val Met Thr Gln Ser Pro Leu Ser Leu Pro Val Thr Leu Gly
1               5                   10                  15

Gln Pro Ala Ser Ile Ser Cys
            20

<210> SEQ ID NO 14
<211> LENGTH: 15
<212> TYPE: PRT
<213> ORGANISM: Artificial Sequence
<220> FEATURE:
<223> OTHER INFORMATION: Synthetic Construct

<400> SEQUENCE: 14

Trp Tyr Gln Gln Arg Pro Gly Gln Ser Pro Arg Leu Leu Ile Tyr
1               5                   10                  15

<210> SEQ ID NO 15
<211> LENGTH: 32
<212> TYPE: PRT
<213> ORGANISM: Artificial Sequence
<220> FEATURE:
<223> OTHER INFORMATION: Synthetic Construct

<400> SEQUENCE: 15

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 16
<211> LENGTH: 10
<212> TYPE: PRT
<213> ORGANISM: Artificial Sequence
<220> FEATURE:
<223> OTHER INFORMATION: Synthetic Construct

<400> SEQUENCE: 16

Phe Gly Gln Gly Thr Lys Leu Glu Ile Lys
1               5                   10

<210> SEQ ID NO 17
<211> LENGTH: 329
<212> TYPE: PRT
<213> ORGANISM: Artificial Sequence
<220> FEATURE:
<223> OTHER INFORMATION: Synthetic Construct

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 18

```
<211> LENGTH: 106
<212> TYPE: PRT
<213> ORGANISM: Artificial Sequence
<220> FEATURE:
<223> OTHER INFORMATION: Synthetic Construct

<400> SEQUENCE: 18
```

| Thr | Val | Ala | Ala | Pro | Ser | Val | Phe | Ile | Phe | Pro | Pro | Ser | Asp | Glu | Gln |
|---|---|---|---|---|---|---|---|---|---|---|---|---|---|---|---|
| 1 | | | | 5 | | | | | 10 | | | | | 15 | |

| Leu | Lys | Ser | Gly | Thr | Ala | Ser | Val | Val | Cys | Leu | Leu | Asn | Asn | Phe | Tyr |
|---|---|---|---|---|---|---|---|---|---|---|---|---|---|---|---|
| | | | 20 | | | | | 25 | | | | | 30 | | |

| Pro | Arg | Glu | Ala | Lys | Val | Gln | Trp | Lys | Val | Asp | Asn | Ala | Leu | Gln | Ser |
|---|---|---|---|---|---|---|---|---|---|---|---|---|---|---|---|
| | | 35 | | | | | 40 | | | | | 45 | | | |

| Gly | Asn | Ser | Gln | Glu | Ser | Val | Thr | Glu | Gln | Asp | Ser | Lys | Asp | Ser | Thr |
|---|---|---|---|---|---|---|---|---|---|---|---|---|---|---|---|
| | 50 | | | | | 55 | | | | | 60 | | | | |

| Tyr | Ser | Leu | Ser | Ser | Thr | Leu | Thr | Leu | Ser | Lys | Ala | Asp | Tyr | Glu | Lys |
|---|---|---|---|---|---|---|---|---|---|---|---|---|---|---|---|
| 65 | | | | | 70 | | | | | 75 | | | | | 80 |

| His | Lys | Val | Tyr | Ala | Cys | Glu | Val | Thr | His | Gln | Gly | Leu | Ser | Ser | Pro |
|---|---|---|---|---|---|---|---|---|---|---|---|---|---|---|---|
| | | | | 85 | | | | | 90 | | | | | 95 | |

| Val | Thr | Lys | Ser | Phe | Asn | Arg | Gly | Glu | Cys |
|---|---|---|---|---|---|---|---|---|---|
| | | | 100 | | | | | 105 | |

```
<210> SEQ ID NO 19
<211> LENGTH: 329
<212> TYPE: PRT
<213> ORGANISM: Artificial Sequence
<220> FEATURE:
<223> OTHER INFORMATION: Synthetic Construct

<400> SEQUENCE: 19
```

| Ala | Ser | Thr | Lys | Gly | Pro | Ser | Val | Phe | Pro | Leu | Ala | Pro | Ser | Ser | Lys |
|---|---|---|---|---|---|---|---|---|---|---|---|---|---|---|---|
| 1 | | | | 5 | | | | | 10 | | | | | 15 | |

| Ser | Thr | Ser | Gly | Gly | Thr | Ala | Ala | Leu | Gly | Cys | Leu | Val | Lys | Asp | Tyr |
|---|---|---|---|---|---|---|---|---|---|---|---|---|---|---|---|
| | | | 20 | | | | | 25 | | | | | 30 | | |

| Phe | Pro | Glu | Pro | Val | Thr | Val | Ser | Trp | Asn | Ser | Gly | Ala | Leu | Thr | Ser |
|---|---|---|---|---|---|---|---|---|---|---|---|---|---|---|---|
| | | 35 | | | | | 40 | | | | | 45 | | | |

| Gly | Val | His | Thr | Phe | Pro | Ala | Val | Leu | Gln | Ser | Ser | Gly | Leu | Tyr | Ser |
|---|---|---|---|---|---|---|---|---|---|---|---|---|---|---|---|
| | 50 | | | | | 55 | | | | | 60 | | | | |

| Leu | Ser | Ser | Val | Val | Thr | Val | Pro | Ser | Ser | Ser | Leu | Gly | Thr | Gln | Thr |
|---|---|---|---|---|---|---|---|---|---|---|---|---|---|---|---|
| 65 | | | | | 70 | | | | | 75 | | | | | 80 |

| Tyr | Ile | Cys | Asn | Val | Asn | His | Lys | Pro | Ser | Asn | Thr | Lys | Val | Asp | Lys |
|---|---|---|---|---|---|---|---|---|---|---|---|---|---|---|---|
| | | | | 85 | | | | | 90 | | | | | 95 | |

| Lys | Val | Glu | Pro | Lys | Ser | Cys | Asp | Lys | Thr | His | Thr | Cys | Pro | Pro | Cys |
|---|---|---|---|---|---|---|---|---|---|---|---|---|---|---|---|
| | | | 100 | | | | | 105 | | | | | 110 | | |

| Pro | Ala | Pro | Glu | Leu | Leu | Gly | Gly | Pro | Cys | Val | Phe | Leu | Phe | Pro | Pro |
|---|---|---|---|---|---|---|---|---|---|---|---|---|---|---|---|
| | | 115 | | | | | 120 | | | | | 125 | | | |

| Lys | Pro | Lys | Asp | Thr | Leu | Met | Ile | Ser | Arg | Thr | Pro | Glu | Val | Thr | Cys |
|---|---|---|---|---|---|---|---|---|---|---|---|---|---|---|---|
| | 130 | | | | | 135 | | | | | 140 | | | | |

| Val | Val | Val | Asp | Val | Ser | His | Glu | Asp | Pro | Glu | Val | Lys | Phe | Asn | Trp |
|---|---|---|---|---|---|---|---|---|---|---|---|---|---|---|---|
| 145 | | | | | 150 | | | | | 155 | | | | | 160 |

| Tyr | Val | Asp | Gly | Val | Glu | Val | His | Asn | Ala | Lys | Thr | Lys | Pro | Arg | Glu |
|---|---|---|---|---|---|---|---|---|---|---|---|---|---|---|---|
| | | | | 165 | | | | | 170 | | | | | 175 | |

| Glu | Gln | Tyr | Asn | Ser | Thr | Tyr | Arg | Val | Val | Ser | Val | Leu | Thr | Val | Leu |
|---|---|---|---|---|---|---|---|---|---|---|---|---|---|---|---|
| | | | 180 | | | | | 185 | | | | | 190 | | |

| His | Gln | Asp | Trp | Leu | Asn | Gly | Lys | Glu | Tyr | Lys | Cys | Lys | Val | Ser | Asn |
|---|---|---|---|---|---|---|---|---|---|---|---|---|---|---|---|
| | | 195 | | | | | 200 | | | | | 205 | | | |

| Lys | Ala | Leu | Pro | Ala | Pro | Ile | Glu | Lys | Thr | Ile | Ser | Lys | Ala | Lys | Gly |
|---|---|---|---|---|---|---|---|---|---|---|---|---|---|---|---|

```
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 20
<211> LENGTH: 112
<212> TYPE: PRT
<213> ORGANISM: Artificial Sequence
<220> FEATURE:
<223> OTHER INFORMATION: Synthetic Construct

<400> SEQUENCE: 20

Asp Phe Val Met Thr Gln Ser Pro Leu Ser Leu Pro Val Thr Leu Gly
1               5                   10                  15

Gln Pro Ala Ser Ile Ser Cys Arg Ala Ser Gln Ser Leu Val His Ser
            20                  25                  30

Asn Gly Asn Thr Tyr Leu His Trp Tyr Gln Gln Arg Pro Gly Gln Ser
        35                  40                  45

Pro Arg Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Thr Phe Gly Gln Gly Thr Lys Leu Glu Ile Lys
            100                 105                 110

<210> SEQ ID NO 21
<211> LENGTH: 119
<212> TYPE: PRT
<213> ORGANISM: Mus musculus

<400> SEQUENCE: 21

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Asp Ser Gly Ile Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Phe Val Thr Ala Glu Asp Thr Ala Thr Tyr Asn Cys Ala
                85                  90                  95
```

Arg Arg Thr Leu Ala Thr Tyr Tyr Ala Met Asp Tyr Trp Gly Gln Gly
            100                 105                 110

Thr Ser Val Thr Val Ser Ser
        115

<210> SEQ ID NO 22
<211> LENGTH: 97
<212> TYPE: PRT
<213> ORGANISM: Mus musculus

<400> SEQUENCE: 22

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Ser Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg

<210> SEQ ID NO 23
<211> LENGTH: 112
<212> TYPE: PRT
<213> ORGANISM: Homo sapiens

<400> SEQUENCE: 23

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Tyr Phe Asp Tyr Trp Gly Gln Gly Thr Leu Val Thr Val Ser Ser
            100                 105                 110

<210> SEQ ID NO 24
<211> LENGTH: 119
<212> TYPE: PRT
<213> ORGANISM: Artificial Sequence
<220> FEATURE:
<223> OTHER INFORMATION: Synthetic Construct

<400> SEQUENCE: 24

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Ser Gly
            20                  25                  30

```
Tyr Trp Asn Trp Ile Arg Gln Phe Pro Gly Lys Gly Leu Glu Tyr Met
            35                  40                  45

Gly Tyr Ile Ser Asp Ser Gly Ile Thr Tyr Tyr Asn Pro Ser Leu Lys
        50                  55                  60

Ser Arg Ile Thr Ile Ser Arg Asp Thr Ser Lys Asn Gln Tyr Ser Leu
 65                  70                  75                  80

Lys Leu Ser Ser Val Thr Ala Ala Asp Thr Ala Val Tyr Tyr Cys Ala
                85                  90                  95

Arg Arg Thr Leu Ala Thr Tyr Tyr Ala Met Asp Tyr Trp Gly Gln Gly
                100                 105                 110

Thr Leu Val Thr Val Ser Ser
            115
```

<210> SEQ ID NO 25
<211> LENGTH: 119
<212> TYPE: PRT
<213> ORGANISM: Artificial Sequence
<220> FEATURE:
<223> OTHER INFORMATION: Synthetic Construct

<400> SEQUENCE: 25

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Thr Ser Gly
                20                  25                  30

Tyr Trp Asn Trp Ile Arg Gln Phe Pro Gly Lys Gly Leu Glu Tyr Met
            35                  40                  45

Gly Tyr Ile Ser Asp Ser Gly Ile Thr Tyr Tyr Asn Pro Ser Leu Lys
        50                  55                  60

Ser Arg Ile Thr Ile Ser Arg Asp Thr Ser Lys Asn Gln Tyr Ser Leu
 65                  70                  75                  80

Lys Leu Ser Phe Val Thr Ala Ala Asp Thr Ala Val Tyr Asn Cys Ala
                85                  90                  95

Arg Arg Thr Leu Ala Thr Tyr Tyr Ala Met Asp Tyr Trp Gly Gln Gly
                100                 105                 110

Thr Leu Val Thr Val Ser Ser
            115
```

<210> SEQ ID NO 26
<211> LENGTH: 112
<212> TYPE: PRT
<213> ORGANISM: Mus musculus

<400> SEQUENCE: 26

```
Asp Phe Val Met Thr Gln Thr Pro Leu Ser Leu Pro Val Ser Leu Gly
 1               5                  10                  15

Asp Gln Ala Ser Ile Ser Cys Arg Ala Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Arg Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                85                  90                  95
```

Thr His Val Pro Pro Thr Phe Gly Gly Gly Thr Lys Leu Glu Ile Lys
            100                 105                 110

<210> SEQ ID NO 27
<211> LENGTH: 100
<212> TYPE: PRT
<213> ORGANISM: Mus musculus

<400> SEQUENCE: 27

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro
            100

<210> SEQ ID NO 28
<211> LENGTH: 112
<212> TYPE: PRT
<213> ORGANISM: Homo sapiens

<400> SEQUENCE: 28

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

<210> SEQ ID NO 29
<211> LENGTH: 112
<212> TYPE: PRT
<213> ORGANISM: Artificial Sequence
<220> FEATURE:
<223> OTHER INFORMATION: Synthetic Construct

<400> SEQUENCE: 29

Asp Phe Val Met Thr Gln Ser Pro Leu Ser Leu Pro Val Thr Leu Gly
1               5                   10                  15

Gln Pro Ala Ser Ile Ser Cys Arg Ala Ser Gln Ser Leu Val His Ser
            20                  25                  30

Asn Gly Asn Thr Tyr Leu His Trp Phe Gln Gln Arg Pro Gly Gln Ser
        35                  40                  45

```
Pro Arg Arg Leu Ile Tyr Arg Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Val Pro Pro Thr Phe Gly Gln Gly Thr Lys Leu Glu Ile Lys
            100                 105                 110
```

<210> SEQ ID NO 30
<211> LENGTH: 4
<212> TYPE: PRT
<213> ORGANISM: Artificial Sequence
<220> FEATURE:
<223> OTHER INFORMATION: Synthetic Construct

<400> SEQUENCE: 30

```
Gly Phe Leu Gly
 1
```

<210> SEQ ID NO 31
<211> LENGTH: 113
<212> TYPE: PRT
<213> ORGANISM: Mus musculus

<400> SEQUENCE: 31

```
Asp Phe Val Met Thr Gln Thr Pro Leu Ser Leu Pro Val Ser Leu Gly
 1               5                  10                  15

Asp Gln Ala Ser Ile Ser Cys Arg Ala Ser Gln Ser Leu Val His Ser
             20                  25                  30

Asn Gly Asn Thr Tyr Leu His Trp Tyr Leu Gln Lys Pro Gly Gln Ser
         35                  40                  45

Pro Lys Leu Leu Ile Tyr Arg Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Pro Thr Phe Gly Gly Gly Thr Lys Leu Glu Ile Lys
            100                 105                 110

Arg
```

<210> SEQ ID NO 32
<211> LENGTH: 113
<212> TYPE: PRT
<213> ORGANISM: Homo sapiens

<400> SEQUENCE: 32

```
Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
             20                  25                  30

Asp Gly Asn Thr Tyr Leu Asn Trp Phe Gln Gln Arg Pro Gly Gln Ser
         35                  40                  45

Pro Arg Arg Leu Ile Tyr Lys Val Ser Asn Arg Asp Ser Gly Val Pro
     50                  55                  60

Asp Arg Phe Ser Gly Ser Gly Ser Gly Thr Asp Phe Thr Leu Lys Ile
 65                  70                  75                  80
```

Ser Arg Val Glu Ala Glu Asp Val Gly Val Tyr Tyr Cys Met Gln Gly
            85                  90                  95

Thr His Trp Pro Tyr Thr Phe Gly Gln Gly Thr Lys Leu Glu Ile Lys
            100                 105                 110

Arg

<210> SEQ ID NO 33
<211> LENGTH: 113
<212> TYPE: PRT
<213> ORGANISM: Artificial Sequence
<220> FEATURE:
<223> OTHER INFORMATION: Synthetic Construct

<400> SEQUENCE: 33

Asp Phe Val Met Thr Gln Ser Pro Leu Ser Leu Pro Val Thr Leu Gly
1               5                   10                  15

Gln Pro Ala Ser Ile Ser Cys Arg Ala Ser Gln Ser Leu Val His Ser
            20                  25                  30

Asn Gly Asn Thr Tyr Leu His Trp Phe Gln Gln Arg Pro Gly Gln Ser
        35                  40                  45

Pro Arg Arg Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
            85                  90                  95

Thr His Val Pro Pro Thr Phe Gly Gln Gly Thr Lys Leu Glu Ile Lys
            100                 105                 110

Arg

<210> SEQ ID NO 34
<211> LENGTH: 113
<212> TYPE: PRT
<213> ORGANISM: Artificial Sequence
<220> FEATURE:
<223> OTHER INFORMATION: Synthetic Construct

<400> SEQUENCE: 34

Asp Phe Val Met Thr Gln Ser Pro Leu Ser Leu Pro Val Thr Leu Gly
1               5                   10                  15

Gln Pro Ala Ser Ile Ser Cys Arg Ala Ser Gln Ser Leu Val His Ser
            20                  25                  30

Asn Gly Asn Thr Tyr Leu His Trp Tyr Gln Gln Arg Pro Gly Gln Ser
        35                  40                  45

Pro Arg Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
            85                  90                  95

Thr His Val Pro Pro Thr Phe Gly Gln Gly Thr Lys Leu Glu Ile Lys
            100                 105                 110

Arg

<210> SEQ ID NO 35
<211> LENGTH: 113
<212> TYPE: PRT

```
<213> ORGANISM: Artificial Sequence
<220> FEATURE:
<223> OTHER INFORMATION: Synthetic Construct

<400> SEQUENCE: 35

Asp Phe Val Met Thr Gln Ser Pro Leu Ser Leu Pro Val Thr Leu Gly
1               5                   10                  15

Gln Pro Ala Ser Ile Ser Cys Arg Ala Ser Gln Ser Leu Val His Ser
            20                  25                  30

Asp Gly Asn Thr Tyr Leu His Trp Tyr Gln Gln Arg Pro Gly Gln Ser
        35                  40                  45

Pro Arg Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Thr Phe Gly Gln Gly Thr Lys Leu Glu Ile Lys
                100                 105                 110

Arg
```

ANTI-CD228 ANTIBODIES AND ANTIBODY-DRUG CONJUGATES

CROSS-REFERENCE TO RELATED APPLICATIONS

This application claims priority to U.S. Provisional Application Nos. 62/801,590 filed on Feb. 5, 2019, 62/824,923 filed Mar. 27, 2019, 62/879,660 filed Jul. 29, 2019, 62/882,016 filed Aug. 2, 2019, and 62/934,424 filed on Nov. 12, 2019, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 761682001300SEQLIST.TXT, date recorded: Jan. 21, 2020, size: 28 KB).

TECHNICAL FIELD

The present invention relates to novel anti-CD228 antibodies and antibody-drug conjugates and methods of using such anti-CD228 antibodies and antibody-drug conjugates to treat cancer.

BACKGROUND

CD228, which is also known as melanotransferrin, MELTF, p97 and MF12, is a glycosylphosphatidylinositol-anchored glycoprotein and was first identified as a 97-kDa cell-surface marker for malignant melanoma cells. CD228 is overexpressed on a majority of clinical melanoma isolates and is also observed on many human carcinomas. CD228 has been shown to be expressed in a variety of cancers. CD228 belongs to the transferrin family of iron-binding proteins.

Melanoma, also known as malignant melanoma, is a type of cancer that develops from melanocytes, which are pigment-containing cells. Melanoma is the most dangerous type of skin cancer. In 2015, were 3.1 million people with active disease and melanoma resulted in 59,800 deaths. Surgery can be effective for early stage melanoma, but may not be a treatment option for disease that has metastasized to distant organs. Melanomas that spread often do so to the lymph nodes in the area before spreading elsewhere. Attempts to improve survival by removing lymph nodes surgically were associated with many complications, but no overall survival benefit. Immunotherapy, chemotherapy and radiation therapy have all been used, but are often not curative, particularly for late stage melanoma. When there is distant metastasis, the cancer is generally considered incurable. The five-year survival rate of stage IV disease is 15-20%. Therefore, there is a need for improved treatments for melanoma.

All references cited herein, including patent applications, patent publications, and scientific literature, are herein incorporated by reference in their entirety, as if each individual reference were specifically and individually indicated to be incorporated by reference.

SUMMARY

Provided herein is an isolated anti-CD228 antibody, or antigen-binding fragment thereof, comprising a heavy chain variable region and a light chain variable region, wherein the heavy chain variable region comprises:

(i) a CDR-H1 comprising the amino acid sequence of SEQ ID NO:1;

(ii) a CDR-H2 comprising the amino acid sequence of SEQ ID NO:2; and (iii) a CDR-H3 comprising the amino acid sequence of SEQ ID NO:3; and wherein the light chain variable region comprises:

(i) a CDR-L1 comprising the amino acid sequence of SEQ ID NO:4;

(ii) a CDR-L2 comprising the amino acid sequence of SEQ ID NO:5; and (iii) a CDR-L3 comprising the amino acid sequence of SEQ ID NO:6. In some embodiments, the antibody is humanized.

Also provided herein is a humanized anti-CD228 antibody, or antigen-binding fragment thereof, comprising a heavy chain variable region comprising an amino acid sequence at least 90% identical to SEQ ID NO: 7 provided that position H27 is occupied by D, position H30 is occupied by T, position H47 is occupied by Y, position H71 is occupied by R, and position H78 is occupied by Y, and a light chain variable region comprising an amino acid sequence at least 90% identical to SEQ ID NO: 8, provided that position L2 is occupied by F, position L36 is occupied by Y and position L46 is occupied by L. In some embodiments, position L28 is occupied by D.

Also provided herein is a humanized anti-CD228 antibody, or antigen-binding fragment thereof, comprising a heavy chain variable region comprising the three Kabat CDRs of SEQ ID NO: 7, wherein position H27 is occupied by D, position H30 is occupied by T, position H47 is occupied by Y, position H71 is occupied by R, and position H78 is occupied by Y, and a light chain variable region comprising the three Kabat CDRs of SEQ ID NO: 8, wherein position L2 is occupied by F, position L36 is occupied by Y and position L46 is occupied by L.

In some of any of the embodiments herein, the heavy chain variable region comprises an amino acid sequence having at least 95% sequence identity to the amino acid sequence of SEQ ID NO: 7 and the light chain variable region comprises an amino acid sequence having at least 95% sequence identity to the amino acid sequence of SEQ ID NO: 8. In some of any of the embodiments herein, the heavy chain variable region comprises the amino acid sequence of SEQ ID NO: 7 and the light chain variable region comprises the amino acid sequence of SEQ ID NO:8. In some of any of the embodiments herein, the antibody or antigen-binding fragment is an antigen-binding fragment. In some of any of the embodiments herein, the antibody or antigen-binding fragment is a full-length antibody.

Also provided herein is an antibody-drug conjugate comprising the antibody or antigen-binding fragment provided herein conjugated to a cytotoxic or cytostatic agent. In some embodiments, the linker is a MDpr-PEG(12)-gluc linker. In some of any of the embodiments herein, the cytotoxic or cytostatic agent is a monomethyl auristatin. In some embodiments, the monomethyl auristatin is monomethyl auristatin E (MMAE). In some of any of the embodiments herein, the he linker is attached to monomethyl auristatin E forming an antibody-drug conjugate having the structure:

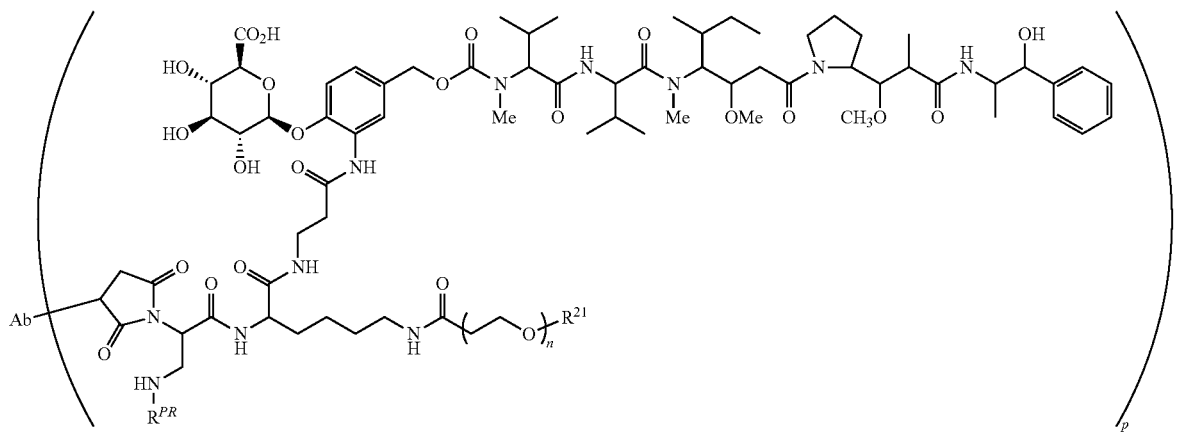

wherein Ab is the antibody hL49, n is 12, $R^{PR}$ is hydrogen, $R^{21}$ is $CH_3$, and p denotes a number from 1 to 16. In some of any of the embodiments herein, the antibody-drug conjugate is hL49-MDpr-PEG(12)-gluc-MMAE.

Also provided herein is a nucleic acid encoding the heavy chain variable region and/or the light chain variable region of an antibody described herein. Also provided herein is a vector comprising a nucleic acid provided herein. Also provided herein is a host cell comprising a nucleic acid provided herein.

Also provided herein is a method of producing an anti-CD228 antibody or antigen-binding fragment provided herein, comprising culturing a host cell provided herein under a condition suitable for production of the anti-CD228 antibody or antigen-binding fragment thereof.

Also provided herein is a method of producing an anti-CD228 antibody-drug conjugate provided herein, comprising culturing a host cell provided herein under a condition suitable for production of an anti-CD228 antibody; isolating the anti-CD228 antibody produced from the host cell; and conjugating the anti-CD228 antibody to a cytotoxic or cytostatic agent.

Also provided herein is a method of treating cancer in a subject, the method comprising administering to the subject an antibody or antigen-binding fragment provided herein or an antibody-drug conjugate provided herein. In some embodiments, the cancer is selected from the group consisting of melanoma, pancreatic cancer, mesothelioma, colorectal cancer, lung cancer, thyroid cancer, breast cancer, choliangiocarcinoma, esophageal cancer and head and neck cancer. In some embodiments, the subject is a human.

Also provided herein is a kit comprising: (a) an antibody or antigen-binding fragment provided herein or an antibody-drug conjugate provided herein; and (b) instructions for using the antibody or antigen-binding fragment or antibody-drug conjugate according to a method provided herein.

Also provided herein is a pharmaceutical composition comprising an antibody or antigen-binding fragment provided herein or an antibody-drug conjugate provided herein and one or more agents selected from the group consisting of a physiologically acceptable carrier, a diluent, an excipient and an auxiliary.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8 shows an alignment of the heavy chain variable region amino acid sequences of the parental murine anti-CD228 monoclonal antibody (referred to as Mu L49 vH (SEQ ID NO: 21)) with the human acceptor sequence (referred to as Hu IGHV4-59/HJ4 (SEQ ID NO: 23)) and humanized versions of the L49 antibody (referred to as hvHA (SEQ ID NO: 7), hvHB (SEQ ID NO: 24), and hvHC (SEQ ID NO: 25)). The CDR positions are designated using both the Kabat and IMGT numbering schemes.

FIG. 9 shows an alignment of the heavy chain variable region amino acid sequences of humanized versions of the L49 antibody (referred to as hvHA (SEQ ID NO: 7), hvHB (SEQ ID NO: 24) and hvHC (SEQ ID NO: 25)). The CDR positions are designated using both the Kabat and IMGT numbering schemes.

FIG. 10 shows an alignment of the light chain variable region amino acid sequences of the parental murine anti-CD228 monoclonal antibody (referred to as Mu L49 vL (SEQ ID NO: 31)) with the human acceptor sequence (referred to as Hu IGKV2-30/KJ2 (SEQ ID NO: 32)) and humanized versions of the L49 antibody (referred to as hvLA (SEQ ID NO: 33), hvLB (SEQ ID NO: 34) and hvLC (SEQ ID NO: 35)). The CDR positions are designated using both the Kabat and IMGT numbering schemes.

FIG. 11 shows an alignment of the light chain variable region amino acid sequences of humanized versions of the L49 antibody (referred to as hvLA (SEQ ID NO: 33), hvLB (SEQ ID NO: 34) and hvLC (SEQ ID NO: 35)). The CDR positions are designated using both the Kabat and IMGT numbering schemes.

FIG. 27 shows the percent change in tumor volume in response to treatment with hL49-MDpr-PEG(12)-gluc-MMAE (8) in 22 different mouse PDX models of triple-negative breast cancer.

DETAILED DESCRIPTION

I. Definitions

Figure 1:
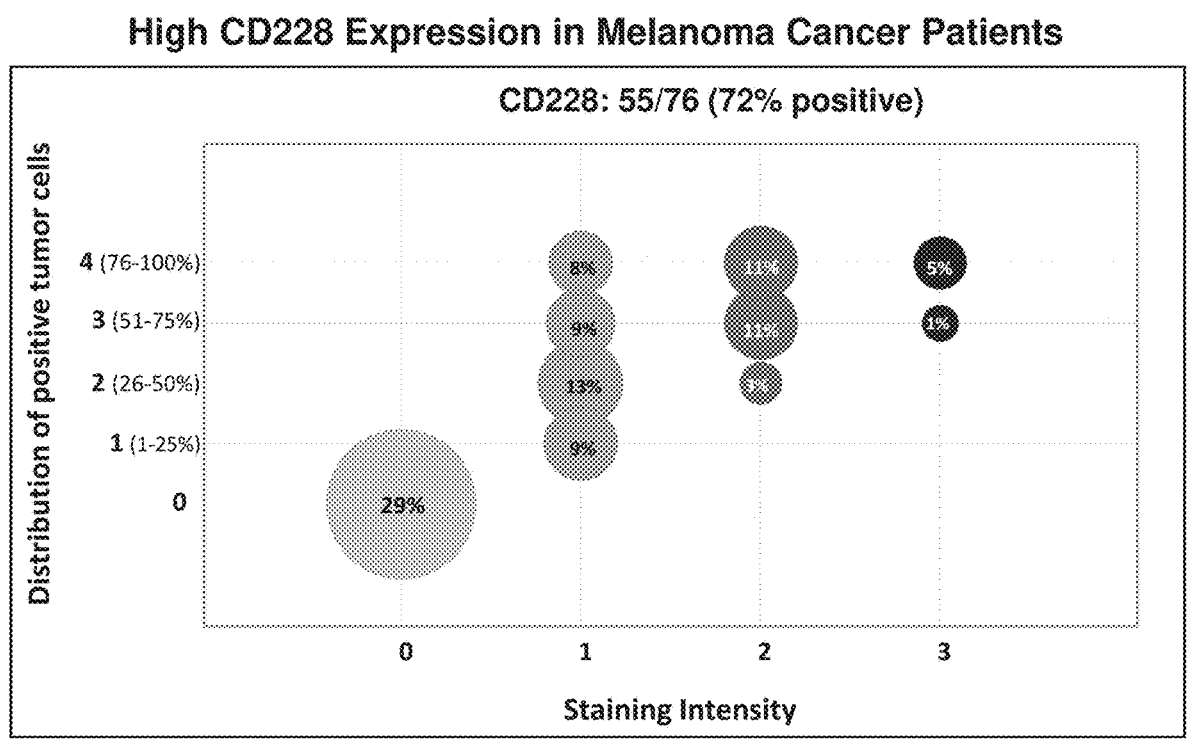
FIG. 1 shows an analysis of CD228 protein expression by IHC on melanoma cancer patient samples.

In order that the present disclosure can be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that aspects and embodiments of the invention described herein include "comprising," "consisting," and "consisting essentially of" aspects and embodiments.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

The terms "CD228," "p97," "melanotransferrin," "MELTF," and "MF12" are used interchangeably herein, and, unless specified otherwise, include any variants, isoforms and species homologs of human CD228 which are generally expressed by cells or expressed on cells transfected with the CD228 gene.

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$ or VH) and a heavy chain constant region ($C_H$ or CH). The heavy chain constant region typically is comprised of three domains, $C_H1$, $C_H2$, and $C_H3$. The heavy chains are generally inter-connected via disulfide bonds in the so-called "hinge region." Each light chain typically is comprised of a light chain variable region (abbreviated herein as $V_L$ or VL) and a light chain constant region ($C_L$ or CL). The light chain constant region typically is comprised of one domain, $C_L$. The CL can be of κ (kappa) or λ (lambda) isotype. The terms "constant domain" and "constant region" are used interchangeably herein. An immunoglobulin can derive from any of the commonly known isotypes, including but not limited to IgA, secretory IgA, IgG, and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes.

The term "variable region" or "variable domain" refers to the domain of an antibody heavy or light chain that is involved in binding the antibody to antigen. The variable regions of the heavy chain and light chain ($V_H$ and $V_L$, respectively) of a native antibody may be further subdivided into regions of hypervariability (or hypervariable regions, which may be hypervariable in sequence and/or form of structurally defined loops), also termed complementarity-determining regions (CDRs), interspersed with regions that are more conserved, termed framework regions (FRs). The terms "complementarity determining regions" and "CDRs," synonymous with "hypervariable regions" or "HVRs" are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). Within each $V_H$ and $V_L$, three CDRs and four FRs are typically arranged from amino-terminus to carboxy-terminus in the following order: FR1, CDR1, FR2, CDR2, FR3, CDR3, FR4 (See also Chothia and Lesk *J. Mot. Biol.*, 195, 901-917 (1987)).

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half-life of significant periods of time, such as at least about 30 min, at least about 45 min, at least about one hour (h), at least about two hours, at least about four hours, at least about eight hours, at least about 12 hours (h), about 24 hours or more, about 48 hours or more, about three, four, five, six, seven or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. An antibody may also be a bispecific antibody, diabody, multispecific antibody or similar molecule.

The term "monoclonal antibody" as used herein refers to a preparation of antibody molecules that are recombinantly produced with a single primary amino acid sequence. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal non-human animal, such as a transgenic mouse, having a genome comprising a human heavy chain transgene and a light chain transgene, fused to an immortalized cell.

An "isolated antibody" refers to an antibody that is substantially free of other antibodies having different antigenic specificities (e.g., an isolated antibody that binds specifically to CD228 is substantially free of antibodies that bind specifically to antigens other than CD228). An isolated antibody that binds specifically to CD228 can, however, have cross-reactivity to other antigens, such as CD228 molecules from different species. Moreover, an isolated antibody can be substantially free of other cellular material and/or chemicals. In one embodiment, an isolated antibody includes an antibody conjugate attached to another agent (e.g., small molecule drug). In some embodiments, an isolated anti-CD228 antibody includes a conjugate of an anti-CD228 antibody with a small molecule drug (e.g., MMAE or MMAF).

A "human antibody" (HuMAb) refers to an antibody having variable regions in which both the FRs and CDRs are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human antibodies" and "fully human antibodies" and are used synonymously.

The term "humanized antibody" as used herein, refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), which together form the antigen binding site, onto a homologous human acceptor framework region (FR) (see WO92/22653 and EP0629240). In order to fully reconstitute the binding affinity and specificity of the parental antibody, the substitution of framework residues from the parental antibody (i.e. the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties.

The term "chimeric antibody" as used herein, refers to an antibody wherein the variable region is derived from a non-human species (e.g. derived from rodents) and the constant region is derived from a different species, such as human. Chimeric antibodies may be generated by antibody engineering. "Antibody engineering" is a term used generic for different kinds of modifications of antibodies, and which is a well-known process for the skilled person. In particular, a chimeric antibody may be generated by using standard DNA techniques as described in Sambrook et al., 1989, Molecular Cloning: A laboratory Manual, New York: Cold Spring Harbor Laboratory Press, Ch. 15. Thus, the chimeric antibody may be a genetically or an enzymatically engineered recombinant antibody. It is within the knowledge of the skilled person to generate a chimeric antibody, and thus, generation of the chimeric antibody according to the present invention may be performed by other methods than described herein. Chimeric monoclonal antibodies for therapeutic applications are developed to reduce antibody immunogenicity. They may typically contain non-human (e.g. murine) variable regions, which are specific for the antigen of interest, and human constant antibody heavy and light chain domains. The terms "variable region" or "variable domains" as used in the context of chimeric antibodies, refers to a region which comprises the CDRs and framework regions of both the heavy and light chains of the immunoglobulin.

An "anti-antigen antibody" refers to an antibody that binds to the antigen. For example, an anti-CD228 antibody is an antibody that binds to the antigen CD228.

An "antigen-binding portion" or antigen-binding fragment" of an antibody refers to one or more fragments of an antibody that retain the ability to bind specifically to the antigen bound by the whole antibody. Examples of antibody fragments (e.g., antigen-binding fragment) include but are not limited to Fv, Fab, Fab', Fab'-SH, F(ab')$_2$; diabodies; linear antibodies; single-chain antibody molecules (e.g. scFv); and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Percent (%) sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For example, the % sequence identity of a given amino acid sequence A to, with, or against a given amino acid sequence B (which can alternatively be phrased as a given amino acid sequence A that has or comprises a certain % sequence identity to, with, or against a given amino acid sequence B) is calculated as follows:

$$100 \text{ times the fraction } X/Y$$

where X is the number of amino acid residues scored as identical matches by the sequence in that program's alignment of A and B, and where Y is the total number of amino acid residues in B. It will be appreciated that where the length of amino acid sequence A is not equal to the length of amino acid sequence B, the % sequence identity of A to B will not equal the % sequence identity of B to A.

As used herein, the terms "binding", "binds" or "specifically binds" in the context of the binding of an antibody to a pre-determined antigen typically is a binding with an affinity corresponding to a $K_D$ of about $10^{-6}$ M or less, e.g. $10^{-7}$ M or less, such as about $10^{-8}$ M or less, such as about $10^{-9}$ M or less, about $10^{-10}$ M or less, or about $10^{-11}$ M or even less when determined by for instance BioLayer Interferometry (BLI) technology in a Octet HTX instrument using the antibody as the ligand and the antigen as the analyte, and wherein the antibody binds to the predetermined antigen with an affinity corresponding to a $K_D$ that is at least ten-fold lower, such as at least 100-fold lower, for instance at least 1,000-fold lower, such as at least 10,000- fold lower, for instance at least 100,000-fold lower than its $K_D$ of binding to a non-specific antigen (e.g., BSA, casein) other than the predetermined antigen or a closely related antigen. The amount with which the $K_D$ of binding is lower is dependent on the $K_D$ of the antibody, so that when the $K_D$ of the antibody is very low, then the amount with which the $K_D$ of binding to the antigen is lower than the $K_D$ of binding to a non-specific antigen may be at least 10,000-fold (that is, the antibody is highly specific).

The term "$K_D$" (M), as used herein, refers to the dissociation equilibrium constant of a particular antibody-antigen interaction. Affinity, as used herein, and $K_D$ are inversely related, that is that higher affinity is intended to refer to lower $K_D$, and lower affinity is intended to refer to higher $K_D$.

The term "ADC" refers to an antibody-drug conjugate, which in the context of the present invention refers to an anti-CD228 antibody, which is coupled to a drug moiety (e.g., MMAE or MMAF) as described in the present application.

The abbreviations "vc" and "val-cit" refer to the dipeptide valine-citrulline.

The abbreviation "PAB" refers to the self-immolative spacer:

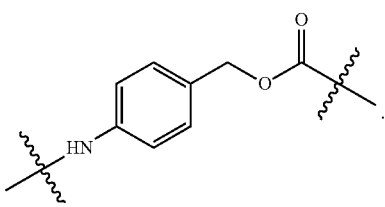 [SMILES: *Nc1ccc(COC(*)=O)cc1]

The abbreviation "MC" refers to the stretcher maleimidocaproyl:

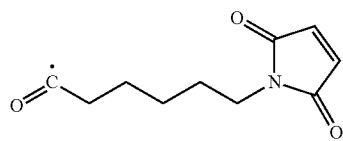

The abbreviation "MP" refers to the stretcher maleimidopropionyl:

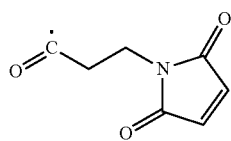

A "cancer" refers to a broad group of various diseases characterized by the uncontrolled growth of abnormal cells in the body. A "cancer" or "cancer tissue" can include a tumor. Unregulated cell division and growth results in the formation of malignant tumors that invade neighboring tissues and can also metastasize to distant parts of the body through the lymphatic system or bloodstream. Following metastasis, the distal tumors can be said to be "derived from" the pre-metastasis tumor.

The term "antibody-dependent cellular cytotoxicity", or ADCC, is a mechanism for inducing cell death that depends upon the interaction of antibody-coated target cells with immune cells possessing lytic activity (also referred to as effector cells). Such effector cells include natural killer cells, monocytes/macrophages and neutrophils. The effector cells attach to an Fc effector domain(s) of Ig bound to target cells via their antigen-combining sites. Death of the antibody-coated target cell occurs as a result of effector cell activity.

The term "antibody-dependent cellular phagocytosis", or ADCP, refers to the process by which antibody-coated cells are internalized, either in whole or in part, by phagocytic immune cells (e.g., macrophages, neutrophils and dendritic cells) that bind to an Fc effector domain(s) of Ig.

The term "complement-dependent cytotoxicity", or CDC, refers to a mechanism for inducing cell death in which an Fc effector domain(s) of a target-bound antibody activates a series of enzymatic reactions culminating in the formation of holes in the target cell membrane. Typically, antigen-antibody complexes such as those on antibody-coated target cells bind and activate complement component C1q which in turn activates the complement cascade leading to target cell death. Activation of complement may also result in deposition of complement components on the target cell surface that facilitate ADCC by binding complement receptors (e.g., CR3) on leukocytes.

A "cytostatic effect" refers to the inhibition of cell proliferation. A "cytostatic agent" refers to an agent that has a cytostatic effect on a cell, thereby inhibiting the growth and/or expansion of a specific subset of cells. Cytostatic agents can be conjugated to an antibody or administered in combination with an antibody.

"Treatment" or "therapy" of a subject refers to any type of intervention or process performed on, or the administration of an active agent to, the subject with the objective of reversing, alleviating, ameliorating, inhibiting, slowing down, or preventing the onset, progression, development, severity, or recurrence of a symptom, complication, condition, or biochemical indicia associated with a disease. In some embodiments, the disease is cancer.

A "subject" includes any human or non-human animal. The term "non-human animal" includes, but is not limited to, vertebrates such as non-human primates, sheep, dogs, and rodents such as mice, rats, and guinea pigs. In some embodiments, the subject is a human. The terms "subject" and "patient" and "individual" are used interchangeably herein.

An "effective amount" or "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

By way of example for the treatment of tumors, a therapeutically effective amount of an anti-cancer agent inhibits cell growth or tumor growth by at least about 10%, by at least about 20%, by at least about 30%, by at least about 40%, by at least about 50%, by at least about 60%, by at least about 70%, or by at least about 80%, by at least about 90%, by at least about 95%, by at least about 96%, by at least about 97%, by at least about 98%, or by at least about 99% in a treated subject(s) (e.g., one or more treated subjects) relative to an untreated subject(s) (e.g., one or more untreated subjects). In some embodiments, a therapeutically effective amount of an anti-cancer agent inhibits cell growth or tumor growth by 100% in a treated subject(s) (e.g., one or more treated subjects) relative to an untreated subject(s) (e.g., one or more untreated subjects).

In other embodiments of the disclosure, tumor regression can be observed and continue for a period of at least about 20 days, at least about 30 days, at least about 40 days, at least about 50 days, or at least about 60 days.

A therapeutically effective amount of a drug (e.g., anti-CD228 antibody-drug conjugate) includes a "prophylactically effective amount," which is any amount of the drug that, when administered alone or in combination with an anti-cancer agent to a subject at risk of developing a cancer (e.g., a subject having a pre-malignant condition) or of suffering a recurrence of cancer, inhibits the development or recurrence of the cancer. In some embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

As used herein, "subtherapeutic dose" means a dose of a therapeutic compound (e.g., an anti-CD228 antibody-drug conjugate) that is lower than the usual or typical dose of the therapeutic compound when administered alone for the treatment of a hyperproliferative disease (e.g., cancer).

An "immune-related response pattern" refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents can require long-term monitoring of the effects of these agents on the target disease.

By way of example, an "anti-cancer agent" promotes cancer regression in a subject. In some embodiments, a therapeutically effective amount of the drug promotes cancer regression to the point of eliminating the cancer. "Promoting cancer regression" means that administering an effective amount of the drug, alone or in combination with an anti-cancer agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity or other adverse physiological effects at the cellular, organ and/or organism level (adverse effects) resulting from administration of the drug.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration that is at least the same as the treatment duration, or at least 1.5, 2.0, 2.5, or 3 times longer than the treatment duration.

As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started.

As used herein, "progression free survival" or "PFS" refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall response rate" or "ORR" refers to the sum of complete response (CR) rate and partial response (PR) rate.

As used herein, "overall survival" or "OS" refers to the percentage of individuals in a group who are likely to be alive after a particular duration of time.

The phrase "pharmaceutically acceptable" indicates that the substance or composition must be compatible chemically and/or toxicologically, with the other ingredients comprising a formulation, and/or the mammal being treated therewith.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, methanesulfonate "mesylate", ethanesulfonate, benzenesulfonate, p-toluenesulfonate, pamoate (i.e., 4,4'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

"Administering" or "administration" refer to the physical introduction of a therapeutic agent to a subject, using any of the various methods and delivery systems known to those skilled in the art. Exemplary routes of administration for the anti-CD228 antibody-drug conjugate include intravenous, intramuscular, subcutaneous, intraperitoneal, spinal or other parenteral routes of administration, for example by injection or infusion (e.g., intravenous infusion). The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. A therapeutic agent can be administered via a non-parenteral route, or orally. Other non-parenteral routes include a topical, epidermal or mucosal route of administration, for example, intranasally, vaginally, rectally, sublingually or topically. Administration can also be performed, for example, once, a plurality of times, and/or over one or more extended periods.

The terms "baseline" or "baseline value" used interchangeably herein can refer to a measurement or characterization of a symptom before the administration of the therapy (e.g., an anti-CD228 antibody-drug conjugate as described herein) or at the beginning of administration of the therapy. The baseline value can be compared to a reference value in order to determine the reduction or improvement of a symptom of a CD228-associated disease contemplated herein (e.g., cancer). The terms "reference" or "reference value" used interchangeably herein can refer to a measurement or characterization of a symptom after administration of the therapy (e.g., an anti-CD228 antibody-drug conjugate as described). The reference value can be measured one or more times during a dosage regimen or treatment cycle or at the completion of the dosage regimen or treatment cycle. A "reference value" can be an absolute value; a relative value; a value that has an upper and/or lower limit; a range of values; an average value; a median value: a mean value; or a value as compared to a baseline value.

Similarly, a "baseline value" can be an absolute value; a relative value; a value that has an upper and/or lower limit; a range of values; an average value; a median value; a mean value; or a value as compared to a reference value. The reference value and/or baseline value can be obtained from one individual, from two different individuals or from a group of individuals (e.g., a group of two, three, four, five or more individuals).

The term "monotherapy" as used herein means that the anti-CD228 antibody-drug conjugate is the only anti-cancer agent administered to the subject during the treatment cycle. Other therapeutic agents, however, can be administered to the subject. For example, anti-inflammatory agents or other agents administered to a subject with cancer to treat symptoms associated with cancer, but not the underlying cancer itself, including, for example inflammation, pain, weight loss, and general malaise, can be administered during the period of monotherapy.

An "adverse event" (AE) as used herein is any unfavorable and generally unintended or undesirable sign (including an abnormal laboratory finding), symptom, or disease associated with the use of a medical treatment. A medical treatment can have one or more associated AEs and each AE can have the same or different level of severity. Reference to methods capable of "altering adverse events" means a treatment regime that decreases the incidence and/or severity of one or more AEs associated with the use of a different treatment regime.

A "serious adverse event" or "SAE" as used herein is an adverse event that meets one of the following criteria:

Is fatal or life-threatening (as used in the definition of a serious adverse event, "life-threatening" refers to an event in which the patient was at risk of death at the time of the event; it does not refer to an event which hypothetically might have caused death if it was more severe.
Results in persistent or significant disability/incapacity
Constitutes a congenital anomaly/birth defect
Is medically significant, i.e., defined as an event that jeopardizes the patient or may require medical or surgical intervention to prevent one of the outcomes listed above.

Medical and scientific judgment must be exercised in deciding whether an AE is "medically significant"
Requires inpatient hospitalization or prolongation of existing hospitalization, excluding the following: 1) routine treatment or monitoring of the underlying disease, not associated with any deterioration in condition; 2) elective or pre-planned treatment for a pre-existing condition that is unrelated to the indication under study and has not worsened since signing the informed consent; and 3) social reasons and respite care in the absence of any deterioration in the patient's general condition.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

Reference to "about" a value or parameter herein includes (and describes) embodiments that are directed to that value or parameter per se. For example, description referring to "about X" encompasses and describes "X."

As described herein, any concentration range, percentage range, ratio range, or integer range is to be understood to include the value of any integer within the recited range and, when appropriate, fractions thereof (such as one tenth and one hundredth of an integer), unless otherwise indicated.

Various aspects of the disclosure are described in further detail in the following subsections.

II. General

The invention provides antibodies that specifically bind CD228. The present invention is based, in part, on the discovery that antibody-drug conjugates, including pegylated-MMAE antibody-drug conjugates, targeted to CD228 are particularly effective at killing CD228+ expressing cells. CD228 has been shown to be expressed in a variety of cancers, including melanoma, thyroid cancer, lung cancer, liver cancer, pancreatic cancer, head and neck cancer, stomach cancer, colorectal cancer, urothelial cancer, breast cancer and cervical cancer.

III. Target Molecules

Unless otherwise indicated, CD228 refers to human CD228. An exemplary human protein sequence is assigned UniProt ID NO. P08582.

IV. Antibodies of the Invention

The invention provides antibodies, such as humanized antibodies, derived from the mouse antibody L49. L49 is a murine immunoglobulin G1 (IgG1) monoclonal antibody against CD228, which was derived from BALB/c mice immunized with lung carcinoma and melanoma cell lines (Siemers et al., 1997, Bioconjug. Chem. 8:510-9).

The binding affinity of humanized forms of the mouse L49 antibody (i.e., dissociation constant, $K_D$) is preferably within a factor of five or a factor of two of that of the mouse antibody L49 for human. CD228. Humanized L49 antibodies specifically bind to human CD228 as does the mouse antibody from which they were derived. These antibodies bind CD228 both in its native form and as recombinantly expressed, for example from Chinese hamster ovary (CHO) cells or Human embryonic kidney (HEK) cells. Preferred humanized L49 antibodies have an affinity the same as or greater than (i.e., greater than beyond margin of error in measurement) that of L49 for human CD228 (e.g., 1.1-5 fold, 1.1 to 3 fold, 1.5 to 3-fold, 1.7 to 2.3-fold or 1.7-2.1- fold the affinity or about twice the affinity of L49). Preferred humanized L49 antibodies bind to the same epitope and/or compete with mouse L49 for binding to human CD228.

Preferred antibodies of the invention inhibit cancer (e.g., growth of cells, metastasis and/or lethality to the organisms) as shown on cancerous cells propagating in culture, in an animal model or clinical trial. Animal models can be formed by implanting CD228-expressing human tumor cell lines into appropriate immunodeficient rodent strains, e.g., athymic nude mice or SCID mice. These tumor cell lines can be established in immunodeficient rodent hosts either as solid tumor by subcutaneous injections or as disseminated tumors by intravenous injections.

Once established within a host, these tumor models can be applied to evaluate the therapeutic efficacies of the anti-CD228 antibodies or conjugated forms thereof as described in the Examples.

Generally, anti-CD228 antibodies and/or anti-CD228 antibody-drug conjugates of the disclosure bind CD228, e.g., human CD228, and exert cytostatic and cytotoxic effects on malignant cells, such as cancer cells. Anti-CD228 antibodies of the disclosure are preferably monoclonal, and may be multispecific, human, humanized or chimeric antibodies, single chain antibodies, Fab fragments, F(ab') fragments, fragments produced by a Fab expression library, and CD228 binding fragments of any of the above. In some embodiments, the anti-CD228 antibodies of the disclosure specifically bind CD228. The immunoglobulin molecules of the disclosure can be of any type (e.g., IgG, IgE, IgM, IgD, IgA and IgY), class (e.g., IgG1, IgG2, IgG3, IgG4, IgA1 and IgA2) or subclass of immunoglobulin molecule.

In certain embodiments of the disclosure, the anti-CD228 antibodies are antigen-binding fragments (e.g., human antigen-binding fragments) as described herein and include, but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Antigen-binding fragments, including single-chain antibodies, may comprise the variable region(s) alone or in combination with the entirety or a portion of the following: hinge region, CH1, CH2, CH3 and CL domains. Also included in the present disclosure are antigen-binding fragments comprising any combination of variable region(s) with a hinge region, CH1, CH2, CH3 and CL domains. In some embodiments, the anti-CD228 antibodies or antigen-binding fragments thereof are human, murine (e.g., mouse and rat), donkey, sheep, rabbit, goat, guinea pig, camelid, horse, or chicken.

The anti-CD228 antibodies of the present disclosure may be monospecific, bispecific, trispecific or of greater multi specificity. Multispecific antibodies may be specific for different epitopes of CD228 or may be specific for both CD228 as well as for a heterologous protein. See, e.g., PCT publications WO 93/17715; WO 92/08802; WO 91/00360; WO 92/05793; Tutt, et al., 1991, J. Immunol. 147:60 69; U.S. Pat. Nos. 4,474,893; 4,714,681; 4,925,648; 5,573,920; 5,601,819; Kostelny et al., 1992, J. Immunol. 148:1547 1553.

Anti-CD228 antibodies of the present disclosure may be described or specified in terms of the particular CDRs they comprise. The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme); Al-Lazikani et al., (1997) JMB 273,927-948 ("Chothia" numbering scheme); MacCallum et al., J. Mol. Biol. 262:732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Plückthun A, "Yet another numbering scheme for immunoglobulin variable domains: an automatic modeling and analysis tool," J Mol Biol, 2001 Jun. 8; 309(3):657-70, ("Aho" numbering scheme); and Martin et al., "Modeling antibody hypervariable loops: a combined algorithm," PNAS, 1989, 86(23): 9268-9272, ("AbM" numbering scheme). The boundaries of a given CDR may vary depending on the scheme used for identification. In some embodiments, a "CDR" or "complementarity determining region," or individual specified CDRs (e.g., CDR-H1, CDR-H2, CDR-H3), of a given antibody or region thereof (e.g., variable region thereof) should be understood to encompass a (or the specific) CDR as defined by any of the aforementioned schemes. For example, where it is stated that a particular CDR (e.g., a CDR-H3) contains the amino acid sequence of a corresponding CDR in a given $V_H$ or $V_L$ region amino acid sequence, it is understood that such a CDR has a sequence of the corresponding CDR (e.g., CDR-H3) within the variable region, as defined by any of the aforementioned schemes. The scheme for identification of a particular CDR or CDRs may be specified, such as the CDR as defined by the Kabat, Chothia, AbM or IMGT method.

CDR sequences of the anti-CD228 antibodies and of the anti-CD228 antibody-drug conjugates described herein are according to the Kabat numbering scheme as described in Kabat et al. (1991), "Sequences of Proteins of Immunological Interest," 5th Ed. Public Health Service, National Institutes of Health, Bethesda, Md.

In one aspect, provided herein is an anti-CD228 antibody comprising a heavy chain variable region and a light chain variable region, wherein the heavy chain variable region comprises (i) CDR-H1 comprising the amino acid sequence of SEQ ID NO:1, (ii) CDR-H2 comprising the amino acid sequence of SEQ ID NO:2, and (iii) CDR-H3 comprising the amino acid sequence of SEQ ID NO:3; and/or wherein the light chain variable region comprises (i) CDR-L1 comprising the amino acid sequence of SEQ ID NO:4, (ii) CDR-L2 comprising the amino acid sequence of SEQ ID NO:5, and (iii) CDR-L3 comprising the amino acid sequence of SEQ ID NO:6, wherein the CDRs of the anti-CD228 antibody are defined by the Kabat numbering scheme.

An anti-CD228 antibody described herein may comprise any suitable framework variable domain sequence, provided that the antibody retains the ability to bind CD228 (e.g., human CD228). As used herein, heavy chain framework regions are designated "HC-FR1-FR4," and light chain framework regions are designated "LC-FR1-FR4." In some embodiments, the anti-CD228 antibody comprises a heavy chain variable domain framework sequence of SEQ ID NO:9, 10, 11, and 12 (HC-FR1, HC-FR2, HC-FR3, and HC-FR4, respectively). In some embodiments, the anti-CD228 antibody comprises a light chain variable domain framework sequence of SEQ ID NO:13, 14, 15, and 16 (LC-FR1, LC-FR2, LC-FR3, and LC-FR4, respectively).

In some embodiments of the anti-CD228 antibodies described herein, the heavy chain variable domain comprises the amino acid sequence of QVQLQESGPGLVKPSETLSLTCTVSGDSITSGYWNWIRQPPGKGLEYIGYISDSGITYYNPSLKSRVTISRDTSKNQYSLKLSSVTAADTAVYYCARRTLATYYAMDYWGQGTLVTVSS (SEQ ID NO:7) and the light chain variable domain comprises the amino acid sequence of DFVMTQSPLSLPVTLGQPASISCRASQSLVHSDGNTYLHWYQQRPGQSPRLLIYRVSNRFSGVPDRFSGSGSGTDFTLKISRVEAEDVGVYYCSQSTHVPPTFGQGTKLEIK (SEQ ID NO:8).

In some embodiments of the anti-CD228 antibodies described herein, the heavy chain CDR sequences comprise the following:

a) CDR-H1
(SGYWN (SEQ ID NO: 1));

b) CDR-H2
(YISDSGITYYNPSLKS (SEQ ID NO: 2));
and c) CDR-H3
(RTLATYYAMDY (SEQ ID NO: 3)).

In some embodiments of the anti-CD228 antibodies described herein, the heavy chain FR sequences comprise the following:

a) HC-FR1
(QVQLQESGPGLVKPSETLSLTCTVSGDSIT (SEQ ID NO: 9));

b) HC-FR2
(WIRQPPGKGLEYIG (SEQ ID NO: 10));

c) HC-FR3
(RVTISRDTSKNQYSLKLSSVTAADTAVYYCAR (SEQ ID NO: 11));
and d) HC-FR4
(WGQGTLVTVSS (SEQ ID NO: 12)).

In some embodiments of the anti-CD228 antibodies described herein, the light chain CDR sequences comprise the following:

a) CDR-L1
(RASQSLVHSDGNTYLH (SEQ ID NO: 4));

b) CDR-L2
(RVSNRFS (SEQ ID NO: 5));
and c) CDR-L3
(SQSTHVPPT (SEQ ID NO: 6)).

In some embodiments of the anti-CD228 antibodies described herein, the light chain FR sequences comprise the following:

a) LC-FR1
(DFVMTQSPLSLPVTLGQPASISC (SEQ ID NO: 13));

b) LC-FR2
(WYQQRPGQSPRLLIY (SEQ ID NO: 14));

c) LC-FR3
(GVPDRFSGSGSGTDFTLKISRVEAEDVGVYYC (SEQ ID NO: 15));
and d) LC-FR4
(FGQGTKLEIK (SEQ ID NO: 16)).

In some embodiments, provided herein is an anti-CD228 antibody and/or anti-CD228 antibody-drug conjugate that binds to CD228 (e.g., human CD228), wherein the antibody or antibody-drug conjugate comprises a heavy chain variable region and a light chain variable region, wherein the antibody comprises:

(a) heavy chain variable domain comprising:
(1) an HC-FR1 comprising the amino acid sequence of SEQ ID NO:9;
(2) an CDR-H1 comprising the amino acid sequence of SEQ ID NO:1;
(3) an HC-FR2 comprising the amino acid sequence of SEQ ID NO:10;
(4) an CDR-H2 comprising the amino acid sequence of SEQ ID NO:2;
(5) an HC-FR3 comprising the amino acid sequence of SEQ ID NO:11;
(6) an CDR-H3 comprising the amino acid sequence of SEQ ID NO:3; and
(7) an HC-FR4 comprising the amino acid sequence of SEQ ID NO:12, and/or
(b) a light chain variable domain comprising:
(1) an LC-FR1 comprising the amino acid sequence of SEQ ID NO:13;
(2) an CDR-L1 comprising the amino acid sequence of SEQ ID NO:4;
(3) an LC-FR2 comprising the amino acid sequence of SEQ ID NO:14;
(4) an CDR-L2 comprising the amino acid sequence of SEQ ID NO:5;
(5) an LC-FR3 comprising the amino acid sequence of SEQ ID NO:15;
(6) an CDR-L3 comprising the amino acid sequence of SEQ ID NO:6; and
(7) an LC-FR4 comprising the amino acid sequence of SEQ ID NO:16.

In one aspect, provided herein is an anti-CD228 antibody and/or anti-CD228 antibody-drug conjugate comprising a heavy chain variable domain comprising the amino acid sequence of SEQ ID NO:7 or comprising a light chain variable domain comprising the amino acid sequence of SEQ ID NO:8. In some embodiments, the N-terminal glutamine of the heavy chain variable domain is cyclized to form pyroglutamic acid. In one aspect, provided herein is an anti-CD228 antibody comprising a heavy chain variable domain comprising the amino acid sequence of SEQ ID NO:7 and comprising a light chain variable domain comprising the amino acid sequence of SEQ ID NO:8. In some embodiments, the N-terminal glutamine of the heavy chain variable domain is cyclized to form pyroglutamic acid.

In some embodiments, provided herein is an anti-CD228 antibody and/or anti-CD228 antibody-drug conjugate comprising a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:7. In some embodiments, the N-terminal glutamine of the heavy chain variable domain is cyclized to form pyroglutamic acid. In certain embodiments, a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:7 contains substitutions (e.g., conservative substitutions), insertions, or deletions relative to the reference sequence and retains the ability to bind to a CD228 (e.g., human CD228). In certain embodiments, a total of 1 to 10 amino acids have been substituted, inserted and/or deleted in SEQ ID NO:7. In certain embodiments, substitutions, insertions, or deletions (e.g., 1, 2, 3, 4, or 5 amino acids) occur in regions outside the CDRs (i.e., in the FRs). In some embodiments, the anti-CD228 antibody comprises a heavy chain variable domain sequence of SEQ ID NO:7 including post-translational modifications of that sequence. In some embodiments, the N-terminal glutamine of the heavy chain variable domain is cyclized to form pyroglutamic acid. In a particular embodiment, the heavy chain variable domain comprises one, two or three CDRs selected from: (a) CDR-H1 comprising the amino acid sequence of SEQ ID NO:1, (b) CDR-H2 comprising the amino acid sequence of SEQ ID NO:2, and (c) CDR-H3 comprising the amino acid sequence of SEQ ID NO:3.

In some embodiments, provided herein is an anti-CD228 antibody and/or anti-CD228 antibody-drug conjugate comprising a light chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:8. In certain embodiments, a light chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:8 contains substitutions (e.g., conservative substitutions), insertions, or deletions relative to the reference sequence and retains the ability to bind to a CD228 (e.g., human CD228). In certain embodiments, a total of 1 to 10 amino acids have been substituted, inserted and/or deleted in SEQ ID NO:8. In certain embodiments, substitutions, insertions, or deletions (e.g., 1, 2, 3, 4, or 5 amino acids) occur in regions outside the CDRs (i.e., in the FRs). In some embodiments, the anti-CD228 antibody comprises a light chain variable domain sequence of SEQ ID NO:8 including post-translational modifications of that sequence. In a particular embodiment, the light chain variable domain comprises one, two or three CDRs selected from: (a) CDR-L1 comprising the amino acid sequence of SEQ ID NO:4, (b) CDR-L2 comprising the amino acid sequence of SEQ ID NO:5, and (c) CDR-L3 comprising the amino acid sequence of SEQ ID NO:6.

In some embodiments, the anti-CD228 antibody and/or the anti-CD228 antibody-drug conjugate comprises a heavy chain variable domain as in any of the embodiments provided above, and a light chain variable domain as in any of the embodiments provided above. In one embodiment, the antibody comprises the heavy chain variable domain sequence of SEQ ID NO:7 and the light chain variable domain sequence of SEQ ID NO:8, including post-translational modifications of those sequences. In some embodiments, the N-terminal glutamine of the heavy chain variable domain is cyclized to form pyroglutamic acid.

In some embodiments, the anti-CD228 antibody and/or the anti-CD228 antibody-drug conjugate comprises: i) a heavy chain CDR1 comprising the amino acid sequence of SEQ ID NO: 1, a heavy chain CDR2 comprising the amino acid sequence of SEQ ID NO: 2, a heavy chain CDR3 comprising the amino acid sequence of SEQ ID NO: 3; and ii) a light chain CDR1 comprising the amino acid sequence of SEQ ID NO: 4, a light chain CDR2 comprising the amino acid sequence of SEQ ID NO: 5, and a light chain CDR3 comprising the amino acid sequence of SEQ ID NO: 6, wherein the CDRs of the anti-CD228 antibody are defined by the Kabat numbering scheme.

In some embodiments, the anti-CD228 antibody and/or the anti-CD228 antibody-drug conjugate comprises: i) an amino acid sequence having at least 85% sequence identity to a heavy chain variable region comprising the amino acid sequence of SEQ ID NO: 7, and ii) an amino acid sequence having at least 85% sequence identity to a light chain variable region comprising the amino acid sequence of SEQ ID NO: 8. In some embodiments, the N-terminal glutamine of the heavy chain variable domain is cyclized to form pyroglutamic acid.

In some embodiments, the anti-CD228 antibody or the anti-CD228 antibody of the anti-CD228 antibody-drug conjugate is a monoclonal antibody.

Anti-CD228 antibodies of the present invention may also be described or specified in terms of their binding affinity to CD228 (e.g., human CD228). Preferred binding affinities include those with a dissociation constant or $K_D$ less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

In some embodiments, the binding of an anti-CD228 antibody of the present invention is pH dependent, such that the antibody displays differential binding across a pH gradient. In some embodiments, the anti-CD228 antibody displays maximal binding between a pH of about 5.5 and a pH of about 6.3. In some embodiments, the anti-CD228 antibody displays maximal binding at a pH of about 5.6. In some embodiments, the anti-CD228 antibody displays maximal binding at a pH of about 6.3. In some embodiments, the anti-CD228 antibody displays minimal binding at a pH of about 5.1 or less.

There are five classes of immunoglobulins: IgA, IgD, IgE, IgG and IgM, having heavy chains designated α, δ, ε, γ and μ, respectively. The y and a classes are further divided into subclasses e.g., humans express the following subclasses: IgG1, IgG2, IgG3, IgG4, IgA1 and IgA2. IgG1 antibodies can exist in multiple polymorphic variants termed allotypes (reviewed in Jefferis and Lefranc 2009. mAbs Vol 1 Issue 4 1-7) any of which are suitable for use in some of the embodiments herein. Common allotypic variants in human populations are those designated by the letters a, f, n, z or combinations thereof. In any of the embodiments herein, the antibody may comprise a heavy chain Fc region comprising a human IgG Fc region. In further embodiments, the human IgG Fc region comprises a human IgG1.

In some embodiments, the anti-CD228 antibody and/or the anti-CD228 antibody-drug conjugate comprises a heavy chain variable domain as in any of the embodiments provided above, and a light chain variable domain as in any of the embodiments provided above. In one embodiment, the antibody comprises a heavy chain constant region comprising the amino acid sequence of ASTKGPSVFPLAPSSKST-SGGTAALGCLVKDYFPEPVTVSWNSGALT-SGVHTFPAVLQSS
GLYS-
LSSVVTVPSSSLGTQTYICNVNHKPSNTKVDKKVE- PKSCDKTHTCPPCPAPELLGG
PSVFLFPPKPKDTLMISRTPEVTCVVVDVSHEDPE-
VKFNWYVDGVEVHNAKTKPREEQY
NSTYRVVSVLTVLHQDWLNGKEYKCKVSNKALPA-
PIEKTISKAKGQPREPQVYTLPPSR DELTKNQVSLT-
CLVKGFYPSDIAVEWESNGQPEN-
NYKTTPPVLDSDGSFFLYSKLTVDK
SRWQQGNVFSCSVMHEALHNHYTQKSLSLSPG (SEQ ID NO:17) and a light chain constant region comprising the amino acid sequence of TVAAPSVFIFPPSDEQLKSG-TASVVCLLNNFYPREAKVQWKVD-
NALQSGNSQESVTEQD SKDSTYSLSSTLTL-
SKADYEKHKVYACEVTHQGLSSPVTKSFNRGEC
(SEQ ID NO:18), including post-translational modifications of those sequences. In another embodiment, the antibody comprises a heavy chain constant region comprising the amino acid sequence of ASTKGPSVFPLAPSSKST-SGGTAALGCLVKDYFPEPVTVSWNSGALT-
SGVHTFPAVLQSS GLYS-
LSSVVTVPSSSLGTQTYICNVNHKPSNTKVDKKVEP
KSCDKTHTCPPCPAPELLGG PCVFLFPPKPKDTLMIS-
RTPEVTCVVVDVSHEDPE-
VKFNWYVDGVEVHNAKTKPREEQ
YNSTYRVVSVLTVLHQDWLNGKEYKCKVSNKAL-
PAPIEKTISKAKGQPREPQVYTLPPS RDELT-
KNQVSLTCLVKGFYPSDIAVEWESNGQPEN-
NYKTTPPVLDSDGSFFLYSKLTVD
KSRWQQGNVFSCSVMHEALHNHYTQKSLSLSPG
(SEQ ID NO:19) and a light chain constant region comprising the amino acid sequence of TVAAPSVFIFPPSD-EQLKSGTASVVCLLNNFYPREAKVQWKVD-
NALQSGNSQESVTEQD
SKDSTYSLSSTLTLSKADYEKHKVYACE-
VTHQGLSSPVTKSFNRGEC (SEQ ID NO:18), including post-translational modifications of those sequences. SEQ ID NO:19 comprises a serine to cysteine substitution at amino acid position 239 of human IgG1 isotype. The presence of an additional cysteine residue allows interchain disulfide bond formation. Such interchain disulfide bond formation can cause steric hindrance, thereby reducing the affinity of the Fc region-FcγR binding interaction. The cysteine residue introduced in or in proximity to the Fc region of an IgG constant region can also serve as a site for conjugation to therapeutic agents (i.e., coupling cytotoxic drugs using thiol specific reagents such as maleimide derivatives of drugs). The presence of a therapeutic agent causes steric hindrance, thereby further reducing the affinity of the Fc region-FcγR binding interaction. Other substitutions at any of positions 234, 235, 236 and/or 237 reduce affinity for Fcγ receptors, particularly FcγR1 receptor (see, e.g., U.S. Pat. Nos. 6,624,821, 5,624, 821.)

In some embodiments, the anti-CD228 antibody or the anti-CD228 antibody of the antibody-drug conjugate is the humanized antibody hL49 HALC. hL49 HALC comprises a heavy chain variable region sequence of SEQ ID NO:7 and a light chain variable region sequence of SEQ ID NO:8. In some embodiments, the N-terminal glutamine of the heavy chain variable domain is cyclized to form pyroglutamic acid. In some embodiments, the anti-CD228 antibody or the anti-CD228 antibody of the antibody-drug conjugate is the humanized antibody hL49. hL49 comprises a heavy chain variable region comprising the amino acid sequence of SEQ ID NO:7, a light chain variable region comprising the amino acid sequence of SEQ ID NO:8, a heavy chain constant region comprising the amino acid sequence of SEQ ID NO:17, and a light chain constant region comprising the amino acid sequence of SEQ ID NO:18.

The antibodies also include derivatives that are modified, i.e., by the covalent attachment of any type of molecule to the antibody such that covalent attachment does not prevent the antibody from binding to CD228 or from exerting a cytostatic or cytotoxic effect on HD cells. For example, but not by way of limitation, the antibody derivatives include antibodies that have been modified, e.g., by glycosylation, acetylation, PEGylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Humanized Antibodies

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence. A preferred acceptor sequence for the heavy chain is the germline $V_H$ exon $V_H1$-2 (also referred to in the literature as HV1-2) (Shin et al, 1991, EMBO J. 10:3641-3645) and for the hinge region ($J_H$), exon $J_H$-6 (Mattila et al, 1995, Eur. J. Immunol. 25:2578-2582). For the light chain, a preferred acceptor sequence is exon VK2-30 (also referred to in the literature as KV2-30) and for the hinge region exon JK-4 (Hieter et al, 1982, J. Biol. Chem. 257:1516-1522). Thus, a humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 60%, 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85%, 90%, 95% or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5) CDRs from a mouse antibody (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly,
(2) is adjacent to a CDR region,
(3) otherwise interacts with a CDR region (e.g. is within about 6 A of a CDR region); or
(4) mediates interaction between the heavy and light chains.

One aspect of the invention provides humanized forms of the mouse antibody L49. One such humanized variant of the mouse antibody L49 is designated HALC. HALC comprises a mature heavy chain variable region comprising the amino acid sequence of SEQ ID NO:7 and a mature light chain variable region comprising the amino acid sequence of SEQ ID NO:8. In some embodiments, the N-terminal glutamine of the heavy chain variable domain is cyclized to form pyroglutamic acid. Humanized antibodies of the invention include variants of the HALC humanized antibody in which the humanized heavy chain mature variable region shows at least 90%, 95% or 99% identity to SEQ ID NO: 7 and the humanized light chain mature variable region shows at least 90%, 95% or 99% sequence identity to SEQ ID NO:8. Preferably, in such antibodies some or all of the backmutations in HALC are retained. In other words, at least 1, 2, 3, 4 or preferably all 5 of heavy chain positions H27, H30, H47, H71 and H78 are occupied by D, T, Y, R and Y, respectively. Likewise position L36 is preferably occupied by Y and position L46 is preferably occupied by L. In some embodiments, position L2 is preferably occupied by F. In some embodiments, the CDR regions of such humanized antibodies are identical or substantially identical to the CDR regions of the mouse donor antibody. In a preferred embodiment, the light chain CDR1 position L28 is occupied by D. The CDR regions can be defined by any conventional definition (e.g., Chothia) but are preferably as defined by Kabat. In one embodiment, the humanized antibody comprises a heavy chain comprising the 3 CDRs of SEQ ID NO: 7 and variable region frameworks with at least 95% identity to the variable region frameworks of SEQ ID NO: 7. In another embodiment, the humanized antibody comprises a light chain comprising the 3 CDRs of SEQ ID NO: 8 and variable region frameworks with at least 95% identity to variable region frameworks of SEQ ID NO: 8. In a further embodiment, the humanized antibody comprises a heavy chain comprising the 3 CDRs of SEQ ID NO: 7 and variable region frameworks with at least 95% identity to the variable region frameworks of SEQ ID NO: 7, and a light chain comprising the 3 CDRs of SEQ ID NO: 8, and variable region frameworks with at least 95% identity to the variable region frameworks of SEQ ID NO: 8. In one embodiment, the humanized antibody comprises a heavy chain comprising the 3 CDRs of SEQ ID NO: 7 and variable region frameworks with at least 98% identity to the variable region frameworks of SEQ ID NO: 7. In another embodiment, the humanized antibody comprises a light chain comprising the 3 CDRs of SEQ ID NO: 8 and variable region frameworks with at least 98% identity to variable region frameworks of SEQ ID NO: 8. In a further embodiment, the humanized antibody comprises a heavy chain comprising the 3 CDRs of SEQ ID NO: 7 and variable region frameworks with at least 98% identity to the variable region frameworks of SEQ ID NO: 7, and a light chain comprising the 3 CDRs of SEQ ID NO: 8, and variable region frameworks with at least 98% identity to the variable region frameworks of SEQ ID NO: 8. In one embodiment, the humanized antibody comprises a heavy chain comprising the 3 CDRs of SEQ ID NO: 7 and variable region frameworks with at least 99% identity to the variable region frameworks of SEQ ID NO: 7. In another embodiment, the humanized antibody comprises a light chain comprising the 3 CDRs of SEQ ID NO: 8 and variable region frameworks with at least 99% identity to variable region frameworks of SEQ ID NO: 8. In a further embodiment, the humanized antibody comprises a heavy chain comprising the 3 CDRs of SEQ ID NO: 7 and variable region frameworks with at least 99% identity to the variable region frameworks of SEQ ID NO: 7, and a light chain comprising the 3 CDRs of SEQ ID NO: 8, and variable region frameworks with at least 99% identity to the variable region frameworks of SEQ ID NO: 8.

The humanized antibody HALC comprises an asparagine to aspartic acid substitution at amino acid position L28 compared to the mouse antibody L49, which is in the light chain CDR1. This substitution eliminates the deamidation observed in the humanized L49 variant HALB, and has limited isomerization. In some embodiments, of any of the antibodies described herein, the light chain variable region lacks this substitution at position L28. In some embodiments of the antibodies described herein, the light chain variable region comprises the amino acid sequence DFVMTQSPLSLPVTLGQPASISCRASQSLVHSNGN-TYLHWYQQRPGQSPRLLIYRVSNRF SGVPDRFSGSGSGTDFTLKISRVEAE-DVGVYYCSQSTHVPPTFGQGTKLEIK (SEQ ID NO:20). In some embodiments, the humanized antibody is HALB, which comprises a heavy chain variable region comprising SEQ ID NO:7 and a light chain variable region comprising SEQ ID NO:20.

Insofar as humanized antibodies show any variation from the exemplified HALC humanized antibody, one possibility for such additional variation is additional backmutations in the variable region frameworks. However, such additional backmutations are not preferred because they in general do not improve affinity and introducing more mouse residues may give increased risk of immunogenicity.

Another possible variation is to substitute certain residues in the CDRs of the mouse antibody with corresponding residues from human CDRs sequences, typically from the CDRs of the human acceptor sequences used in designing the exemplified humanized antibodies. In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, J. Mol. Biol. 196:901, 1987), by molecular modeling and/or empirically, or as described in Gonzales et al., Mol. Immunol. 41: 863 (2004). In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

Although not preferred other amino acid substitutions can be made, for example, in framework residues not in contact with the CDRs, or even some potential CDR-contact residues amino acids within the CDRs. Often the replacements made in the variant humanized sequences are conservative with respect to the replaced HALC amino acids. Preferably, replacements relative to HALC (whether or not conservative) have no substantial effect on the binding affinity or potency of the humanized mAb, that is, its ability to bind human CD228 and inhibit growth of cancer cells.

Variants typically differ from the heavy and light chain mature variable region sequences of HALC by a small number (e.g., typically no more than 1, 2, 3, 5 or 10 in either the light chain or heavy chain mature variable region, or both) of replacements, deletions or insertions.

Selection of Constant Region

The heavy and light chain variable regions of humanized antibodies can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotypes IgG1 and IgG3 have strong complement-dependent cytotoxicity, human isotype IgG2 weak complement-dependent cytotoxicity and human. IgG4 lacks complement-dependent cytotoxicity. Human IgG1 and IgG3 also induce stronger cell mediated effector functions than human IgG2 and IgG4. Light chain constant regions can be lambda or kappa. Antibodies can be expressed as tetramers containing two light and two heavy chains, as separate heavy chains, light chains, as Fab, Fab', F(ab')2, and Fv, or as single chain antibodies in which heavy and light chain variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype binds to a non-polymorphic region of a one or more other isotypes.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004).

Exemplary substitution include the amino acid substitution of the native amino acid to a cysteine residue is introduced at amino acid position 234, 235, 237, 239, 267, 298, 299, 326, 330, or 332, preferably an S239C mutation in a human IgG1 isotype (US 20100158909). The presence of an additional cysteine residue allows interchain disulfide bond formation. Such interchain disulfide bond formation can cause steric hindrance, thereby reducing the affinity of the Fc region-FcγR binding interaction. The cysteine residue(s) introduced in or in proximity to the Fc region of an IgG constant region can also serve as sites for conjugation to therapeutic agents (i.e., coupling cytotoxic drugs using thiol specific reagents such as maleimide derivatives of drugs. The presence of a therapeutic agent causes steric hindrance, thereby further reducing the affinity of the Fc region-FcγR binding interaction. Other substitutions at any of positions 234, 235, 236 and/or 237 reduce affinity for Fcγ receptors, particularly FcγRI receptor (see, e.g., U.S. Pat. Nos. 6,624,821, 5,624,821.)

The in vivo half-life of an antibody can also impact on its effector functions. The half-life of an antibody can be increased or decreased to modify its therapeutic activities. FcRn is a receptor that is structurally similar to MHC Class I antigen that non-covalently associates with β2-microglobulin. FcRn regulates the catabolism of IgGs and their transcytosis across tissues (Ghetie and Ward, 2000, Annu. Rev. Immunol. 18:739-766; Ghetie and Ward, 2002, Immunol. Res. 25:97-113). The IgG-FcRn interaction takes place at pH 6.0 (pH of intracellular vesicles) but not at pH 7.4 (pH of blood); this interaction enables IgGs to be recycled back to the circulation (Ghetie and Ward, 2000, Ann. Rev. Immunol. 18:739-766; Ghetie and Ward, 2002, Immunol. Res. 25:97-113). The region on human IgG1 involved in FcRn binding has been mapped (Shields et al, 2001, J. Biol. Chem. 276:6591-604). Alanine substitutions at positions Pro238, Thr256, Thr307, Gln311, Asp312, Glu380, Glu382, or Asn434 of human IgG1 enhance FcRn binding (Shields et al, 2001, J. Biol. Chem. 276:6591-604). IgG1 molecules harboring these substitutions have longer serum half-lives. Consequently, these modified IgG1 molecules may be able to carry out their effector functions, and hence exert their therapeutic efficacies, over a longer period of time compared to unmodified IgG1. Other exemplary substitutions for increasing binding to FcRn include a Gin at position 250 and/or a Leu at position 428. EU numbering is used for all position in the constant region.

Oligosaccharides covalently attached to the conserved Asn297 are involved in the ability of the Fc region of an IgG to bind FcγR (Lund et al, 1996, J. Immunol. 157:4963-69; Wright and Morrison, 1997, Trends Biotechnol. 15:26-32). Engineering of this glycoform on IgG can significantly improve IgG-mediated ADCC. Addition of bisecting N-acetylglucosamine modifications (Umana et al, 1999, Nat. Biotechnol. 17:176-180; Davies et al, 2001, Biotech. Bioeng. 74:288-94) to this glycoform or removal of fucose (Shields et al, 2002, J. Biol. Chem. 277:26733-40; Shinkawa et al, 2003, J. Biol. Chem. 278:6591-604; Niwa et a/., 2004, Cancer Res. 64:2127-33) from this glycoform are two examples of IgG Fc engineering that improves the binding between IgG Fc and FcγR, thereby enhancing Ig-mediated ADCC activity. In some embodiments, an anti-CD228 antibody or an anti-CD228 antibody of the antibody-drug conjugate described herein has a glycan attached to the conserved Asn297 residue of the constant region, wherein the numbering of amino acid residues in the constant region is according to the EU-index as described in Kabat et al., Sequences of Proteins of Immunological Interest, 5th Ed. Public Health Service, National Institutes of Health, Bethesda, Md. (1991). In some embodiments, the glycan is biantennary. In some embodiments, the glycan is core fucosylated. In some embodiments, the glycan has zero terminal galactose residues. In some embodiments, the glycan is biantennary and core fucosylated. In some embodiments, the glycan is biantennary and has zero terminal galactose residues. In some embodiments, the glycan is core fucosylated and has zero terminal galactose residues. In some embodiments, the glycan is biantennary, core fucosylated and has zero galactose residues. In some embodiments, in a population of anti-CD228 antibodies or anti-CD228 antibodies of the antibody-drug conjugates described herein the conserved Asn297 residues of the constant regions, wherein the numbering of amino acid residues in the constant region is according to the EU-index as described in Kabat et al., Sequences of Proteins of Immunological Interest, 5th Ed. Public Health Service, National Institutes of Health, Bethesda, Md. (1991), are predominantly occupied by biantennary, core fucosylated glycans with zero terminal galactose residues.

A systemic substitution of solvent-exposed amino acids of human IgG1 Fc region has generated IgG variants with altered FcγR binding affinities (Shields et al, 2001, J. Biol. Chem. 276:6591-604). When compared to parental IgG1, a subset of these variants involving substitutions at Thr256/Ser298, Ser298/Glu333, Ser298/Lys334, or Ser298/Glu333 Lys334 to Ala demonstrate increased in both binding affinity toward FcγR and ADCC activity (Shields et al, 2001, J. Biol. Chem. 276:6591-604; Okazaki et al, 2004, J. Mol. Biol. 336:1239-49).

Complement fixation activity of antibodies (both C1q binding and CDC activity) can be improved by substitutions at Lys326 and Glu333 (Idusogie et al., 2001, J. Immunol. 166:2571-2575). The same substitutions on a human IgG2 backbone can convert an antibody isotype that binds poorly to C1q and is severely deficient in complement activation activity to one that can both bind C1q and mediate CDC (Idusogie et al, 2001, J. Immunol. 166:2571-75). Several other methods have also been applied to improve complement fixation activity of antibodies. For example, the grafting of an 18-amino acid carboxyl-terminal tail piece of IgM to the carboxyl-termini of IgG greatly enhances their CDC activity. This is observed even with IgG4, which normally has no detectable CDC activity (Smith et al, 1995, J. Immunol. 154:2226-36). Also, substituting Ser444 located close to the carboxy-terminal of IgG 1 heavy chain with Cys induced tail-to-tail dimerization of IgG 1 with a 200-fold increase of CDC activity over monomeric IgG1 (Shopes et al, 1992, J. Immunol. 148:2918-22). In addition, a bispecific diabody construct with specificity for C1q also confers CDC activity (Kontermann et a/., 1997, Nat. Biotech. 15:629-31).

Complement activity can be reduced by mutating at least one of the amino acid residues 318, 320, and 322 of the heavy chain to a residue having a different side chain, such as Ala. Other alkyl-substituted non-ionic residues, such as Gly, He, Leu, or Val, or such aromatic non-polar residues as Phe, Tyr, Trp and Pro in place of any one of the three residues also reduce or abolish C1q binding. Ser, Thr, Cys, and Met can be used at residues 320 and 322, but not 318, to reduce or abolish C1q binding activity.

Replacement of the 318 (Glu) residue by a polar residue may modify but not abolish C1q binding activity. Replacing residue 297 (Asn) with Ala results in removal of lytic activity but only slightly reduces (about three fold weaker) affinity for C1q. This alteration destroys the glycosylation site and the presence of carbohydrate that is required for complement activation. Any other substitution at this site also destroys the glycosylation site. The following mutations and any combination thereof also reduce C1q binding: D270A, K322A, P329A, and P31 IS (see WO 06/036291).

Reference to a human constant region includes a constant region with any natural allotype or any permutation of residues occupying polymorphic positions in natural allotypes. Also, up to 1, 2, 5, or 10 mutations may be present relative to a natural human constant region, such as those indicated above to reduce Fcgamma receptor binding or increase binding to FcRN.

In some embodiments, an anti-CD228 and/or anti-CD228 antibody-drug conjugate antibody described herein comprises a heavy chain constant region comprising the amino acid sequence of SEQ ID NO:17. In some embodiments, an anti-CD228 and/or anti-CD228 antibody-drug conjugate antibody described herein comprises a light chain constant region comprising the amino acid sequence of SEQ ID NO:18. In some embodiments, an anti-CD228 and/or anti-CD228 antibody-drug conjugate antibody described herein comprises a heavy chain constant region comprising the amino acid sequence of SEQ ID NO:17 and a light chain constant region comprising the amino acid sequence of SEQ ID NO:18. In some embodiments, an anti-CD228 and/or anti-CD228 antibody-drug conjugate antibody described herein comprises a heavy chain constant region comprising the amino acid sequence of SEQ ID NO:19. In some embodiments, an anti-CD228 and/or anti-CD228 antibody-drug conjugate antibody described herein comprises a heavy chain constant region comprising the amino acid sequence of SEQ ID NO:19 and a light chain constant region comprising the amino acid sequence of SEQ ID NO:18.

V. Expression of Recombinant Antibodies

Humanized antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

Mammalian cells are a preferred host for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed in the art, and include CHO cell lines (e.g., DG44), various COS cell lines, HeLa cells, HEK293 cells, L cells, and non-antibody-producing myelomas including Sp2/0 and NS0. Preferably, the cells are nonhuman. Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., J. Immunol. 148:1149 (1992).

Once expressed, antibodies can be purified according to standard procedures of the art, including HPLC purification, column chromatography, gel electrophoresis and the like (see generally, Scopes, Protein Purification (Springer-Verlag, NY, 1982)).

VI. Nucleic Acids

The invention further provides nucleic acids encoding any of the humanized heavy and light chains described above. Typically, the nucleic acids also encode a signal peptide fused to the mature heavy and light chains. Coding sequences on nucleic acids can be in operable linkage with regulatory sequences to ensure expression of the coding sequences, such as a promoter, enhancer, ribosome binding site, transcription termination signal and the like. The nucleic acids encoding heavy and light chains can occur in isolated form or can be cloned into one or more vectors. The nucleic acids can be synthesized by for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

In some aspects, also provided herein are nucleic acids encoding an anti-CD228 antibody or antigen-binding fragment thereof as described herein. Further provided herein are vectors comprising the nucleic acids encoding an anti-CD228 antibody or antigen-binding fragment thereof as described herein. Further provided herein are host cells expressing the nucleic acids encoding an anti-CD228 antibody or antigen-binding fragment thereof as described herein. Further provided herein are host cells comprising the vectors comprising the nucleic acids encoding an anti-CD228 antibody or antigen-binding fragment thereof as described herein.

The anti-CD228 antibodies described herein may be prepared by well-known recombinant techniques using well known expression vector systems and host cells. In one embodiment, the antibodies are prepared in a CHO cell using the GS expression vector system as disclosed in De la Cruz Edmunds et al., 2006, *Molecular Biotechnology* 34; 179-190, EP216846, U.S. Pat. No. 5,981,216, WO 87/04462, EP323997, U.S. Pat. Nos. 5,591,639, 5,658,759, EP338841, U.S. Pat. Nos. 5,879,936, and 5,891,693.

Monoclonal anti-CD228 antibodies described herein may e.g. be produced by the hybridoma method first described by Kohler et al., *Nature*, 256, 495 (1975), or may be produced by recombinant DNA methods. Monoclonal antibodies may also be isolated from phage antibody libraries using the techniques described in, for example, Clackson et al., *Nature*, 352, 624-628 (1991) and Marks et al., *J Mol, Biol.*, 222(3):581-597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

VII. Antibody-Drug Conjugates

Anti-CD228 antibodies can be conjugated to cytotoxic or cytostatic moieties (including pharmaceutically compatible salts thereof) to form an antibody drug conjugate (ADC). Particularly suitable moieties for conjugation to antibodies are cytotoxic agents (e.g., chemotherapeutic agents), prodrug converting enzymes, radioactive isotopes or compounds, or toxins (these moieties being collectively referred to as a therapeutic agent). For example, an anti-CD288 antibody can be conjugated to a cytotoxic agent such as a chemotherapeutic agent, or a toxin (e.g., a cytostatic or cytocidal agent such as, e.g., abrin, ricin A, pseudomonas exotoxin, or diphtheria toxin).

An anti-CD228 antibody can be conjugated to a pro-drug converting enzyme. The pro-drug converting enzyme can be recombinantly fused to the antibody or chemically conjugated thereto using known methods. Exemplary pro-drug converting enzymes are carboxypeptidase G2, beta-glucuronidase, penicillin-V-amidase, penicillin-G-amidase, β-lactamase, β-glucosidase, nitroreductase and carboxypeptidase A.

Techniques for conjugating therapeutic agents to proteins, and in particular to antibodies, are well-known. (See, e.g., Arnon et al, "Monoclonal Antibodies For Immunotargeting Of Drugs In Cancer Therapy," in Monoclonal Antibodies And Cancer Therapy (Reisfeld et al. eds., Alan R. Liss, Inc., 1985); Hellstrom et al, "Antibodies For Drug Delivery," in Controlled Drug Delivery (Robinson et al. eds., Marcel Dekker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al. eds., 1985); "Analysis, Results, and Future Prospective of the Therapeutic Use of Radiolabeled Antibody In Cancer Therapy," in Monoclonal Antibodies For Cancer Detection And Therapy (Baldwin et al. eds., Academic Press, 1985); and Thorpe et al, 1982, Immunol. Rev. 62:119-58. See also, e.g., PCT publication WO 89/12624.)

The therapeutic agent can be conjugated in a manner that reduces its activity unless it is cleaved off the antibody (e.g., by hydrolysis, by antibody degradation or by a cleaving agent). Such therapeutic agent is attached to the antibody with a cleavable linker that is sensitive to cleavage in the intracellular environment of the CD228-expressing cancer cell but is not substantially sensitive to the extracellular environment, such that the conjugate is cleaved from the antibody when it is internalized by the CD228-expressing cancer cell (e.g., in the endosomal or, for example by virtue of pH sensitivity or protease sensitivity, in the lysosomal environment or in the caveolear environment).

Typically the ADC comprises a linker region between the therapeutic agent and the anti-CD228 antibody. As noted supra, typically, the linker is cleavable under intracellular conditions, such that cleavage of the linker releases the therapeutic agent from the antibody in the intracellular environment (e.g., within a lysosome or endosome or caveolea). The linker can be, e.g., a peptidyl linker that is cleaved by an intracellular peptidase or protease enzyme, including a lysosomal or endosomal protease. Typically, the peptidyl linker is at least two amino acids long or at least three amino acids long. Cleaving agents can include cathepsins B and D and plasmin (see, e.g., Dubowchik and Walker, 1999, Pharm. Therapeutics 83:67-123). Most typical are peptidyl linkers that are cleavable by enzymes that are present in CD228-expressing cells. For example, a peptidyl linker that is cleavable by the thiol-dependent protease cathepsin-B, which is highly expressed in cancerous tissue, can be used (e.g., a linker comprising a Phe-Leu or a Gly-Phe-Leu-Gly peptide (SEQ ID NO: 30)). Other such linkers are described, e.g., in U.S. Pat. No. 6,214,345. In specific embodiments, the peptidyl linker cleavable by an intracellular protease comprises a Val-Cit linker or a Phe-Lys dipeptide (see, e.g., U.S. Pat. No. 6,214,345, which describes the synthesis of doxorubicin with the Val-Cit linker). One advantage of using intracellular proteolytic release of the therapeutic agent is that the agent is typically attenuated when conjugated and the serum stabilities of the conjugates are typically high.

The cleavable linker can be pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, Pharm. Therapeutics 83:67-123; Neville et al, 1989, Biol. Chem. 264: 14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thio-ether linker (such as, e.g., a thioether attached to the therapeutic agent via an acylhydrazone bond (see, e.g., U.S. Pat. No. 5,622,929)).

Other linkers are cleavable under reducing conditions (e.g., a disulfide linker). Disulfide linkers include those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT. {See, e.g., Thorpe et al, 1987, Cancer Res. 47:5924-5931; Wawrzynczak et al, In Immunoconjugates: Antibody Conjugates in Radioimagery and Therapy of Cancer (C. W. Vogel ed., Oxford U. Press, 1987. See also U.S. Pat. No. 4,880,935.)

The linker can also be a malonate linker (Johnson et al, 1995, Anticancer Res. 15:1387-93), a maleimidobenzoyl linker (Lau et al, 1995, Bioorg-Med-Chem. 3(10):1299-1304), or a 3'-N-amide analog (Lau et al, 1995, Bioorg-Med-Chem. 3(10):1305-12). The linker can also be a malonate linker (Johnson et al, 1995, Anticancer Res. 15:1387-93), a maleimidobenzoyl linker (Lau et al, 1995, Bioorg-Med-Chem. 3(10):1299-1304), or a 3'-N-amide analog (Lau et al, 1995, Bioorg-Med-Chem. 3(10):1305-12).

The linker also can be a non-cleavable linker, such as an maleimido-alkylene- or maleimide-aryl linker that is directly attached to the therapeutic agent (e.g., a drug). An active drug-linker is released by degradation of the antibody.

Typically, the linker is not substantially sensitive to the extracellular environment meaning that no more than about 20%, typically no more than about 15%, more typically no more than about 10%, and even more typically no more than about 5%, no more than about 3%, or no more than about 1% of the linkers in a sample of the ADC is cleaved when the ADC present in an extracellular environment (e.g., in plasma).

Whether a linker is not substantially sensitive to the extracellular environment can be determined, for example, by incubating independently with plasma both (a) the ADC (the "ADC sample") and (b) an equal molar amount of unconjugated antibody or therapeutic agent (the "control sample") for a predetermined time period (e.g., 2, 4, 8, 16, or 24 hours) and then comparing the amount of unconjugated antibody or therapeutic agent present in the ADC sample with that present in control sample, as measured, for example, by high performance liquid chromatography.

The linker can also promote cellular internalization. The linker can promote cellular internalization when conjugated to the therapeutic agent (i.e., in the milieu of the linker-therapeutic agent moiety of the ADC or ADC derivative as described herein). Alternatively, the linker can promote cellular internalization when conjugated to both the therapeutic agent and the anti-CD228 antibody (i.e., in the milieu of the ADC as described herein).

The anti-CD228 antibody can be conjugated to the linker via a heteroatom of the antibody. These heteroatoms can be present on the antibody in its natural state or can be introduced into the antibody. In some aspects, the anti-CD228 antibody will be conjugated to the linker via a nitrogen atom of a lysine residue. In other aspects, the anti-CD228 antibody will be conjugated to the linker via a sulfur atom of a cysteine residue. The cysteine residue can be naturally-occurring or one that is engineered into the antibody. Methods of conjugating linkers and drug-linkers to antibodies via lysine and cysteine residues are known in the art.

Exemplary antibody-drug conjugates include auristatin based antibody-drug conjugates (i.e., the drug component is an auristatin drug). Auristatins bind tubulin, have been shown to interfere with microtubule dynamics and nuclear and cellular division, and have anticancer activity. Typically the auristatin based antibody-drug conjugate comprises a linker between the auristatin drug and the anti-CD228 antibody. The linker can be, for example, a cleavable linker (e.g., a peptidyl linker, a carbohydrate linker) or a non-cleavable linker (e.g., linker released by degradation of the antibody). Auristatins include auristatin T, MMAF, and MMAE. The synthesis and structure of exemplary auristatins are described in U.S. Publication Pat. Nos. 7,659,241, 7,498,298, 2009-0111756, 2009-0018086, and 7,968, 687 each of which is incorporated herein by reference in its entirety and for all purposes.

Other exemplary antibody-drug conjugates include maytansinoid antibody-drug conjugates (i.e., the drug component is a maytansinoid drug), and benzodiazepine antibody drug conjugates (i.e., the drug component is a benzodiazepine (e.g., pyrrolo[1,4]benzodiazepine dimers (PBD dimer), indolinobenzodiazepine dimers, and oxazolidinobenzodiazepine dimers)).

In some embodiments, a PBD dimer for use in the present invention is represented by formula I. The preferred stereochemistry of the PBD dimer is as shown in formula Ia:

(I)

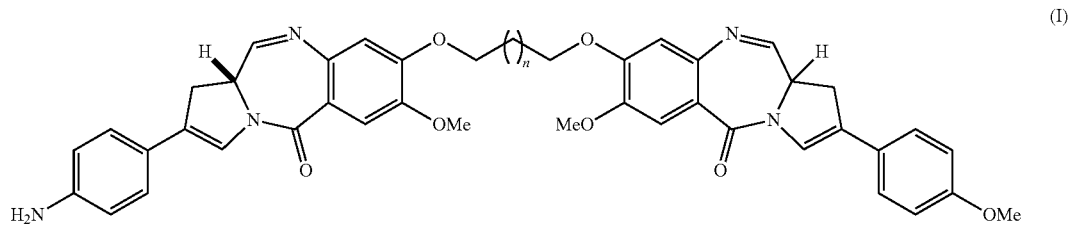

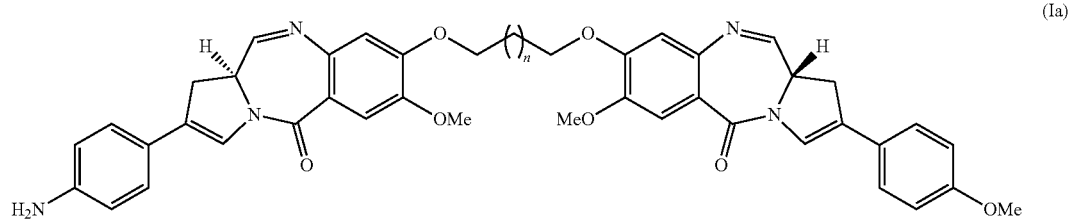
(Ia)

or a pharmaceutically salt, solvate, or solvate of the salt; wherein the subscript n is 1 or 3.

Solvates of formula (I) and (Ia) are typically formed from addition of water or alcoholic solvent across the imine functional group of one or both PBD monomers to form carbinolamine(s) and/or carbinolamine ethers. For example, at the N10-C11 position, there can be an imine (N=C), a carbinolamine (NH—CH(OH)), or a carbinolamine ether (NH—CH(OMe)) as represented by formulas I' and Ia' below:

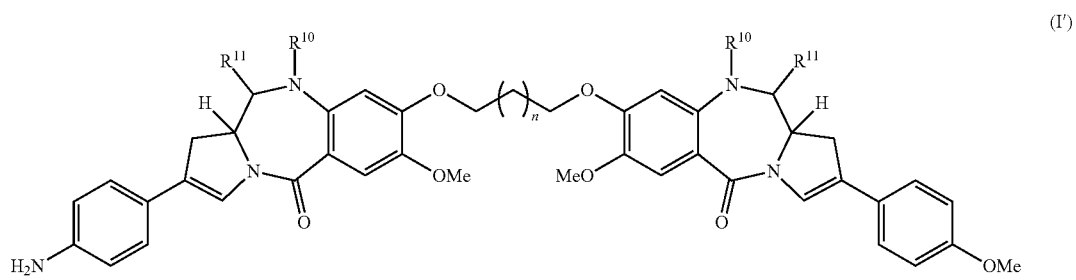
(I')

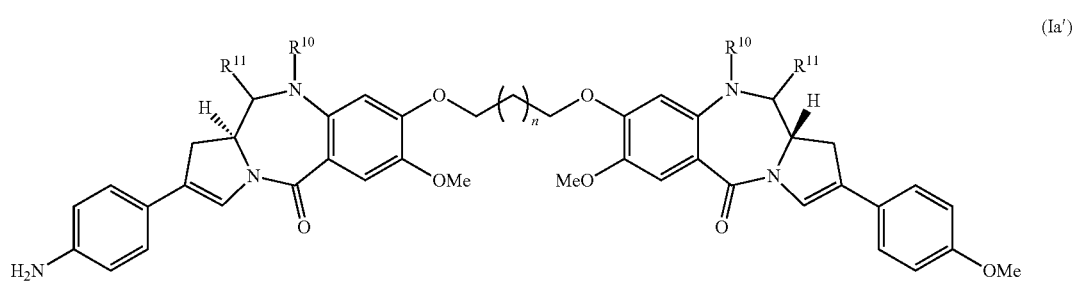
(Ia')

wherein either:
(a) $R^{10}$ is H, and $R^{11}$ is OH or $OR^A$, where $R^A$ is saturated $C_{1-4}$ alkyl (preferably methyl); or
(b) $R^{10}$ and $R^{11}$ form a nitrogen-carbon double bond between the nitrogen and carbon atoms to which they are bound; or
(c) one of $R^{10}$ is H, and $R^{11}$ is OH or $OR^A$, where $R^A$ is saturated $C_{1-4}$ alkyl (preferably methyl); and the other of $R^{10}$ and $R^{11}$ form a nitrogen-carbon double bond between the nitrogen and carbon atoms to which they are bound.

The PBD dimer of formula I or Ia (or a pharmaceutically salt, solvate, or solvate of the salt thereof) is typically linked to the antibody via a Linker Unit, LU. The Linker Unit acts to release the PBD dimer of formula I or Ia (or a pharmaceutically salt, solvate, or solvate of the salt thereof) at the target site (e.g., inside the cancer cell). A PBD drug-linker compound for use in the present invention is represented below by formula II (preferred stereochemistry as shown in IIa) wherein LU is a Linker Unit. The Linker Unit can be, for example, a cleavable peptide Linker Unit (e.g., a linker comprising the valine-alanine peptide) or a cleavable disulfide Linker Unit:

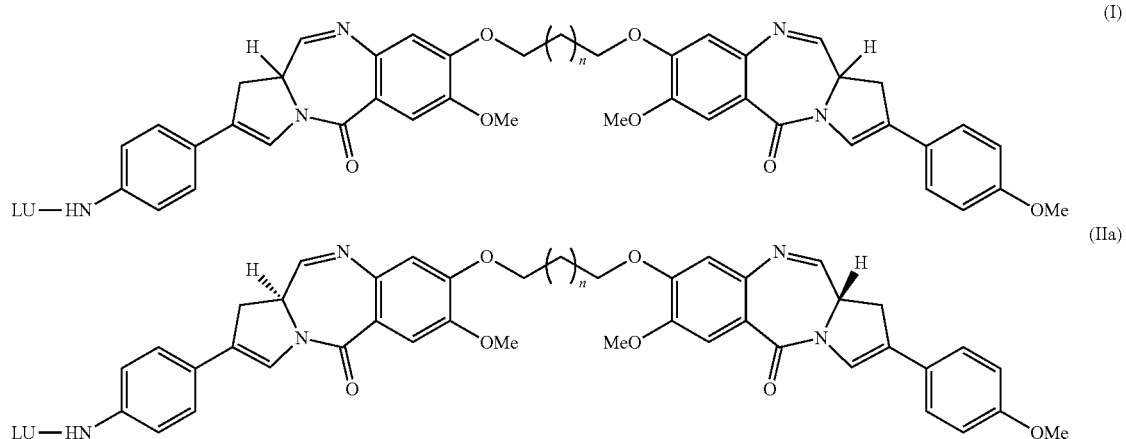

or a pharmaceutically salt, solvate, or solvate of the salt; wherein the subscript n is 1 or 3.

A preferred PBD drug-linker compound for use in the present invention is represented by Formula III below:

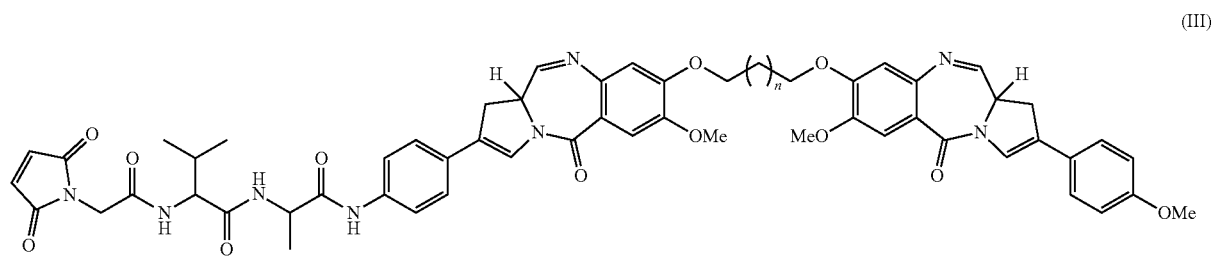

or a pharmaceutically salt, solvate, or solvate of the salt; wherein the subscript n is 1 or 3 and the subscript m is an integer from 2 to 5.

The PBD drug-linker is conjugated to an anti-CD228 antibody to produce a CD228 targeted antibody-drug conjugate. For example, the antibody can be conjugated to a drug-linker of formula II or formula III. An exemplary C2248 targeted antibody-drug conjugate is shown below in formulas IV, IVa, and IVb:

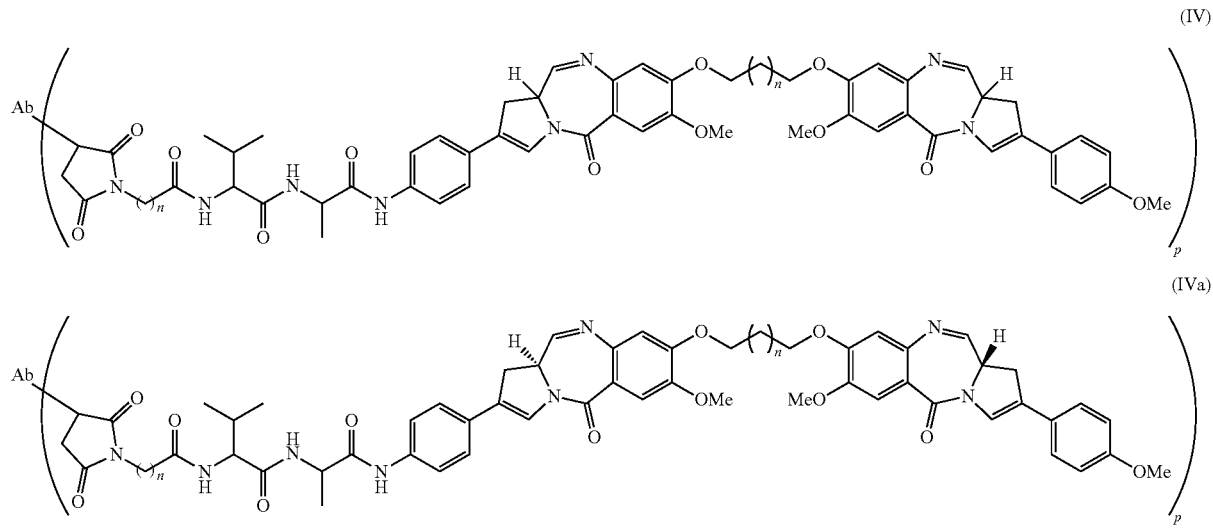

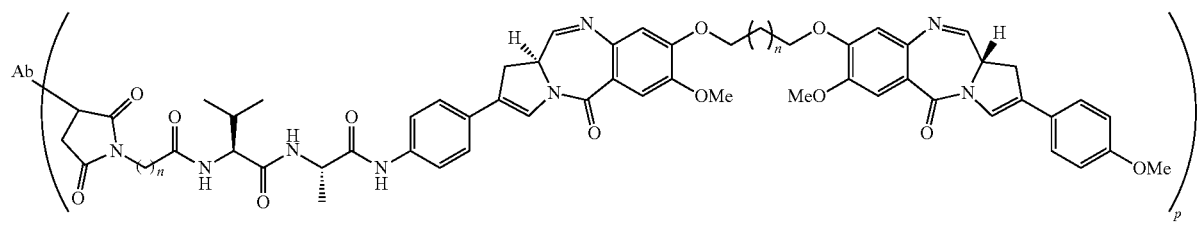

(IVb)

or a pharmaceutically salt, solvate, or solvate of the salt; wherein the subscript n is 1 or 3; the subscript m is an integer from 2 to 5; and the subscript p is from 1 to 4.

Exemplary drug-linkers include MMAE drug-linkers. The present inventors have found that the incorporation of a polyethylene glycol polymer as a side chain into a cleavable β-glucuronide MMAE drug-linker provides antibody drug-conjugates with descreased plasma clearance and increased antitumor activity in xenograft models as compared to a non-PEGylated control. Accordingly, particularly advantageous drug-linkers for attachment to the antibodies of the present invention are as follows in formula V:

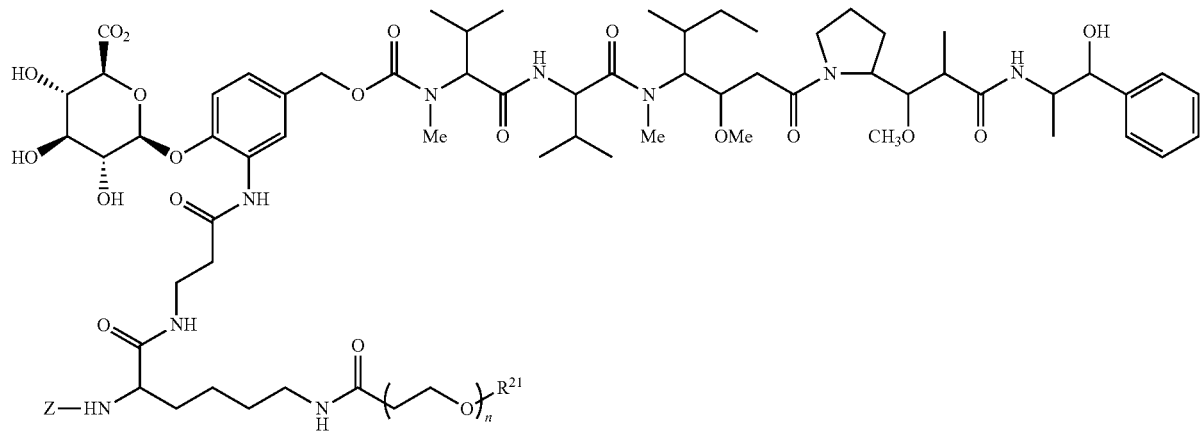

(V)

or a pharmaceutically acceptable salt thereof.

A preferred stereochemistry for such drug-linker is shown below in formula Va:

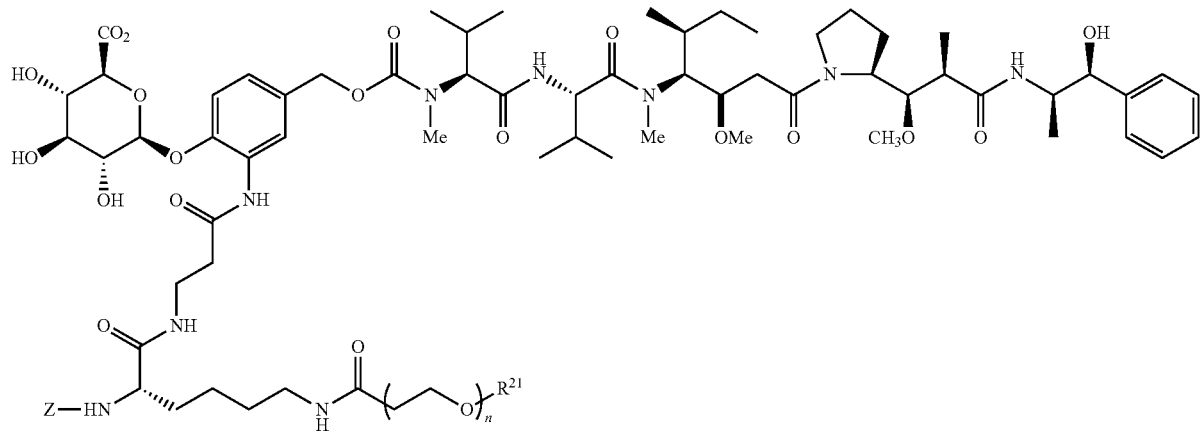

(Va)

or a pharmaceutically acceptable salt thereof wherein for formulas V and Va, Z represents an organic moiety having a reactive site capable of reacting with a functional group on the antibody to form a covalent attachment thereto, n ranges from 8 to 36 and most preferably ranges from 8 to 14 (most preferably 12), $R^{21}$ is a capping unit for the polyethylene glycol moiety, preferably —$CH_3$ or —$CH_2CH_2CO_2H$.

A preferred Z moiety is a maleimido-containing moiety. Particularly preferred Z moieties are shown in the drug-linkers below:

(VI)

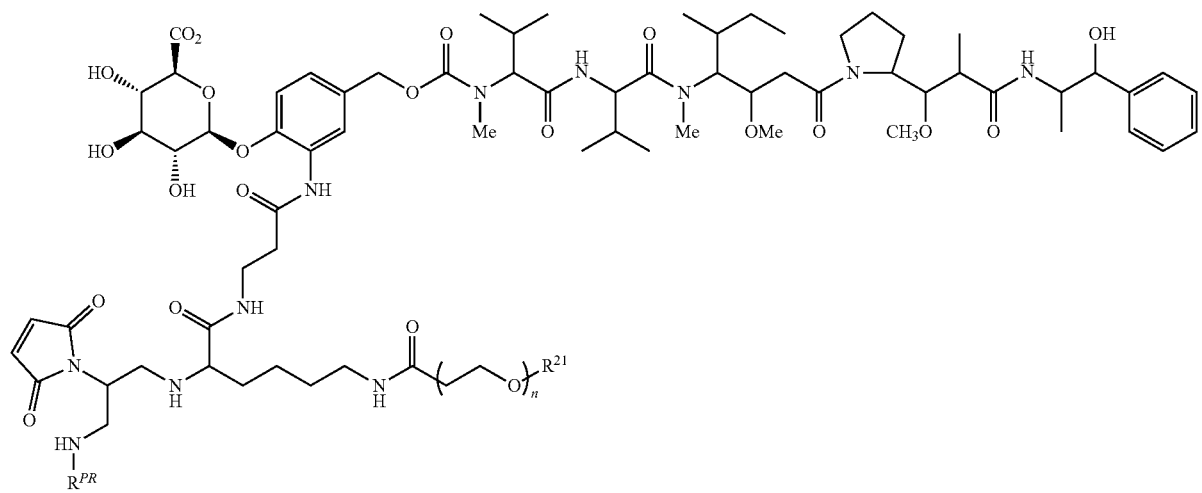

(VII)

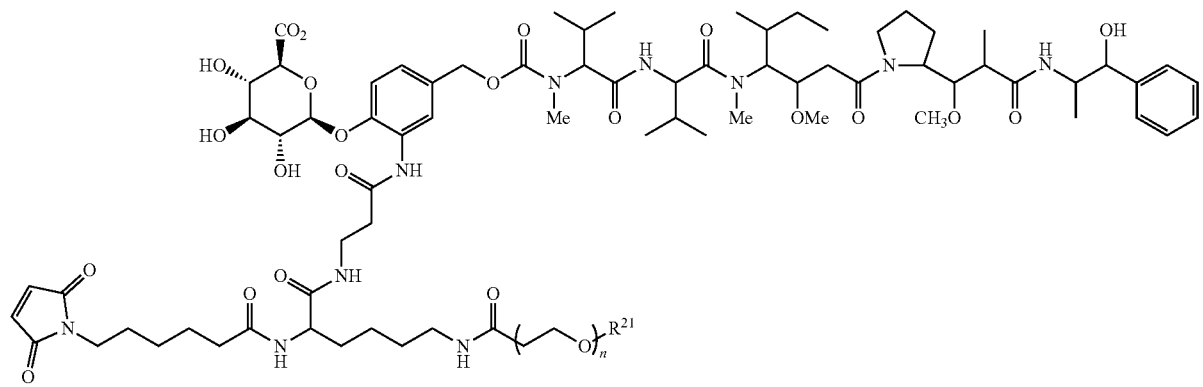

or a pharmaceutically acceptable salt thereof.

A preferred stereochemistry for such drug-linkers is shown below:

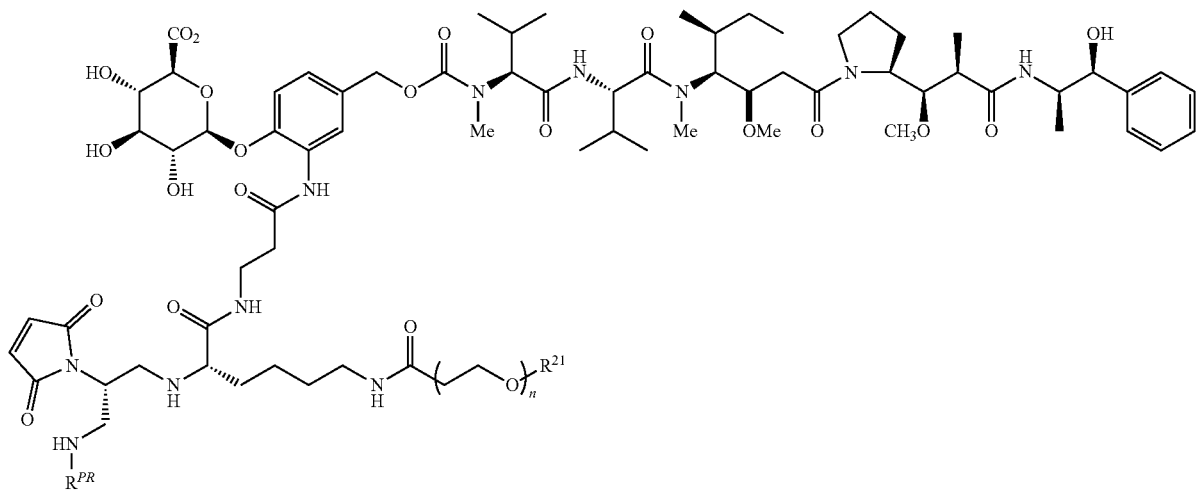

(VIa)

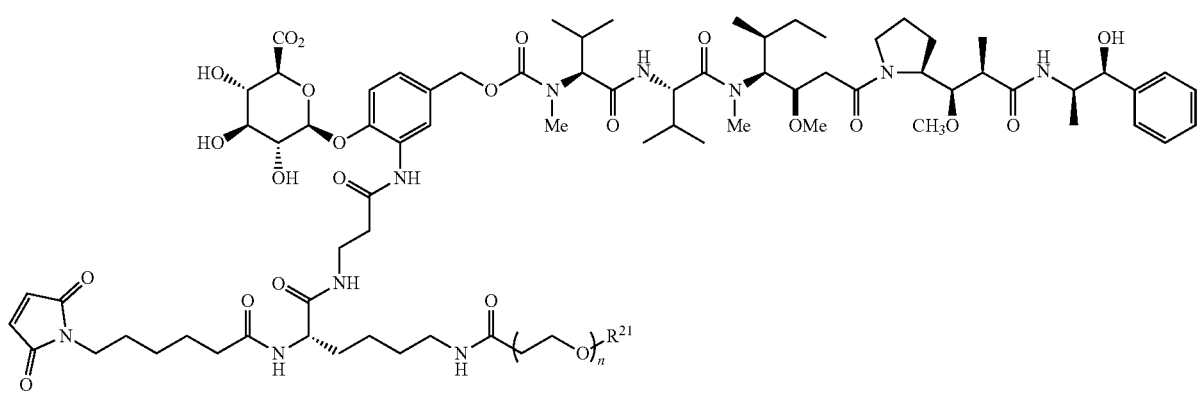

(VIIa)

or a pharmaceutically acceptable salt thereof wherein for formulas VI, VIa, VII and VIIa, n ranges from 8 to 36 and most preferably ranges from 8 to 14 (most preferably 12), $R^{PR}$ is hydrogen or a protecting group, e.g., acid labile protecting group, e.g., BOC, $R^{21}$ is a capping unit for the polyethylene glycol moiety, preferably —CH$_3$ or —CH$_2$CH$_2$CO$_2$H.

As noted above, $R^{PR}$ can be hydrogen or a protecting group. Protective groups as used herein refer to groups which selectively block, either temporarily or permanently, a reactive site in a multifunctional compound. A protecting group is a suitable protecting group when it is capable of preventing or avoiding unwanted side-reactions or premature loss of the protecting group under reaction conditions required to effect desired chemical transformation elsewhere in the molecule and during purification of the newly formed molecule when desired, and can be removed under conditions that do not adversely affect the structure or stereochemical integrity of that newly formed molecule. Suitable amine protecting groups include acid-labile nitrogen protecting groups, including those provided by Isidro-Llobel et al. "Amino acid-protecting groups" Chem. Rev. (2009) 109: 2455-2504. Typically, an acid-labile nitrogen-protecting group transforms a primary or secondary amino group to its corresponding carbamate and includes t-butyl, allyl, and benzyl carbamates.

As noted above, $R^{21}$ is a capping unit for the polyethylene glycol moiety. As will be appreciated by the skilled artisan, polyethylene glycol units can be terminally capped with a wide diversity of organic moieties, typically those that are relatively non-reactive. Alkyl and substituted alkyl groups are preferred.

Generally, there are 1 to 16 drug-linkers attached to each antibody.

Referring to the CD228 targeted antibody-drug conjugates, the subscript p represents the drug load and, depending on the context, can represent the number of molecules of drug-linker molecules attached to an individual antibody molecule and as such, is an integer value, or can represent an average drug load and, as such, can be an integer or non-integer value but is typically a non-integer value. An average drug load represents the average number of drug-linker molecules per antibody in a population. Often, but not always, when we refer to an antibody, e.g., a monoclonal antibody, we are referring to a population of antibody molecules. In a composition comprising a population of antibody-drug conjugate molecules, the average drug load is an important quality attribute as it determines the amount of drug that can be delivered to a target cell. The percentage of unconjugated antibody molecules in the composition is included in the average drug load value.

In preferred aspects of the present invention, the average drug load when referring to a composition comprising a population of antibody-drug conjugate compounds is from 1 to about 16, preferably about 2 to about 14, more preferably about 2 to about 10. For PBD antibody drug conjugates, such as those exemplified herein, a particularly preferred average drug load is about 2. In some aspects, the actual drug load for individual antibody molecules in the population of antibody-drug conjugate compounds is from 1 to 4, 1 to 3 or 1 to 2 with a predominant drug loading of 2. In preferred aspects, the average drug load of 2 is achieved via site specific conjugation techniques (e.g., engineered cysteines introduced to the antibody including at position 239, according to the EU Index numbering system).

For the MMAE PEGylated ADCs, such as those exemplified herein, a particularly preferred average drug load is about 8. In exemplary embodiments, the drug-linkers are conjugated to the cysteine residues of the reduced interchain disulfides. In some aspects, the actual drug load for individual antibody molecules in the population of antibody-drug conjugate compounds is from 1 to 10 (or from 6 to 10 or from 6 to 8) with a predominant drug loading of 8. A higher drug load can be achieved, for example, if, in addition to the interchain disulfides, drug-linker is conjugated to introduced cysteine residues (such as a cysteine residue introduced at position 239, according to the EU index).

Exemplary ADCs include the following:

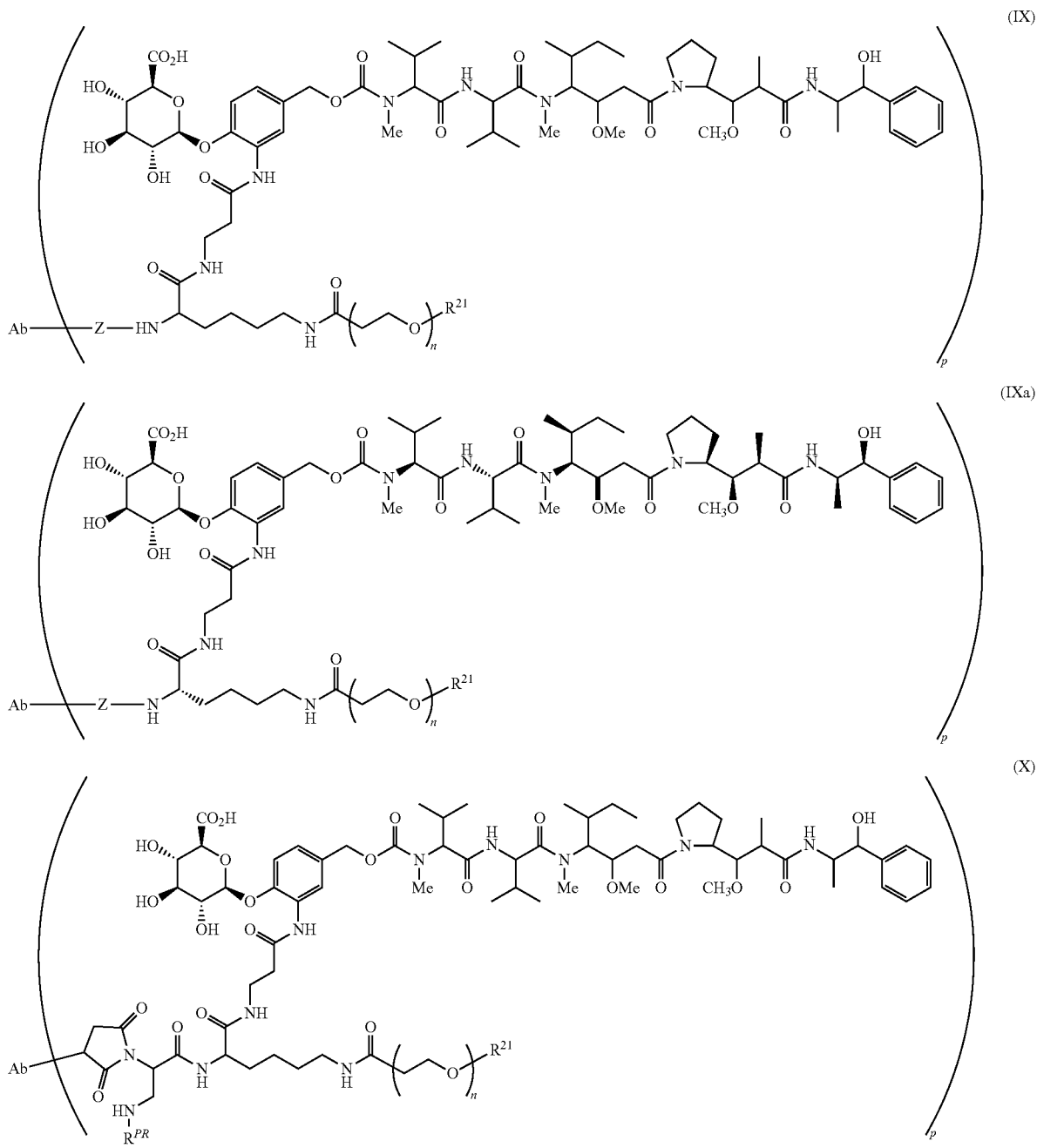

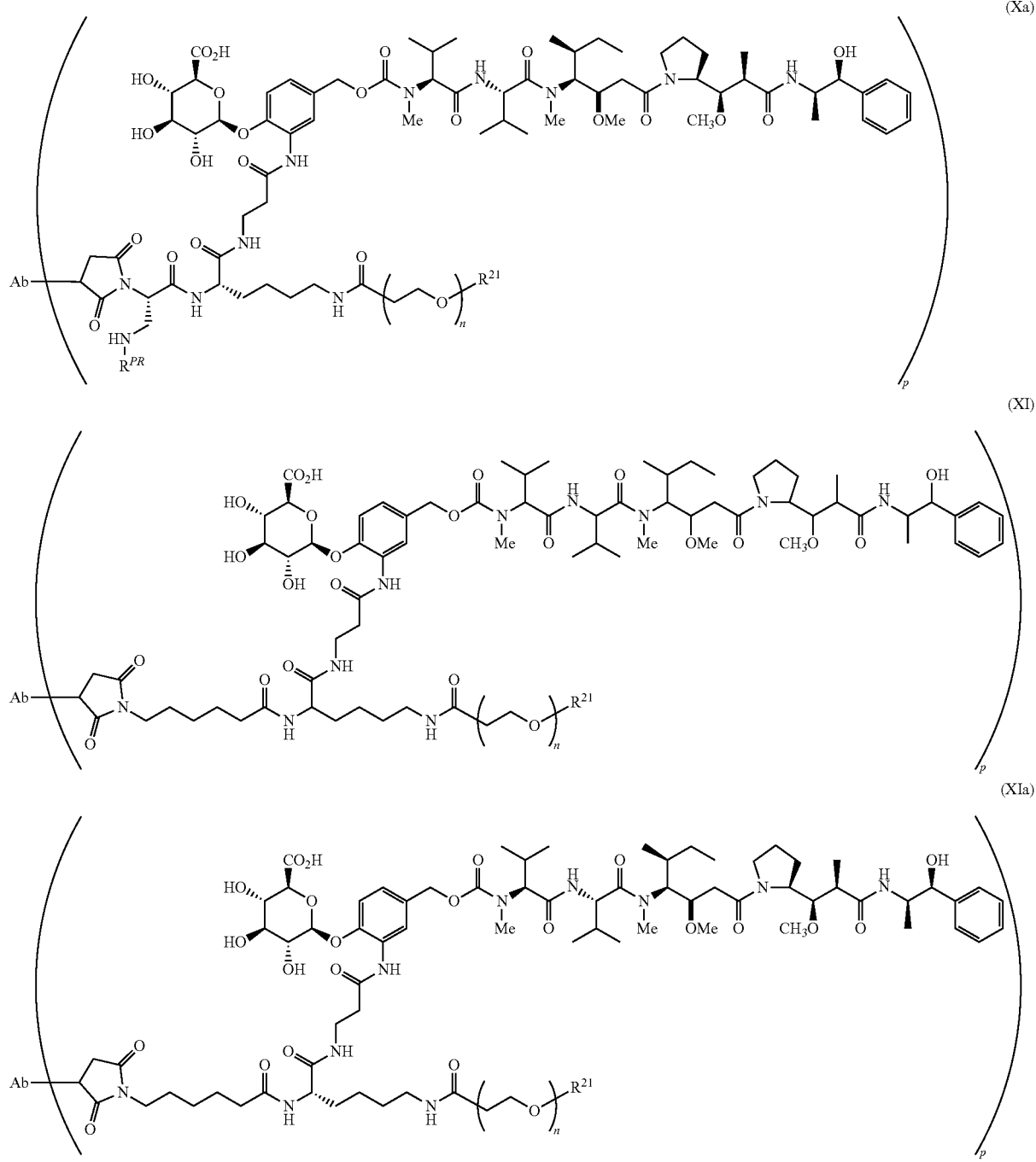

or a pharmaceutically acceptable salt thereof wherein n ranges from 8 to 36 and most preferably ranges from 8 to 14 (most preferably 12), $R^{PR}$ is hydrogen or a protecting group, e.g., acid labile protecting group, e.g., BOC, $R^{21}$ is a capping unit for the polyethylene glycol moiety, preferably —$CH_3$ or —$CH_2CH_2CO_2H$, Ab represents an anti-CD228 antibody and p represents an integer ranging from 1 to 16, preferably 1 to 14, 6 to 12, 6 to 10, or 8 to 10 when referring to individual antibody molecules or to an average drug load of from about 4 or about 6 to about 14, preferably about 8 when referring to a population of antibody molecules.

As noted above, the PEG (polyethylene glycol) portion of the drug linker can range from 8 to 36, however, it has been found that a PEG of 12 ethylene oxide units is particularly preferably. It has been found that longer PEG chains can result in slower clearance whereas shorter PEG chains can result in diminished activity. Accordingly, the subscript n in all of the embodiments above is preferably 8 to 14, 8 to 12, 10 to 12 or 10 to 14 and is most preferably 12.

Polydisperse PEGS, monodisperse PEGS and discrete PEGs can be used to make the PEGylated antibody drug conjugates of the present invention. Polydisperse PEGs are a heteregenous mixture of sizes and molecular weights whereas monodisperse PEGs are typically purified from heterogenous mixtures and are therefore provide a single chain length and molecular weight. Preferred PEG Units are discrete PEGs, compounds that are synthesized in step-wise fashion and not via a polymerization process. Discrete PEGs provide a single molecule with defined and specified chain length. As with the subscript "p", when referring to populations of antibody-drug conjugates, the value for the subscript "n" can be an average number and can be an integer or non-integer number.

In preferred embodiments, covalent attachment of the antibody to the drug-linker is accomplished through a sulfhydryl functional group of the antibody interacting with a maleimide functional group of a drug linker to form a thio-substituted succinimide. The sulfhydryl functional group can be present on the Ligand Unit in the Ligand's natural state, for example, in a naturally-occurring residue (inter-chain disulfide resides), or can be introduced into the Ligand via chemical modification or by biological engineering, or a combination of the two. It will be understood that an antibody-substituted succinimide may exist in hydrolyzed form(s). For example, in preferred embodiments, an ADC is comprised of a succinimide moiety that when bonded to the antibody is represented by the structure of:

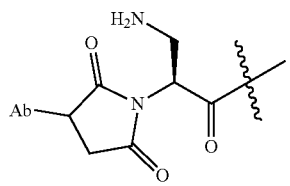

or is comprised of its corresponding acid-amide moiety that when bonded to the antibody is represented by the structure of:

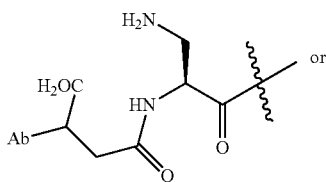

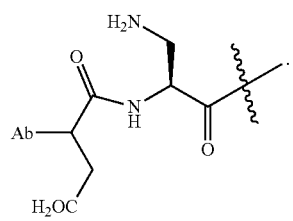

The wavy line indicates linkage to the remainder of the drug-linker.

Useful classes of cytotoxic agents to conjugate to anti-CD228 antibodies include, for example, antitubulin agents, DNA minor groove binding agents, DNA replication inhibitors, chemotherapy sensitizers, or the like. Other exemplary classes of cytotoxic agents include anthracyclines, auristatins, camptothecins, duocarmycins, etoposides, maytansinoids and vinca alkaloids. Some exemplary cytotoxic agents include auristatins (e.g., auristatin T, auristatin E, AFP, monomethyl auristatin F (MMAF), lipophilic monomethyl aurstatin F, monomethyl auristatin E (MMAE)), DNA minor groove binders (e.g., enediynes and lexitropsins), duocarmycins, taxanes (e.g., paclitaxel and docetaxel), vinca alkaloids, nicotinamide phosphoribosyltranferase inhibitor (NAMPTi), tubulysin M, doxorubicin, morpholino-doxorubicin, and cyanomorpholino-doxorubicin.

The cytotoxic agent can be a chemotherapeutic such as, for example, doxorubicin, paclitaxel, melphalan, vinca alkaloids, methotrexate, mitomycin C or etoposide. The agent can also be a CC-1065 analogue, calicheamicin, maytansine, an analog of dolastatin 10, rhizoxin, or palytoxin.

The cytotoxic agent can also be an auristatin. The auristatin can be an auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatins include auristatin T, AFP, MMAF, and MMAE. The synthesis and structure of various auristatins are described in, for example, US 2005-0238649 and US2006-0074008.

The cytotoxic agent can be a DNA minor groove binding agent. (See, e.g., U.S. Pat. No. 6,130,237.) For example, the minor groove binding agent can be a CBI compound or an enediyne (e.g., calicheamicin).

The cytotoxic or cytostatic agent can be an anti-tubulin agent. Examples of anti-tubulin agents include taxanes (e.g., Taxol® (paclitaxel), Taxotere® (docetaxel)), T67 (Tularik), vinca alkyloids (e.g., vincristine, vinblastine, vindesine, and vinorelbine), and auristatins (e.g., auristatin E, AFP, MMAF, MMAE, AEB, AEVB). Exemplary auristatins are shown below in formulae III-XIII. Other suitable antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermoide and eleuthrobin.

The cytotoxic agent can be a maytansinoid, another group of anti-tubulin agents (e.g., DM1, DM2, DM3, DM4). For example, the maytansinoid can be maytansine or a maytansine containing drug linker such as DM-1 or DM-4 (ImmunoGen, Inc.; see also Chari et al., 1992, Cancer Res.)

In some embodiments, an anti-CD228 antibody of the invention is conjugated to monomethyl auristatin E via a MDpr-PEG(12)-gluc linker forming an antibody-drug conjugate having the structure:

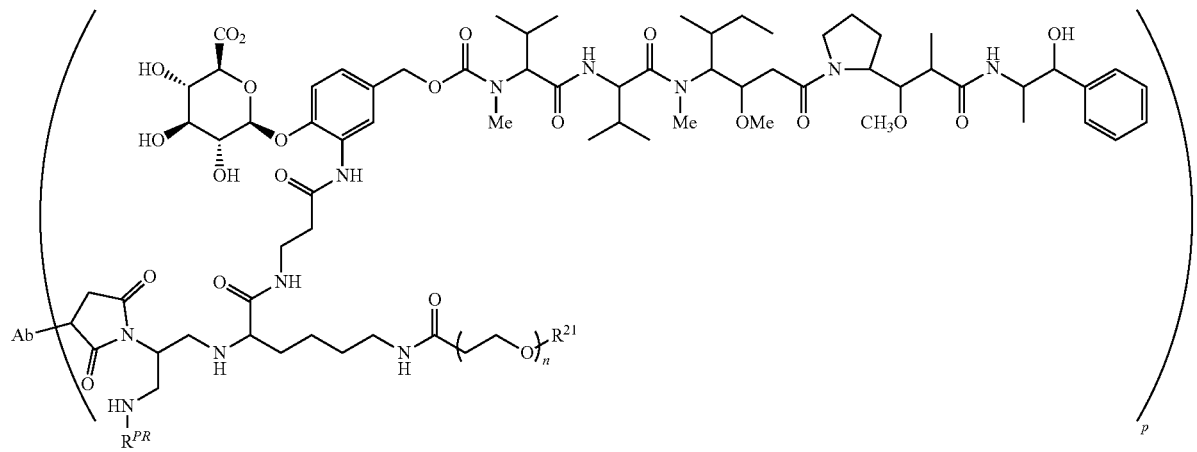

(X)

or a pharmaceutically acceptable salt thereof wherein n ranges from 8 to 36 and most preferably ranges from 8 to 14 (most preferably 12), $R^{PR}$ is hydrogen or a protecting group, e.g., acid labile protecting group, e.g., BOC, $R^{21}$ is a capping unit for the polyethylene glycol moiety, preferably —$CH_3$ or —$CH_2CH_2CO_2H$, Ab represents an anti-CD228 antibody and p represents an integer ranging from 1 to 16, preferably 1 to 14, 6 to 12, 6 to 10, or 8 to 10 when referring to individual antibody molecules or to an average drug load of from about 4 or about 6 to about 14, preferably about 8 when referring to a population of antibody molecules. In some embodiments, the anti-CD228 is hL49 and the resulting antibody-drug conjugate is hL49-Mdpr-PEG(12)-gluc-MMAE. hL49-Mdpr-PEG(12)-gluc-MMAE is also referred to as hL49-5088. The term hL49-5088(8) refers to the hL49-5088 with an average drug load of about 8 drug-linkers per antibody.

VIII. Therapeutic Applications

The antibodies of the invention, alone or as anti-CD228 antibody-drug conjugates thereof, can be used to treat cancer in a subject. Some such cancers show detectable levels of CD228 measured at either the protein (e.g., by immunoassay using one of the exemplified antibodies) or mRNA level. Some such cancers show elevated levels of CD228 relative to noncancerous tissue of the same type, preferably from the same patient. An exemplary level of CD228 on cancer cells amenable to treatment is 5000-500,000 CD228 molecules per cell, although higher or lower levels can be treated. Optionally, a level of CD228 in a cancer is measured before performing treatment. In some embodiments, the subject has been previously treated with one or more therapeutic agents and did not respond to the treatment, wherein the one or more therapeutic agents is not the antibody, antigen-binding fragment, or antibody-drug conjugate. In some embodiments, the subject has been previously treated with one or more therapeutic agents and relapsed after the treatment, wherein the one or more therapeutic agents is not the antibody, antigen-binding fragment, or antibody-drug conjugate. In some embodiments, the subject has been previously treated with one or more therapeutic agents and has experienced disease progression during treatment, wherein the one or more therapeutic agents is not the antibody, antigen-binding fragment, or antibody-drug conjugate. In some embodiments, the cancer is an advanced stage cancer. In some embodiments, the advanced stage cancer is a stage 3 or stage 4 cancer. In some embodiments, the advanced stage cancer is metastatic cancer. In some embodiments, the cancer is recurrent cancer. In some embodiments, the subject received prior treatment with standard of care therapy for the cancer and failed the prior treatment. In some embodiments, the subject is a human.

Examples of cancers associated with CD228 expression and amenable to treatment include melanoma and other carcinomas, including pancreatic cancer, lung cancer, such as non-small lung cancer, thyroid cancer, esophageal cancer, head and neck cancer, breast cancer, such as triple negative breast cancer, colorectal cancer, mesothelioma and cholangiocarcinoma. In some embodiments, the antibodies or antibody-drug conjugates of the invention are used in methods of treating melanoma in a subject. In some embodiments, the melanoma is cutaneous melanoma. In some embodiments, the cutaneous melanoma is selected from the group consisting of superficial spreading melanoma, nodular melanoma, acral lentiginous melanoma, lentigo maligna melanoma, and desmoplastic melanoma. In some embodiments, the cutaneous melanoma is superficial spreading melanoma. In some embodiments, the cutaneous melanoma is nodular melanoma. In some embodiments, the cutaneous melanoma is acral lentiginous melanoma. In some embodiments, the acral lentiginous melanoma is subungual melanoma. In some embodiments, the cutaneous melanoma is lentigo maligna melanoma. In some embodiments, the cutaneous melanoma is desmoplastic melanoma. In some embodiments, the subject received prior therapy with an inhibitor of PD-1 or PD-L1 for the cutaneous melanoma. In some embodiments, the subject received prior therapy with an inhibitor of PD-1. In some embodiments, the inhibitor of PD-1 is selected from the group consisting of nivolumab (OPDIVO®, BMS-936558 or MDX-1106), pembrolizumab (KEYTRUDA®, MK-3475), pidilizumab (CT-011) and cemiplimab (REGN2810). In some embodiments, the subject received prior therapy with an inhibitor of PD-L1. In some embodiments, the PD-L1 inhibitor is selected from the group consisting of atezolizumab (TECENTRIQ®, MPDL3280A), avelumab (BAVENCIO®), durvalumab and BMS-936559. In some embodiments, the melanoma is subcutaneous melanoma. In some embodiments, the sub-cutaneous melanoma is ocular melanoma or mucosal melanoma.

In some embodiments, the melanoma is non-cutaneous melanoma. In some embodiments, the antibodies or antibody-drug conjugates of the invention are used in methods of treating pancreatic cancer in a subject. In some embodiments, the pancreatic cancer is an exocrine cancer or a neuroendocrine cancer. In some embodiments, the pancreatic cancer is an exocrine cancer. In some embodiments, the exocrine pancreatic cancer is selected from the group consisting of pancreatic adenocarcinoma, acinar cell carcinoma, cystadenocarcinoma, pancreatoblastoma, adenosquamous carcinoma, signet ring carcinoma, hepatoid carcinoma, colloid carcinoma, undifferentiated carcinoma, and pancreatic mucinous cystic neoplasm. In some embodiments, the subject received one or more prior line of therapy for the exocrine pancreatic cancer. In some embodiments, the subject received one prior line of therapy for the exocrine pancreatic cancer. In some embodiments, the subject received more than one prior line of therapy for the exocrine pancreatic cancer. In some embodiments, the pancreatic cancer is pancreatic adenocarcinoma. In some embodiments, the pancreatic adenocarcinoma is pancreatic ductal adenocarcinoma. In some embodiments, the pancreatic cancer is acinar cell carcinoma. In some embodiments, the pancreatic cancer is cystadenocarcinoma. In some embodiments, the pancreatic cancer is pancreatoblastoma. In some embodiments, the pancreatic cancer is adenosquamous carcinoma. In some embodiments, the pancreatic cancer is signet ring carcinoma. In some embodiments, the pancreatic cancer is hepatoid carcinoma. In some embodiments, the pancreatic cancer is colloid carcinoma. In some embodiments, the pancreatic cancer is undifferentiated carcinoma. In some embodiments, the pancreatic cancer is pancreatic mucinous cystic neoplasm. In some embodiments, the pancreatic cancer is a neuroendocrine cancer. In some embodiments, the antibodies or antibody-drug conjugates of the invention are used in methods of treating lung cancer in a subject. In some embodiments, the antibodies or antibody-drug conjugates of the invention are used in methods of treating non-small cell lung cancer in a subject. In some embodiments, the non-small cell lung cancer has a mutant form of epidermal growth factor receptor (EGFR). In some embodiments, the non-small cell lung cancer has wild-type EGFR. In some embodiments, the subject has received prior therapy with a platinum-based therapy for the non-small cell lung cancer. In some embodiments, the platinum-based therapy is selected from the group consisting of carboplatin, cisplatin, oxaliplatin, nedaplatin, triplatin tetranitrate, phenanthriplatin, picoplatin and satraplatin. In some embodiments, the platinum-based therapy is carboplatin. In some embodiments, the platinum-based therapy is cisplatin. In some embodiments, the platinum-based therapy is oxaliplatin. In some embodiments, the platinum-based therapy is nedaplatin. In some embodiments, the platinum-based therapy is triplatin tetranitrate. In some embodiments, the platinum-based therapy is phenanthriplatin. In some embodiments, the platinum-based therapy is picoplatin. In some embodiments, the platinum-based therapy is satraplatin. In some embodiments, the subject received prior therapy with an inhibitor of PD-1 or PD-L1 for the non-small cell lung cancer. In some embodiments, the subject received prior therapy with an inhibitor of PD-1. In some embodiments, the PD-1 inhibitor is selected from the group consisting of nivolumab (OPDIVO®, BMS-936558 or MDX-1106), pembrolizumab (KEYTRUDA®, MK-3475), pidilizumab (CT-011) and cemiplimab (REGN2810). In some embodiments, the subject received prior therapy with an inhibitor of PD-L1. In some embodiments, the PD-L1 inhibitor is selected from the group consisting of atezolizumab (TECENTRIQ®, MPDL3280A), avelumab (BAVENCIO®), durvalumab and BMS-936559. In some embodiments, the subject has received prior therapy with a platinum-based therapy and an inhibitor of PD-1 or PD-L1 for the non-small cell lung cancer. In some embodiments, the antibodies or antibody-drug conjugates of the invention are used in methods of treating thyroid cancer in a subject. In some embodiments, the antibodies or antibody-drug conjugates of the invention are used in methods of treating esophageal cancer in a subject. In some embodiments, the antibodies or antibody-drug conjugates of the invention are used in methods of treating head and neck cancer in a subject. In some embodiments, the antibodies or antibody-drug conjugates of the invention are used in methods of treating breast cancer in a subject. In some embodiments, the breast cancer is selected from the group consisting of HER2 positive, HER2 negative, Estrogen Receptor (ER) positive, ER negative, Progesterone Receptor (PR) positive, PR negative, and triple negative breast cancer. In some embodiments, the breast cancer is HER2 positive breast cancer. In some embodiments, the breast cancer is HER2 negative breast cancer. In some embodiments, the subject received one or more prior line of therapy for the HER2 negative breast cancer. In some embodiments, the one or more prior line of therapy comprised treatment with a taxane. In some embodiments, the taxane is selected from the group consisting of paclitaxel, docetaxel, and cabazitaxel. In some embodiments, the taxane is paclitaxel. In some embodiments, the taxane is docetaxel. In some embodiments, the taxane is cabazitaxel. In some embodiments, the subject with HER2 negative breast cancer is hormone receptor positive. In some embodiments, the subject with HER2 negative, hormone receptor positive breast cancer received prior therapy with an inhibitor of CDK4/6. In some embodiments, the subject with HER2 negative, hormone receptor positive breast cancer received prior therapy with a hormonally-directed therapy. In some embodiments, the breast cancer is ER positive breast cancer. In some embodiments, the breast cancer is ER negative breast cancer. In some embodiments, the breast cancer is PR positive breast cancer. In some embodiments, the breast cancer is PR negative breast cancer. In some embodiments, the antibodies or antibody-drug conjugates of the invention are used in methods of treating triple negative breast cancer in a subject. A triple negative breast cancer is a term of art for a cancer lacking detectable estrogen and progesterone receptors and lacking overexpression of HER2/neu. In some embodiments, the antibodies or antibody-drug conjugates of the invention are used in methods of treating colorectal cancer in a subject. In some embodiments, the colorectal cancer is selected from the group consisting of a colorectal adenocarcinoma, a gastrointestinal stromal tumor, a primary colorectal lymphoma, a gastrointestinal carcinoid tumor, and a leiomyosarcoma. In some embodiments, the colorectal cancer is a colorectal adenocarcinoma. In some embodiments, the colorectal cancer is a gastrointestinal stromal tumor. In some embodiments, the colorectal cancer is a primary colorectal lymphoma. In some embodiments, the colorectal cancer is a gastrointestinal carcinoid tumor. In some embodiments, the colorectal cancer is a leiomyosarcoma. In some embodiments, the subject received two or more prior lines of therapy for the colorectal cancer. In some embodiments, the subject received two prior lines of therapy for the colorectal cancer. In some embodiments, the subject received more than two prior lines of therapy for the colorectal cancer. In some embodiments, the antibodies or antibody-drug conjugates of the invention are used in methods of treating mesothelioma in a subject. In some embodiments, the mesothelioma is selected from the group consisting of pleural mesothelioma, peritoneal mesothelioma, pericardial mesothelioma, and testicular mesothelioma. In some embodiments, the mesothelioma is pleural mesothelioma. In some embodiments, the subject has received prior therapy with a platinum-based therapy for the pleural mesothelioma. In some embodiments, the platinum-based therapy is selected from the group consisting of carboplatin, cisplatin, oxaliplatin, nedaplatin, triplatin tetranitrate, phenanthriplatin, picoplatin and satraplatin. In some embodiments, the platinum-based therapy is carboplatin. In some embodiments, the platinum-based therapy is cisplatin. In some embodiments, the platinum-based therapy is oxaliplatin. In some embodiments, the platinum-based therapy is nedaplatin. In some embodiments, the platinum-based therapy is triplatin tetranitrate. In some embodiments, the platinum-based therapy is phenanthriplatin. In some embodiments, the platinum-based therapy is picoplatin. In some embodiments, the platinum-based therapy is satraplatin. In some embodiments, the subject received prior therapy with pemetrexed for the pleural mesothelioma. In some embodiments, the mesothelioma is peritoneal mesothelioma. In some embodiments, the mesothelioma is pericardial mesothelioma. In some embodiments, the mesothelioma is testicular mesothelioma. In some embodiments, the antibodies or antibody-drug conjugates of the invention are used in methods of treating choliangiocarcinoma. The treatment can be applied to patients having primary or metastatic tumors of these kinds. The treatment can also be applied to patients who are refractory to conventional treatments, or who have relapsed following a response to such treatments. In some embodiments, the subject is a human.

Antibodies of the present invention, such as humanized antibodies, alone or as conjugates thereof, are administered in an effective regime meaning a dosage, route of administration and frequency of administration that delays the onset, reduces the severity, inhibits further deterioration, and/or ameliorates at least one sign or symptom of cancer. If a patient is already suffering from cancer, the regime can be referred to as a therapeutically effective regime. If the patient is at elevated risk of the caner relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Exemplary dosages for a monoclonal antibody are 0.1 mg/kg to 50 mg/kg of the patient's body weight, more typically 1 mg/kg to 30 mg/kg, 1 mg/kg to 20 mg/kg, 1 mg/kg to 15 mg/kg, 1 mg/kg to 12 mg/kg, or 1 mg/kg to 10 mg/kg 1, or 2 mg/kg to 30 mg/kg, 2 mg/kg to 20 mg/kg, 2 mg/kg to 15 mg/kg, 2 mg/kg to 12 mg/kg, or 2 mg/kg to 10 mg/kg, or 3 mg/kg to 30 mg/kg, 3 mg/kg to 20 mg/kg, 3 mg/kg to 15 mg/kg, 3 mg/kg to 12 mg/kg, or 3 mg/kg to 10 mg/kg. Exemplary dosages for a monoclonal antibody or antibody drug conjugates thereof are 1 mg/kg to 7.5 mg/kg, or 2 mg/kg to 7.5 mg/kg or 3 mg/kg to 7.5 mg/kg of the subject's body weight, or 0.1-20, or 0.5-5 mg/kg body weight (e.g., 0.5, 1, 2, 3, 4, 5, 6, 7, 8, 9 or 10 mg/kg) or 10-1500 mg or 200-1500 mg as a fixed dosage. In some methods, the patient is administered a dose of at least 1.5 mg/kg, at least 2 mg/kg or at least 3 mg/kg, administered once every three weeks or greater. The dosage depends on the frequency of administration, condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Administration can also be localized directly into a tumor. Administration into the systemic circulation by intravenous or subcutaneous administration is preferred. Intravenous administration can be, for example, by infusion over a period such as 30-90 min or by a single bolus injection.

The frequency of administration depends on the half-life of the antibody or conjugate in the circulation, the condition of the patient and the route of administration among other factors. The frequency can be daily, weekly, monthly, quarterly, or at irregular intervals in response to changes in the patient's condition or progression of the cancer being treated. An exemplary frequency for intravenous administration is between twice a week and quarterly over a continuous course of treatment, although more or less frequent dosing is also possible. Other exemplary frequencies for intravenous administration are between weekly or three out of every four weeks over a continuous course of treatment, although more or less frequent dosing is also possible. For subcutaneous administration, an exemplary dosing frequency is daily to monthly, although more or less frequent dosing is also possible.

The number of dosages administered depends on the nature of the cancer (e.g., whether presenting acute or chronic symptoms) and the response of the disorder to the treatment. For acute disorders or acute exacerbations of a chronic disorder between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use. The concentration of antibody in a liquid formulation can be e.g., 1-100 mg/ml, such as 10 mg/ml.

Treatment with antibodies of the invention can be combined with chemotherapy, radiation, stem cell treatment, surgery other treatments effective against the disorder being treated. Useful classes of other agents that can be administered with antibodies and antibody-drug conjugates to CD228 as described herein include, for example, antibodies to other receptors expressed on cancerous cells, antitubulin agents (e.g., auristatins), DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

Treatment with the anti-CD228 antibody or antibody-drug conjugate, optionally in combination with any of the other agents or regimes described above alone or as an antibody drug conjugate, can increase the median progression-free survival or overall survival time of patients with tumors (e.g., melanoma, pancreatic cancer, non-small lung cancer, thyroid cancer, head and neck cancer, triple negative breast cancer, colorectal cancer, mesothelioma, choliangiocarcinoma), especially when relapsed or refractory, by at least 30% or 40% but preferably 50%, 60% to 70% or even 100% or longer, compared to the same treatment (e.g., chemotherapy) but without an anti-CD228 antibody alone or as a conjugate. In addition or alternatively, treatment (e.g., standard chemotherapy) including the anti-CD228 antibody alone or as a conjugate can increase the complete response rate, partial response rate, or objective response rate (complete+partial) of patients with tumors by at least 30% or 40% but preferably 50%, 60% to 70% or even 100% compared to the same treatment (e.g., chemotherapy) but without the anti-CD228 antibody alone or as a conjugate.

Typically, in a clinical trial (e.g., a phase II, phase or phase III trial), the aforementioned increases in median progression-free survival and/or response rate of the patients treated with standard therapy plus the anti-CD228 antibody alone or as conjugate, relative to the control group of patients receiving standard therapy alone (or plus placebo), are statistically significant, for example at the p=0.05 or 0.01 or even 0.001 level. The complete and partial response rates are determined by objective criteria commonly used in clinical trials for cancer, e.g., as listed or accepted by the National Cancer Institute and/or Food and Drug Administration.

IX. Articles of Manufacture and Kits

In another aspect, an article of manufacture or kit is provided which comprises an anti-CD228 antibody or anti-CD228 antibody-drug conjugate described herein. The article of manufacture or kit may further comprise instructions for use of the anti-CD228 antibody or anti-CD228 antibody-drug conjugate described herein in the methods of the invention. Thus, in certain embodiments, the article of manufacture or kit comprises instructions for the use of an anti-CD228 antibody or anti-CD228 antibody-drug conjugate described herein in methods for treating cancer (e.g., melanoma and other carcinomas, including pancreatic cancer, non-small lung cancer, thyroid cancer, head and neck cancer, breast cancer, such as triple negative breast cancer, colorectal cancer, mesothelioma or choliangiocarcinoma) in a subject comprising administering to the subject an effective amount of an anti-CD228 antibody or anti-CD228 antibody-drug conjugate described herein. In some embodiments, the cancer is melanoma. In some embodiments, the cancer is pancreatic cancer. In some embodiments, the cancer is non-small lung cancer. In some embodiments, the cancer is thyroid cancer. In some embodiments, the cancer is head and neck cancer. In some embodiments, the cancer is breast cancer. In some embodiments, the breast cancer is triple negative breast cancer. In some embodiments, the cancer is colorectal cancer. In some embodiments, the cancer is mesothelioma. In some embodiments, the cancer is choliangiocarcinoma. In some embodiments, the subject is a human.

The article of manufacture or kit may further comprise a container. Suitable containers include, for example, bottles, vials (e.g., dual chamber vials), syringes (such as single or dual chamber syringes) and test tubes. In some embodiments, the container is a vial. The container may be formed from a variety of materials such as glass or plastic. The container holds the formulation.

The article of manufacture or kit may further comprise a label or a package insert, which is on or associated with the container, may indicate directions for reconstitution and/or use of the formulation. The label or package insert may further indicate that the formulation is useful or intended for subcutaneous, intravenous (e.g., intravenous infusion), or other modes of administration for treating cancer in a subject (e.g., melanoma and other carcinomas, including pancreatic cancer, non-small lung cancer, thyroid cancer, head and neck cancer, breast cancer, such as triple negative breast cancer, colorectal cancer, mesothelioma or choliangiocarcinoma). The container holding the formulation may be a single-use vial or a multi-use vial, which allows for repeat administrations of the reconstituted formulation. The article of manufacture or kit may further comprise a second container comprising a suitable diluent. The article of manufacture or kit may further include other materials desirable from a commercial, therapeutic, and user standpoint, including other buffers, diluents, filters, needles, syringes, and package inserts with instructions for use.

The article of manufacture or kit herein optionally further comprises a container comprising a second medicament, wherein the anti-CD228 antibody or anti-CD228 antibody-drug conjugate is a first medicament, and which article or kit further comprises instructions on the label or package insert for treating the subject with the second medicament, in an effective amount. In some embodiments, the second medicament is for eliminating or reducing the severity of one or more adverse events.

In some embodiments, the anti-CD228 antibody or anti-CD228 antibody-drug conjugate is present in the container as a lyophilized powder. In some embodiments, the lyophilized powder is in a hermetically sealed container, such as a vial, an ampoule or sachette, indicating the quantity of the active agent. Where the pharmaceutical is administered by injection, an ampoule of sterile water for injection or saline can be, for example, provided, optionally as part of the kit, so that the ingredients can be mixed prior to administration. Such kits can further include, if desired, one or more of various conventional pharmaceutical components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components can also be included in the kit.

X. Other Applications

The anti-CD228 antibodies described herein, such as humanized anti-CD228, antibodies can be used for detecting CD228 in the context of clinical diagnosis or treatment or in research. Expression of CD228 on a cancer provides an indication that the cancer is amenable to treatment with the antibodies of the present invention. The antibodies can also be sold as research reagents for laboratory research in detecting cells bearing CD228 and their response to various stimuli. In such uses, monoclonal antibodies can be labeled with fluorescent molecules, spin-labeled molecules, enzymes or radioisotopes, and can be provided in the form of kit with all the necessary reagents to perform the assay for CD228. The antibodies described herein, can be used to detect CD228 protein expression and determine whether a cancer is amenable to treatment with CD228 ADCs. As an example, hL49 (HALC) can be used to detect CD228 expression on melanoma cells, pancreatic cancer cells, non-small cell lung cancer cells, thyroid cancer cells, and head and neck cancer cells. The antibodies can also be used to purify CD228, e.g., by affinity chromatography.

All patent filings, website, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

XI. Variable Domain Sequences

For each of the following variable region sequences, the CDRs according to the Kabat numbering scheme are underlined and the CDRs according to the IMGT numbering scheme are in bold and italics.

```
Murine L49 vH
                                              (SEQ ID NO: 21)
EVQLQESGPSLVKPSQTLSLTCSVTGDSITSGYWNWIRKFPGNKLEYMGYISDSGITYYN
PSLKSRISITRDTSKNQYYLQLNFVTAEDTATYNCARRTLATYYAMDYWGQGTSVTVSS Mu IGHV3-8 vH
                                              (SEQ ID NO: 22)
EVQLQESGPSLVKPSQTLSLTCSVTGDSITSGYWNWIRKFPGNKLEYMGYISYSGSTYYN
PSLKSRISITRDTSKNQYYLQLNSVTTEDTATYYCAR Hu IGHV4-59/HJ4
                                              (SEQ ID NO: 23)
QVQLQESGPGLVKPSETLSLTCTVSGGSISSYYWSWIRQPPGKGLEWIGYIYYGSGTNYNP
SLKSRVTISVDTSKNQFSLKLSSVTAADTAVYYCARYFDYWGQGTLVTVSS hvHA
                                              (SEQ ID NO: 7)
QVQLQESGPGLVKPSETLSLTCTVSGDSITSGYWNWIRQPPGKGLEYIGYISDSGITYYNP
SLKSRVTISRDTSKNQYSLKLSSVTAADTAVYYCARRTLATYYAMDYWGQGTLVTVSS hvHB
                                              (SEQ ID NO: 24)
QVQLQESGPGLVKPSETLSLTCTVSGDSITSGYWNWIRQFPGKGLEYMGYISDSGITYYN
PSLKSRITISRDTSKNQYSLKLSSVTAADTAVYYCARRTLATYYAMDYWGQGTLVTVSS hvHC
                                              (SEQ ID NO: 25)
QVQLQESGPGLVKPSETLSLTCTVSGDSITSGYWNWIRQFPGKGLEYMGYISDSGITYYN
PSLKSRITISRDTSKNQYSLKLSFVTAADTAVYNCARRTLATYYAMDYWGQGTLVTVSS Mu L49 vL
                                              (SEQ ID NO: 26)
DFVMTQTPLSLPVSLGDQASISCRASQSLVHSNGNTYLHWYLQKPGQSPKWYRVSNRF
SGVPDRFSGSGSGTDFTLKISRVEAEDLGVYFCSQSTHVPPTFGGGTKLEIK Mu IGKV1-110 vL
                                              (SEQ ID NO: 27)
DVVMTQTPLSLPVSLGDQASISCRSSQSLVHSNGNTYLHWYLQKPGQSPKWYKVSNRF
SGVPDRFSGSGSGTDFTLKISRVEAEDLGVYFCSQSTHVP Hu IGKV2-30/KJ2
                                              (SEQ ID NO: 28)
DVVMTQSPLSLPVTLGQPASISCRSSQSLVYSDGNTYLNWFQQRPGQSPRRLIYKVSNRD
SGVPDRFSGSGSGTDFTLKISRVEAEDVGVYYCMQGTHWPYTFGQGTKLEIK hvLA
                                              (SEQ ID NO: 29)
DFVMTQSPLSLPVTLGQPASISCRASQSLVHSNGNTYLHWFQQRPGQSPRRLIYRVSNRF
SGVPDRFSGSGSGTDFTLKISRVEAEDVGVYYCSQSTHVPPTFGQGTKLEIK hvLB
                                              (SEQ ID NO: 20)
DFVMTQSPLSLPVTLGQPASISCRASQSLVHSNGNTYLHWYQQRPGQSPRLLIYRVSNRF
```

```
                                                            -continued
SGVPDRFSGSGSGTDFTLKISRVEAEDVGVYYCSQSTHVPPTFGQGTKLEIK hvLC
                                                                                  (SEQ ID NO: 8)
DFVMTQSPLSLPVTLGQPASISCRASQSLVHSDGNTYLHWYQQRPGQSPRLLIYRVSNRF
SGVPDRFSGSGSGTDFTLKISRVEAEDVGVYYCSQSTHVPPTFGQGTKLEIK.
```

XII. Exemplary Embodiments

Among the embodiments provided herein are:

1. An isolated anti-CD228 antibody, or antigen-binding fragment thereof, comprising a heavy chain variable region and a light chain variable region, wherein the heavy chain variable region comprises:
   (i) a CDR-H1 comprising the amino acid sequence of SEQ ID NO:1;
   (ii) a CDR-H2 comprising the amino acid sequence of SEQ ID NO:2; and
   (iii) a CDR-H3 comprising the amino acid sequence of SEQ ID NO:3; and
   wherein the light chain variable region comprises:
   (i) a CDR-L1 comprising the amino acid sequence of SEQ ID NO:4;
   (ii) a CDR-L2 comprising the amino acid sequence of SEQ ID NO:5; and
   (iii) a CDR-L3 comprising the amino acid sequence of SEQ ID NO:6.

2. The antibody or antigen-binding fragment of embodiment 1, wherein the antibody is humanized.

3. A humanized anti-CD228 antibody, or antigen-binding fragment thereof, comprising a heavy chain variable region comprising an amino acid sequence at least 90% identical to SEQ ID NO: 7 provided that position H27 is occupied by D, position H30 is occupied by T, position H47 is occupied by Y, position H71 is occupied by R, and position H78 is occupied by Y, and a light chain variable region comprising an amino acid sequence at least 90% identical to SEQ ID NO: 8, provided that position L2 is occupied by F, position L36 is occupied by Y and position L46 is occupied by L.

4. The antibody or antigen-binding fragment of embodiment 3, further provided that position L28 is occupied by D.

5. A humanized anti-CD228 antibody, or antigen-binding fragment thereof, comprising a heavy chain variable region comprising the three Kabat CDRs of SEQ ID NO: 7, wherein position H27 is occupied by D, position H30 is occupied by T, position H47 is occupied by Y, position H71 is occupied by R, and position H78 is occupied by Y, and a light chain variable region comprising the three Kabat CDRs of SEQ ID NO: 8, wherein position L2 is occupied by F, position L36 is occupied by Y and position L46 is occupied by L.

6. The antibody or antigen-binding fragment of any one of embodiments 1-5, wherein the heavy chain variable region comprises an amino acid sequence having at least 95% sequence identity to the amino acid sequence of SEQ ID NO: 7 and the light chain variable region comprises an amino acid sequence having at least 95% sequence identity to the amino acid sequence of SEQ ID NO: 8.

7. The antibody or antigen-binding fragment of any one of embodiments 1-5, wherein the heavy chain variable region comprises an amino acid sequence having at least 98% sequence identity to the amino acid sequence of SEQ ID NO: 7 and the light chain variable region comprises an amino acid sequence having at least 98% sequence identity to the amino acid sequence of SEQ ID NO: 8.

8. The antibody or antigen-binding fragment of any one of embodiments 1-5, wherein the heavy chain variable region comprises an amino acid sequence having at least 99% sequence identity to the amino acid sequence of SEQ ID NO: 7 and the light chain variable region comprises an amino acid sequence having at least 99% sequence identity to the amino acid sequence of SEQ ID NO: 8.

9. The antibody or antigen-binding fragment of any one of embodiments 1-5, wherein the heavy chain variable region comprises the amino acid sequence of SEQ ID NO: 7 and the light chain variable region comprises the amino acid sequence of SEQ ID NO:8.

10. The antibody or antigen-binding fragment of any one of embodiments 1-9, wherein the antibody or antigen-binding fragment is an antigen-binding fragment.

11. The antibody or antigen-binding fragment of embodiment 10, wherein the antigen-binding fragment is selected from the group consisting of Fab, Fab', F(ab')$_2$, Fab'-SH, Fv, diabody, linear antibody, and single-chain antibody fragment.

12. The antibody or antigen-binding fragment of any one of embodiments 1-9, wherein the antibody or antigen-binding fragment is a full-length antibody.

13. The antibody or antigen-binding fragment of embodiment 12, wherein the heavy chain variable region is fused to a heavy chain constant region and the light chain variable region is fused to a light chain constant region.

14. The antibody or antigen-binding fragment of embodiment 13, wherein the heavy chain constant region is of the IgG1 isotype.

15. The antibody or antigen-binding fragment of embodiment 13 or embodiment 14, wherein the heavy chain constant region has an amino acid sequence comprising SEQ ID NO:17 and the light chain constant region has an amino acid sequence comprising SEQ ID NO:18.

16. The antibody or antigen-binding fragment of embodiment 13 or embodiment 14, wherein the heavy chain constant region is a mutant form of a natural human constant region which has reduced binding to an Fcgamma receptor relative to the natural human constant region.

17. The antibody or antigen-binding fragment of embodiment 13 or embodiment 14, wherein the heavy chain constant region has an amino acid sequence comprising SEQ ID NO:19 (S239C) and the light chain constant region has an amino acid sequence comprising SEQ ID NO:18.

18. An antibody-drug conjugate comprising the antibody or antigen-binding fragment of any one of embodiments 1-17 conjugated to a cytotoxic or cytostatic agent.

19. The antibody-drug conjugate of embodiment 18, wherein the antibody or antigen-binding fragment is conjugated to the cytotoxic or cytostatic agent via a linker.

20. The antibody-drug conjugate of embodiment 19, wherein the linker is a MDpr-PEG(12)-gluc linker.

21. The antibody-drug conjugate of any one of embodiments 18-20, wherein the cytotoxic or cytostatic agent is a monomethyl auristatin.

22. The antibody-drug conjugate of embodiment 21, wherein the monomethyl auristatin is monomethyl auristatin E (MMAE).

23. The antibody-drug conjugate of embodiment 22, wherein the linker is attached to monomethyl auristatin E forming an antibody-drug conjugate having the structure:

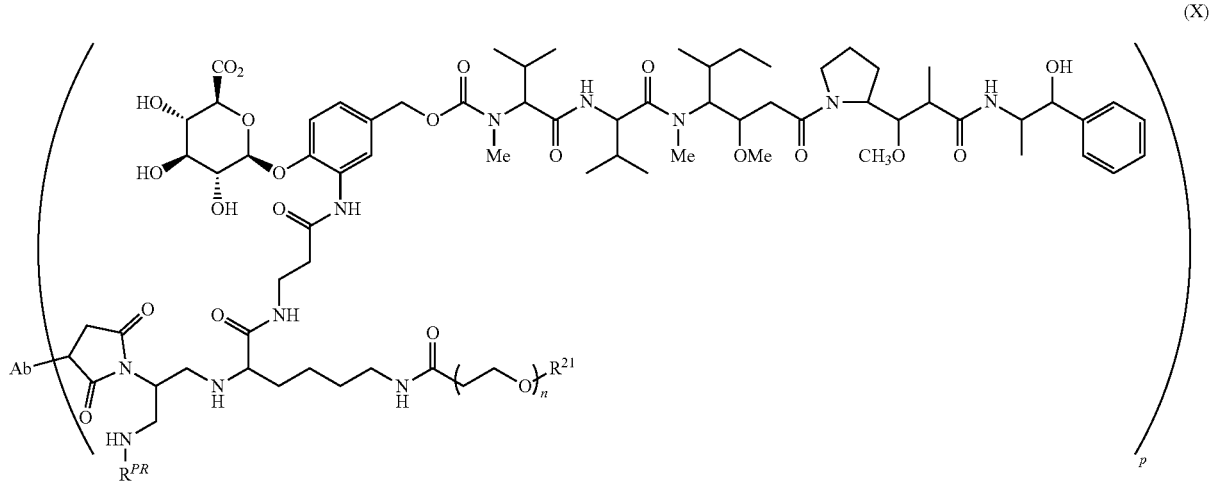

(X)

wherein Ab is the antibody hL49, n is 12, $R^{PR}$ is hydrogen, $R^{21}$ is $CH_3$, and p denotes a number from 1 to 16.

24. The antibody-drug conjugate of embodiment 23, wherein the average value of p in a population of the antibody-drug conjugate is about 8.

25. The antibody-drug conjugate of any one of embodiments 18-24, wherein the antibody-drug conjugate is hL49-MDpr-PEG(12)-gluc-MMAE.

26. A nucleic acid encoding the heavy chain variable region and/or the light chain variable region as defined by any one of embodiments 1-17.

27. A vector comprising the nucleic acid of embodiment 26.

28. The vector of embodiment 27, wherein the vector is an expression vector.

29. A host cell comprising the nucleic acid of embodiment 26.

30. The host cell of embodiment 29, wherein the host cell is a Chinese hamster ovary (CHO) cell.

31. A method of producing an anti-CD228 antibody or antigen-binding fragment thereof comprising culturing the host cell of embodiment 29 or embodiment 30 under a condition suitable for production of the anti-CD228 antibody or antigen-binding fragment thereof.

32. The method of embodiment 31, further comprising isolating the anti-CD228 antibody or antigen-binding fragment thereof produced by the host cell.

33. A method of producing an anti-CD228 antibody-drug conjugate comprising culturing the host cell of embodiment 29 or embodiment 30 under a condition suitable for production of an anti-CD228 antibody; isolating the anti-CD228 antibody produced from the host cell; and conjugating the anti-CD228 antibody to a cytotoxic or cytostatic agent.

34. The method of embodiment 33, wherein the anti-CD228 antibody is conjugated to the cytotoxic or cytostatic agent via a linker.

35. The method of embodiment 34, wherein the linker is a MDpr-PEG(12)-gluc linker.

36. The method of any one of embodiments 33-35, wherein the cytotoxic or cytostatic agent is a monomethyl auristatin.

37. The method of embodiment 36, wherein the monomethyl auristatin is monomethyl auristatin E (MMAE).

38. The method of embodiment 37, wherein the linker is attached to monomethyl auristatin E forming an antibody-drug conjugate having the structure:

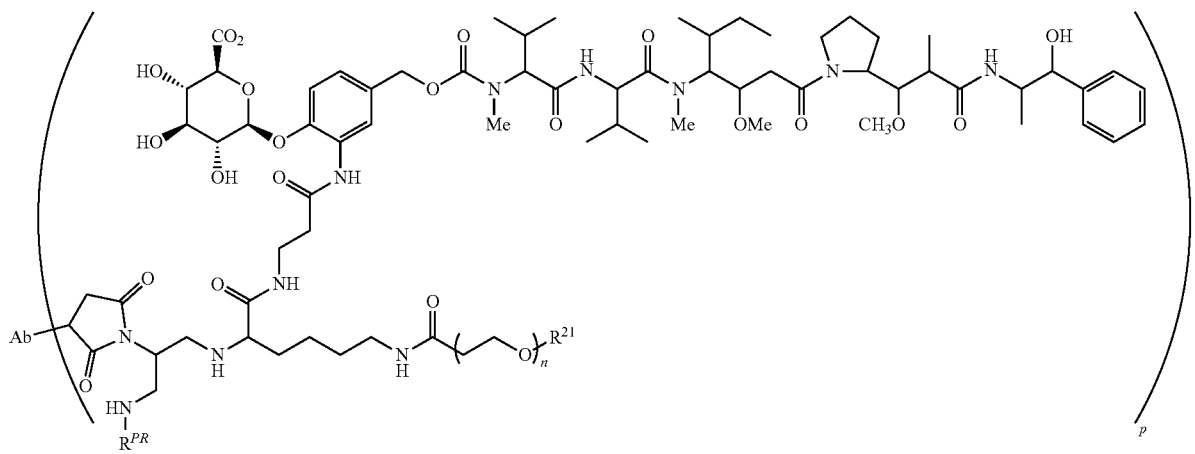

wherein Ab is the antibody hL49, n is 12, $R^{PR}$ is hydrogen, $R^{21}$ is $CH_3$, and p denotes a number from 1 to 16.

39. The method of embodiment 38, wherein the average value of p in a population of the antibody-drug conjugate is about 8.
40. The method of any one of embodiments 33-39, wherein the antibody-drug conjugate is hL49-MDpr-PEG(12)-gluc-MMAE.
41. A method of treating cancer in a subject, the method comprising administering to the subject the antibody or antigen-binding fragment of any one of embodiments 1-17 or the antibody-drug conjugate of any one of embodiments 18-25.
42. The method of embodiment 41, wherein the subject has been previously treated with one or more therapeutic agents and did not respond to the treatment, wherein the one or more therapeutic agents is not the antibody, antigen-binding fragment, or antibody-drug conjugate.
43. The method of embodiment 41, wherein the subject has been previously treated with one or more therapeutic agents and relapsed after the treatment, wherein the one or more therapeutic agents is not the antibody, antigen-binding fragment, or antibody-drug conjugate.
44. The method of embodiment 41, wherein the subject has been previously treated with one or more therapeutic agents and has experienced disease progression during treatment, wherein the one or more therapeutic agents is not the antibody, antigen-binding fragment, or antibody-drug conjugate.
45. The method of any one of embodiments 41-44, wherein the cancer is an advanced stage cancer.
46. The method of embodiment 45, wherein the advanced stage cancer is a stage 3 or stage 4 cancer.
47. The method of embodiment 45 or 46, wherein the advanced stage cancer is metastatic cancer.
48. The method of any one of embodiments 41-47, wherein the cancer is recurrent cancer.
49. The method of any one of embodiments 41-48, wherein the cancer is unresectable.
50. The method of any one of embodiments 41-49, wherein the subject received prior treatment with standard of care therapy for the cancer and failed the prior treatment.
51. The method of any one of embodiments 41-50, wherein the cancer is selected from the group consisting of melanoma, pancreatic cancer, mesothelioma, colorectal cancer, lung cancer, thyroid cancer, breast cancer, choliangiocarcinoma, esophageal cancer and head and neck cancer.
52. The method of embodiment 51, wherein the cancer is melanoma.
53. The method of embodiment 52, wherein the melanoma is cutaneous melanoma.
54. The method of embodiment 53, wherein the cutaneous melanoma is selected from the group consisting of superficial spreading melanoma, nodular melanoma, acral lentiginous melanoma, lentigo maligna melanoma, and desmoplastic melanoma.
55. The method of embodiment 54, wherein the acral lentiginous melanoma is subungual melanoma.
56. The method of any one of embodiments 53-55, wherein the subject received prior therapy with an inhibitor of PD-1 or PD-L1.
57. The method of embodiment 56, wherein the subject received prior therapy with an inhibitor of PD-1.
58. The method of embodiment 52, wherein the melanoma is sub-cutaneous melanoma.
59. The method of embodiment 58, wherein the sub-cutaneous melanoma is ocular melanoma or mucosal melanoma.
60. The method of embodiment 52, wherein the melanoma is non-cutaneous melanoma.
61. The method of embodiment 51, wherein the cancer is mesothelioma.
62. The method of embodiment 61, wherein the mesothelioma is selected from the group consisting of pleural mesothelioma, peritoneal mesothelioma, pericardial mesothelioma, and testicular mesothelioma.
63. The method of embodiment 62, wherein the mesothelioma is pleural mesothelioma.
64. The method of embodiment 63, wherein the subject has received prior therapy with a platinum-based therapy.
65. The method of embodiment 64, wherein the platinum-based therapy is cisplatin.
66. The method of any one of embodiments 63-65, wherein the subject received prior therapy with pemetrexed.
67. The method of embodiment 51, wherein the lung cancer is non-small cell lung cancer.
68. The method of embodiment 67, wherein the non-small cell lung cancer has a mutant form of epidermal growth factor receptor (EGFR).

69. The method of embodiment 67, wherein the non-small cell lung cancer has wild-type EGFR.
70. The method of embodiment 69, wherein the subject has received prior therapy with a platinum-based therapy.
71. The method of embodiment 69 or 70, wherein the subject received prior therapy with an inhibitor of PD-1 or PD-L1.
72. The method of embodiment 71, wherein the subject received prior therapy with an inhibitor of PD-1.
73. The method of embodiment 51, wherein the breast cancer is selected from the group consisting of HER2 positive, HER2 negative, Estrogen Receptor (ER) positive, ER negative, Progesterone Receptor (PR) positive, PR negative, and triple negative breast cancer.
74. The method of embodiment 73, wherein the breast cancer is HER2 negative breast cancer.
75. The method of embodiment 74, wherein the subject received one or more prior line of therapy for the HER2 negative breast cancer.
76. The method of embodiment 75, wherein the one or more prior line of therapy comprised treatment with a taxane.
77. The method of embodiment 75 or 76, wherein the subject is hormone receptor positive.
78. The method of embodiment 77, wherein the subject received prior therapy with an inhibitor of CDK4/6.
79. The method of embodiment 77 or 78, wherein the subject received prior therapy with a hormonally-directed therapy.
80. The method of embodiment 51, wherein the colorectal cancer is selected from the group consisting of a colorectal adenocarcinoma, a gastrointestinal stromal tumor, a primary colorectal lymphoma, a gastrointestinal carcinoid tumor, and a leiomyosarcoma.
81. The method of embodiment 80, wherein the subject received two or more prior lines of therapy for the colorectal cancer.
82. The method of embodiment 51, wherein the pancreatic cancer is an exocrine cancer or a neuroendocrine cancer.
83. The method of embodiment 82, wherein the exocrine cancer is selected from the group consisting of pancreatic adenocarcinoma, acinar cell carcinoma, cystadenocarcinoma, pancreatoblastoma, adenosquamous carcinoma, signet ring carcinoma, hepatoid carcinoma, colloid carcinoma, undifferentiated carcinoma, and pancreatic mucinous cystic neoplasm.
84. The method of embodiment 83, wherein the pancreatic adenocarcinoma is pancreatic ductal adenocarcinoma.
85. The method of embodiment 83 or 84, wherein the subject received one or more prior line of therapy for the pancreatic cancer.
86. The method of any one of embodiments 41-85, wherein the antibody or antigen-binding fragment or antibody-drug conjugate is in a pharmaceutical composition comprising the antibody or antigen-binding fragment or antibody-drug conjugate and a pharmaceutically acceptable carrier.
87. The method of any one of embodiments 41-86, wherein the subject is a human.
88. A kit comprising:
    (a) the antibody or antigen-binding fragment of any one of embodiments 1-17 or the antibody-drug conjugate of any one of embodiments 18-25; and
    (b) instructions for using the antibody or antigen-binding fragment or antibody-drug conjugate according to the method of any one of embodiments 41-87.
89. A pharmaceutical composition comprising the antibody or antigen-binding fragment of any one of embodiments 1-17 or the antibody-drug conjugate of any one of embodiments 18-25 and one or more agents selected from the group consisting of a physiologically acceptable carrier, a diluent, an excipient and an auxiliary.
90. The antibody or antigen-binding fragment of any one of embodiments 1-17 or the antibody-drug conjugate of any one of embodiments 18-25 for use in the treatment of cancer in a subject.
91. The antibody or antigen-binding fragment of embodiment 90, wherein the subject has been previously treated with one or more therapeutic agents and did not respond to the treatment, wherein the one or more therapeutic agents is not the antibody, antigen-binding fragment, or antibody-drug conjugate.
92. The antibody or antigen-binding fragment of embodiment 90, wherein the subject has been previously treated with one or more therapeutic agents and relapsed after the treatment, wherein the one or more therapeutic agents is not the antibody, antigen-binding fragment, or antibody-drug conjugate.
93. The antibody or antigen-binding fragment of embodiment 90, wherein the subject has been previously treated with one or more therapeutic agents and has experienced disease progression during treatment, wherein the one or more therapeutic agents is not the antibody, antigen-binding fragment, or antibody-drug conjugate.
94. The antibody or antigen-binding fragment of any one of embodiments 90-93, wherein the cancer is an advanced stage cancer.
95. The antibody or antigen-binding fragment of embodiment 94, wherein the advanced stage cancer is a stage 3 or stage 4 cancer.
96. The antibody or antigen-binding fragment of embodiment 94 or 95, wherein the advanced stage cancer is metastatic cancer.
97. The antibody or antigen-binding fragment of any one of embodiments 90-96, wherein the cancer is recurrent cancer.
98. The antibody or antigen-binding fragment of any one of embodiments 90-97, wherein the cancer is unresectable.
99. The antibody or antigen-binding fragment of any one of embodiments 90-98, wherein the subject received prior treatment with standard of care therapy for the cancer and failed the prior treatment.
100. The antibody or antigen-binding fragment of any one of embodiments 90-99, wherein the cancer is selected from the group consisting of melanoma, pancreatic cancer, mesothelioma, colorectal cancer, lung cancer, thyroid cancer, breast cancer, choliangiocarcinoma, esophageal cancer and head and neck cancer.
101. The antibody or antigen-binding fragment of embodiment 100, wherein the cancer is melanoma.
102. The antibody or antigen-binding fragment of embodiment 101, wherein the melanoma is cutaneous melanoma.
103. The antibody or antigen-binding fragment of embodiment 102, wherein the cutaneous melanoma is selected from the group consisting of superficial spreading melanoma, nodular melanoma, acral lentiginous melanoma, lentigo maligna melanoma, and desmoplastic melanoma.
104. The antibody or antigen-binding fragment of embodiment 103, wherein the acral lentiginous melanoma is subungual melanoma.
105. The antibody or antigen-binding fragment of any one of embodiments 102-104, wherein the subject received prior therapy with an inhibitor of PD-1 or PD-L1.

106. The antibody or antigen-binding fragment of embodiment 105, wherein the subject received prior therapy with an inhibitor of PD-1.
107. The antibody or antigen-binding fragment of embodiment 101, wherein the melanoma is sub-cutaneous melanoma.
108. The antibody or antigen-binding fragment of embodiment 107, wherein the sub-cutaneous melanoma is ocular melanoma or mucosal melanoma.
109. The antibody or antigen-binding fragment of embodiment 101, wherein the melanoma is non-cutaneous melanoma.
110. The antibody or antigen-binding fragment of embodiment 100, wherein the cancer is mesothelioma.
111. The antibody or antigen-binding fragment of embodiment 110, wherein the mesothelioma is selected from the group consisting of pleural mesothelioma, peritoneal mesothelioma, pericardial mesothelioma, and testicular mesothelioma.
112. The antibody or antigen-binding fragment of embodiment 111, wherein the mesothelioma is pleural mesothelioma.
113. The antibody or antigen-binding fragment of embodiment 112, wherein the subject has received prior therapy with a platinum-based therapy.
114. The antibody or antigen-binding fragment of embodiment 113, wherein the platinum-based therapy is cisplatin.
115. The antibody or antigen-binding fragment of any one of embodiments 112-114, wherein the subject received prior therapy with pemetrexed.
116. The antibody or antigen-binding fragment of embodiment 100, wherein the lung cancer is non-small cell lung cancer.
117. The antibody or antigen-binding fragment of embodiment 116, wherein the non-small cell lung cancer has a mutant form of epidermal growth factor receptor (EGFR).
118. The antibody or antigen-binding fragment of embodiment 116, wherein the non-small cell lung cancer has wild-type EGFR.
119. The antibody or antigen-binding fragment of embodiment 118, wherein the subject has received prior therapy with a platinum-based therapy.
120. The antibody or antigen-binding fragment of embodiment 118 or 119, wherein the subject received prior therapy with an inhibitor of PD-1 or PD-L1.
121. The antibody or antigen-binding fragment of embodiment 120, wherein the subject received prior therapy with an inhibitor of PD-1.
122. The antibody or antigen-binding fragment of embodiment 100, wherein the breast cancer is selected from the group consisting of HER2 positive, HER2 negative, Estrogen Receptor (ER) positive, ER negative, Progesterone Receptor (PR) positive, PR negative, and triple negative breast cancer.
123. The antibody or antigen-binding fragment of embodiment 122, wherein the breast cancer is HER2 negative breast cancer.
124. The antibody or antigen-binding fragment of embodiment 123, wherein the subject received one or more prior line of therapy for the HER2 negative breast cancer.
125. The antibody or antigen-binding fragment of embodiment 124, wherein the one or more prior line of therapy comprised treatment with a taxane.
126. The antibody or antigen-binding fragment of embodiment 124 or 125, wherein the subject is hormone receptor positive.
127. The antibody or antigen-binding fragment of embodiment 126, wherein the subject received prior therapy with an inhibitor of CDK4/6.
128. The antibody or antigen-binding fragment of embodiment 126 or 127, wherein the subject received prior therapy with a hormonally-directed therapy.
129. The antibody or antigen-binding fragment of embodiment 128, wherein the colorectal cancer is selected from the group consisting of a colorectal adenocarcinoma, a gastrointestinal stromal tumor, a primary colorectal lymphoma, a gastrointestinal carcinoid tumor, and a leiomyosarcoma.
130. The antibody or antigen-binding fragment of embodiment 129, wherein the subject received two or more prior lines of therapy for the colorectal cancer.
131. The antibody or antigen-binding fragment of embodiment 100, wherein the pancreatic cancer is an exocrine cancer or a neuroendocrine cancer.
132. The antibody or antigen-binding fragment of embodiment 131, wherein the exocrine cancer is selected from the group consisting of pancreatic adenocarcinoma, acinar cell carcinoma, cystadenocarcinoma, pancreatoblastoma, adenosquamous carcinoma, signet ring carcinoma, hepatoid carcinoma, colloid carcinoma, undifferentiated carcinoma, and pancreatic mucinous cystic neoplasm.
133. The antibody or antigen-binding fragment of embodiment 132, wherein the pancreatic adenocarcinoma is pancreatic ductal adenocarcinoma.
134. The antibody or antigen-binding fragment of embodiment 132 or 133, wherein the subject received one or more prior line of therapy for the pancreatic cancer.
135. The antibody or antigen-binding fragment of any one of embodiments 90-134, wherein the antibody or antigen-binding fragment or antibody-drug conjugate is in a pharmaceutical composition comprising the antibody or antigen-binding fragment or antibody-drug conjugate and a pharmaceutically acceptable carrier.
136. The antibody or antigen-binding fragment of any one of embodiments 90-135, wherein the subject is a human.
137. Use of the antibody or antigen-binding fragment of any one of embodiments 1-17 or the antibody-drug conjugate of any one of embodiments 18-25 for the manufacture of a medicament for treating cancer in subject.
138. The use of embodiment 137, wherein the subject has been previously treated with one or more therapeutic agents and did not respond to the treatment, wherein the one or more therapeutic agents is not the antibody, antigen-binding fragment, or antibody-drug conjugate.
139. The use of embodiment 137, wherein the subject has been previously treated with one or more therapeutic agents and relapsed after the treatment, wherein the one or more therapeutic agents is not the antibody, antigen-binding fragment, or antibody-drug conjugate.
140. The use of embodiment 137, wherein the subject has been previously treated with one or more therapeutic agents and has experienced disease progression during treatment, wherein the one or more therapeutic agents is not the antibody, antigen-binding fragment, or antibody-drug conjugate.
141. The use of any one of embodiments 137-140, wherein the cancer is an advanced stage cancer.
142. The use of embodiment 141, wherein the advanced stage cancer is a stage 3 or stage 4 cancer.
143. The method of embodiment 141 or 142, wherein the advanced stage cancer is metastatic cancer.
144. The use of any one of embodiments 137-143, wherein the cancer is recurrent cancer.

145. The use of any one of embodiments 137-144, wherein the cancer is unresectable.
146. The use of any one of embodiments 137-145, wherein the subject received prior treatment with standard of care therapy for the cancer and failed the prior treatment.
147. The use of any one of embodiments 137-146, wherein the cancer is selected from the group consisting of melanoma, pancreatic cancer, mesothelioma, colorectal cancer, lung cancer, thyroid cancer, breast cancer, choliangiocarcinoma, esophageal cancer and head and neck cancer.
148. The use of embodiment 147, wherein the cancer is melanoma.
149. The use of embodiment 148, wherein the melanoma is cutaneous melanoma.
150. The use of embodiment 149, wherein the cutaneous melanoma is selected from the group consisting of superficial spreading melanoma, nodular melanoma, acral lentiginous melanoma, lentigo maligna melanoma, and desmoplastic melanoma.
151. The use of embodiment 150, wherein the acral lentiginous melanoma is subungual melanoma.
152. The use of any one of embodiments 149-151, wherein the subject received prior therapy with an inhibitor of PD-1 or PD-L1.
153. The use of embodiment 152, wherein the subject received prior therapy with an inhibitor of PD-1.
154. The use of embodiment 148, wherein the melanoma is sub-cutaneous melanoma.
155. The use of embodiment 154, wherein the sub-cutaneous melanoma is ocular melanoma or mucosal melanoma.
156. The use of embodiment 148, wherein the melanoma is non-cutaneous melanoma.
157. The use of embodiment 147, wherein the cancer is mesothelioma.
158. The use of embodiment 157, wherein the mesothelioma is selected from the group consisting of pleural mesothelioma, peritoneal mesothelioma, pericardial mesothelioma, and testicular mesothelioma.
159. The use of embodiment 158, wherein the mesothelioma is pleural mesothelioma.
160. The use of embodiment 159, wherein the subject has received prior therapy with a platinum-based therapy.
161. The use of embodiment 160, wherein the platinum-based therapy is cisplatin.
162. The use of any one of embodiments 158-161, wherein the subject received prior therapy with pemetrexed.
163. The use of embodiment 147, wherein the lung cancer is non-small cell lung cancer.
164. The use of embodiment 163, wherein the non-small cell lung cancer has a mutant form of epidermal growth factor receptor (EGFR).
165. The use of embodiment 163, wherein the non-small cell lung cancer has wild-type EGFR.
166. The use of embodiment 165, wherein the subject has received prior therapy with a platinum-based therapy.
167. The use of embodiment 165 or 166, wherein the subject received prior therapy with an inhibitor of PD-1 or PD-L1.
168. The use of embodiment 167, wherein the subject received prior therapy with an inhibitor of PD-1.
169. The use of embodiment 147, wherein the breast cancer is selected from the group consisting of HER2 positive, HER2 negative, Estrogen Receptor (ER) positive, ER negative, Progesterone Receptor (PR) positive, PR negative, and triple negative breast cancer.
170. The use of embodiment 169, wherein the breast cancer is HER2 negative breast cancer.
171. The use of embodiment 170, wherein the subject received one or more prior line of therapy for the HER2 negative breast cancer.
172. The use of embodiment 171, wherein the one or more prior line of therapy comprised treatment with a taxane.
173. The use of embodiment 171 or 172, wherein the subject is hormone receptor positive.
174. The use of embodiment 173, wherein the subject received prior therapy with an inhibitor of CDK4/6.
175. The use of embodiment 173 or 174, wherein the subject received prior therapy with a hormonally-directed therapy.
176. The use of embodiment 147, wherein the colorectal cancer is selected from the group consisting of a colorectal adenocarcinoma, a gastrointestinal stromal tumor, a primary colorectal lymphoma, a gastrointestinal carcinoid tumor, and a leiomyosarcoma.
177. The use of embodiment 176, wherein the subject received two or more prior lines of therapy for the colorectal cancer.
178. The use of embodiment 147, wherein the pancreatic cancer is an exocrine cancer or a neuroendocrine cancer.
179. The use of embodiment 178, wherein the exocrine cancer is selected from the group consisting of pancreatic adenocarcinoma, acinar cell carcinoma, cystadenocarcinoma, pancreatoblastoma, adenosquamous carcinoma, signet ring carcinoma, hepatoid carcinoma, colloid carcinoma, undifferentiated carcinoma, and pancreatic mucinous cystic neoplasm.
180. The use of embodiment 179, wherein the pancreatic adenocarcinoma is pancreatic ductal adenocarcinoma.
181. The use of embodiment 179 or 180, wherein the subject received one or more prior line of therapy for the pancreatic cancer.
182. The use of any one of embodiments 137-181, wherein the antibody or antigen-binding fragment or antibody-drug conjugate is in a pharmaceutical composition comprising the antibody or antigen-binding fragment or antibody-drug conjugate and a pharmaceutically acceptable carrier.
183. The use of any one of embodiments 137-182, wherein the subject is a human.

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1

CD288 Expression in Cancer Cell Lines

Quantification of CD228 copy number on the cell surface of various cancer cell lines was determined using a murine CD228 mAb as primary antibody and the DAKO QiFiKit flow cytometric indirect assay as described by the manufacturer (DAKO A/S, Glostrup, Denmark) and evaluated with a Attune NxT Flow Cytometer. The resulting number of CD228 molecules expressed per cell are shown in Table 1.

TABLE 1

CD228 molecules per cell for various cell lines

| Cell Line | Number of CD228 molecules per cell |
|---|---|
| A2058 | 51,000 |
| RPMI-7951 | 0 |
| PRMI-7951 + CD228 | 400,000 |
| SK-MEL-5 | 134,000 |
| SK-MEL-28 | 450,000 |
| COLO853 | 92,000 |
| IGR37 | 24,000 |
| A375 | 16,000 |
| HPAF-II | 34,000 |
| C0L0818 | 21,0000 |
| H3677 | 40,000 |
| IGR39 | 6,200 |
| MALME3M | 149,754 |
| SH4 | 106,000 |
| SK-MEL-2 | 264,197 |
| SK-MEL-24 | 151,000 |
| SK-MEL-3 | 26,000 |
| WM115 | 1,000 |
| WM266.4 | 46,700 |
| JL-1 | 185,708 |
| NCI-H2452 | 908,219 |
| NCI-H2052 | 334,559 |
| MSTO211h | 9,416 |
| SW1463 | 18,683 |
| SW1116 | 59,064 |
| SW48 | 16,776 |
| SW480 | 11,197 |
| SK-CO-1 | 104,398 |
| T84 | 28,486 |
| Colo205 | 4,084 |
| HCT15 | 3,701 |
| HCT116 | 40,466 |
| LoVo | 7,441 |
| LS174T | 667 |
| Cal851 | 175,893 |
| HCC70 | 91,994 |
| HCC1937 | 16,467 |
| HCC1143 | 115,430 |
| MDA-MB-231 | 174,640 |
| BT-474 | 968 |
| SK-BR-3 | 1,722 |
| HT1080 | 35,224 |
| Capan1 | 19,250 |
| A549 | 18,799 |
| CorL23 | 47,446 |
| Calu-1 | 59,000 |
| Sk-Mes-1 | 18,000 |
| NCIH226 | 843,430 |
| NCIH441 | 79,460 |
| CORL105 | 236,804 |
| 92-1 | 7,879 |
| Mel202 | 12,527 |
| MP46 | 14,733 |
| MP41 | 23,074 |
| MP65 | 51,397 |
| MM28 | 108,400 |

Example 2

Immunohistochemical Analysis of CD228 Expression

Tumor tissue arrays were obtained from commercial sources. Tumor formalin fixed and paraffin embedded (FFPE) tissues were purchased from US Biomax Inc. All samples were processed on Bond-Max™ autostainer (Leica).

FFPE slides sectioned on glass slides were de-paraffinized using Bond™ Dewax solution (Leica, cat #AR9222) at 72° C. and rehydrated. Antigen retrieval was performed using EDTA based Bond™ Epitope Retrieval Solution 2 (Leica, cat #AR9640) for 20 min at 95-100° C. before incubation with the primary anti-CD228 antibody (Sigma; cat #HPA004880). Isotype-matched rabbit IgG1 was used as negative control for background staining. For automated MC staining we used either a Refine DAB kit or an alkaline phosphatase based detection kit: Bond™ Polymer AP Red Detection kit (Leica, cat #DS9305). Slides were incubated with rabbit monoclonal primary antibodies against rabbit CD228 mAb for 45 min at 1 µg/ml with a preliminary 30 min protein block (DAKO cat #X0909). After chromogen development, sections were counterstained with hematoxylin and coverslipped. Slides were evaluated and scored by a pathologist and images were taken using a Zeiss Axiovert 200M microscope (Carl Zeiss, Inc., Thornwood, N.Y.).

FIG. 1 shows a high level of CD228 expression in melanoma cancer patient samples providing a strong rationale to treat these tumors using a CD228 ADC.

Figure 2:
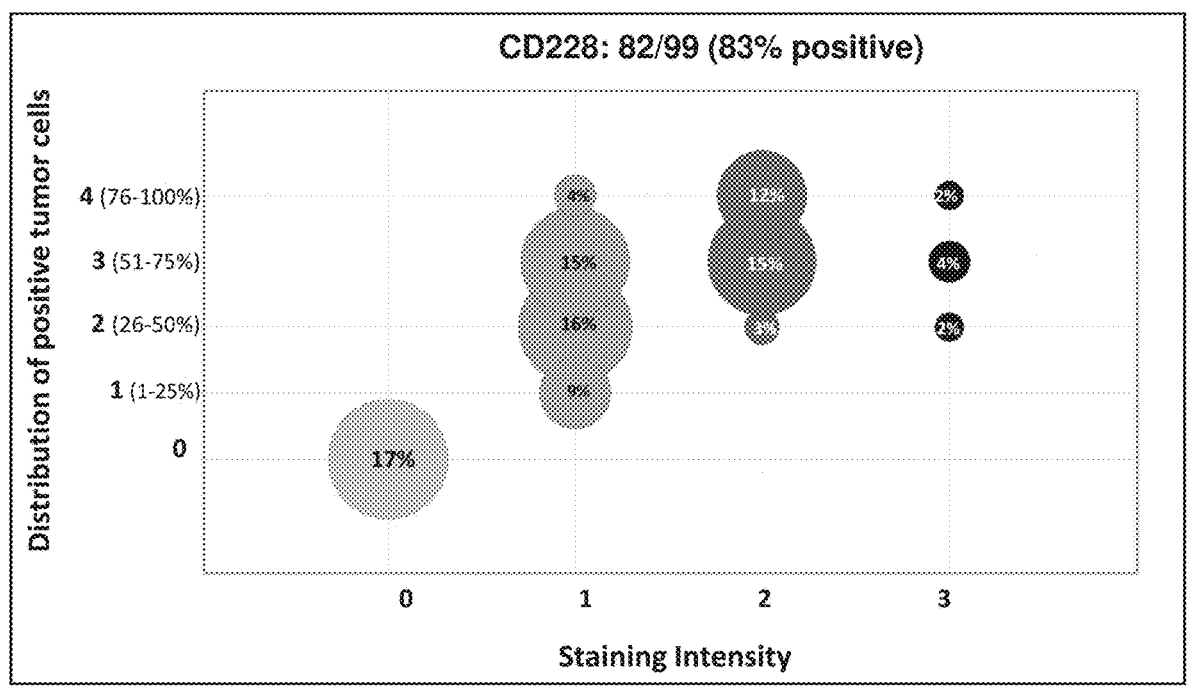
FIG. 2 shows an analysis of CD228 protein expression by IHC on mesothelioma cancer patient samples.

FIG. 2 shows a high level of CD228 expression in mesothelioma cancer patient samples providing a strong rationale to treat these tumors using a CD228 ADC.

Figure 3:
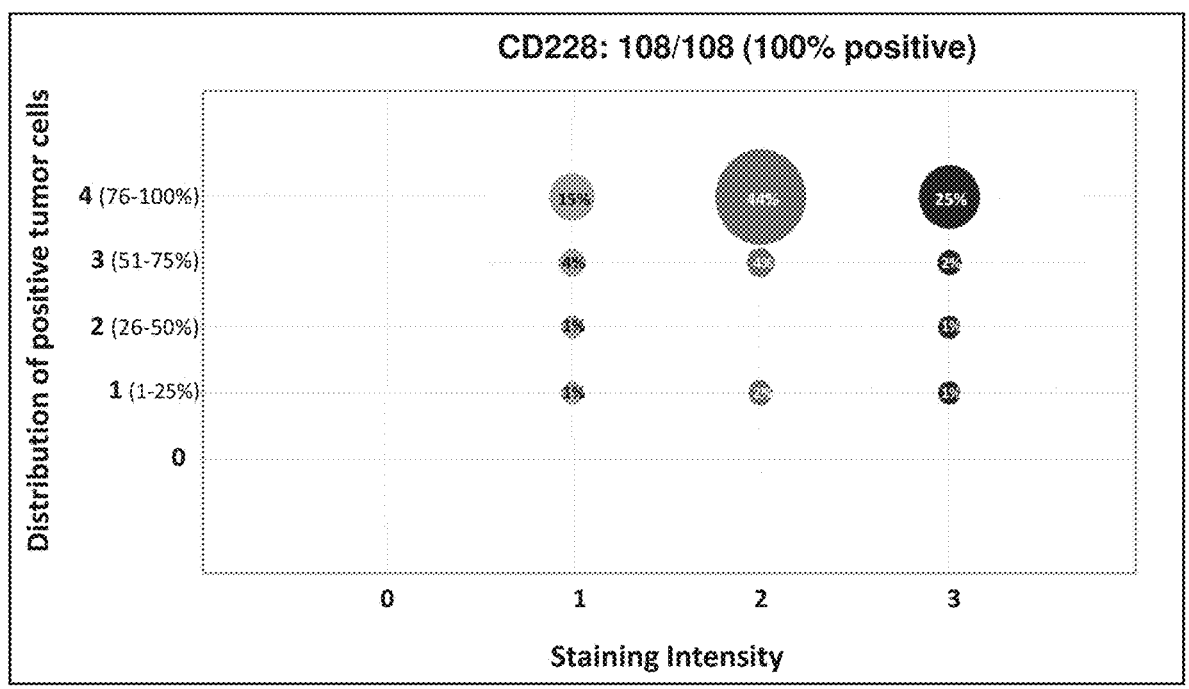
FIG. 3 shows an analysis of CD228 protein expression by IHC on colorectal cancer patient samples.

FIG. 3 shows a high level of CD228 expression in colorectal cancer patient samples providing a strong rationale to treat these tumors using a CD228 ADC.

Figure 4:
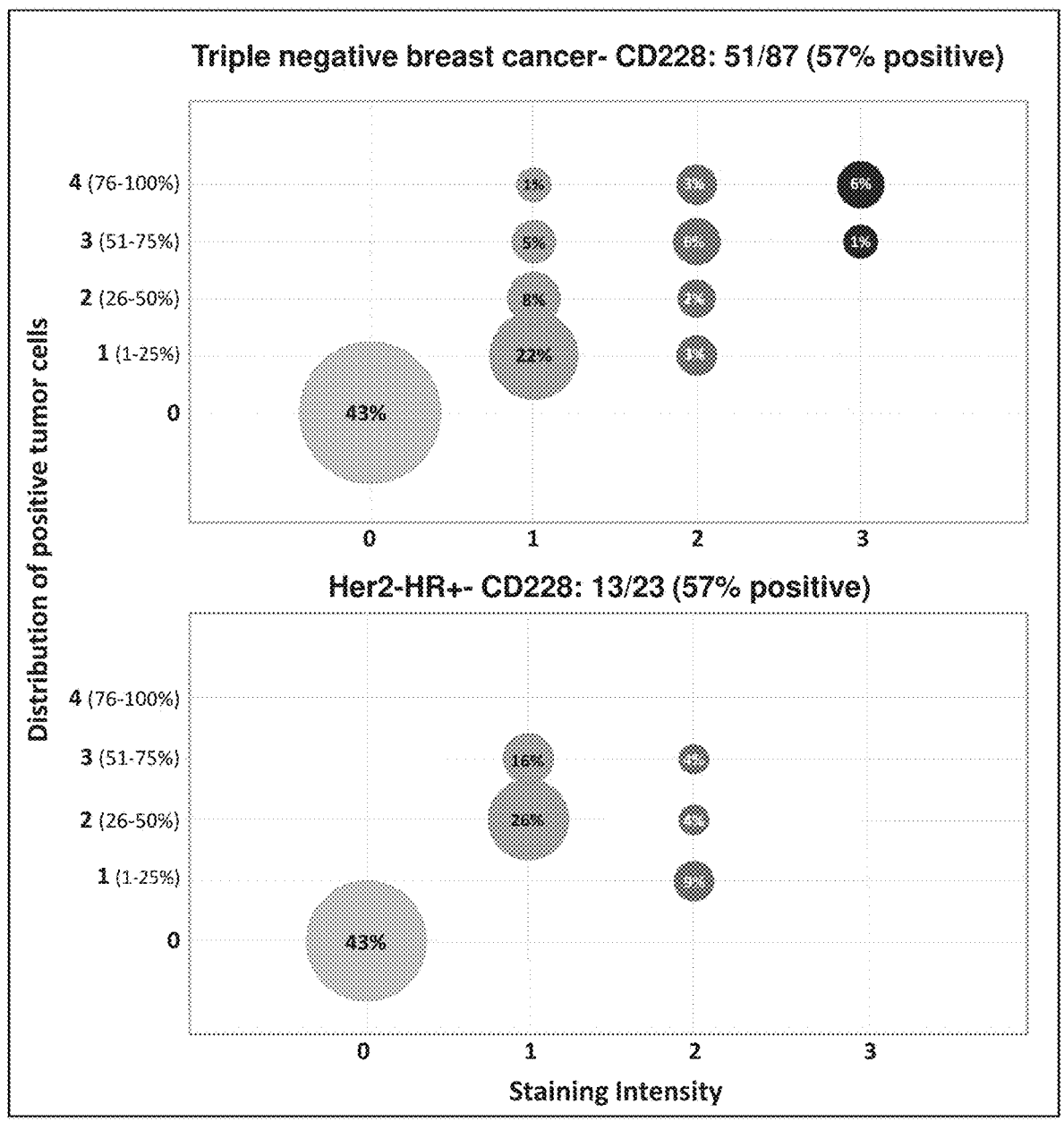
FIG. 4 shows an analysis of CD228 protein expression by IHC on breast cancer patient samples. Upper panel shows an analysis of CD228 protein expression by IHC on triple negative breast cancer patient samples. Lower panel an analysis of CD228 protein expression by IHC on Her2−HR+ breast cancer patient samples.

FIG. 4 shows a high level of CD228 expression in triple negative (HR−, PgR−, Her2−) breast cancer patient samples (upper panel) and Her2−HR+ breast cancer patient samples (lower panel) providing a strong rationale to treat these tumors using a CD228 ADC.

Figure 5:
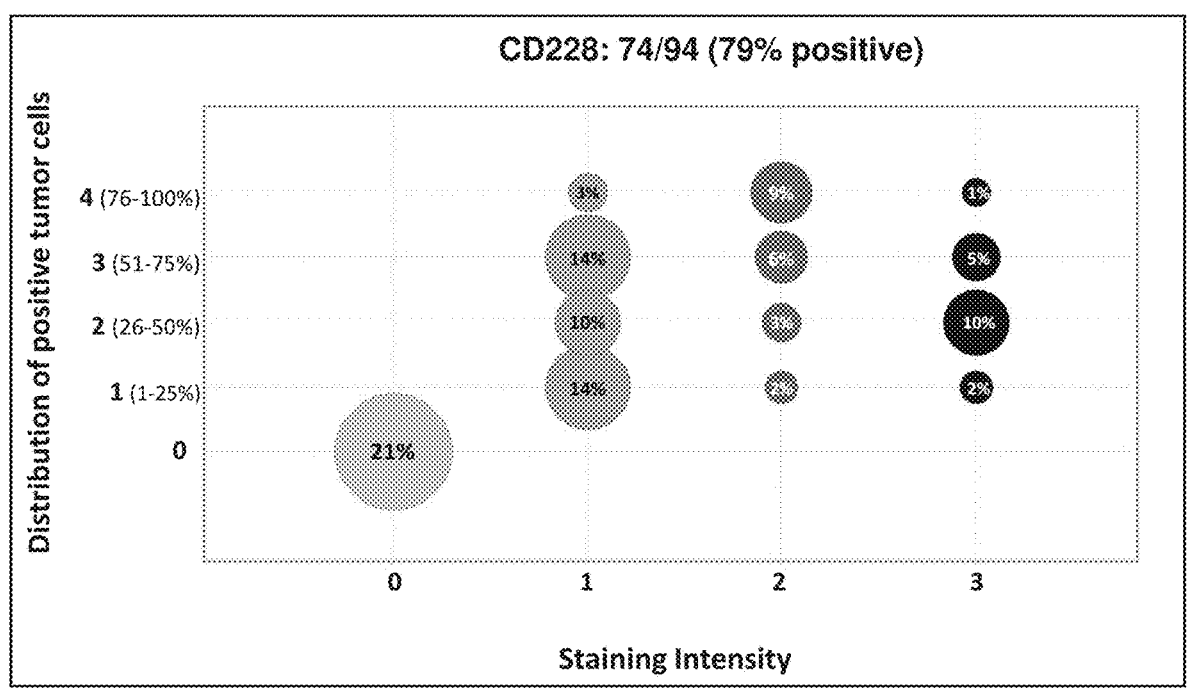
FIG. 5 shows an analysis of CD228 protein expression by IHC on pancreatic cancer patient samples.

FIG. 5 shows a high level of CD228 expression in pancreatic cancer patient samples providing a strong rationale to treat these tumors using a CD228 ADC.

Figure 6:
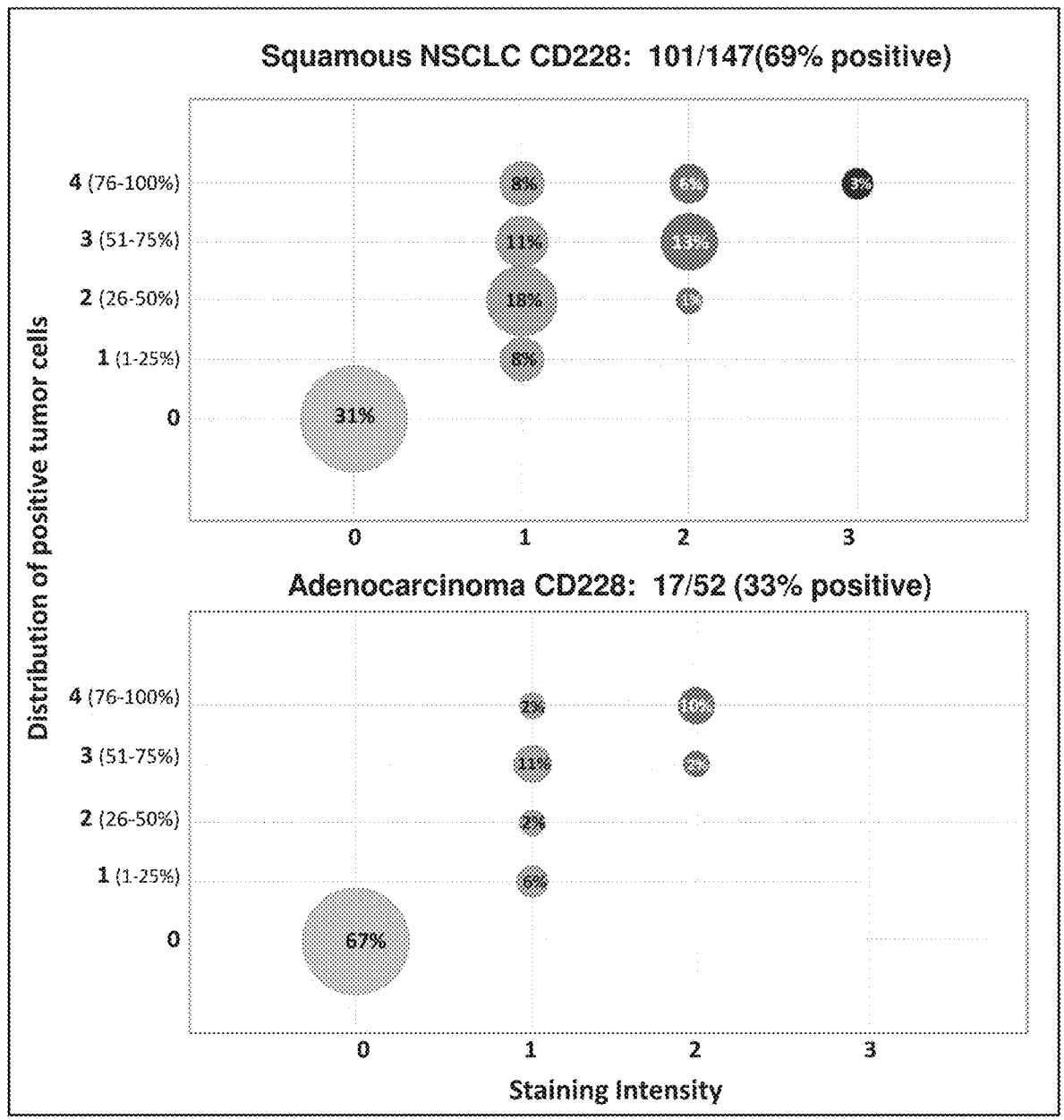
FIG. 6 shows an analysis of CD228 protein expression by IHC on non-small cell lung cancer patient samples. Upper panel shows an analysis of CD228 protein expression by IHC on squamous NSCLC cancer patient samples. Lower panel shows an analysis of CD228 protein expression by IHC on adenocarcinoma NSCLC cancer patient samples.

FIG. 6 shows a high level of CD228 expression in squamous non-small lung cancer patient samples (upper panel) and adenocarcinoma non-small cell lung cancer patient samples (lower panel) providing a strong rationale to treat these tumors using a CD228 ADC.

Figure 7:
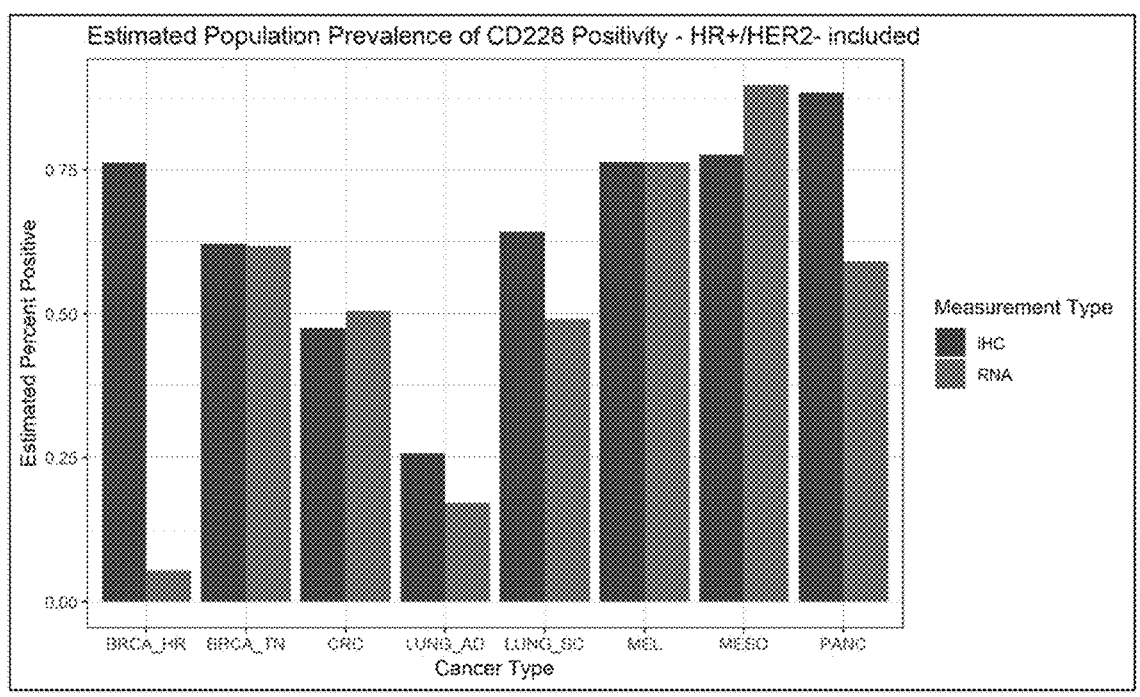
FIG. 7 shows a comparison of the percent of patient samples that are positive for CD228 expression as determined by IHC and by RNA levels as reported by The Cancer Genome Atlas for various tumor types.
Figure 12A:
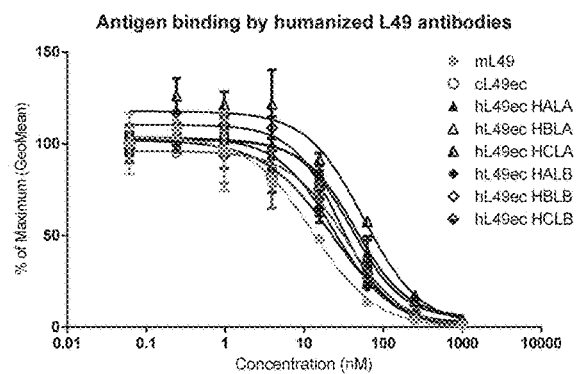
FIG. 12A-12F shows the results of competition binding studies of recombinant humanized anti-CD228 antibodies, the parental murine antibody (referred to as mL49), and a chimeric antibody (cL49ec).
Figure 12B:
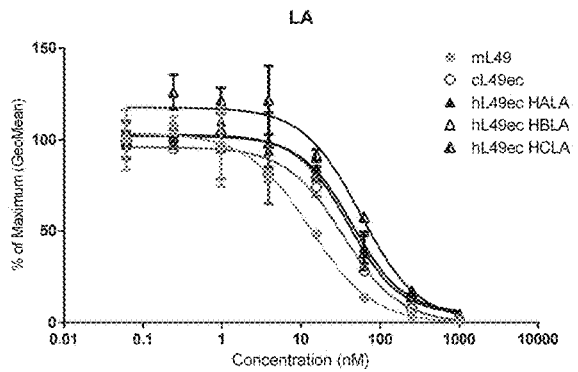
Figure 12C:
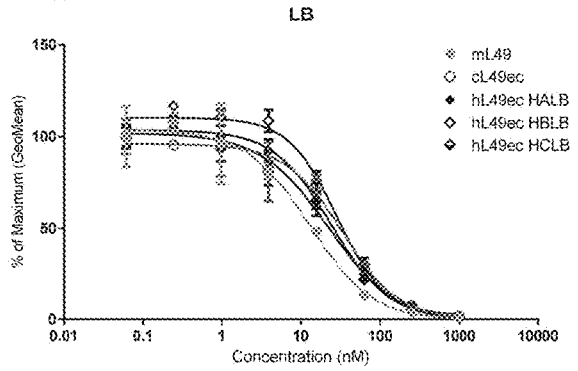
Figure 12D:
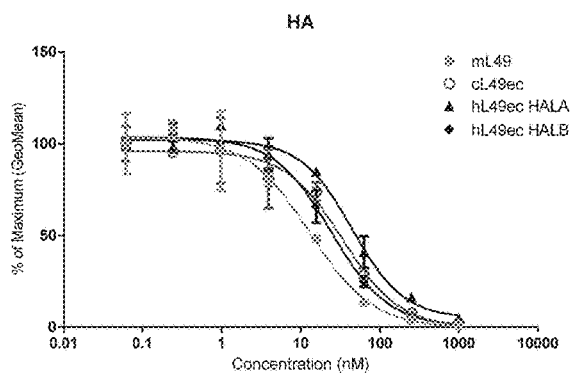
Figure 12E:
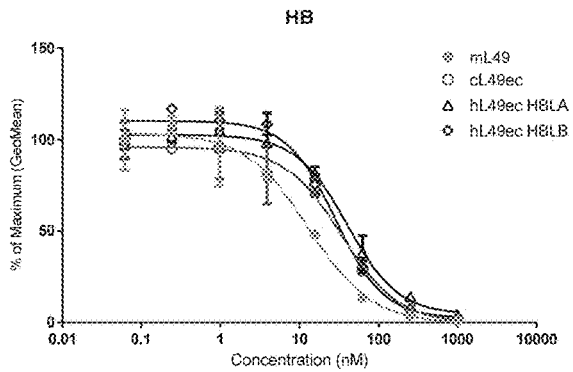
Figure 12F:
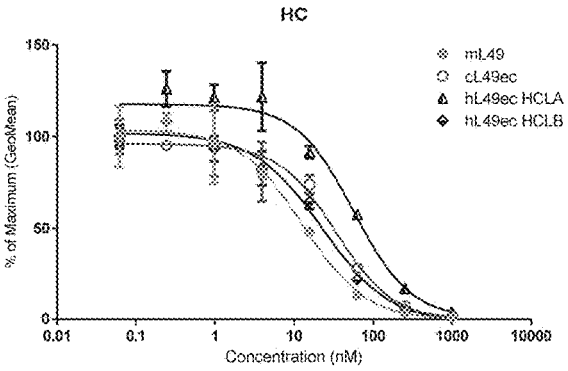

A summary of the immunohistochemical experiments was compared to CD228 RNA levels as reported by The Cancer Genome Atlas for various tumor types. We determined a threshold of CD228 RNA positivity by applying the IHC prevalence of melanoma to TCGA. As can be seen in FIG. 7, most tumor types have a close correlation between RNA expression and immunohistochemistry, with the exception being HER2−/HR+ breast cancer. TNBC=triple negative breast cancer. NSCLC=non-small cell lung cancer. Adeno=adenocarcinoma. Squamous=squamous cell carcinoma. TCGA=The Cancer Genome Atlas.

Example 3

Anti-CD228 Antibody Drug Conjugates

Various anti-CD228 antibodies were conjugated to the drug MMAE via the linker MDpr-PEG(12)-gluc, such that the average drug load per antibody is about 8. The conjugation method is described in U.S. Publ. No. 2018/0092984. Tumor cells were incubated with CD228 antibody drug conjugates (ADCs) for 96-144 hours at 37° C. A human IgG ADC was used as a negative control. Cell viability was measured using Cell Titer Glo according to manufacturer's instructions. Fluorescent signal was measured on a Fusion HT fluorescent plate reader (Perkin Elmer, Waltham, Mass.). The data was normalized to untreated cells, and x50 values were calculated using Graph Pad software. Results are reported in Table 2 as $IC_{50}$, the concentration of compound needed to yield a 50% reduction in viability compared to vehicle-treated cells (control=100%). Chimeric L49 (cL49) and mouse (mL49) ADCs were superior to all other anti-CD228 ADCs, particularly in cell lines with lower CD228 expression.

TABLE 2

IC$_{50}$ of anti-CD228 antibody-drug conjugates against various cancer cells

| | | | Melanoma Cell Lines (# of CD228 molecules per cell) | | | | |
|---|---|---|---|---|---|---|---|
| Antibody | Drug Linker | Drug Load | A2058 (51,000) | RPMI-7951 (0) | RPMI-7951 +p97 (400,000) | SK-MEL-5 (134,000) | SK-MEL-28 (450,000) |
| mL49 | MDpr-PEG (12)-gluc-MMAE | 8 | 12 | >1000 | 3 | 5 | 3 |
| cL49 | MDpr-PEG (12)-gluc-MMAE | 8 | 5 | >1000 | 2 | 2 | 2 |
| mL235 | MDpr-PEG (12)-gluc-MMAE | 8 | 780 | >1000 | 17 | 305 | 114 |
| Santa Cruz (#271633) | MDpr-PEG (12)-gluc-MMAE | 8 | >1000 | >1000 | >1000 | >1000 | >1000 |
| R&D (#893416) | MDpr-PEG (12)-gluc-MMAE | 8 | 444 | >1000 | 4 | 55 | 6 |
| Biolegend (#363101) | MDpr-PEG (12)-gluc-MMAE | 8 | 718 | >1000 | 2 | 100 | 7 |
| hIgG | MDpr-PEG (12)-gluc-MMAE | 8 | >1000 | >1000 | >1000 | >1000 | >1000 |

Example 4

Humanization of Mouse L49 Antibody

The mouse antibody mL49 (Siemers et al., 1997, Bioconjug. Chem. 8:510-9) was used as the starting point or donor antibody for humanization. Suitable human acceptor sequences were genomic sequences provided by hIGHV4-59 and hIGHJ4 for the heavy chain and by hIGKV2-30 and hIGKJ2 for the light chain. The human acceptor sequences show 70 (heavy-chain) and 84 (light-chain) percentage identity to the donor sequences in the variable region frameworks, when the CDRs are defined according to the Kabat numbering scheme.

Alignment of the donor sequences identified 26 positions in the heavy chain and 13 positions in the light chain at which the human acceptor framework sequence differed from the donor framework sequence and that may affect antibody binding as a result of contacting antigen directly, affecting conformation of CDRs or affecting packing between heavy and light chains, when the CDRs are defined according to the Kabat numbering scheme. Three humanized heavy chains (HA, HB, and HC) and three humanized light chains (LA, LB, and LC) were made incorporating back mutations at different permutations of particular positions. See FIGS. 8-11 and Tables 3-6.

TABLE 3

Humanizing Mutations in hL49 Heavy Chain Variants

| vH Variant | HV Exon Acceptor Sequence | Murine Donor Framework Residues | Human Acceptor CDR Residues |
|---|---|---|---|
| hvHA | IGHV4-59/HJ4 | H27, H30, H47, H71, H78 | none |
| hvHB | IGHV4-59/HJ4 | H27, H30, H40, H47, H48, H67, H71, H78 | none |
| hvHC | IGHV4-59/HJ4 | H27, H30, H40, H47, H48, H67, H71, H78, H82B, H91 | none |

TABLE 4

Specific Murine Framework Mutations in hL49 Heavy Chain Variants

| Variant | 27 | 30 | 40 | 47 | 48 | 67 | 71 | 78 | 82B | 91 | % Human |
|---|---|---|---|---|---|---|---|---|---|---|---|
| hvHA | D | T | | Y | | | R | Y | | | 88.8 |
| hvHB | D | T | F | Y | M | I | R | Y | | | 85.7 |
| hvHC | D | T | F | Y | M | I | R | Y | F | N | 83.7 |

TABLE 5

Humanizing Mutations in hL49 Kappa Light Chain Variants

| vK Variant | KV Exon Acceptor Sequence | Murine Donor Framework Residues | Human Acceptor CDR Residues |
|---|---|---|---|
| hvLA | IGKV2-30/KJ2 | L2 | none |
| hvLB | IGKV2-30/KJ2 | L2, L36, L46 | none |
| hvLC | IGKV2-30/KJ2 | L2, L36, L46 | L28 |

TABLE 6

Specific Murine Framework Mutations in hL49 Kappa Light Chain Variants

| Variant | 2 | 36 | 46 | % Human |
|---|---|---|---|---|
| hvLA | F | | | 91.0 |
| hvLB | F | Y | L | 89.0 |
| hvLC | F | Y | L | 90.0 |

Humanized antibodies were then expressed representing every permutation of these chains (9 possibilities) of the humanized heavy and light chains. The antibodies were then compared using peptide map analysis of labile chemical modifications found in the L2 peptide for hL49 HALB (Asn (N)—potential for asparagine deamidation) and hL49 HALC (Asp (D)—potential for aspartate isomerization) after incubation of 1 week at temperatures and pH conditions as shown in Table 7. hL49 HALC (N28D) eliminates the deamidation observed in hL49 HALB as well as has limited isomerization. Overall L2 peptide modifications drops from 13% to 2%.

TABLE 7

Peptide map analysis of humanized anti-CD228 antibodies

| hL49 ec | Temp (° C.) | pH | % Unmodified L2 peptide | % Asn 33 deamidated | % Asp 33 isomerized | % Asn/Asp 33 succinimide | % Asn/Asp 33 clip | % Total modified L2 peptide |
|---|---|---|---|---|---|---|---|---|
| HALB | 4 | 7.4 | 88.9 | 6.7 | NA | 3.5 | 1.0 | 11.1 |
| | 37 | 7.4 | 87.2 | 8.3 | NA | 3.5 | 0.9 | 12.8 |
| | 37 | 6.5 | 86.7 | 9.1 | NA | 3.6 | 0.6 | 13.3 |
| | 37 | 4.4 | 87.1 | 8.7 | NA | 3.5 | 0.6 | 12.9 |
| HALC | 4 | 7.4 | 98.0 | NA | 0.2 | 1.5 | 0.1 | 2.0 |
| | 37 | 7.4 | 98.1 | NA | 0.2 | 1.5 | 0.0 | 1.9 |
| | 37 | 6.5 | 98.0 | NA | 0.3 | 1.7 | 0.1 | 2.0 |
| | 37 | 4.4 | 97.9 | NA | 0.3 | 1.8 | 0.1 | 2.1 |

Binding curves for each resulting antibody was determined by a competition binding assay. Briefly, 1×10⁵ RPMI-7951 cells stably expressing human CD228 were aliquoted per well of a 96-well v-bottom plates on ice. The cells were incubated for 1 hour with 5 nM AlexaFluor-647 (AF) labeled parental murine CD228 mAb and increasing concentrations (from 0.06 nM to 1000 nM) of unlabeled humanized CD228 mAb, with various combinations of humanized light chains LA-LB and humanized heavy chains HA-HC. Cells were pelleted and washed 3 times with PBS/BSA. The cells were pelleted and resuspended in 12.5 μL of PBS/BSA. Fluorescence was analyzed by flow cytometry, using percent of saturated fluorescent signal to determine percent labeled murine CD228 mAb bound. The binding curves for recombinant human anti-CD228 antibodies are shown in FIG. 12A-12F.

Figure 13:
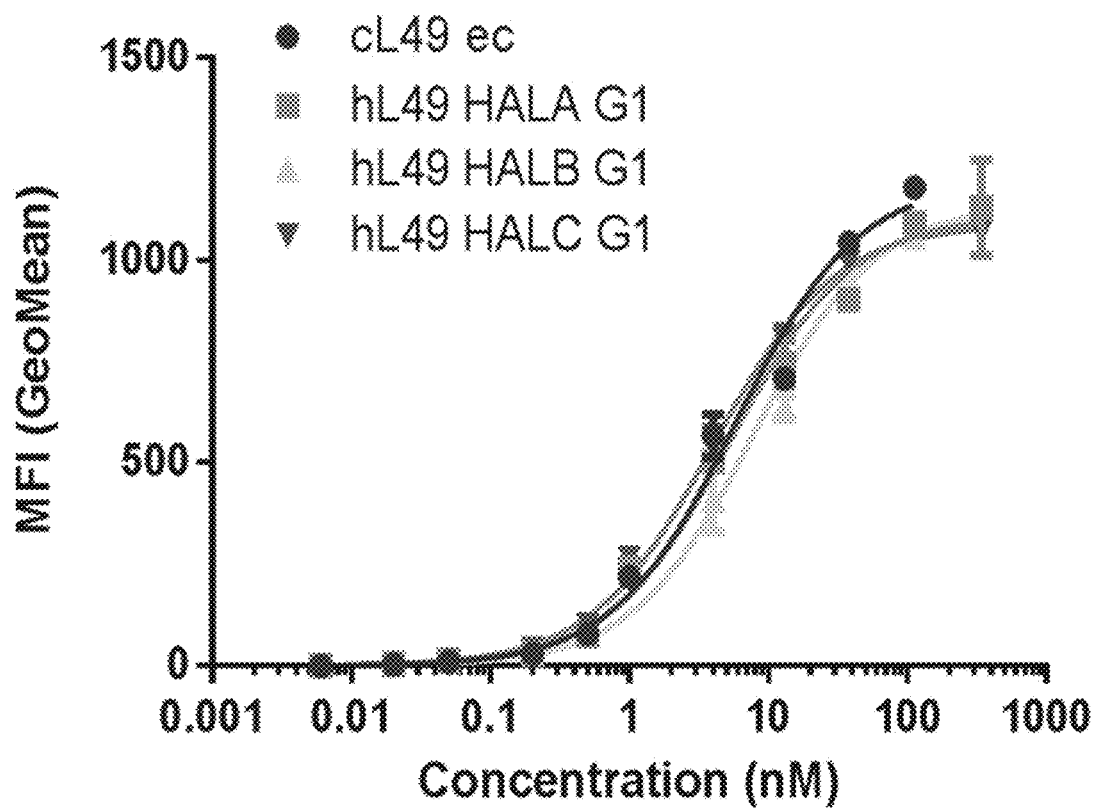
FIG. 13 shows results of saturation binding studies for recombinant humanized anti-CD228 antibodies.

The $K_D$ for each resulting antibody was then determined by a saturation binding assay. Briefly, 1×10⁵ RPMI-7951 cells stably expressing human CD228 were aliquoted per well of a 96-well v-bottom plates. Each CD228 antibody was added in concentrations ranging from 0.05 pM to 340 nM and incubated on ice for 60 minutes. Cells were pelleted and washed 3× with PBS/BSA followed by addition of 10 ug/ml of a PE labeled anti-human IgG goat secondary antibody and incubated on ice for an additional 60 minutes. Cells were pelleted and washed 3× with PBS/BSA and resuspended in 125 μL of PBS/BSA. Fluorescence was analyzed by flow cytometry, using percent of saturated fluorescent signal to determine percent bound and to subsequently calculate apparent $K_D$. The binding curves for recombinant human anti-CD228 antibodies are shown in FIG. 13 and the $K_D$ for cL49ec (chimeric L49 with an S239C mutation in the light chain constant region), hL49 HALA G1, hL49 HALB G1, and hL49 HALC G1 are shown in Table 8. The antibody called "HALC," "hL49," or "hL49-HALC" which comprises heavy chain "HA" and the light chain "LC" was selected for use in all other experiments.

TABLE 8

KD of humanized anti-CD228 antibodies

| | cL49ec | hL49 HALA G1 | hL49 HALB G1 | hL49 HALC G1 |
|---|---|---|---|---|
| $K_D$ (nM) | 5.8 | 5.3 | 7.8 | 4.0 |

Example 5 hL49-HALC Antibody Drug Conjugates with Various Drug Linkers

A. Antibody Drug Conjugation hL49-HALC was conjugated to 8-loads of either MDpr-PEG(12)-gluc-MMAE, Auristatin T, Tubulysin M, or Lipophilic MMAF, 2-loads of either MC-VC-MMAE or MDpr-gluc-MMAE, or 2-loads of PBD. The conjugation method is described in U.S. Publ. No. 2018/0092984. All commercially available anhydrous solvents were used without further purification. PEG reagents were obtained from Quanta BioDesign (Powell, Ohio). Analytical thin layer chromatography was performed on silica gel 60 F254 aluminum sheets (EMD Chemicals, Gibbstown, N.J.). Radial chromatography was performed on Chromatotron apparatus (Harris Research, Palo Alto, Calif.). Column chromatography was performed on a Biotage Isolera One flash purification system (Charlotte, N.C.). Analytical HPLC was performed on a Varian ProStar 210 solvent delivery system configured with a Varian ProStar 330 PDA detector. Samples were eluted over a C12 Phenomenex Synergi 2.0×150 mm, 4 μm, 80 Å reverse-phase column. The acidic mobile phase consisted of acetonitrile and water both containing either 0.05% trifluoroacetic acid or 0.1% formic acid (denoted for each compound). Compounds were eluted with a linear gradient of acidic acetonitrile from 5% at 1 min post injection, to 95% at 11 min, followed by isocratic 95% acetonitrile to 15 min (flow rate=1.0 mL/min). LC-MS was performed on two different systems. LC-MS system 1 consisted of a ZMD Micromass mass spectrometer interfaced to an HP Agilent 1100 HPLC instrument equipped with a C12 Phenomenex Synergi 2.0×150 mm, 4 μm, 80 Å reverse phase column. The acidic eluent consisted of a linear gradient of acetonitrile from 5% to 95% in 0.1% aqueous formic acid over 10 min, followed by isocratic 95% acetonitrile for 5 min (flow rate=0.4 mL/min). LC-MS system 2 consisted of a Waters Xevo G2 Tof mass spectrometer interfaced to a Waters 2695 Separations Module with a Waters 2996 Photodiode Array Detector; the column, mobile phases, gradient, and flow rate were same as for LC-MS system 1. UPLC-MS was carried out on a Waters SQ mass detector interfaced to an Acquity Ultra Performance LC equipped with an Acquity UPLC BEH C18 2.1×50 mm, 1.7 μm reverse phase column. The acidic mobile phase (0.1% formic acid) consisted of a gradient of 3% acetonitrile/97% water to 100% acetonitrile (flow rate=0.5 mL/min). Preparative HPLC was carried out on a Varian ProStar 210 solvent delivery system configured with a Varian ProStar 330 PDA detector. Products were purified over a C12 Phenomenex Synergi 10.0×250 mm, 4 μm, 80 Å reverse phase column eluting with 0.1% formic acid in water (solvent A) and 0.1% formic acid in acetonitrile (solvent B). The purification method consisted of the following gradient of solvent A to solvent B: 90:10 from 0 to 5 min; 90:10 to 10:90 from 5 min to 80 min; followed by isocratic 10:90 for 5 min. The flow rate was 4.6 mL/min with monitoring at 254 nm. Preparative HPLC for compounds in Schemes 3 and 4 was carried out with 0.1% trifluoroacetic acid in both mobile phases, instead of 0.1% formic acid.

Scheme 1.

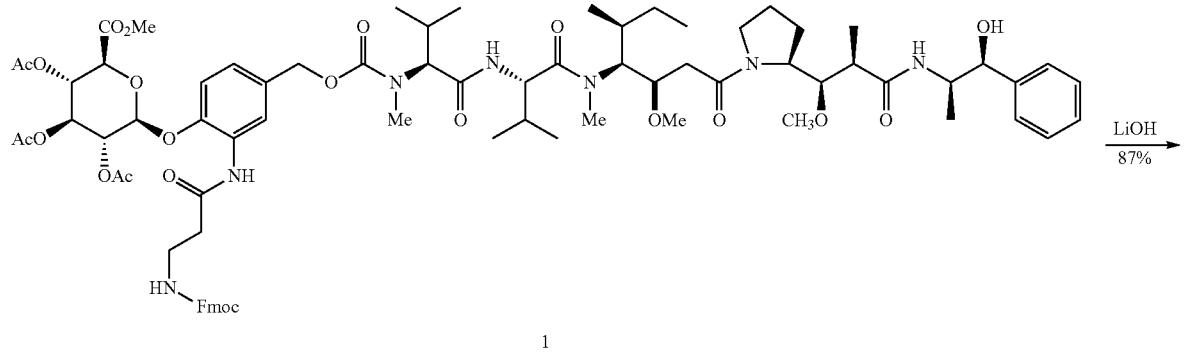

1

(compound 8a in US 2008/0241 128 A1)

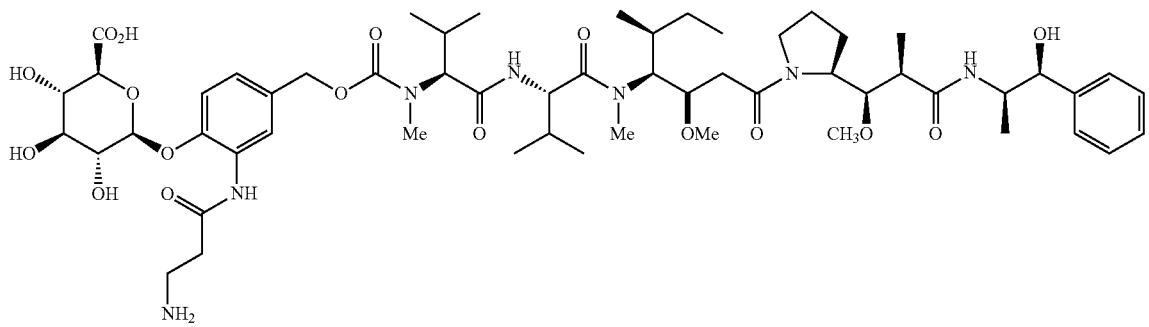

2 le;2q(2S,3S,4S,5R,6S)-6-(2-(3-aminopropanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (2): To a flask containing the known (compound 8a in US 2008/0241128 A1) glucuronide-MMAE intermediate 2 (40 mg, 26.8 μmol) was added 0.9 mL methanol and 0.9 mL tetrahydrofuran. The solution was then cooled in an ice bath and lithium hydroxide monohydrate (6.8 mg, 161 μmol) was added drop wise in as a solution in 0.9 mL water. The reaction was then stirred on ice for 1.5 h, at which time LC/MS revealed complete conversion to product. Glacial acetic acid (9.2 μL, 161 μmol) was then added and the reaction was concentrated to dryness. Preparative HPLC afforded the fully deprotected glucuronide-MMAE linker intermediate 3 (26 mg, 87%) as an oily residue. Analytical HPLC (0.1% formic acid): $t_R$ 9.3 min. LC-MS system 1: $t_R$ 11.10 min, m/z (ES$^+$) found 1130.48 (M+H)$^+$, m/z (ES$^-$) found 1128.63 (M−H)$^-$.

(S)-44-((((9H-fluoren-9-yl)methoxy)carbonyl)amino)-38-oxo-2,5,8,11,14,17,20,23,26,29,32,35-dodecaoaxa-39-azapentatetracontan-45-oic acid (4): To a flask containing $N_\alpha$-Fmoc-lysine 3 (59 mg, 161 μmol) was added 2.9 mL anhydrous dichloromethane, followed by methoxy-PEG12-OSu (100 mg, 146 μmol). DIPEA (127 μL, 730 μmol) was then added and the reaction was stirred under nitrogen at room temperature and followed by TLC and LC/MS. After 2 h, LC/MS revealed conversion to product. The reaction solution was diluted in dichloromethane and purified by silica gel chromatography. The stationary phase was eluted with dichloromethane with increasing amounts of methanol (0% to 20%) to provide the desired product 4 (153 mg, 112%). UPLC-MS: $t_R$ 1.77 min, m/z (ES$^+$) found 939.58 (M+H)$^+$.

(S)-2,5-dioxopyrrolidin-1-yl 44-((((9H-fluoren-9-yl)methoxy)carbonyl)amino)-38-oxo-2,5,8,11,14,17,20,23,26,29,32,35-dodecaoaxa-39-azapentatetracontan-45-oate (5): A flask was charged with $N_\alpha$-Fmoc-lysine(PEG12)-OH 4 (153 mg, 163 μmol) and 1.6 mL anhydrous tetrahydrofuran. N-hydroxysuccinimide (28 mg, 245 μmol) was added, followed by diisopropylcarbodiimide (38 μL, 245 μmol).

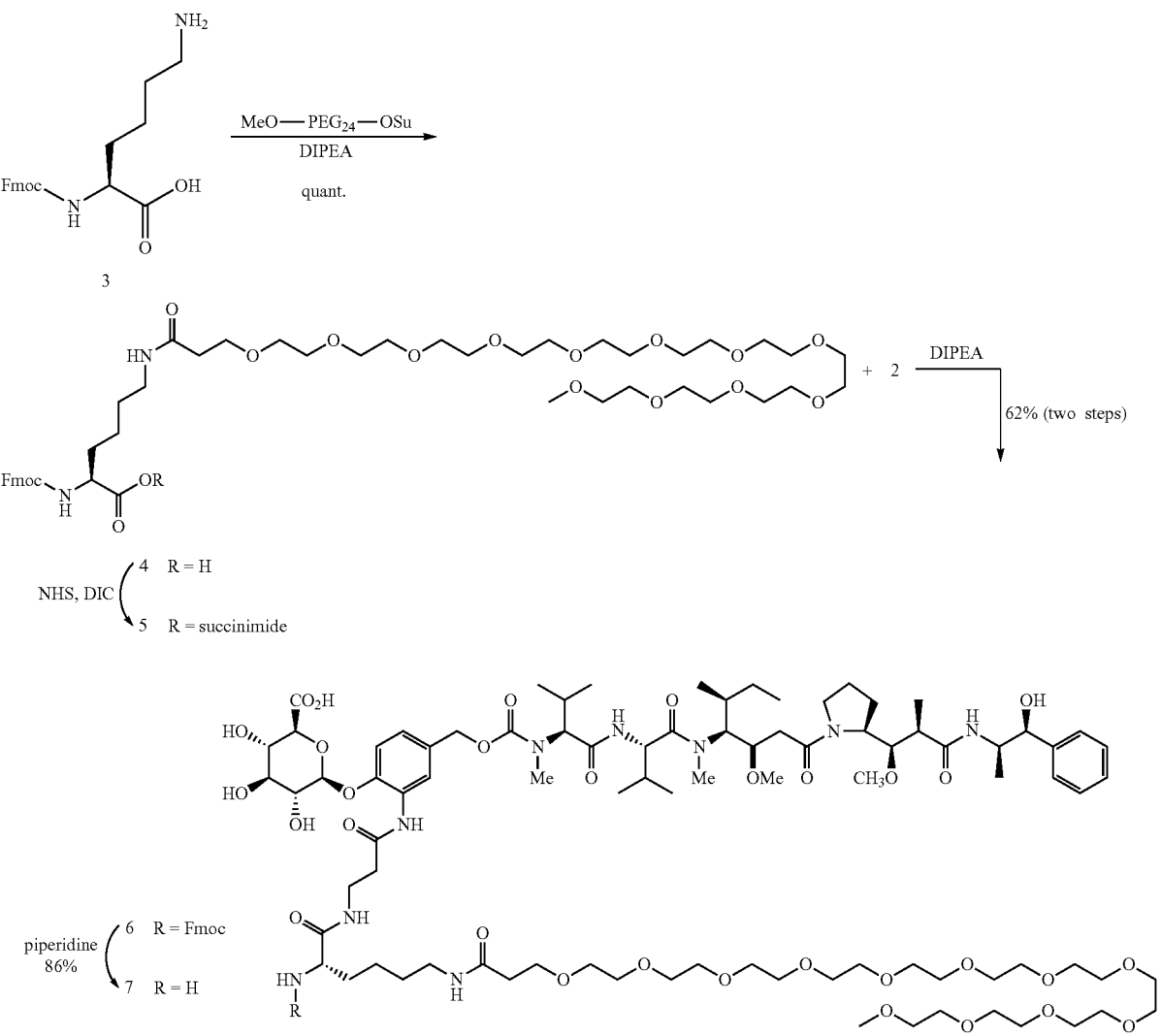

Scheme 2.

The reaction was sealed under nitrogen and stirred overnight. The crude reaction was diluted in dichloromethane and pure over silica gel eluted with dichloromethane with increasing amounts of methanol (0% to 10%) to provide the desired activated ester 5 (155 mg). The material was carried forward without further characterization. UPLC-MS: $t_R$ 1.92 min, m/z (ES$^+$) found 1036.48 (M+H)$^+$.

(2S,3S,4S,5R,6S)-6-(2-((S)-44-((((9H-fluoren-9-yl)methoxy)carbonyl)amino)-38,45-dioxo-2,5,8,11,14,17,20,23,26,29,32,35-dodecaoxa-39,46-diazanonatetracontanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (6): Deprotected glucuronide-MMAE linker intermediate 2 (92 mg, 81 µmol) was dissolved in anhydrous dimethylformamide (1.6 mL) and added to a flask containing Nα-Fmoc-lysine(PEG12)-OSu 5 (101 mg, 97 µmol). Diisopropylethylamine (70 µL, 405 µmol) was then added, the reaction was then stirred under nitrogen at room temperature. After 4.5 h, LC-MS revealed conversion to product. The product was purified by preparative HPLC to provide Fmoc-Lys(PEG12)-glucuronide-MMAE intermediate 6 (111 mg, 62% over two steps) as an oily residue. UPLC-MS: $t_R$ 2.01 min, m/z (ES$^+$) found 2050.92 (M+H)$^+$.

(2S,3S,4S,5R,6S)-6-(2-((S)-44-amino-38,45-dioxo-2,5,8,11,14,17,20,23,26,29,32,35-dodecaoxa-39,46-diazanonatetracontanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (7): Fmoc-Lys(PEG12)-glucuronide-MMAE intermediate 6 (111 mg, 54 µmol) was dissolved in 2.2 mL anhydrous dimethylformamide, followed by addition of 0.5 mL of piperidine. The reaction was stirred under nitrogen for 3 hours and then concentrated to dryness. The product was purified by preparative HPLC to provide H-Lys(PEG12)-glucuronide-MMAE intermediate 7 (85 mg, 86%) as an oily residue. UPLC-MS: $t_R$ 1.50 min, m/z (ES) found 1829.31 (M+H)$^+$.

(S)-2,5-dioxopyrrolidin-1-yl 3-((tert-butoxycarbonyl)amino)-2-(2,5-dioxo-2,5-dihydro-1H-pyrrol-1-yl)propanoate (9): (S)—N$_α$-maleimido-N$_β$-Boc-diaminopropanoic acid 8 (*Nature Biotechnology,* 2014, 32, 1059-1062) (400 mg, 1.4 mmol) was dissolved in 7 mL anhydrous dimethylformamide, N-hydroxysuccinimide (178 mg, 1.5 mmol) was added, followed by 1-ethyl-3-(3-dimethylaminopropyl) carbodiimide (298 mg, 1.5 mmol). The reaction was stirred at room temperature under nitrogen for 3 hours. Aqueous workup was achieved through dilution into 120 mL water; the aqueous layer was then extracted three times with 60 mL ethyl acetate. The combined organic layer was then washed with brine, dried over sodium sulfate, and concentrated to dryness. The product was purified by flash column chromatography, eluting mixtures of hexanes:ethyl acetate (50:50 to 0:100) to provide (S)—N$_α$-maleimido-N$_β$-Boc-diaminopropanoic acid NHS ester [MDpr(Boc)-OSu] 9 (297 mg, 55%). LC-MS system 1: $t_R$ 12.23 min, m/z (ES$^+$) found 282.0599 (M+H-Boc group)$^+$. LC-MS system 2: $t_R$ 11.30 min, m/z (ES$^+$) found 2580.2515 (M+H)$^+$.

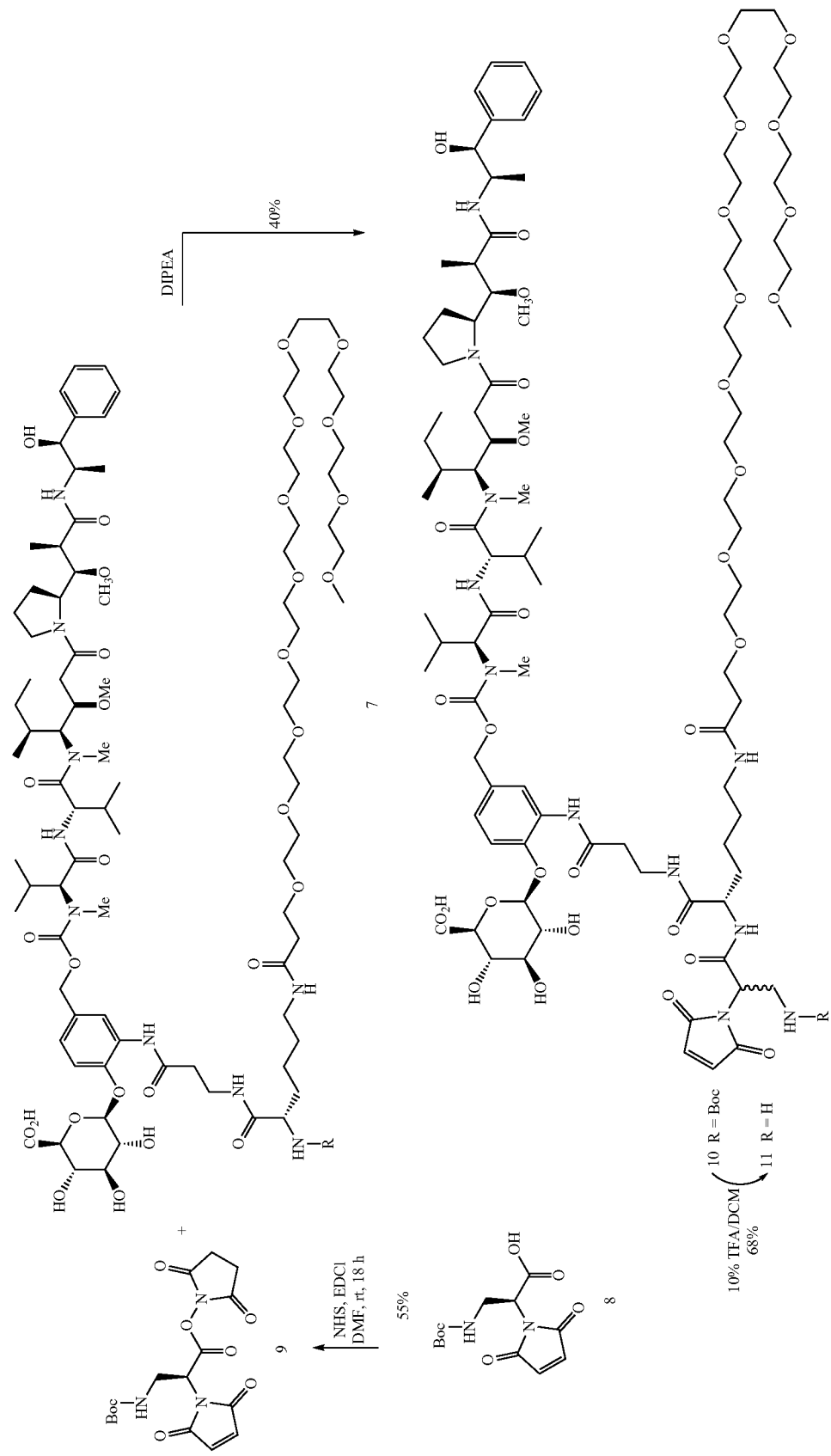

(2R/S,3S,4S,5R,6S)-6-(2-((S)-44-((S)-3-((tert-butoxycarbonyl)amino)-2-(2,5-dioxo-2,5-dihydro-1H-pyrrol-1-yl)propanamido)-38,45-dioxo-2,5,8,11,14,17,20,23,26,29,32,35-dodecaoxa-39,46-diazanonatetracontanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic add (10): MDpr(Boc)-OSu 9 (20 mg, 53 µmol) was dissolved in 2.2. mL of anhydrous dimethylformamide and added to a flask containing H-Lys(PEG12)-glucuronide-MMAE linker intermediate 7 (86 mg, 44 µmol). Diisopropylethylamine (15 µL, 88 µmol) was then added, the reaction was then stirred under nitrogen at room temperature for 2.5 h. The reaction was quenched with 15 µL, glacial acetic acid and purified by preparative HPLC to afford MDpr(Boc)-Lys(PEG12)-glucuronide-MMAE intermediate 10 (37 mg, 40%), as a mixture of diastereomers. The diastereomers were separable by chiral chromatography. UPLC-MS: $t_R$ 1.84 min, m/z (ES$^+$) found 2095.44 (M+H)$^+$.

(2R/S,3S,4S,5R,6S)-6-(2-((S)-44-((R)-3-amino-2-(2,5-dioxo-2,5-dihydro-1H-pyrrol-1-yl)propanamido)-38,45-dioxo-2,5,8,11,14,17,20,23,26,29,32,35-dodecaoxa-39,46-diazanonatetracontanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic add (11): A flask containing MDpr(Boc)-Lys(PEG12)-glucuronide-MMAE intermediate 10 (34 mg, 16 µmol) was cooled to 0° C. in an ice bath under nitrogen. A solution of 10% trifluoroacetic acid in dichloromethane (0.8 mL) was added dropwise. The reaction was then stirred at 0° C. for 2 h, at which time LC-MS revealed complete Boc deprotection. The reaction was concentrated to a crude residue and purified by preparative HPLC to provide MDpr-Lys(PEG12)-glucuronide-MMAE linker 11 (22 mg, 68%). UPLC-MS: $t_R$ 1.50 min, m/z (ES$^+$) found 1995.18 (M+H)$^+$.

Compound 11 was conjugated via its interchain thiols to the anti-CD228 antibody at an average drug loading of 8 drugs per antibody using methods known in the art (see, for example, U.S. Pat. No. 7,659,241).

B. Cytotoxicity of hL49-HALC ADCs In Vitro

Tumor cells were incubated with each antibody drug conjugate (ADC) for 96-144 hours at 37° C. A non-binding (referred to as h00 or IgG) ADC was used as a negative control. Cell viability was measured using Cell Titer Glo according to the manufacturer's instructions. Fluorescent signal was measured on a Fusion HT fluorescent plate reader (Perkin Elmer, Waltham, Mass.). The data was normalized to untreated cells, and x50 values were calculated using Graph Pad software. Results are reported in Table 9 as IC$_{50}$, the concentration of compound needed to yield a 50% reduction in viability compared to vehicle-treated cells (control=100%). hL49 ADCs achieve single digit ng/ml IC$_{50}$ values across a panel of cell lines with CD228 expression ranging from 16,000 to 450,000.

TABLE 9

IC$_{50}$ of Anti-CD228 antibody-drug conjugate against various cancer cells

| | | | Melanoma Cell Lines (# of CD228 molecules per cell) | | | | | |
|---|---|---|---|---|---|---|---|---|
| Antibody | Drug Linker | Drug Load | SKMEL28 (450,000) | SKMEL5 (134,000) | Colo853 (92,000) | A2058 (51,000) | IGR37 (24,000) | A375 (16,000) |
| hL49-HALC | MDpr-PEG (12)-gluc-MMAE | 8 | 2.8 | 2.5 | 3.7 | 7.3 | 13.7 | 14.9 |
| hL49-HALC | Auristatin T | 8 | 0.4 | 0.2 | 0.7 | 0.5 | 1.3 | 0.5 |
| hL49-HALC | Tubulysin M | 8 | 3 | 0.4 | 2 | 1 | 16 | 2 |
| hL49-HALC | Lipophilic MMAF | 8 | 0.3 | 0.05 | 0.2 | 0.3 | 2.0 | 0.7 |
| hL49-HALC | PBD | 2 | 32 | 14 | 68 | 5 | 52 | 12 |
| hL49-HALC | MC-VC-MMAE | 4 | 5.9 | 3.9 | 8.5 | 1823 | 223 | 1556 |
| hL49-HALC | MDpr-gluc-MMAE | 4 | 1.4 | 1.8 | 2.0 | 7.5 | 14.7 | 11.5 |

Figure 14A:
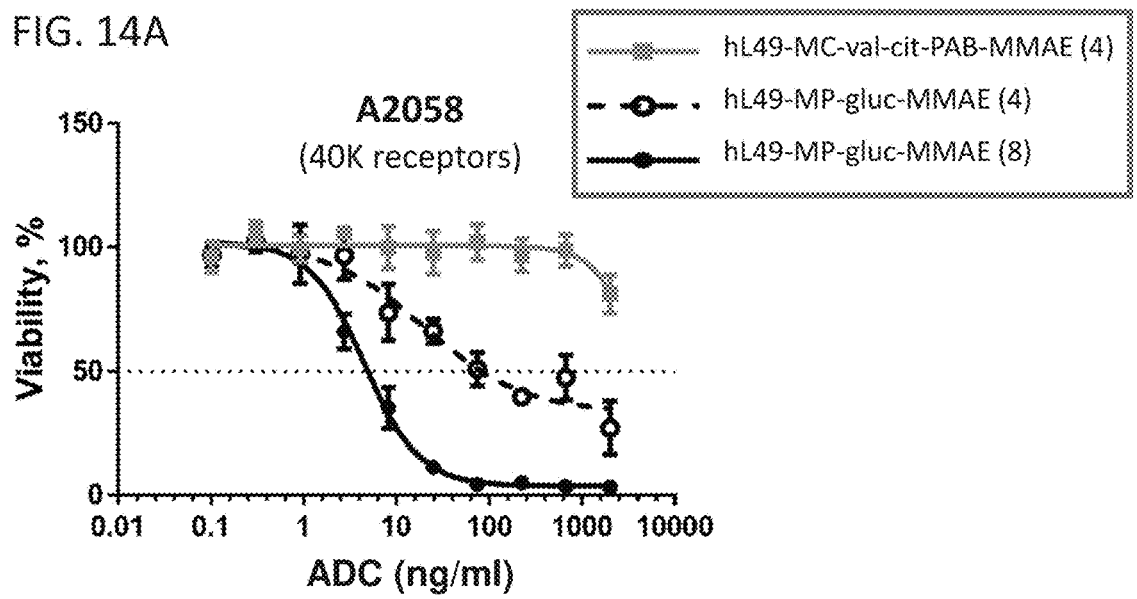
FIG. 14A-14C shows the percent of viable cells over time in A2058, A375 and Colo-853 cell lines treated with hL49-MC-val-cit-PAB-MMAE (4), hL49-MP-gluc-MMAE (4), and hL49-MP-gluc-MMAE (8).

In similar experiments, the percent of viable cells was determined after treatment with various concentrations of hL49 conjugated to different drug linkers with different amounts of MMAE. The resulting percent of viable cells for A2058 cells treated with hL49-MC-val-cit-PAB-MMAE (4), hL49-MP-gluc-MMAE (4), hL49-MP-gluc-MMAE (8) at various antibody-drug conjugate (ADC) concentrations are shown in FIG. 14A. The 8-load MP-gluc-MMAE is superior to the 4-load MP-gluc-MMAE and the MC-val-cit-PAB-MMAE drug linker in vitro. The 4-load MP-gluc-MMAE is superior to the MC-val-cit-PAB-MMAE drug linker in vitro despite containing an identical amount of the same drug (MMAE).

Figure 14B:
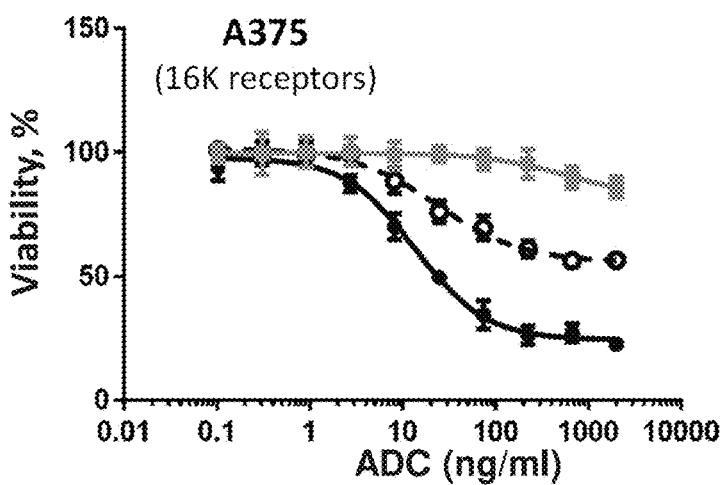

The resulting percent of viable cells for A375 cells treated with hL49-MC-val-cit-PAB-MMAE (4), hL49-MP-gluc-MMAE (4), hL49-MP-gluc-MMAE (8) at various antibody-drug conjugate (ADC) concentrations are shown in FIG. 14B. The 8-load MP-gluc-MMAE is superior to the 4-load MP-gluc-MMAE and the MC-val-cit-PAB-MMAE drug linker in vitro. The 4-load MP-gluc-MMAE is superior to the MC-val-cit-PAB-MMAE drug linker in vitro despite containing an identical amount of the same drug (MMAE).

Figure 14C:
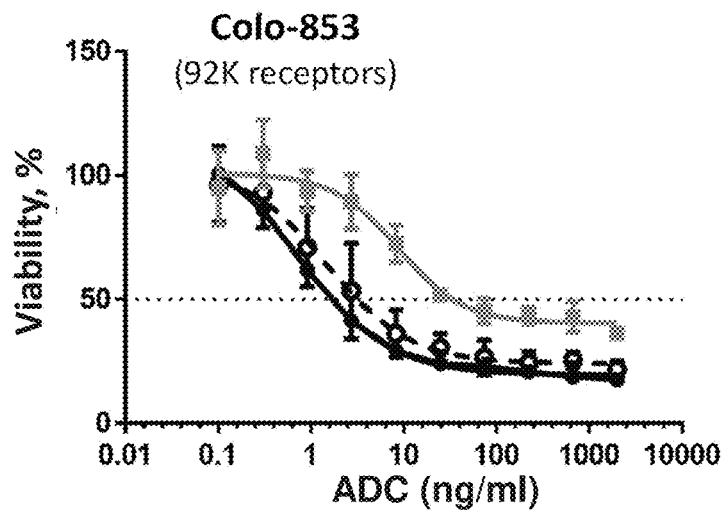

The resulting percent of viable cells for Colo-853 cells treated with hL49-MC-val-cit-PAB-MMAE (4), hL49-MPgluc-MMAE (4), hL49-MP-gluc-MMAE (8) at various antibody-drug conjugate (ADC) concentrations are shown in FIG. 14C. The 8-load MP-gluc-MMAE is superior to the 4-load MP-gluc-MMAE and the MC-val-cit-PAB-MMAE drug linker in vitro.

C. In Vivo Activity of Anti-CD228 ADCs with Various Drug Linkers

Nude (nu/nu) mice (7-8 animals/group) were implanted with $5\times10^6$ cultured A2058 tumor cells in 25% matrigel). Dosing with 1 mg/kg, 3 mg/kg, or 6 mg/kg test ADC began when tumors reached 100 mm³ (q4d×4 intraperitoneal injections). Tumor volumes were monitored using calipers and animals were euthanized when tumor volume reached ~800-1000 mm³. Mean tumor volume plots were continued for each group until one or more animals were euthanized. All animal procedures were performed under a protocol approved by the Institutional Animal Care and Use Committee in a facility accredited by the Association for Assessment and Accreditation of Laboratory Animal Care.

Figure 15:
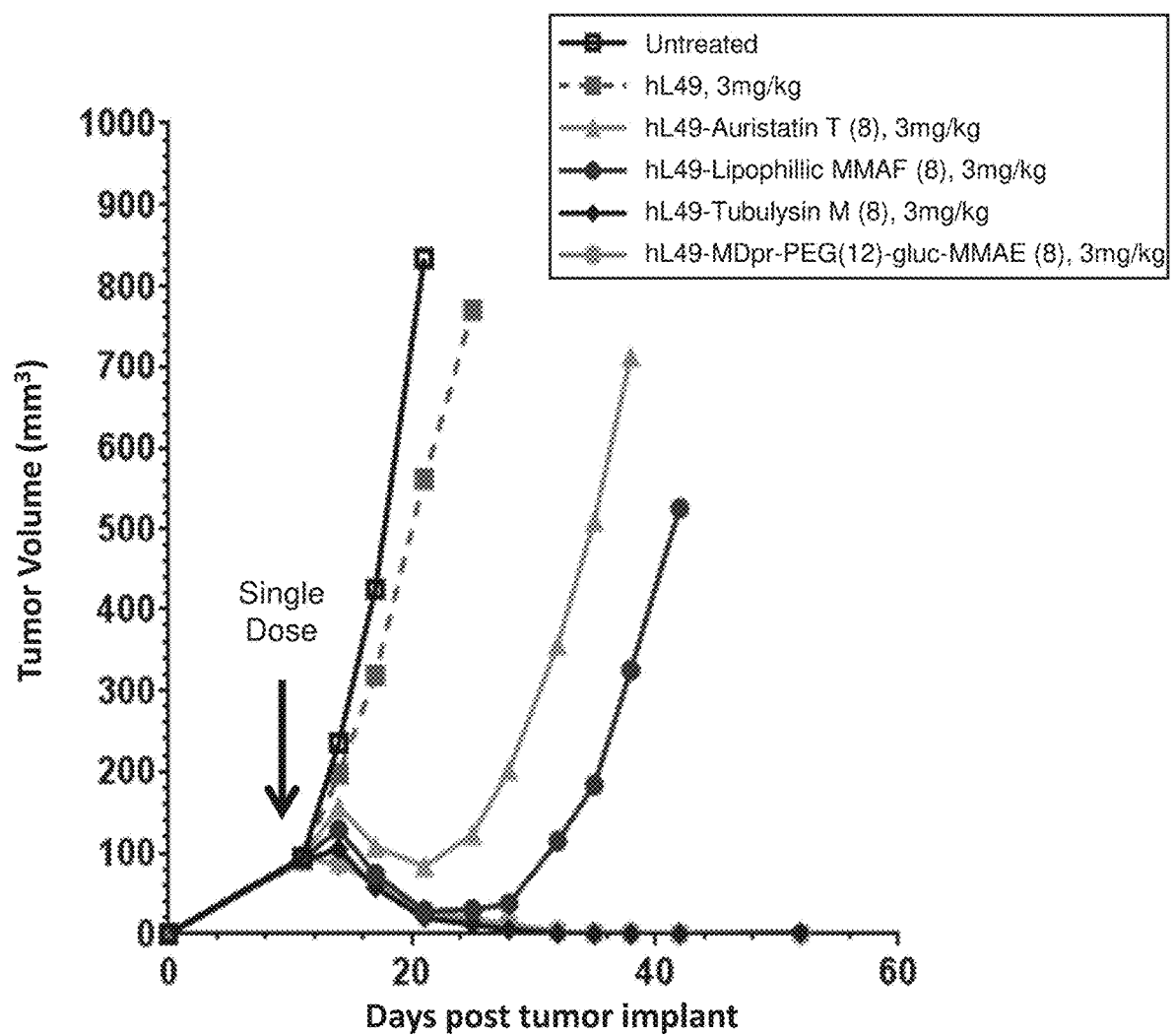
FIG. 15 shows A2058 tumor volumes over time for untreated mice and mice treated with 3 mg/kg hL49-HALC, hL49-HALC-Auristatin T (8), hL49-HALC-Lipophillic MMAF (8), hL49-HALC-Tubulysin M (8), and hL49-HALC-MDpr-PEG(12)-gluc-MMAE (8).

The resulting tumor volumes over time for untreated mice and mice treated with 3 mg/kg hL49, hL49-Auristatin T (8), hL49-Lipophillic MMAF (8), hL49-Tubulysin M (8), and hL49-MDpr-PEG(12)-gluc-MMAE (8) are shown in FIG. 15. Despite superior potency in vitro, Auristatin T and Lipophilic MMAF ADCs are less active than hL49-MDpr-PEG(12)-gluc-MMAE (8) in vivo.

Figure 16:
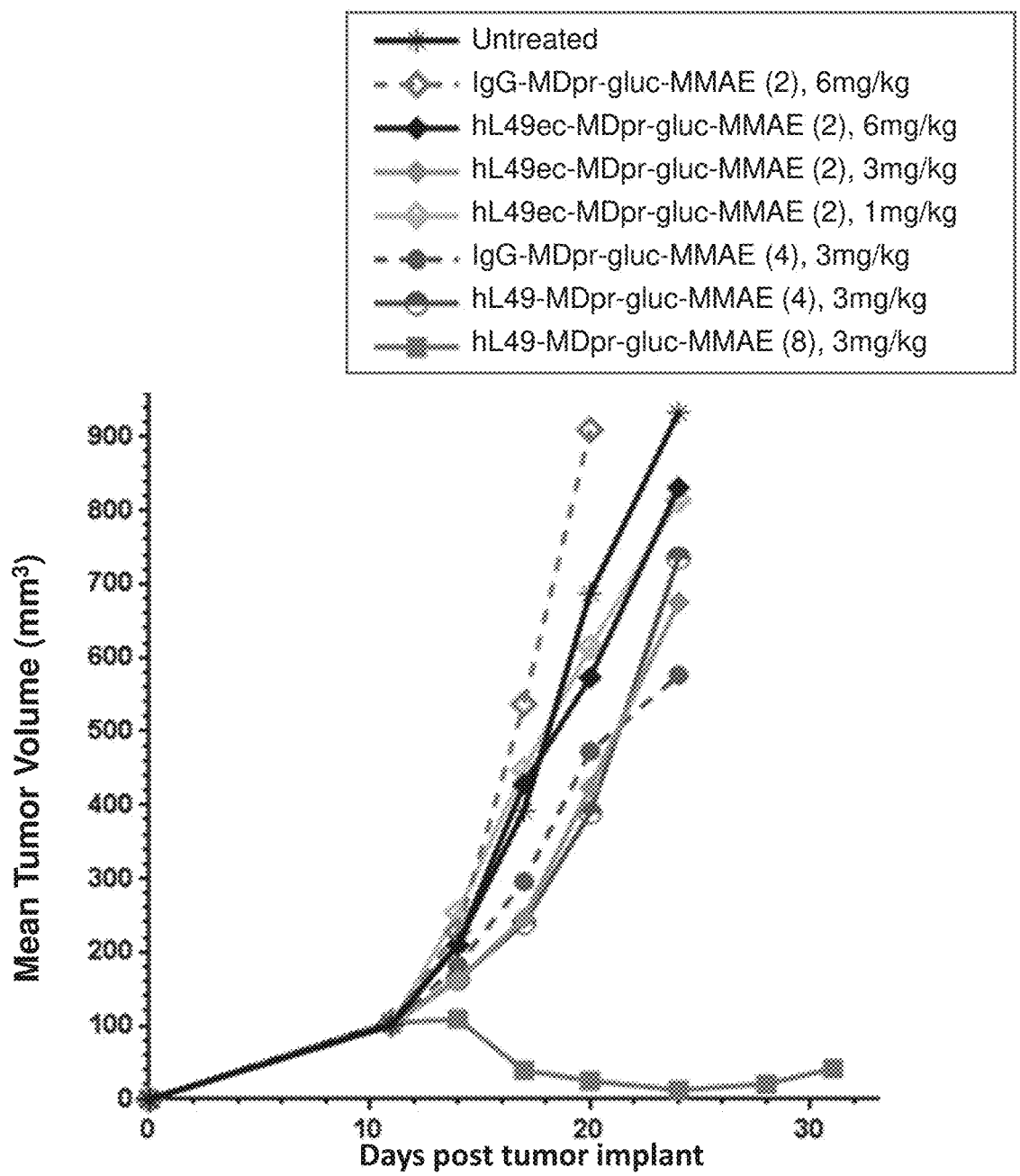
FIG. 16 shows A2058 tumor volumes over time for untreated mice and mice treated with 6 mg/kg IgG-MDpr-gluc-MMAE (2), 6 mg/kg hL49ec-MDpr-gluc-MMAE (2), 3 mg/kg hL49ec-MDpr-gluc-MMAE (2), 1 mg/kg hL49ec-MDpr-gluc-MMAE (2), 3 mg/kg IgG-MDpr-gluc-MMAE (4), 3 mg/kg hL49-MDpr-gluc-MMAE (4), and 3 mg/kg hL49-MDpr-gluc-MMAE (8).

The resulting tumor volumes over time for untreated mice and mice treated with 6 mg/kg IgG-MDpr-gluc-MMAE (2), 6 mg/kg hL49ec-MDpr-gluc-MMAE (2), 3 mg/kg hL49ec-MDpr-gluc-MMAE (2), 1 mg/kg hL49ec-MDpr-gluc-MMAE (2), 3 mg/kg IgG-MDpr-gluc-MMAE (4), 3 mg/kg hL49-MDpr-gluc-MMAE (4), and 3 mg/kg hL49-MDpr-gluc-MMAE (8) are shown in FIG. 16. The 8-load MMAE with PEG is superior to the 2-load or 4-load MMAE with PEG in vivo.

Figure 17:
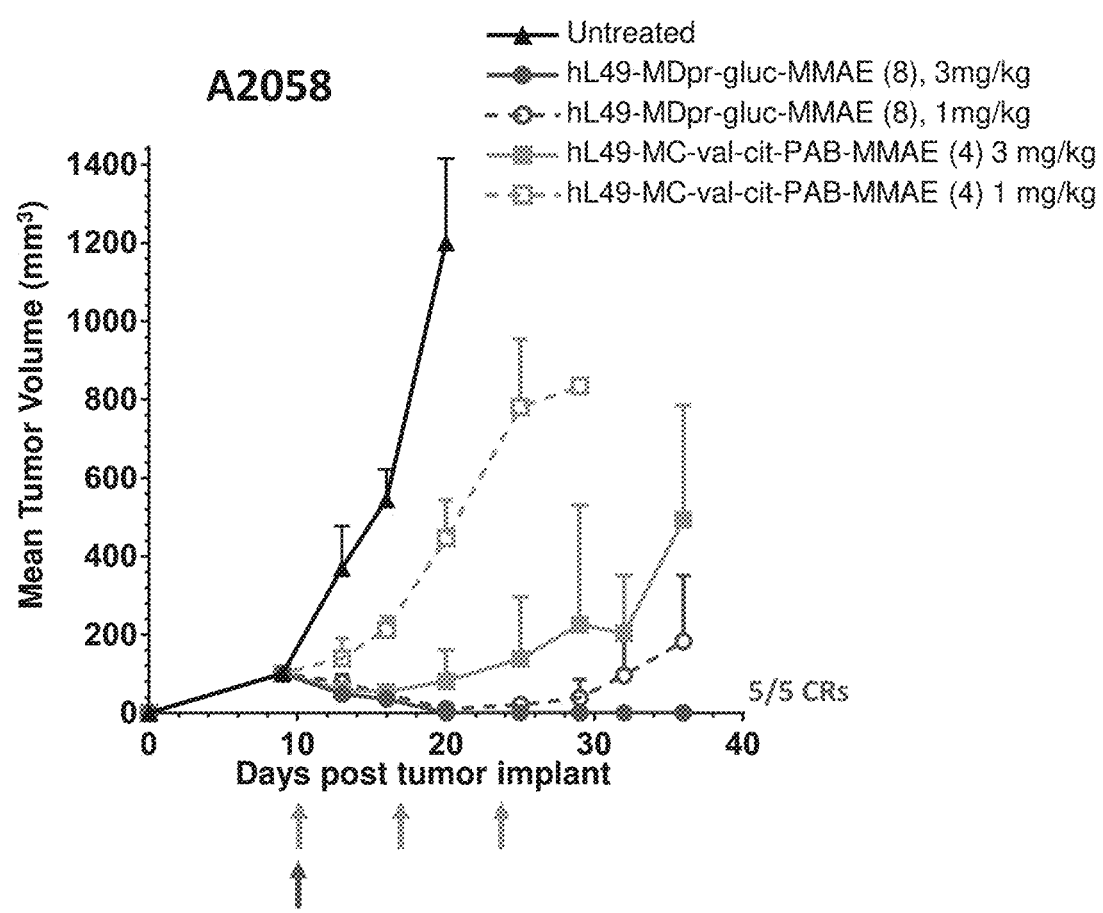
FIG. 17 shows A2058 tumor volumes over time for untreated mice and mice treated with 1 mg/kg hL49-MC-val-cit-PAB-MMAE (4), 3 mg/kg hL49-MC-val-cit-PAB-MMAE (4), 1 mg/kg hL49-MDpr-gluc-MMAE (8), and 3 mg/kg hL49-MDpr-gluc-MMAE (8).

The resulting tumor volumes over time for untreated mice and mice treated with 1 mg/kg hL49-MC-val-cit-PAB-MMAE (4), 3 mg/kg hL49-MC-val-cit-PAB-MMAE (4), 1 mg/kg hL49-MDpr-gluc-MMAE (8), and 3 mg/kg hL49-MDpr-gluc-MMAE (8) are shown in FIG. 17. 3 mg/kg hL49-MDpr-gluc-MMAE (8) is superior to 1 mg/kg hL49-MDpr-gluc-MMAE (8) or either concentration of hL49-MC-val-cit-PAB-MMAE (4) in vivo.

Figure 18:
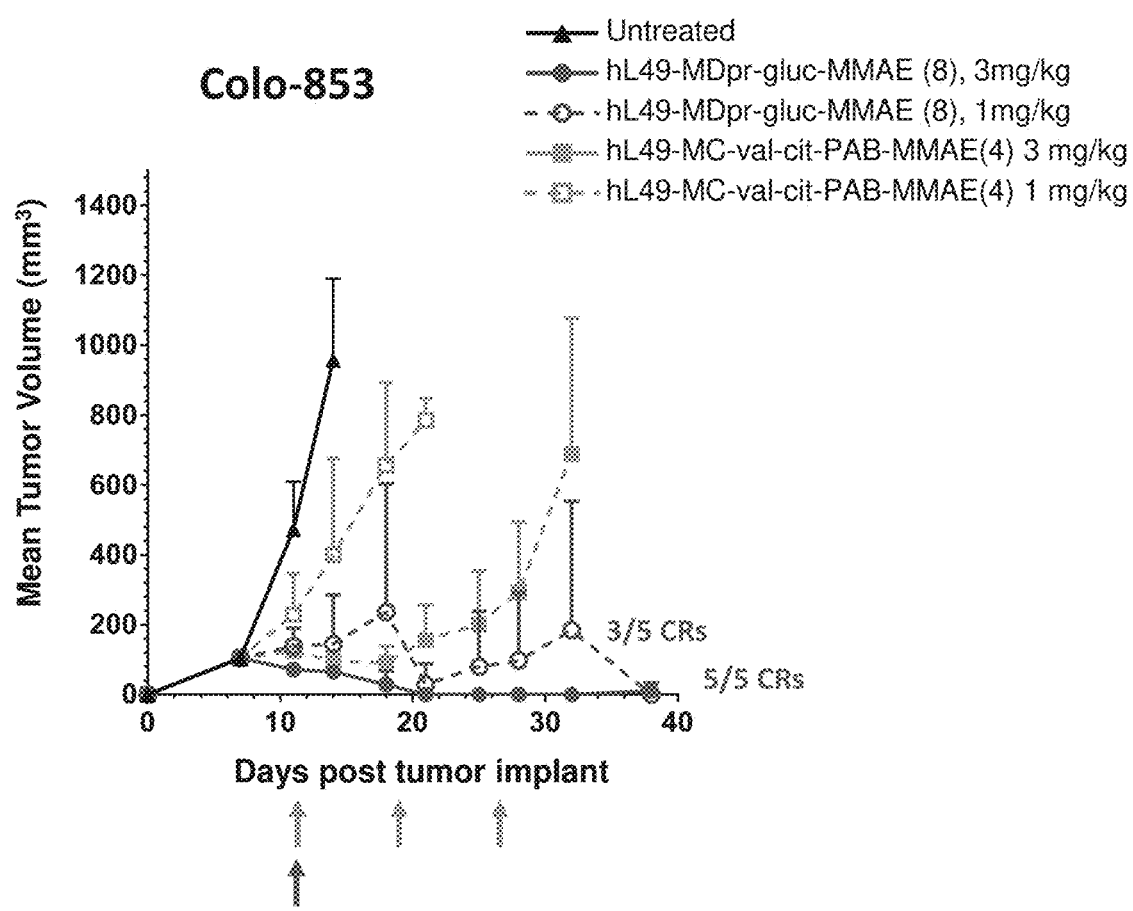
FIG. 18 shows Colo-853 tumor volumes over time for untreated mice and mice treated with 1 mg/kg hL49-MC-val-cit-PAB-MMAE (4), 3 mg/kg hL49-MC-val-cit-PAB-MMAE (4), 1 mg/kg hL49-MDpr-gluc-MMAE (8), and 3 mg/kg hL49-MDpr-gluc-MMAE (8).

The resulting tumor volumes over time for untreated mice and mice treated with 1 mg/kg hL49-MC-val-cit-PAB-MMAE (4), 3 mg/kg hL49-MC-val-cit-PAB-MMAE (4), 1 mg/kg hL49-MDpr-gluc-MMAE (8), and 3 mg/kg hL49-MDpr-gluc-MMAE (8) are shown in FIG. 18. 3 mg/kg hL49-MDpr-gluc-MMAE (8) is superior to 1 mg/kg hL49-MDpr-gluc-MMAE (8) or either concentration of hL49-MC-val-cit-PAB-MMAE (4) in vivo.

Example 6

In Vivo Comparison of ADCs with Tubulysin M and MDpr-PEG(12)-gluc-MMAE hL49 conjugated to Tubulysin M or MDpr-PEG(12)-gluc-MMAE showed superiority to other ADCs against A2058 cells, so these ADCs were selected for further assessment at different dosages and with different tumor cell types.

Nude (nu/nu) mice (6-8 animals/group) were implanted with $2.5\times10^5$ cultured A2058, $1\times10^6$ SK-MEL-5, $1\times10^5$ IGR-37, $1\times10^6$ Colo-853, or $1\times10^6$ HPAF-II tumor cells in 25% matrigel. NOD/SCID/gc KO (NSG) mice were implanted with $5\times10^5$ cultured MDA-MB-231 tumor cells. For PDX models, LU0697 squamous NSCLC model was grown in NOD/SCID mice and the LU5200 Adenocarcinoma NSCLC models was grown in BALB/c Nude mice (3 animals/group). Dosing with 0.3 mg/kg, 0.5 mg/kg, 1 mg/kg, or 3 mg/kg test ADC began when tumors reached approximately 100 mm³ (single intraperitoneal injection). Tumor volumes were monitored using calipers and animals were euthanized when tumor volume reached ~1000 mm³. For the PDX studies, they were terminated 28 days post the final dose regardless of tumor size. Mean tumor volume plots were continued for each group until one or more animals were euthanized. All animal procedures were performed under a protocol approved by the Institutional Animal Care and Use Committee in a facility accredited by the Association for Assessment and Accreditation of Laboratory Animal Care.

Figure 19:
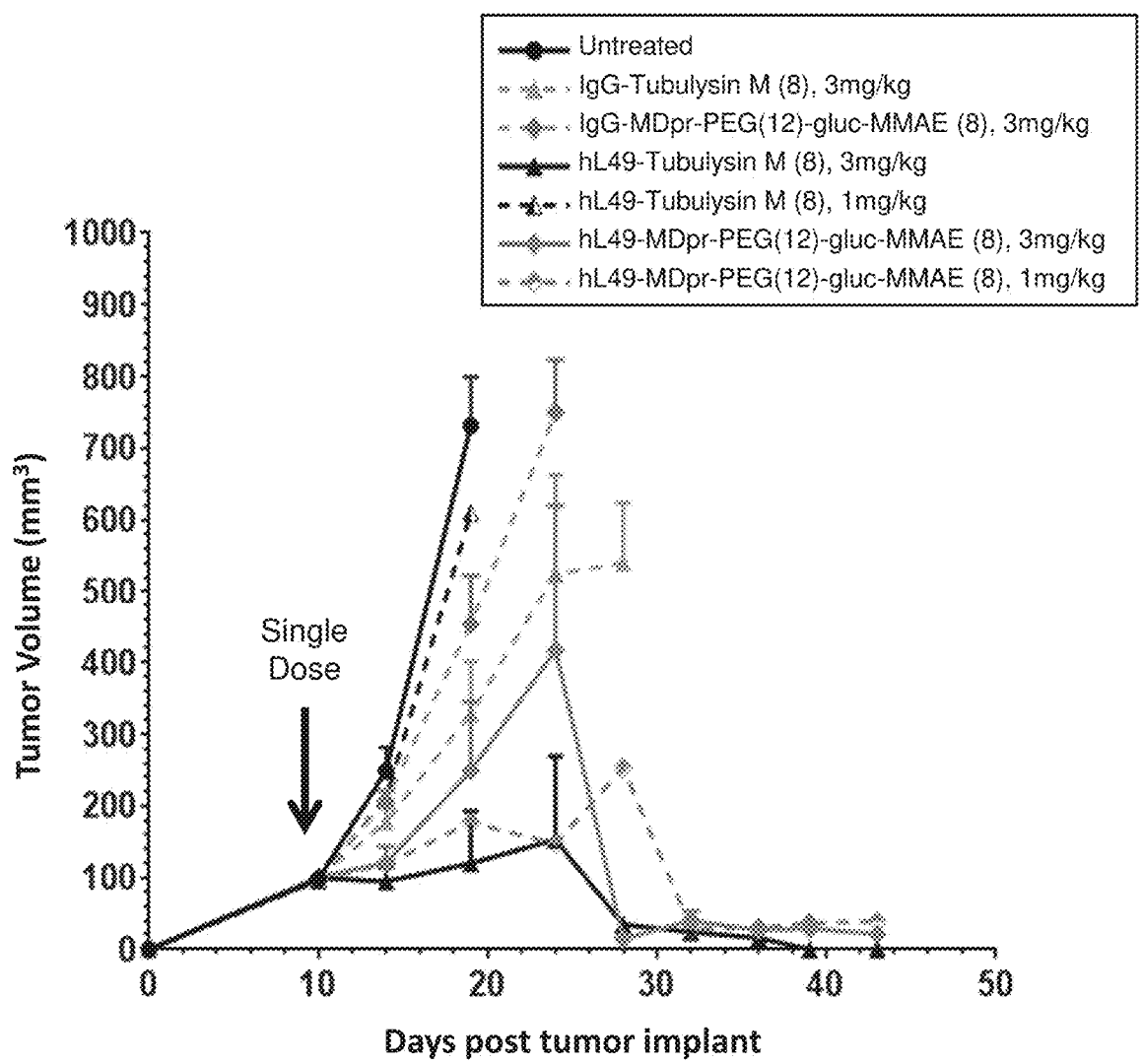
FIG. 19 shows A2058 tumor volumes over time for untreated mice and mice treated with 3 mg/kg IgG-MDpr-PEG(12)-gluc-MMAE (8), 3 mg/kg IgG-Tubulysin M (8), 1 mg/kg or 3 mg/kg hL49-Tubulysin M (8), or 1 mg/kg or 3 mg/kg hL49-MDpr-PEG(12)-gluc-MMAE (8).

The resulting A2058 tumor volumes for over time for untreated mice and mice treated with 3 mg/kg IgG-MDpr-PEG(12)-gluc-MMAE (8), 3 mg/kg IgG-Tubulysin M (8), 1 mg/kg or 3 mg/kg hL49-Tubulysin M (8), or 1 mg/kg or 3 mg/kg hL49-MDpr-PEG(12)-gluc-MMAE (8) are shown in FIG. 19. hL49-Tubulysin M and hL49-MDpr-PEG(12)-gluc-MMAE have similar complete response (CR) rates at 3 mg/kg, but hL49-MDpr-PEG(12)-gluc-MMAE is superior at 1 mg/kg.

Figure 20:
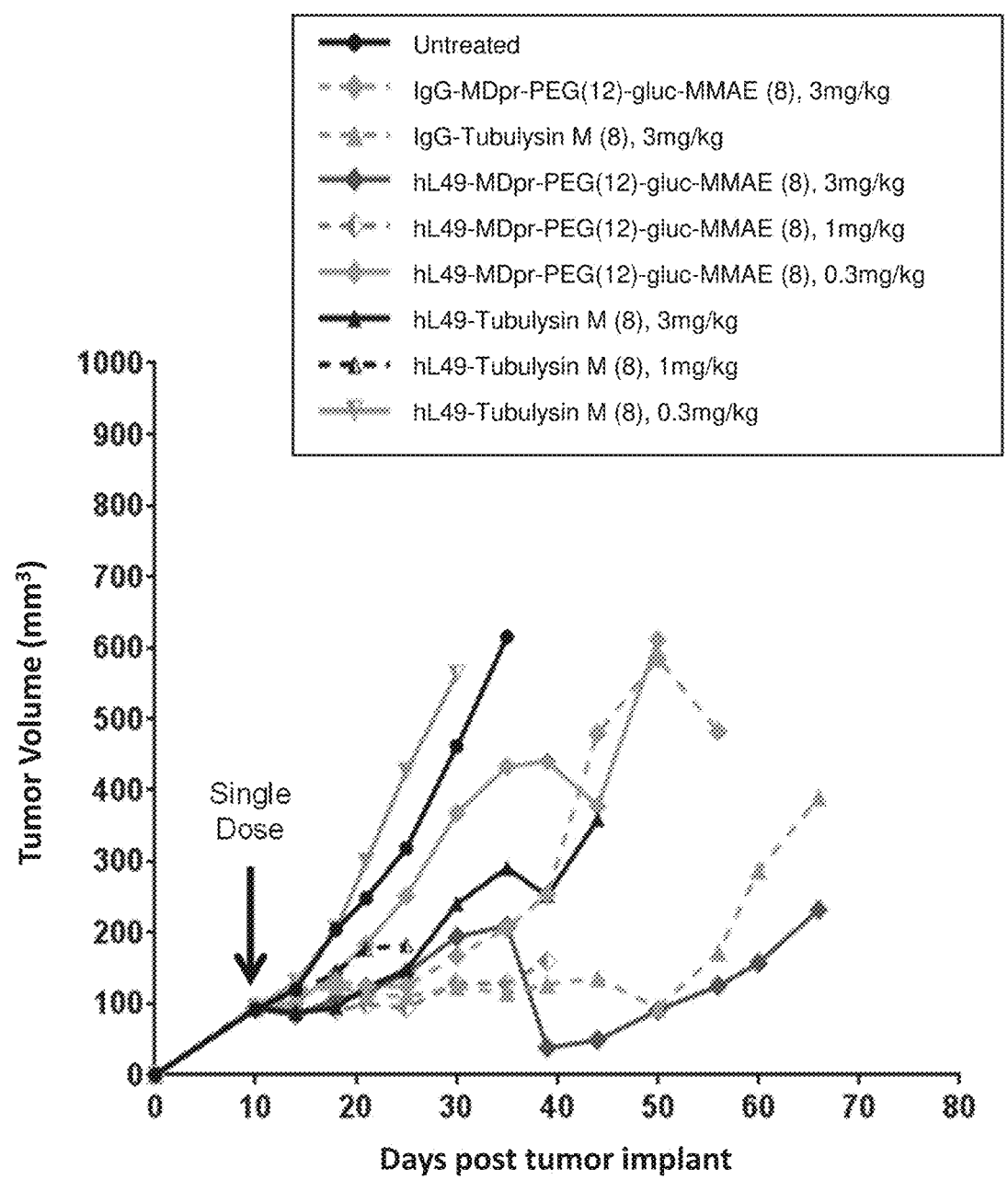
FIG. 20 shows SK-MEL-5 tumor volumes over time for untreated mice and mice treated with 3 mg/kg IgG-MDpr-PEG(12)-gluc-MMAE (8), 3 mg/kg IgG-Tubulysin M (8), 0.3 mg/kg, 1 mg/kg, or 3 mg/kg hL49-Tubulysin M (8), or 0.3 mg/kg, 1 mg/kg or 3 mg/kg hL49-MDpr-PEG(12)-gluc-MMAE (8)

The resulting SK-MEL-5 tumor volumes over time for untreated mice and mice treated with 3 mg/kg IgG-MDpr-PEG(12)-gluc-MMAE (8), 3 mg/kg IgG-Tubulysin M (8), 0.3 mg/kg, 1 mg/kg, or 3 mg/kg hL49-Tubulysin M (8), or 0.3 mg/kg, 1 mg/kg or 3 mg/kg hL49-MDpr-PEG(12)-gluc-MMAE (8) are shown in FIG. 20. hL49-MDpr-PEG(12)-gluc-MMAE is superior to hL49-Tubulysin M for SK-MEL-5 tumors.

Figure 21:
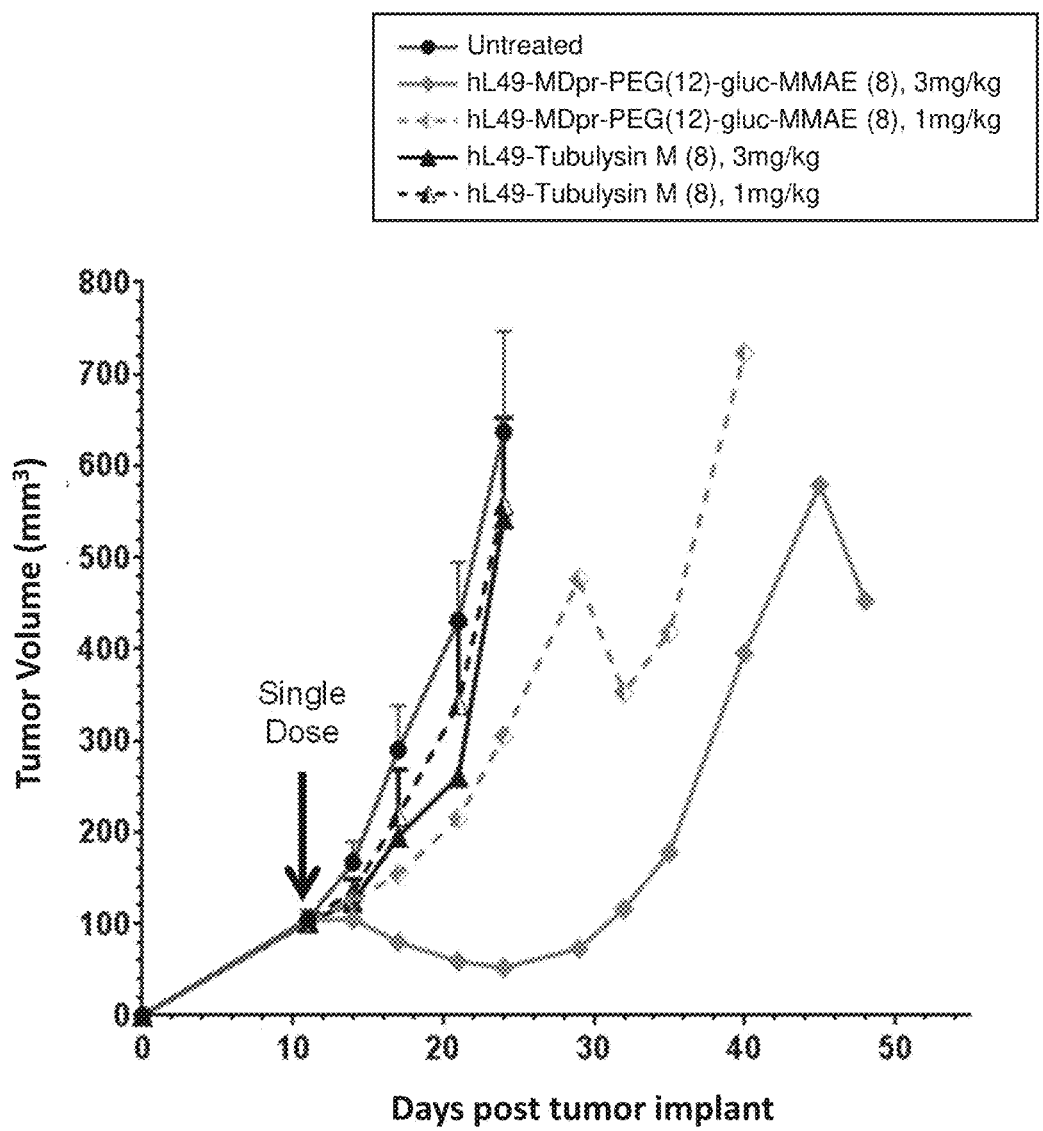
FIG. 21 shows IGR-37 tumor volumes over time for untreated mice and mice treated with 1 mg/kg or 3 mg/kg hL49-Tubulysin M (8), or 1 mg/kg or 3 mg/kg hL49-MDpr-PEG(12)-gluc-MMAE (8).

The resulting IGR-37 tumor volumes over time for untreated mice and mice treated with 1 mg/kg or 3 mg/kg hL49-Tubulysin M (8), or 1 mg/kg or 3 mg/kg hL49-MDpr-PEG(12)-gluc-MMAE (8) are shown in FIG. 21. hL49-MDpr-PEG(12)-gluc-MMAE is superior to hL49-Tubulysin M for IGR-37 tumors.

Figure 22:
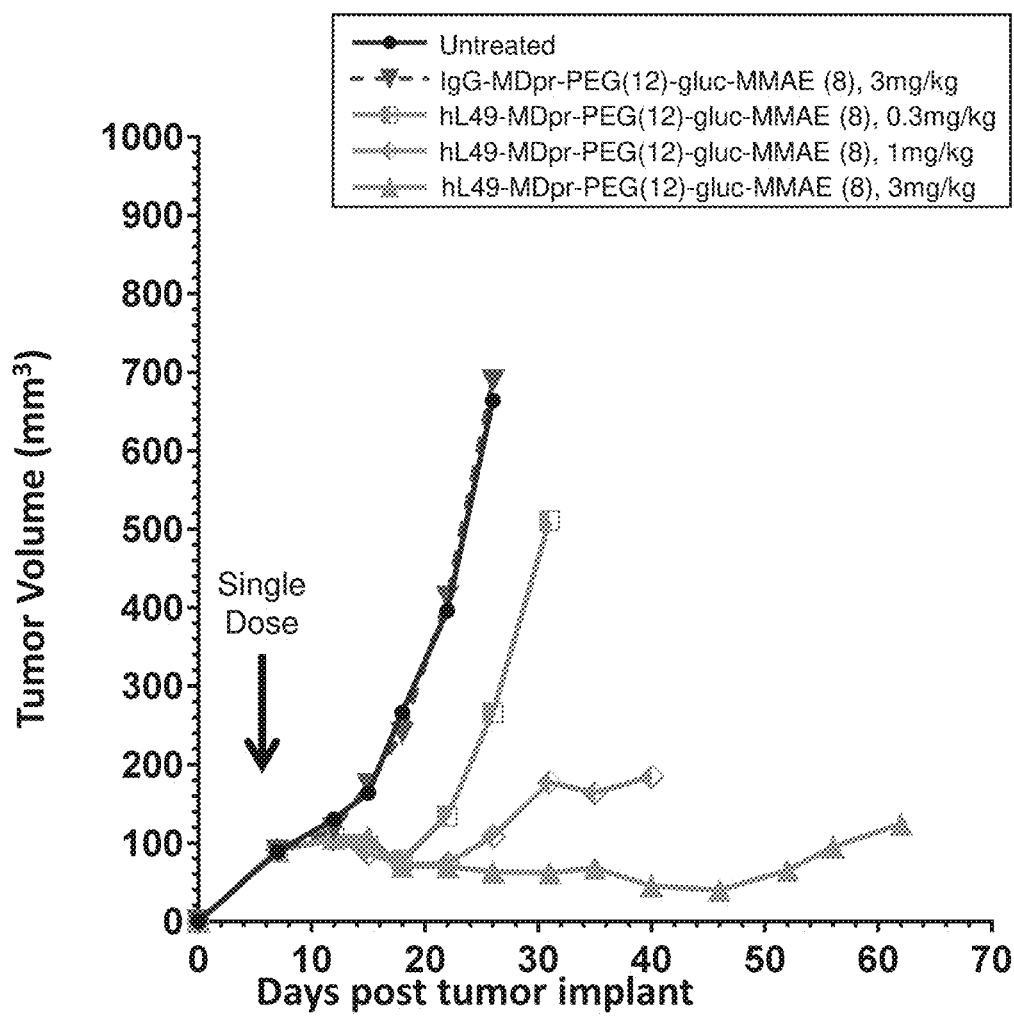
FIG. 22 shows Colo-853 tumor volumes over time for untreated mice and mice treated with 0.3, 1 mg/kg or 3 mg/kg hL49-MDpr-PEG(12)-gluc-MMAE (8), or 3 mg/kg IgG-MDpr-PEG(12)-gluc-MMAE (8).

The resulting Colo-853 tumor volumes over time for untreated mice and mice treated with 0.3, 1 mg/kg or 3 mg/kg hL49-MDpr-PEG(12)-gluc-MMAE (8), or 3 mg/kg IgG-MDpr-PEG(12)-gluc-MMAE (8) are shown in FIG. 22. Colo-853 tumors are responsive to treatment by hL49-MDpr-PEG(12)-gluc-MMAE.

Figure 23:
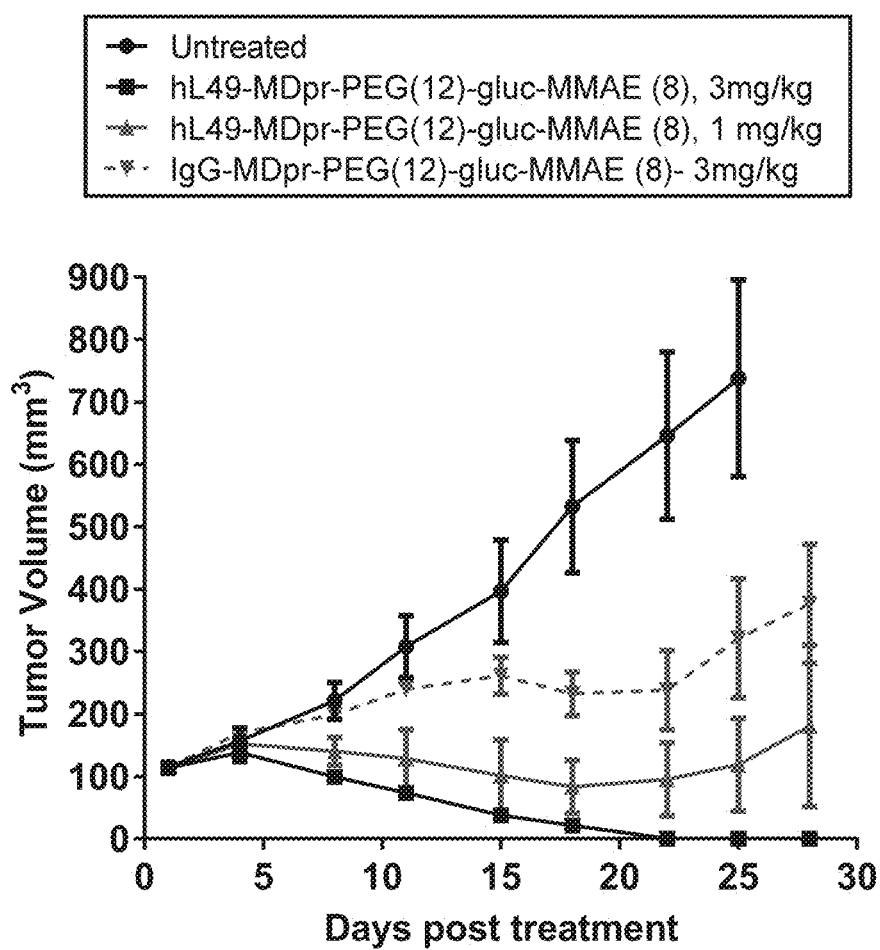
FIG. 23 shows LU0697 squamous NSCL PDX model tumor volumes over time for untreated mice and mice treated with 1 mg/kg or 3 mg/kg hL49-MDpr-PEG(12)-gluc-MMAE (8), or 3 mg/kg IgG-MDpr-PEG(12)-gluc-MMAE (8).

The resulting LU0697 squamous NSCLC PDX model tumor volumes over time for untreated mice and mice treated with 1 mg/kg or 3 mg/kg hL49-MDpr-PEG(12)-gluc-MMAE (8), or 3 mg/kg IgG-MDpr-PEG(12)-gluc-MMAE (8) are shown in FIG. 23. LU0697 squamous NSCL PDX model tumors are responsive to treatment by hL49-MDpr-PEG(12)-gluc-MMAE.

Figure 24:
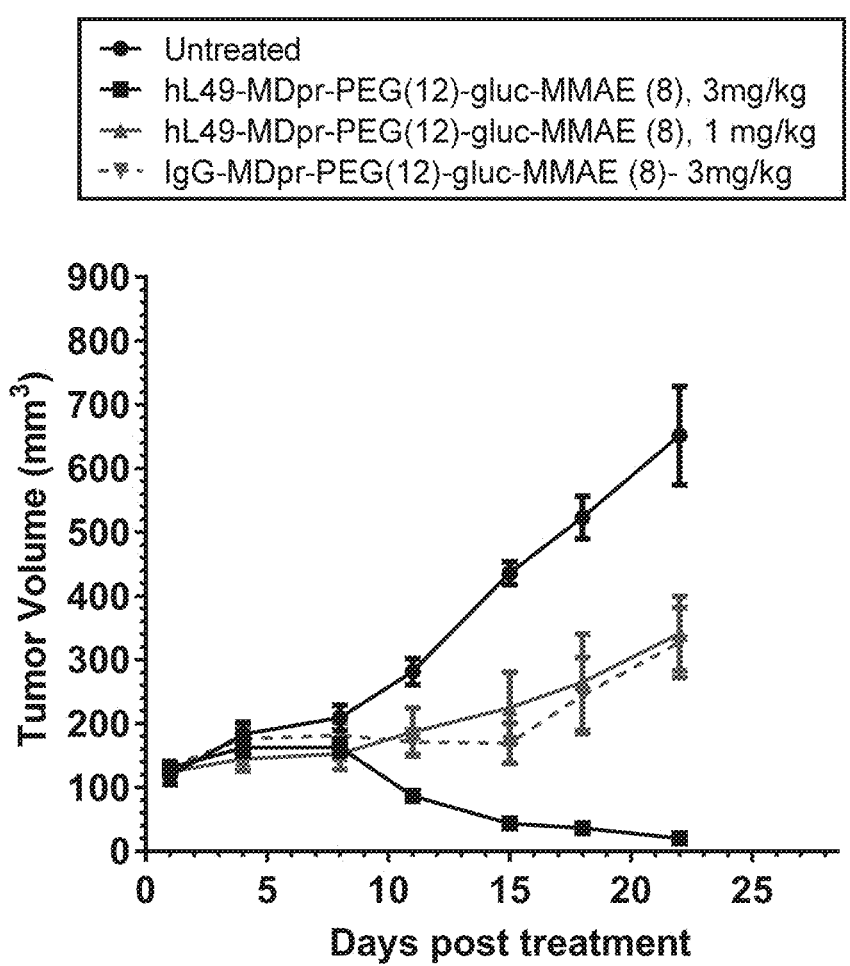
FIG. 24 shows LU0697 adenocarcinoma NSCL PDX model tumor volumes over time for untreated mice and mice treated with 1 mg/kg or 3 mg/kg hL49-MDpr-PEG(12)-gluc-MMAE (8), or 3 mg/kg IgG-MDpr-PEG(12)-gluc-MMAE (8).

The resulting LU0697 adenocarcinoma NSCLC PDX model tumor volumes over time for untreated mice and mice treated with 1 mg/kg or 3 mg/kg hL49-MDpr-PEG(12)-gluc-MMAE (8), or 3 mg/kg IgG-MDpr-PEG(12)-gluc-MMAE (8) are shown in FIG. 24. LU0697 adenocarcinoma NSCL PDX model tumors are responsive to treatment by hL49-MDpr-PEG(12)-gluc-MMAE.

Figure 25:
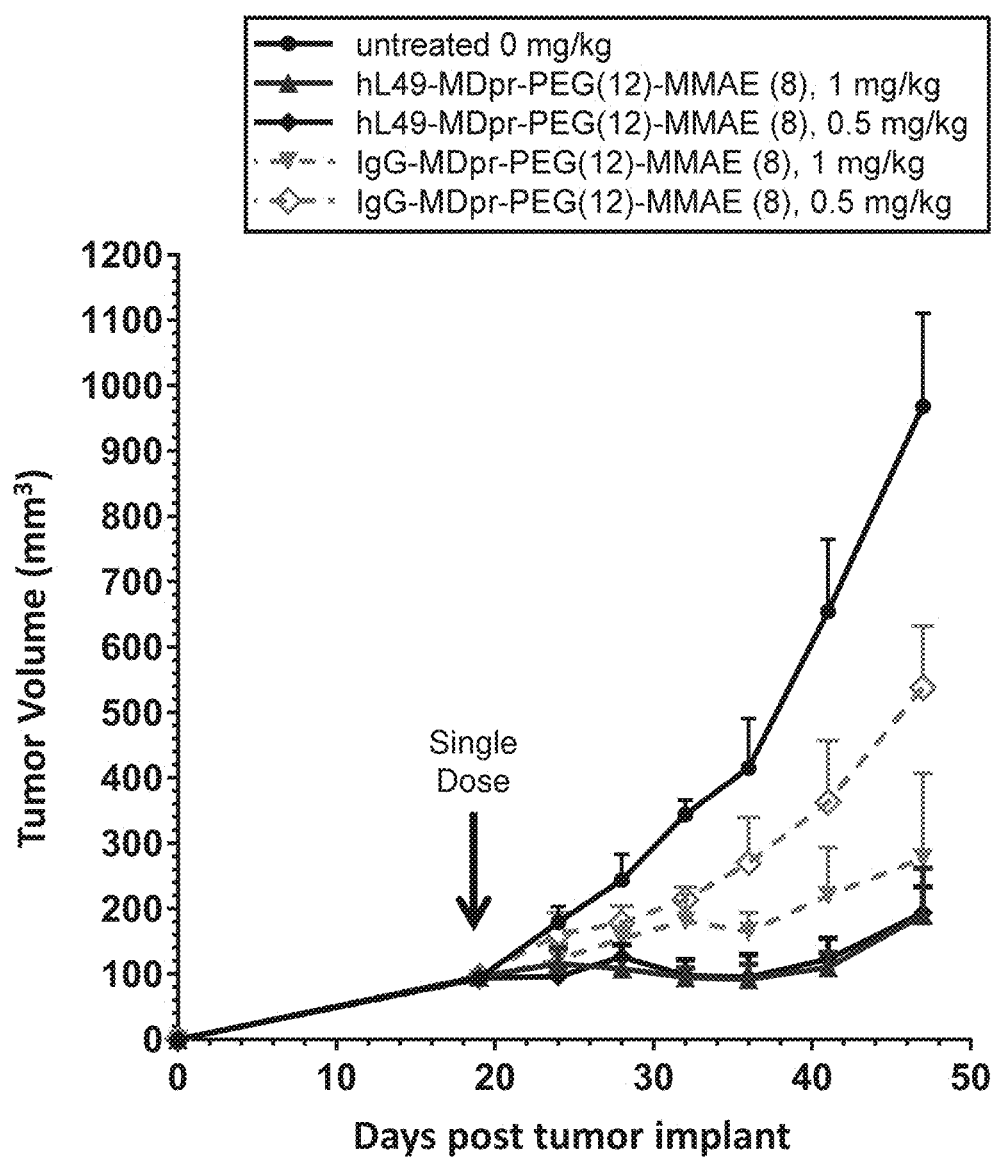
FIG. 25 shows MDA-MB-231 TNBC tumor volumes over time for untreated mice and mice treated with 0.5 mg/kg or 1 mg/kg hL49-MDpr-PEG(12)-gluc-MMAE (8), or 0.5 mg/kg or 1 mg/kg IgG-MDpr-PEG(12)-gluc-MMAE (8).

The resulting MDA-MB-231 TNBC tumor volumes over time for untreated mice and mice treated with 0.5 mg/kg or 1 mg/kg hL49-MDpr-PEG(12)-gluc-MMAE (8), or 0.5 mg/kg or 1 mg/kg IgG-MDpr-PEG(12)-gluc-MMAE (8) are shown in FIG. 25. MDA-MB-231 TNBC tumor are responsive to treatment by hL49-MDpr-PEG(12)-gluc-MMAE.

Figure 26:
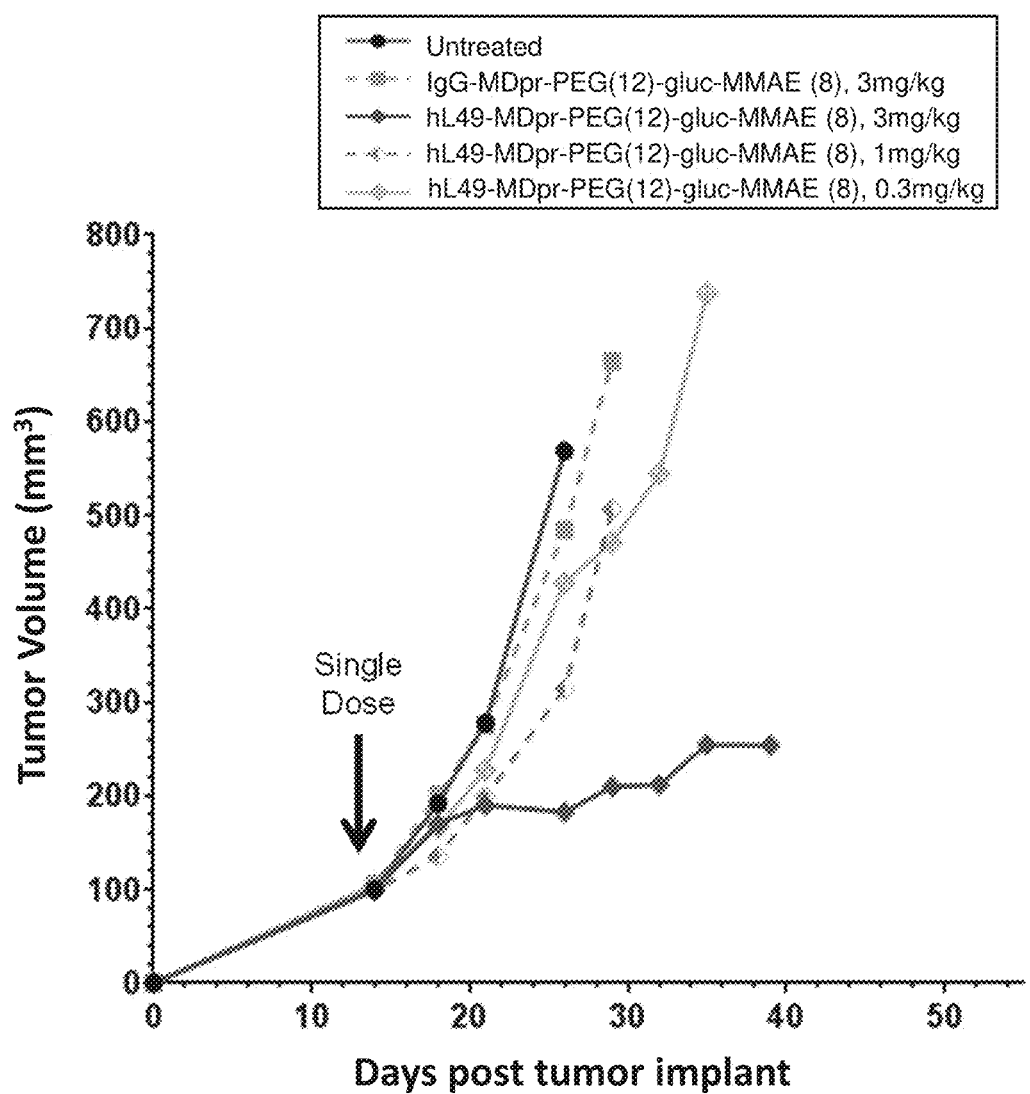
FIG. 26 shows HPAF-II tumor volumes over time for untreated mice and mice treated with 3 mg/kg IgGhL49-MDpr-PEG(12)-gluc-MMAE (8), or 0.3 mg/kg, 1 mg/kg or 3 mg/kg hL49-MDpr-PEG(12)-gluc-MMAE (8).

The resulting HPAF-II tumor volumes over time for untreated mice and mice treated with 3 mg/kg IgG-MDpr-PEG(12)-gluc-MMAE (8), or 0.3 mg/kg, 1 mg/kg or 3 mg/kg hL49-MDpr-PEG(12)-gluc-MMAE (8) are shown in FIG. 26. HPAF-II tumors are responsive to treatment by hL49-MDpr-PEG(12)-gluc-MMAE.

Example 7

Triple-Negative Breast Cancer Mouse Clinical Trial

The percent change in tumor volume in response to treatment with hL49-MDpr-PEG(12)-gluc-MMAE (8) was assessed in 22 different PDX models of triple-negative breast cancer. NCr or Nude mice were implanted with an amount of tumor cells empirically determined for each model. Dosing with 3 mg/kg of hL49-MDpr-PEG(12)-gluc-MMAE (8) began when tumors reached approximately 150-300 mm³. Tumor volumes were monitored using calipers. The percent change in tumor volume for each mouse was calculated at either the time of best response or 7 days post dose with hL49-MDpr-PEG(12)-gluc-MMAE (8) and is shown in FIG. 27. Treatment with hL49-MDpr-PEG(12)-gluc-MMAE (8) achieved a 60% response rate, with 31% of animals achieving a partial response and 29% of animals achieving a complete response. All animal procedures were performed under a protocol approved by the Institutional Animal Care and Use Committee in a facility accredited by the Association for Assessment and Accreditation of Laboratory Animal Care.

Example 7-1

Patient-Derived Xenograft Models of Various CD228-Expressing Cancers

Figure 36A:
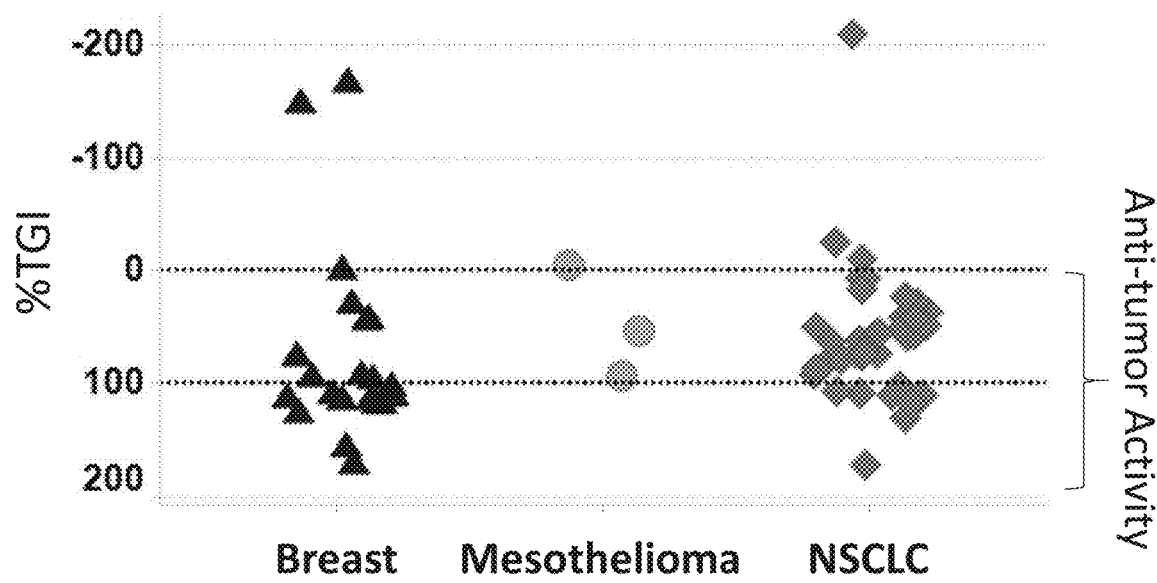
FIG. 36A-36B shows that a single dose of hL49-MDpr-PEG(12)-gluc-MMAE (8) has anti-tumor activity in patient derived tumor (PDX) models.
Figure 36B:
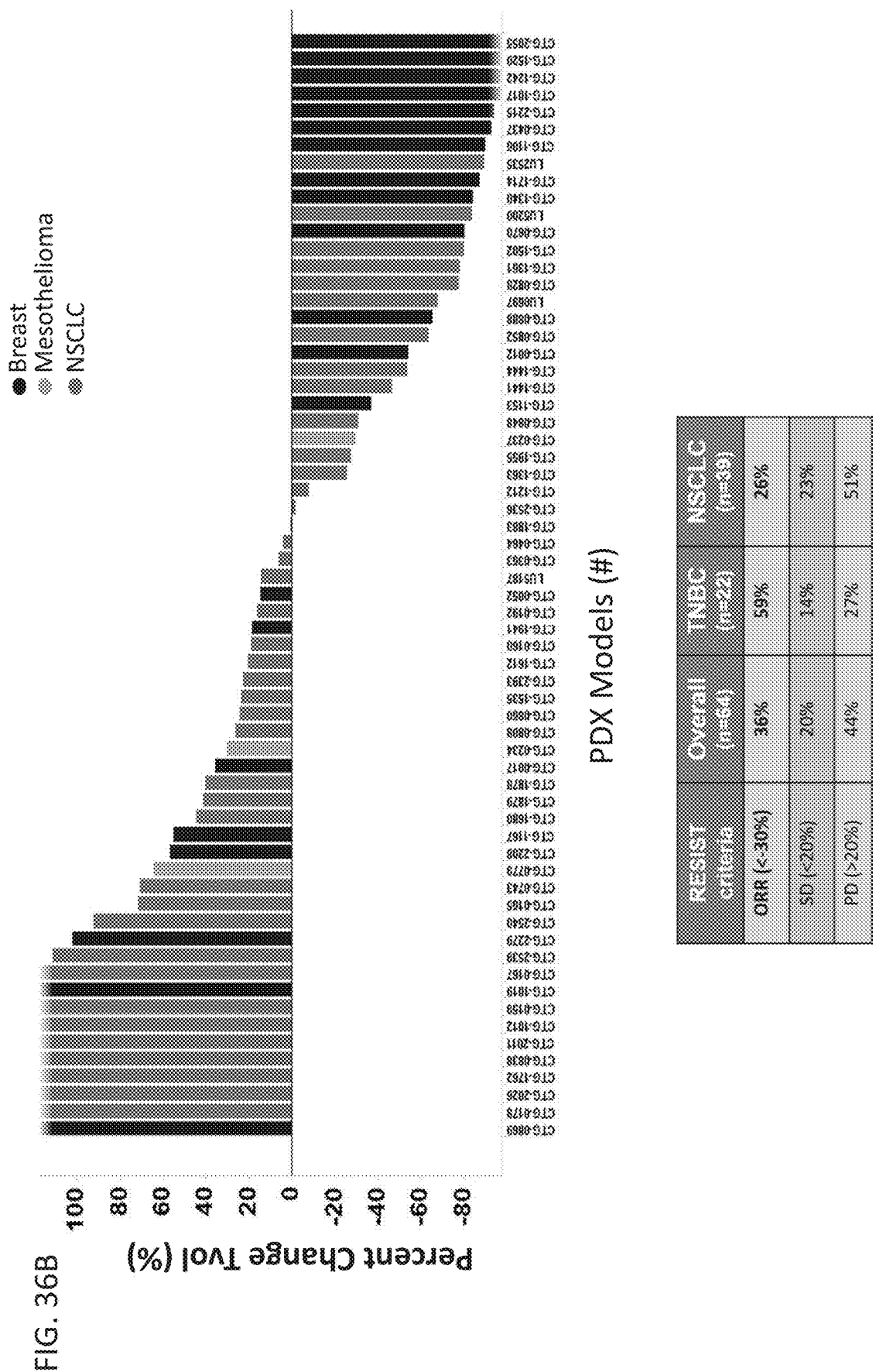

Additional experiments were performed as described in Example 7 to assess the ability of hL49-MDpr-PEG(12)-gluc-MMAE (8) to inhibit tumor growth in various CD228-expressing cancers. Patient-derived xenograft models were generated by isolating tumors from 60 human patients (triple negative breast cancer (TNBC)=22 patients, mesothelioma=3 patients, and non-small cell lung cancer (NSCLC)=35 patients) and implanting the tumors in immunodeficient mice as described in Example 7. After implantation, mice were treated with a single dose of hL49-MDpr-PEG(12)-gluc-MMAE (8). Blood was drawn from the mice 48 hours after treatment with hL49-MDpr-PEG(12)-gluc-MMAE (8) and used for pharmacokinetic assessments. The percent tumor growth inhibition (percent TGI (%)) and percent change in tumor volume from baseline to best response (Percent Change Tvol (%)) were assessed in FIG. 36A and FIG. 36B, respectively. As can be seen, administration of a single dose of hL49-MDpr-PEG(12)-gluc-MMAE (8) had anti-tumor activity in various tumor models.

Example 8

In Vitro Evaluation of Antibody Effector Functions

Figure 28A:
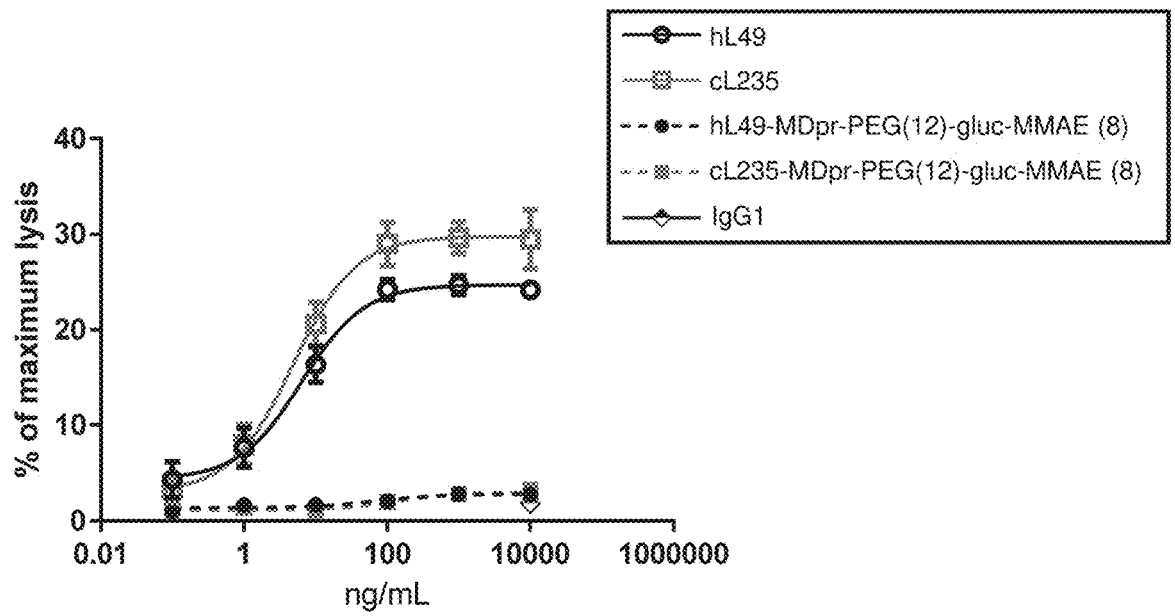
FIG. 28A-28B shows the % specific lysis (ADCC activity) of hL49 and another CD228 antibody, cL235, alone or conjugated to MDpr-PEG(12)-gluc-MMAE for two patients.
Figure 28B:
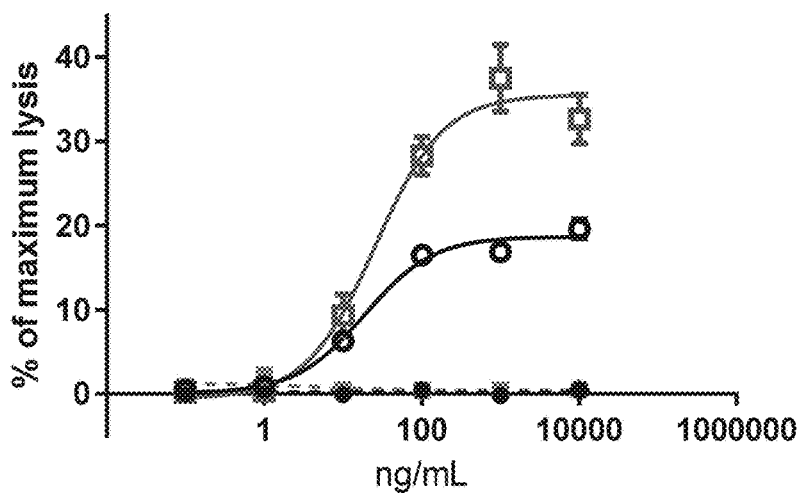

Antibody-dependent Cellular Cytotoxicity (ADCC) activity was measured using the standard $^{51}$Cr-release assay. Briefly, the tumor cells were labeled with 100 µCi Na$^{51}$CrO$_4$, washed, and preincubated with test ADCs prior to addition of effector (natural killer, NK) cells. NK (CD16$^+$ CD56$^+$ cells were prepared from non-adherent peripheral blood mononuclear cells (PBMCs) obtained from normal FcγRIIIA 158V/V donors (Lifeblood, Memphis, Tenn.) with immunomagnetic beads (EasySep, StemCell Technologies, Vancouver, BC, Canada). Viable NK cells were added to target cells at an effector to target cell ratio of 10:1. A human IgG1κ (Ancell, Bayport, Minn.) was used as negative control in this assay. After 4 hours of incubation, supernatants were collected and dried overnight on Luma plates. Gamma radiation emitted from lysed cells was then detected using the TopCount Microplate Scintillation and Luminescence Counter (Perkin Elmer, Waltham, Mass.). The % specific lysis (ADCC activity) for two patients is shown in FIG. 28A-28B. hL49-MDpr-PEG(12)-gluc-MMAE (hL49-5088) has reduced ADCC activity compared to hL49 mAb.

Example 9

Pharmacokinetic Assessment in Mice and Rats

Figure 29A:
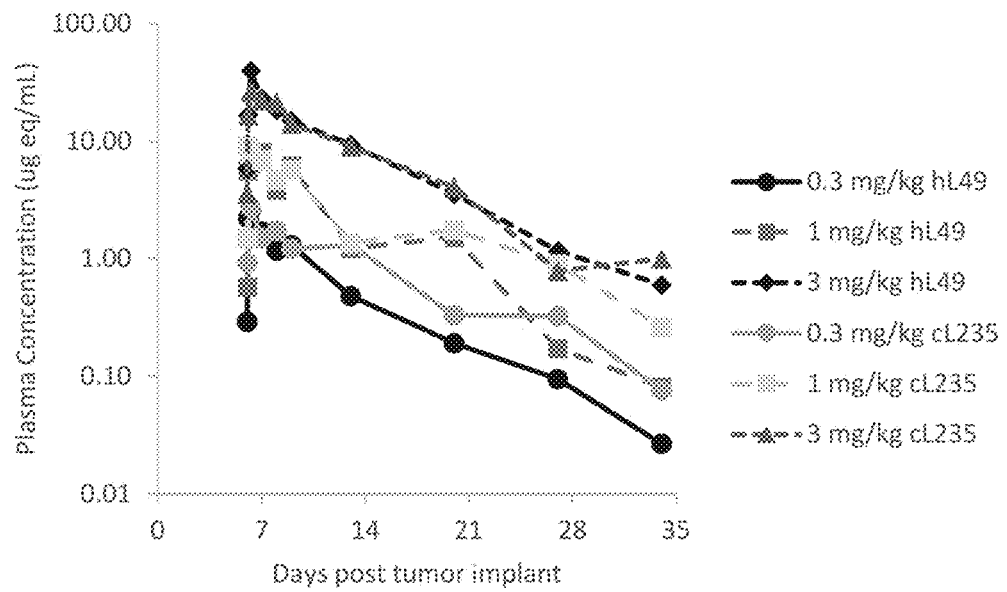
FIG. 29A shows the plasma concentrations of the ADC over time in nude mice.
Figure 29B:
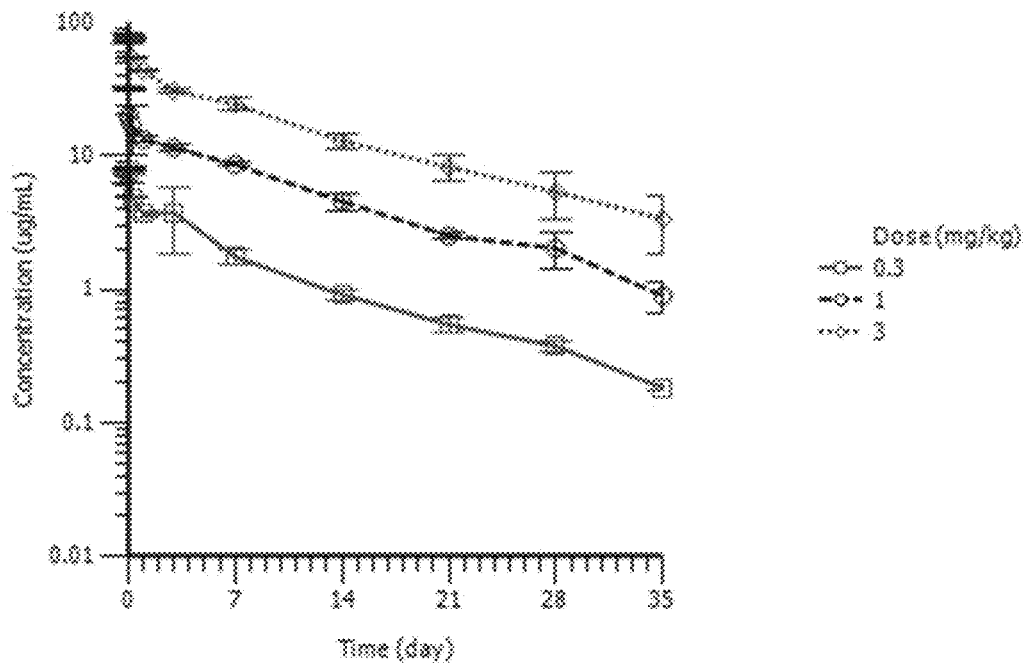
FIG. 29B shows the plasma concentrations of the ADC over time in rats.

Nude mice were intravenously administered hL49-MDpr-PEG(12)-gluc-MMAE or cL235-MDpr-PEG(12)-gluc-MMAE and Sprague-Dawley rats were intravenously administered hL49-MDpr-PEG(12)-gluc-MMAE. Plasma concentrations of the ADC were measured over time using Tab ELISA with an anti-human antibody as the capture antibody. The results are shown in FIG. 29A (mice) and FIG. 29B (rats). Resulting PK parameters are shown in Table 10 (mice) and Table 11 (rats).

TABLE 10

Pharmacokinetic (PK) parameters for hL49-MDpr-PEG(12)-gluc-MMAE in mice

| $AUC_{inf}$/Dose (day * kg * µg/mL/mg) | $C_{max}$/Dose (kg * µg/mL/mg) | $T_{max}$ (day) | Half-life (day) |
|---|---|---|---|
| 41 | 8.8 | 0.25 | 4.7 |
| 50 | 8.1 | 1.0 | 4.4 |
| 63 | 13.3 | 0.25 | 5.1 |

TABLE 11

Pharmacokinetic (PK) parameters for hL49-MDpr-PEG(12)-gluc-MMAE in rats hL49-5088(8)

| $AUC_{inf}$/Dose (day * kg * µg/mL/mg) | $C_{max}$/Dose (kg * µg/mL/mg) | $T_{max}$ (day) | Half-life (day) |
|---|---|---|---|
| 41 | 8.8 | 0.25 | 4.7 |
| 50 | 8.1 | 1.0 | 4.4 |
| 63 | 13.3 | 0.25 | 5.1 |

Example 10

Additional Anti-CD228 Antibodies

Additional anti-CD228 antibodies were conjugated to MDpr-PEG(12)-gluc-MMAE. These additional anti-CD228 antibodies (designated cL235 (see Rolland Y., Pigment Cell Melanoma Res 2009, 22:86-98) and Ab1-9) have binding affinities that are similar to that of hL49, unlike the commercial antibodies tested in Table 2 (Santa Cruz Cat. #271633, R&D Cat. #893416, and Biolegend Cat. No. #363101).

A. In Vitro Cytotoxicity

Tumor cells were incubated with CD228 antibody drug conjugates (ADCs) for 96-144 hours at 37° C. A non-binding (h00-5088(8)) ADC was used as a negative control. Cell viability was measured using Cell Titer Glo according to manufacturer's instructions. Fluorescent signal was measured on a Fusion HT fluorescent plate reader (Perkin Elmer, Waltham, Mass.). The data was normalized to untreated cells, and x50 values were calculated using Graph Pad software. Results are reported in Table 12 as IC$_{50}$, the concentration of compound needed to yield a 50% reduction in viability compared to vehicle-treated cells (control=100%). The percent viable cells remaining at highest dose is shown in Table 13.

TABLE 12

IC$_{50}$ of anti-CD228 antibody-drug conjugate against various cancer cells

| Cell Line | #CD228 | hL49 | cL235 | Ab1 | Ab2 | Ab3 | Ab4 | Ab5 | Ab6 | Ab7 | Ab8 | Ab9 |
|---|---|---|---|---|---|---|---|---|---|---|---|---|
| A2058 | 51K | 2 | 277 | 38 | 10 | 54 | 9 | 47 | 786 | 62 | 1142 | 297 |
| A375 | 16K | 9 | >2000 | 233 | >2000 | >2000 | >2000 | 179 | >200 | 144 | 47 | 203 |
| Colo853 | 92K | 1 | 32 | 10 | 2 | 5 | 1 | 11 | 28 | 11 | 1 | 0.4 |
| IGR37 | 24K | 8 | >2000 | 325 | >2000 | 837 | 1694 | 350 | >200 | 3220 | 1448 | 1738 |
| SKMel5 | 134K | 1 | 71 | 5 | 2 | 3 | 2 | 5 | 17 | 6 | 32 | 2 |
| SKMel28 | 450K | 2 | 13 | 3 | 2 | 2 | 2 | 5 | 7 | 4 | 8 | 1 |

TABLE 13

Percent viable cells remaining at highest dose of anti-CD228 antibody-drug conjugate for various cancer cells

| Cell Line | #CD228 | hL49 | cL235 | Ab1 | Ab2 | Ab3 | Ab4 | Ab5 | Ab6 | Ab7 | Ab8 | Ab9 |
|---|---|---|---|---|---|---|---|---|---|---|---|---|
| A2058 | 51,000 | 4 | 26 | 7 | 31 | 15 | 27 | 9 | 34 | 19 | 40 | 40 |
| A375 | 16,000 | 13 | 62 | 25 | 59 | 62 | 65 | 29 | 54 | 25 | 22 | 22 |
| Colo853 | 92,000 | 24 | 33 | 19 | 31 | 26 | 35 | 25 | 39 | 29 | 20 | 21 |
| IGR37 | 24,000 | 14 | 65 | 22 | 59 | 39 | 53 | 29 | 51 | 35 | 43 | 46 |
| SKMel5 | 134,000 | 13 | 16 | 11 | 22 | 18 | 21 | 12 | 18 | 14 | 9 | 16 |
| SKMel28 | 450,000 | 28 | 21 | 24 | 24 | 24 | 24 | 21 | 24 | 22 | 27 | 31 |

B. In Vivo Activity of Additional Anti-CD228 ADCs

Nude (nu/nu) mice (6 animals/group) were implanted with 1×10$^6$ cultured A375, 1×10$^5$ IGR37, or 2.5×10$^5$ A2058 tumor cells in 25% matrigel). Dosing with 1 mg/kg (A2058) or 3 mg/kg test ADC began when tumors reached 100 mm$^3$ (single dose intraperitoneal injections). Tumor volumes were monitored using calipers and animals were euthanized when tumor volume reached ~800 mm$^3$. Mean tumor volume plots were continued for each group until one or more animals were euthanized. All animal procedures were performed under a protocol approved by the Institutional Animal Care and Use Committee in a facility accredited by the Association for Assessment and Accreditation of Laboratory Animal Care.

Figure 30A:
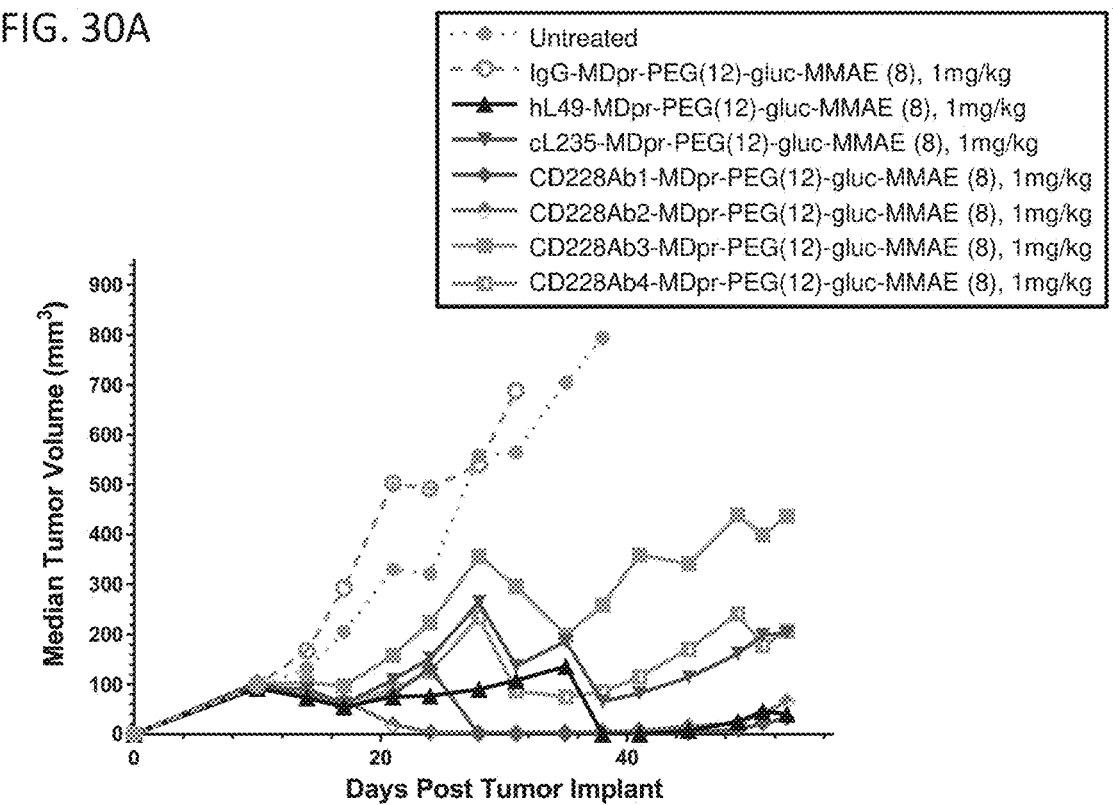
FIG. 30A shows A2058 tumor volumes over time for untreated mice and mice treated with various CD228 antibodies.
Figure 30B:
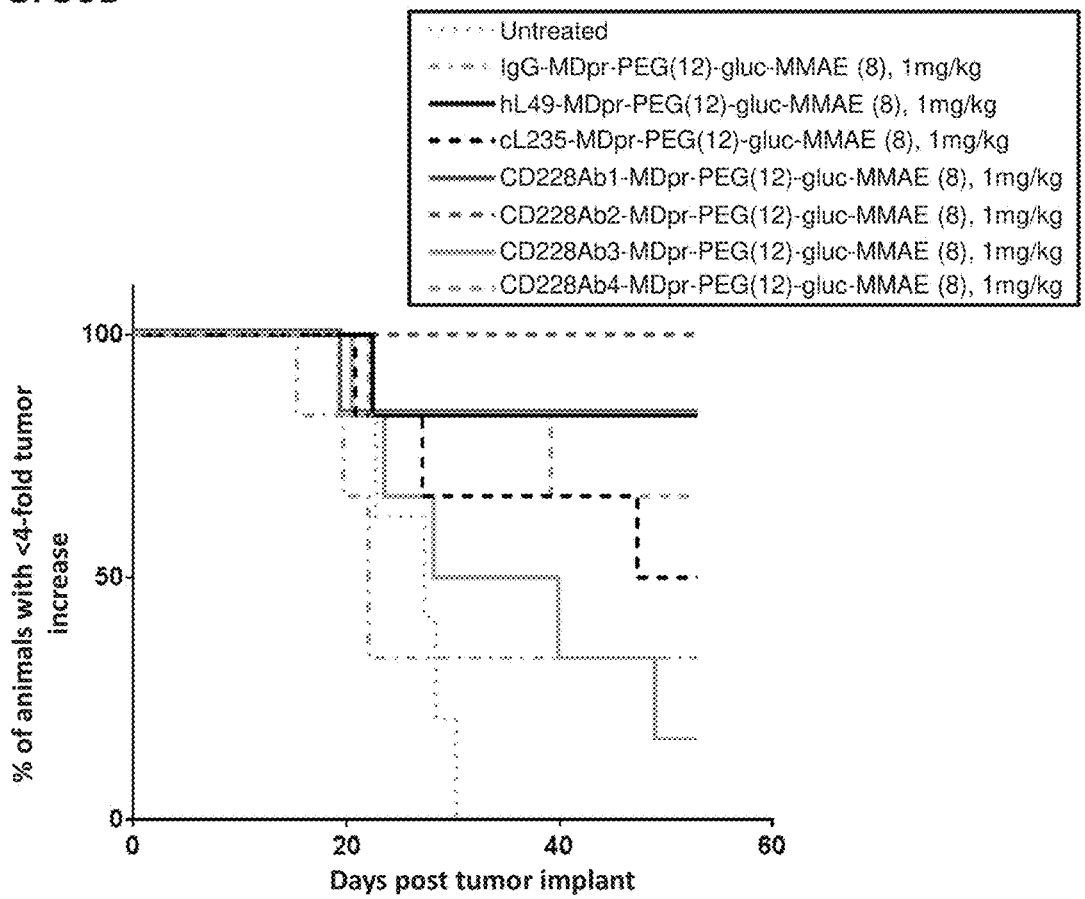
FIG. 30B shows the percent of animals with <4-fold tumor increase over time for each treatment condition.

The resulting A2058 tumor volumes over time for untreated mice and mice treated with various antibodies are shown in FIG. 30A. FIG. 30B shows the percent of animals with <4-fold tumor increase over time for each treatment condition. The number of complete responses (CRs) and median tumor quadrupling time for each ADC and each cell line are shown in Table 14.

TABLE 14

In vivo response to additional anti-CD228 ADCs

| Antibody | A375 | | IGR37 | | A2058 | |
|---|---|---|---|---|---|---|
| | CRs | Median Tumor Quadrupling | CRs | Median Tumor Quadrupling | CRs | Median Tumor Quadrupling |
| Untreated | 0/6 | 25 days | 0/6 | 24 days | 0/6 | 27 days |
| h00 | 0/6 | 34 days | 1/6 | 40 days | 0/6 | 22 days |
| hL49 | 3/6 | — | 1/6 | 51 days | 3/6 | — |
| cL235 | 0/6 | 42 days | 0/6 | 45 days | 0/6 | 50 days |
| CD228Ab1 | 5/6 | — | 2/6 | — | 4/6 | — |
| CD228Ab2 | 2/6 | 50 days | 0/6 | 38 days | 2/6 | — |
| CD228Ab3 | 2/6 | 45 days | 1/6 | 49 days | 0/6 | 34 days |
| CD228Ab4 | 3/6 | — | 1/6 | 55 days | 0/6 | — |

Example 11

Linker Cleavage and CD228 Turnover

Figure 31A:
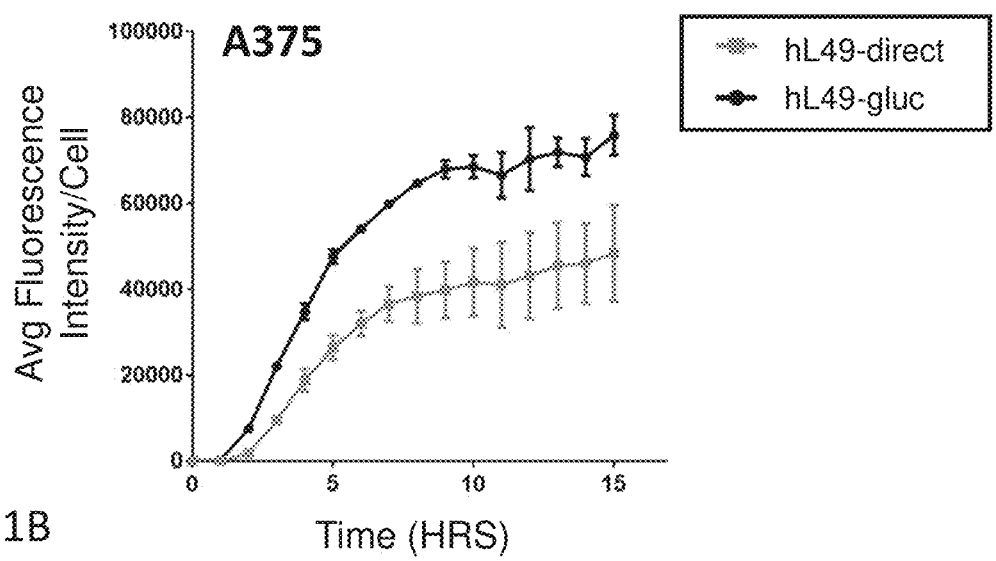
FIG. 31A-31B shows the rate of conjugate cleavage over time in A375 and Colo-853 cells.
Figure 31B:
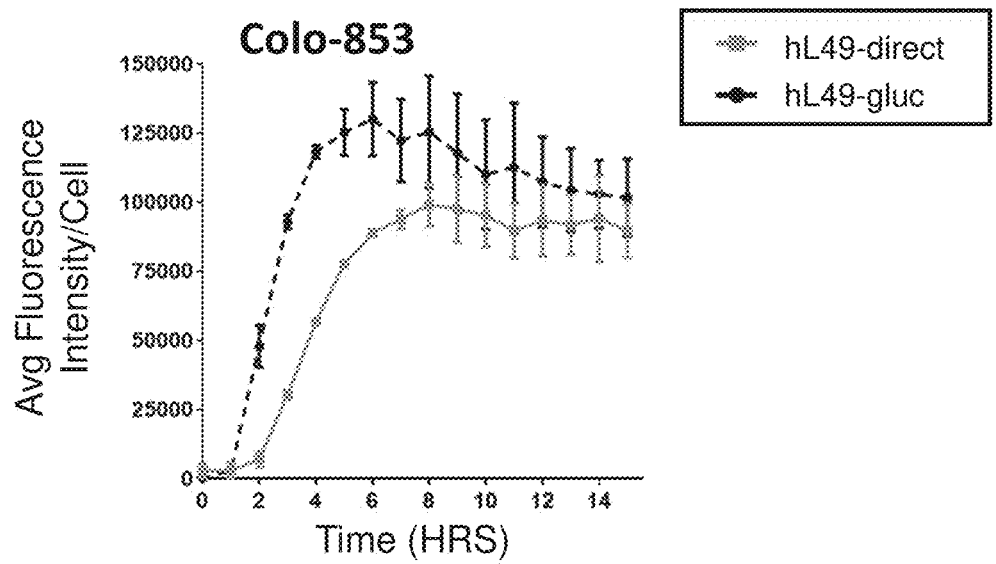

The rate of conjugate cleavage over time was investigated using a fluorescence assay. The fluorescent moiety AF647 was conjugated to the anti-CD228 antibody hL49 either directly to the 8 native cysteines or via a glucuronide linker. Additionally, a quenching reagent, Tide Quencher 5WS succinimidyl ester (TQ5WS) was added via lysine residues such that there were approximately 4 per antibody. When both the quencher and AF647 are attached to the antibody, the fluorescence is quenched. Either cleavage of AF647 from the antibody or antibody degradation results in liberation of the AF647 molecule from the quencher and a subsequent increase in fluorescence. In both A375 cells (FIG. 31A) and Colo-853 cells (FIG. 31B) conjugation of AF647 to the antibody via the glucuronide linker results in a more rapid increase in fluorescence activity than direct conjugation of AF647 to the antibody.

Figure 32:
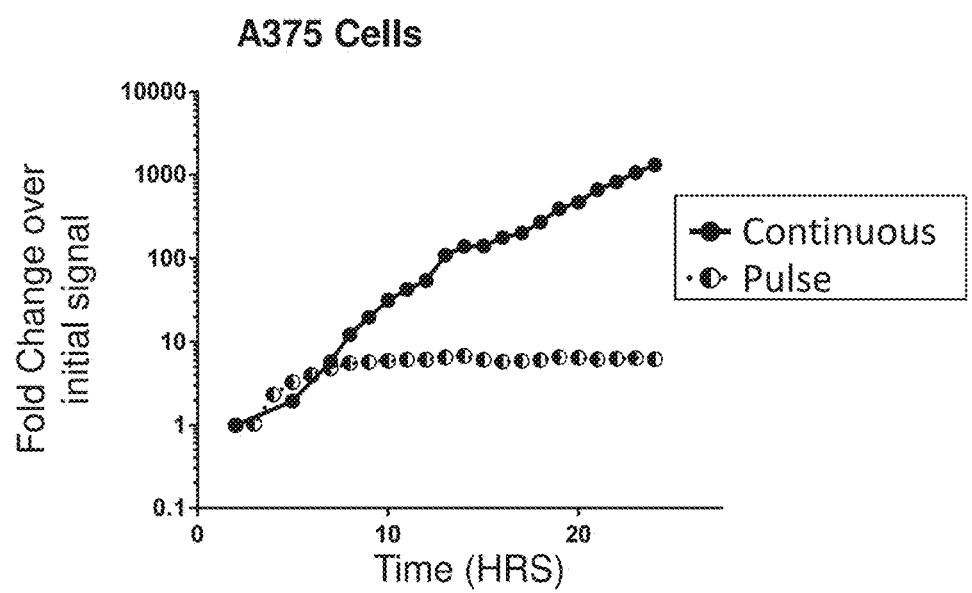
FIG. 32 shows that CD228 is replenished on the cell surface over time by comparing the rates of conjugate cleavage over time in cells treated with fluorescently labeled hL49 antibodies using either a pulse or continuous treatment of labeled antibody.
Figure 33A:
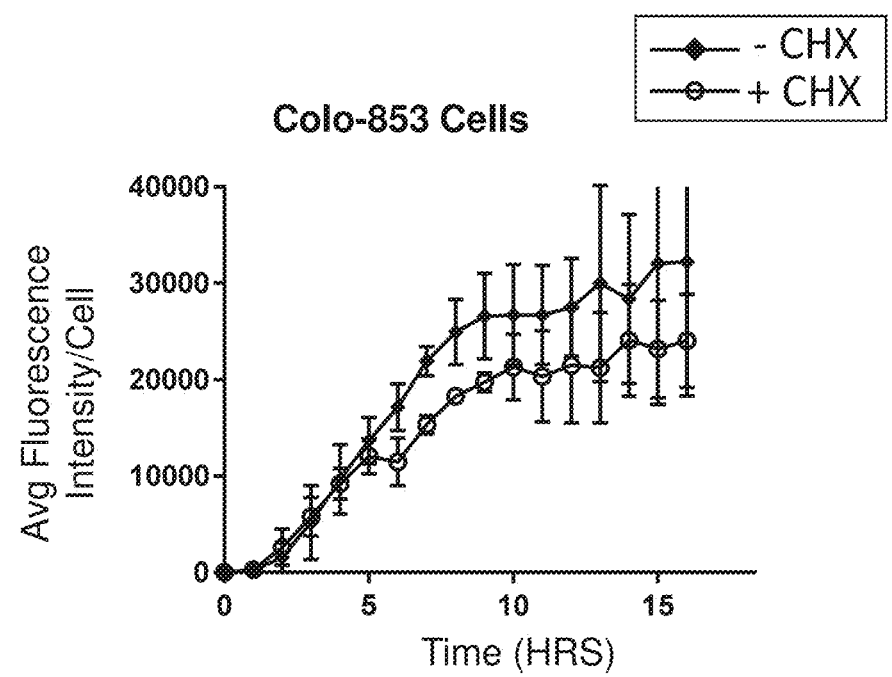
FIG. 33A-33B shows the average fluorescence intensity per cell over time in cells incubated with fluorescently labeled hL49 antibodies in the presence or absence of cycloheximide, which inhibits protein synthesis.
Figure 33B:
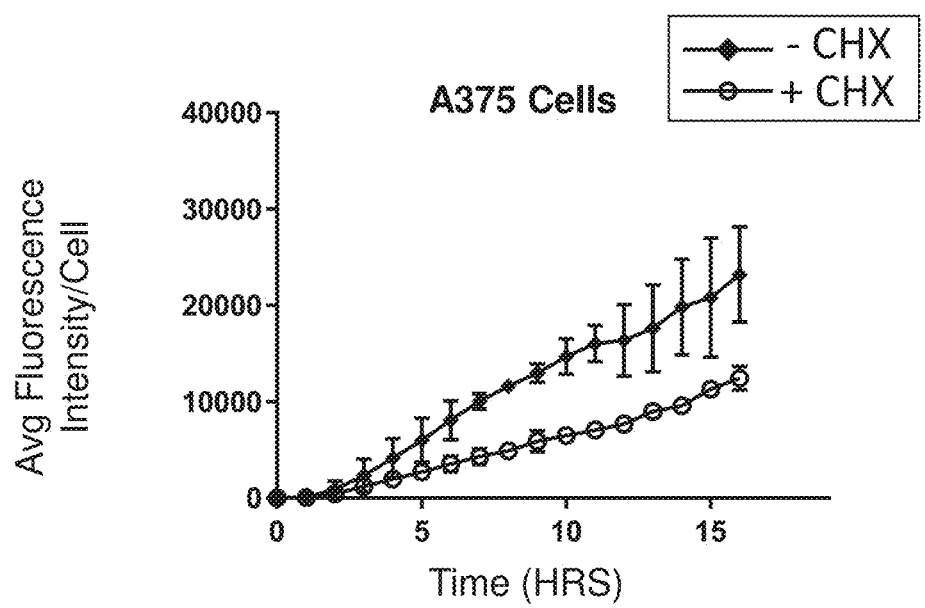
Figure 34A:
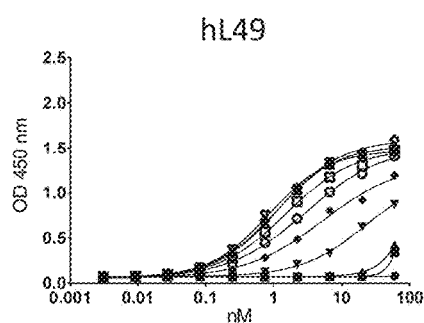
FIG. 34A-34F shows binding of various anti-CD228 antibodies to CD228 at pH values ranging from 4 to 7.4.
Figure 34B:
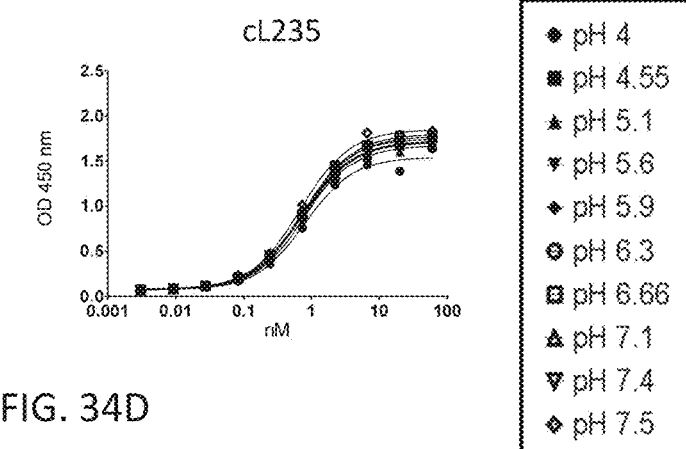
Figure 34C:
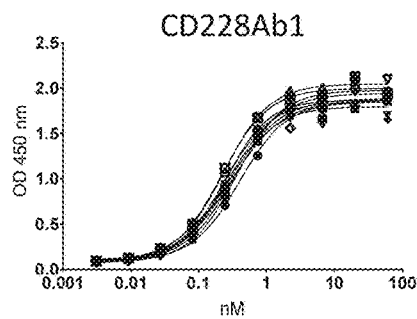
Figure 34D:
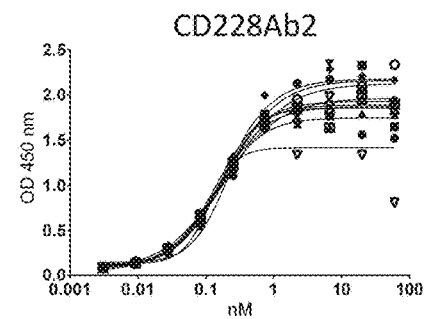
Figure 34E:
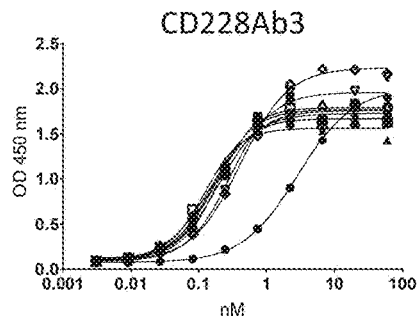
Figure 34F:
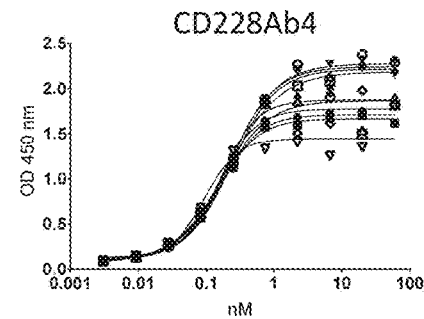

A375 cells were treated with hL49 antibodies that were conjugated to a vcQF01, which is comprised of the TQ5WS linked to a Cy5 fluorophore via a Val-Cit-PAB linker at an approximate ratio of 2 molecules per antibody. Similar to the reagent described in the previous section, Cy5 remains quenched when it is intact on the antibody and will only be fluorescent when it is cleaved away from the TQ5WS quencher. 2 μg/ml of hL49-vcQF01 was then added and allowed to bind to cells. For the pulse treatment, labeled hL49 antibodies were washed after 30 minutes to remove unbound labeled hL49 antibodies. For the continuous treatment with labeled hL49 antibodies, unbound labeled hL49 antibodies were not washed from the cells. As shown in FIG. 32, the pulse treatment resulted in a rapid plateau in the Cy5 signal while continuous exposure to labeled hL49 resulted in a steady increase in the signal of the Cy5 fluorophore. This demonstrates that additional CD228 is added to the cell surface over 24 hours that can then be bound by the labeled hL49 antibody, internalized into the cell, and cleaved to release Cy5. In further experiments, the effect of protein synthesis on CD228 binding by fluorescently labeled hL49 antibodies was investigated by comparing fluorescence intensity per cell over time in the presence and absence of cycloheximide. Cycloheximide (CHX) was used to inhibit protein synthesis. An increase in fluorescence signal over time occurred in the presence of cycloheximide in both Colo-853 (FIG. 33A) and A375 (FIG. 33B cells), but was reduced compared to cells not treated with cycloheximide. This suggests that CD228 is recycled back to the cell surface, even in the absence of protein synthesis. Together these experiments demonstrate that CD228 is both recycled and replenished on the cell surface, which contributes to antibody-drug conjugate activity.

Example 12 pH-Dependent Binding of ADCs

The ability of various anti-CD228 ADCs to bind to CD228 was evaluated at pH values ranging from 4 to 7.5 using a standard ELISA protocol. Briefly, 100 ng of human CD228 (R&D Systems Custom02; Lot DCWR021505A) or BSA (Sigma; Catalog No. A7030-100G) were diluted in PBS and added to each well overnight at 4° C. Plates were then washed three times with PBS-T (EMD Millipore; Catalog No. 5246531 EA). After washing, plates were blocked with 3% (w/v) BSA in PBS-T for 1 hour at room temperature. Excess blocking buffer was then removed and the primary antibody was added in 3-fold dilutions in diluent buffer (0.15M citrate-phosphate buffer pH 4.0-7.5) starting at an antibody concentration of 60 nM. After incubating for 1 hour at room temperature, the plates were washed 3 times and then incubated with secondary antibody (Goat anti-human IgG Fc-specific HRP-conjugated, Jackson ImmunoResearch code #109-035-098) in PBS-T with 1% BSA. After incubating for 30 minutes at room temperature, plates were washed 3 times. 100 µl TMB substrate (Life Technologies; Cat #002023) was then added to each well. After incubating 10 minutes at room temperature, 100 µl H2SO4 was added to each well to stop the reaction, plates were covered with clear plate seal and read on an Envision at 450 nM. pH-dependent binding for hL49, cL235, CD228Ab1, CD228Ab2 and CD228Ab3, CD228Ab4are shown in FIG. 34A-34F. The resulting $EC_{50}$ for each ADC is shown in Table 15. hL49 is the only ADC that displays differential binding across a pH gradient.

TABLE 15

| | $EC_{50}$ for each ADC in nM | | | | | |
|---|---|---|---|---|---|---|
| | hL49 | cL235 | CD228Ab1 | CD228Ab2 | CD228Ab3 | CD228Ab4 |
| pH 4 | — | 0.809 | 0.404 | 0.188 | 2.887 | 0.158 |
| pH 4.55 | — | 0.727 | 0.295 | 0.158 | 0.194 | 0.150 |
| pH 5.1 | — | 0.756 | 0.285 | 0.146 | 0.123 | 0.209 |
| pH 5.6 | 21.820 | 0.740 | 0.254 | 0.196 | 0.162 | 0.223 |
| pH 5.9 | 5.307 | 0.838 | 0.243 | 0.186 | 0.161 | 0.235 |
| pH 6.3 | 2.963 | 0.749 | 0.285 | 0.202 | 0.166 | 0.217 |
| pH 6.66 | 1.542 | 0.757 | 0.221 | 0.146 | 0.152 | 0.161 |
| pH 7.1 | 1.099 | 0.724 | 0.238 | 0.140 | 0.196 | 0.170 |
| pH 7.4 | 0.856 | 0.767 | 0.359 | 0.110 | 0.294 | 0.093 |
| pH 7.5 | 1.178 | 0.694 | 0.294 | 0.169 | 0.415 | 0.148 |

Example 13

Internalization and Catabolism of ADCs

Figure 35A:
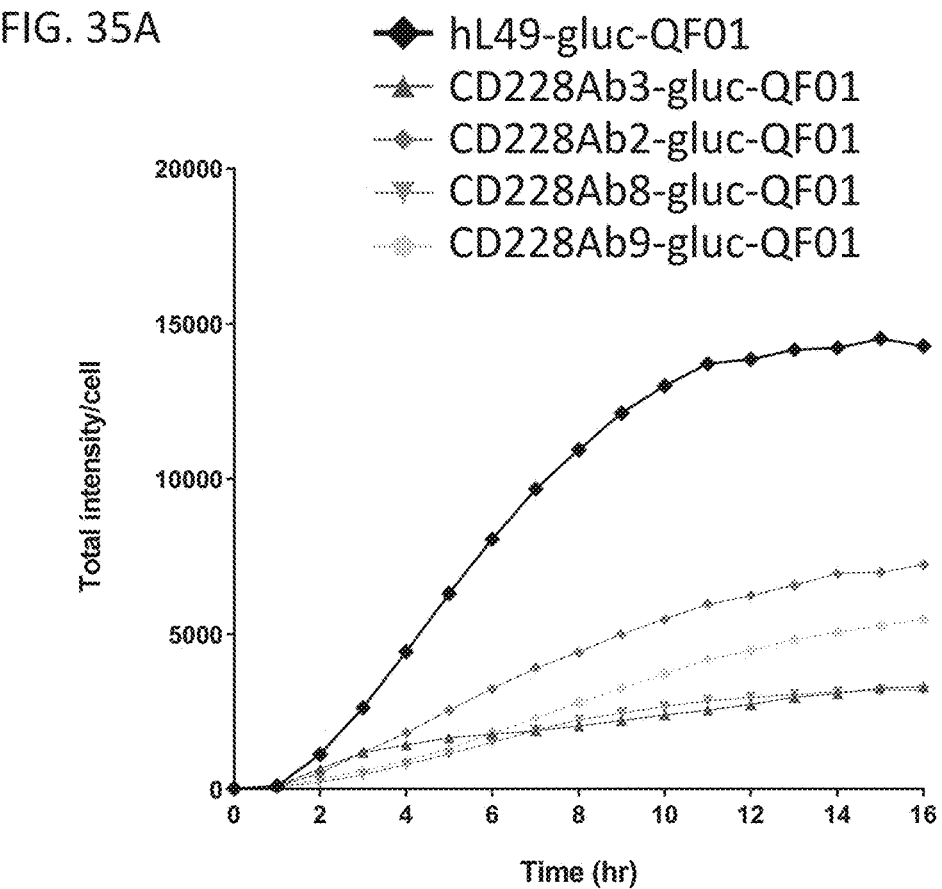
FIG. 35A-35B shows the ability of antibodies with similar binding affinities to internalize and catabolize drug.
Figure 35B:
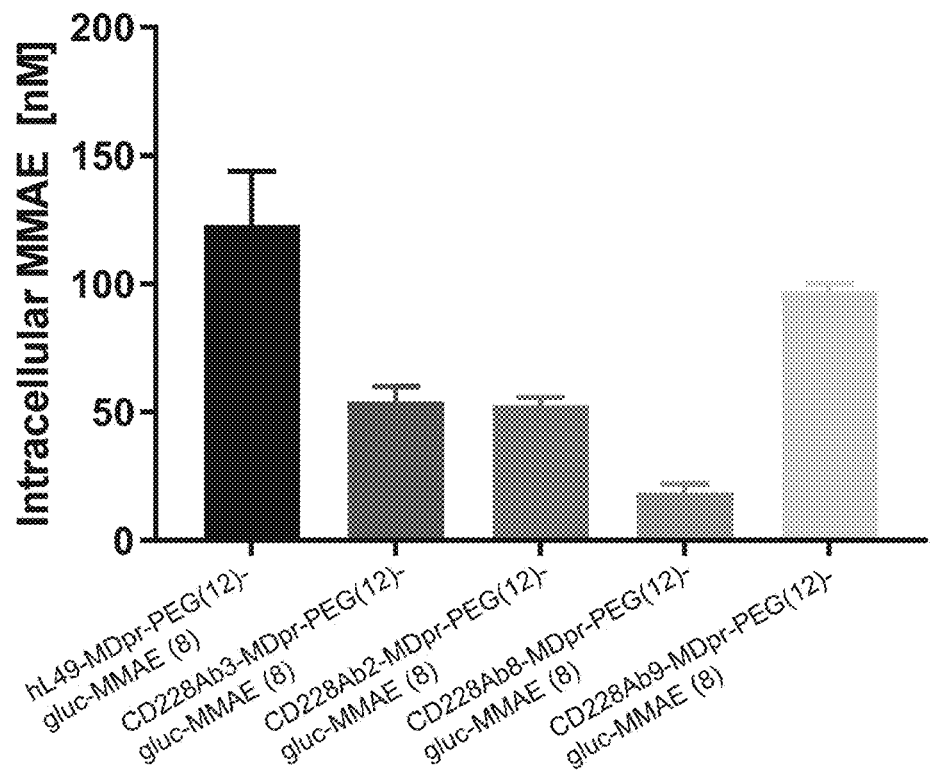

Various additional anti-CD228 antibodies were assessed for their ability to internalize and catabolize the fluorescent moiety AF647. A375 cells were treated with anti-CD228 antibodies that were conjugated to QF01, which is comprised of the quenching agent Tide Quencher 5WS succinimidyl ester (TQ5WS) linked to a Cy5 fluorophore via a glucuronide linker (gluc) at an approximate ratio of 2 molecules per antibody. Cy5 remains quenched when it is intact on the antibody and will only be fluorescent when it is cleaved away from the TQ5WS quencher. Labeled anti-CD228 antibodies were washed after 30 minutes to remove unbound labeled anti-CD228 antibodies. These anti-CD228 antibodies have binding affinities that are similar to that of hL49. Tumor cells were incubated with anti-CD228 antibodies and imaging assays were conducted to determine the fluorescence intensity per cell over time (FIG. 35A). Similar experiments were conducted using hL49 or other anti-CD228 antibodies conjugated to MDpr-PEG(12)-gluc-MMAE (8). After 24 hours, intracellular drug concentration was measured for each ADC (FIG. 35B). These experiments demonstrate that despite similar binding affinities, some antibodies, such as hL49, internalize faster and deliver drug to a greater extent than other antibodies. This suggests that hL49-MDpr-PEG(12)-gluc-MMAE (8) can deliver drug to tumor cells more effectively than other ADCs.

The invention claimed is:

1. An isolated anti-CD228 antibody, or antigen-binding fragment thereof, comprising a heavy chain variable region and a light chain variable region, wherein the heavy chain variable region comprises:
   (i) a CDR-H1 comprising the amino acid sequence of SEQ ID NO:1;
   (ii) a CDR-H2 comprising the amino acid sequence of SEQ ID NO:2; and
   (iii) a CDR-H3 comprising the amino acid sequence of SEQ ID NO:3; and
wherein the light chain variable region comprises:
   (i) a CDR-L1 comprising the amino acid sequence of SEQ ID NO:4;
   (ii) a CDR-L2 comprising the amino acid sequence of SEQ ID NO:5; and
   (iii) a CDR-L3 comprising the amino acid sequence of SEQ ID NO:6.

2. The antibody, or antigen-binding fragment of claim 1, wherein the antibody, or antigen-binding fragment thereof is a humanized anti-CD228 antibody.

3. The humanized anti-CD228 antibody, or antigen-binding fragment thereof of claim 2, comprising a heavy chain variable region comprising an amino acid sequence at least 90% identical to SEQ ID NO: 7 provided that position H27 is occupied by D, position H30 is occupied by T, position H47 is occupied by Y, position H71 is occupied by R, and position H78 is occupied by Y, and a light chain variable region comprising an amino acid sequence at least 90% identical to SEQ ID NO: 8, provided that position L2 is occupied by F, position L36 is occupied by Y and position L46 is occupied by L, wherein amino acid positions are according to Kabat.

4. The antibody or antigen-binding fragment of claim 3, further provided that position L28 is occupied by D, wherein amino acid positions are according to Kabat.

5. A humanized anti-CD228 antibody, or antigen-binding fragment thereof, comprising a heavy chain variable region comprising the three Kabat CDRs of SEQ ID NO: 7, wherein position H27 is occupied by D, position H30 is occupied by T, position H47 is occupied by Y, position H71 is occupied by R, and position H78 is occupied by Y, and a light chain variable region comprising the three Kabat CDRs of SEQ ID NO: 8, wherein position L2 is occupied by F, position L36 is occupied by Y and position L46 is occupied by L, wherein amino acid positions are according to Kabat.

6. The antibody or antigen-binding fragment of claim 1, wherein the heavy chain variable region comprises an amino acid sequence having at least 95% sequence identity to the amino acid sequence of SEQ ID NO: 7 and the light chain variable region comprises an amino acid sequence having at least 95% sequence identity to the amino acid sequence of SEQ ID NO: 8.

7. The antibody or antigen-binding fragment of claim 1, wherein the heavy chain variable region comprises an amino acid sequence having at least 98% sequence identity to the amino acid sequence of SEQ ID NO: 7 and the light chain variable region comprises an amino acid sequence having at least 98% sequence identity to the amino acid sequence of SEQ ID NO: 8.

8. The antibody or antigen-binding fragment of claim 1, wherein the heavy chain variable region comprises an amino acid sequence having at least 99% sequence identity to the amino acid sequence of SEQ ID NO: 7 and the light chain variable region comprises an amino acid sequence having at least 99% sequence identity to the amino acid sequence of SEQ ID NO: 8.

9. The antibody or antigen-binding fragment of claim 1, wherein the heavy chain variable region comprises the amino acid sequence of SEQ ID NO: 7 and the light chain variable region comprises the amino acid sequence of SEQ ID NO:8.

10. The antibody or antigen-binding fragment of claim 1, wherein the antibody or antigen-binding fragment is an antigen-binding fragment.

11. The antibody or antigen-binding fragment of claim 10, wherein the antigen-binding fragment is selected from the group consisting of Fab, Fab', F(ab')$_2$, Fab'-SH, Fv, diabody, linear antibody, and single-chain antibody fragment.

12. The antibody or antigen-binding fragment of claim 1, wherein the antibody or antigen-binding fragment is a full-length antibody.

13. The antibody or antigen-binding fragment of claim 12, wherein the heavy chain variable region is fused to a heavy chain constant region and the light chain variable region is fused to a light chain constant region.

14. The antibody or antigen-binding fragment of claim 13, wherein the heavy chain constant region is of the IgG1 isotype.

15. The antibody or antigen-binding fragment of claim 13, wherein the heavy chain constant region has an amino acid sequence comprising SEQ ID NO:17 and the light chain constant region has an amino acid sequence comprising SEQ ID NO:18.

16. The antibody or antigen-binding fragment of claim 13, wherein the heavy chain constant region is a mutant form of a natural human constant region which has reduced binding to an Fcgamma receptor relative to the natural human constant region.

17. The antibody or antigen-binding fragment of claim 13, wherein the heavy chain constant region has an amino acid sequence comprising SEQ ID NO:19 and the light chain constant region has an amino acid sequence comprising SEQ ID NO:18.

18. An antibody-drug conjugate comprising an anti-CD228 antibody, or antigen-binding fragment thereof, comprising a heavy chain variable region and a light chain variable region, wherein the heavy chain variable region comprises:
    (i) a CDR-H1 comprising the amino acid sequence of SEQ ID NO:1;
    (ii) a CDR-H2 comprising the amino acid sequence of SEQ ID NO:2; and
    (iii) a CDR-H3 comprising the amino acid sequence of SEQ ID NO:3; and
wherein the light chain variable region comprises:
    (i) a CDR-L1 comprising the amino acid sequence of SEQ ID NO:4;
    (ii) a CDR-L2 comprising the amino acid sequence of SEQ ID NO:5; and
    (iii) a CDR-L3 comprising the amino acid sequence of SEQ ID NO:6, wherein the anti-antibody or antigen-binding fragment is conjugated to a cytotoxic or cytostatic agent.

19. The antibody-drug conjugate of claim 18, wherein the antibody or antigen-binding fragment is conjugated to the cytotoxic or cytostatic agent via a linker.

20. The antibody-drug conjugate of claim 19, wherein the linker is a MDpr-PEG(12)-gluc linker.

21. The antibody-drug conjugate of claim 18, wherein the cytotoxic or cytostatic agent is a monomethyl auristatin.

22. The antibody-drug conjugate of claim 21, wherein the monomethyl auristatin is monomethyl auristatin E (MMAE).

23. The antibody-drug conjugate of claim 22, wherein the linker is attached to monomethyl auristatin E forming an antibody-drug conjugate having the structure:

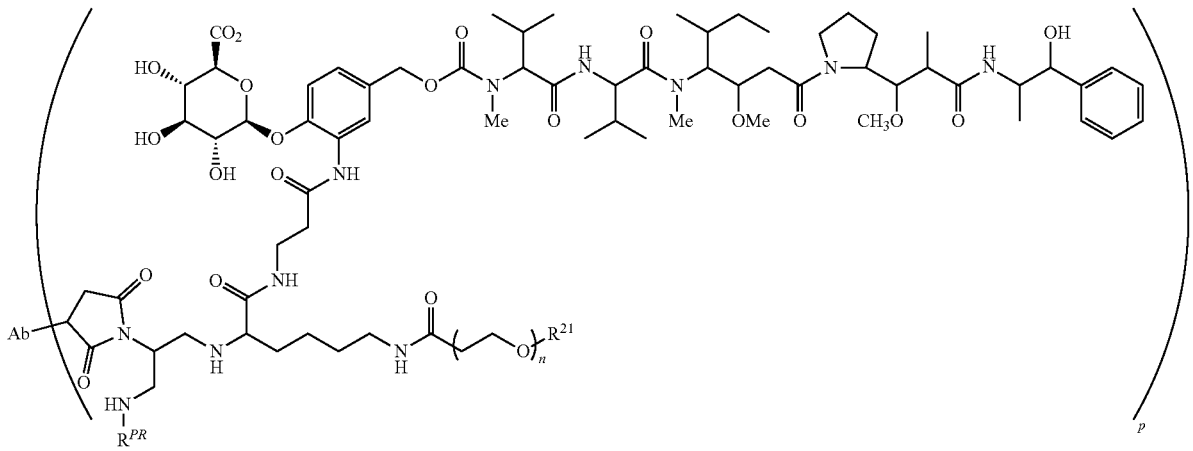

wherein Ab is the antibody hL49, n is 12, $R^{PR}$ is hydrogen, $R^{21}$ is $CH_3$, and p denotes a number from 1 to 16.

24. The antibody-drug conjugate of claim 23, wherein the average value of p in a population of the antibody-drug conjugate is about 8.

25. The antibody-drug conjugate of claim 18, wherein the antibody-drug conjugate is hL49-MDpr-PEG(12)-gluc-MMAE.

26. A nucleic acid encoding a heavy chain variable region and/or a light chain variable region of an anti-CD228 antibody, or antigen-binding fragment thereof, comprising the heavy chain variable region and the light chain variable region, wherein the heavy chain variable region comprises:
    (i) a CDR-H1 comprising the amino acid sequence of SEQ ID NO:1;
    (ii) a CDR-H2 comprising the amino acid sequence of SEQ ID NO:2; and
    (iii) a CDR-H3 comprising the amino acid sequence of SEQ ID NO:3; and
wherein the light chain variable region comprises:
    (i) a CDR-L1 comprising the amino acid sequence of SEQ ID NO:4;
    (ii) a CDR-L2 comprising the amino acid sequence of SEQ ID NO:5; and
    (iii) a CDR-L3 comprising the amino acid sequence of SEQ ID NO:6.

27. A vector comprising the nucleic acid of claim 26.

28. The vector of claim 27, wherein the vector is an expression vector.

29. A host cell comprising the nucleic acid of claim 26.

30. The host cell of claim 29, wherein the host cell is a Chinese hamster ovary (CHO) cell.

31. A method of producing an anti-CD228 antibody or antigen-binding fragment thereof comprising culturing the host cell of claim 29 under a condition suitable for production of the anti-CD228 antibody or antigen-binding fragment thereof.

32. The method of claim 31, further comprising isolating the anti-CD228 antibody or antigen-binding fragment thereof produced by the host cell.

33. A method of producing an anti-CD228 antibody-drug conjugate comprising culturing a host cell comprising a nucleic acid encoding the heavy chain variable region and/or the light chain variable region of a humanized anti-CD228 antibody, or antigen-binding fragment thereof, under a condition suitable for production of the anti-CD228 antibody, or antigen-binding fragment thereof; isolating the anti-CD228 antibody, or antigen-binding fragment thereof, produced from the host cell; and conjugating the anti-CD228 antibody, or antigen-binding fragment thereof, to a cytotoxic or cytostatic agent, wherein the anti-CD228 antibody, or antigen-binding fragment thereof, comprises the heavy chain variable region and the light chain variable region, wherein the heavy chain variable region comprises:
  (i) a CDR-H1 comprising the amino acid sequence of SEQ ID NO:1;
  (ii) a CDR-H2 comprising the amino acid sequence of SEQ ID NO:2; and
  (iii) a CDR-H3 comprising the amino acid sequence of SEQ ID NO:3; and
wherein the light chain variable region comprises:
  (i) a CDR-L1 comprising the amino acid sequence of SEQ ID NO:4;
  (ii) a CDR-L2 comprising the amino acid sequence of SEQ ID NO:5; and
  (iii) a CDR-L3 comprising the amino acid sequence of SEQ ID NO:6.

34. The method of claim 33, wherein the anti-CD228 antibody is conjugated to the cytotoxic or cytostatic agent via a linker.

35. The method of claim 34, wherein the linker is a MDpr-PEG(12)-gluc linker.

36. The method of claim 33, wherein the cytotoxic or cytostatic agent is a monomethyl auristatin.

37. The method of claim 36, wherein the monomethyl auristatin is monomethyl auristatin E (MMAE).

38. The method of claim 37, wherein the linker is attached to monomethyl auristatin E forming an antibody-drug conjugate having the structure:

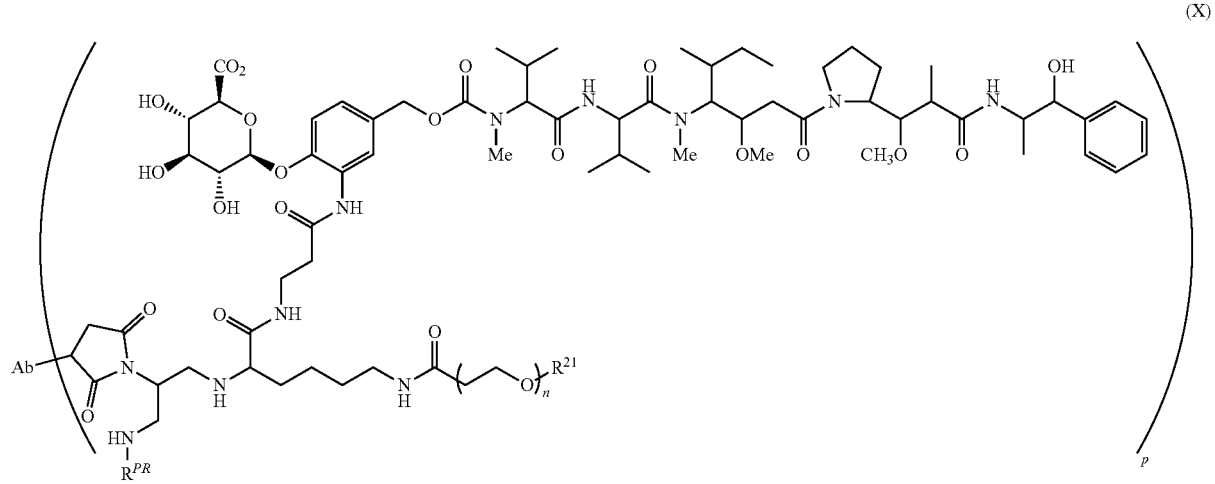

(X)

wherein Ab is the antibody hL49, n is 12, $R^{PR}$ is hydrogen, $R^{21}$ is $CH_3$, and p denotes a number from 1 to 16.

39. The method of claim 38, wherein the average value of p in a population of the antibody-drug conjugate is about 8.

40. The method of claim 33, wherein the antibody-drug conjugate is hL49-MDpr-PEG(12)-gluc-MMAE.

41. A method of treating cancer in a subject, the method comprising administering to the subject the antibody or antigen-binding fragment of claim 1.

42. The method of claim 41, wherein the subject has been previously treated with one or more therapeutic agents and did not respond to the treatment, wherein the one or more therapeutic agents is not the antibody or antigen-binding fragment.

43. The method of claim 41, wherein the subject has been previously treated with one or more therapeutic agents and relapsed after the treatment, wherein the one or more therapeutic agents is not the antibody or antigen-binding fragment.

44. The method of claim 41, wherein the subject has been previously treated with one or more therapeutic agents and has experienced disease progression during treatment, wherein the one or more therapeutic agents is not the antibody or antigen-binding fragment.

45. The method of claim 41, wherein the cancer is an advanced stage cancer.

46. The method of claim 45, wherein the advanced stage cancer is a stage 3 or stage 4 cancer.

47. The method of claim 45, wherein the advanced stage cancer is metastatic cancer.

48. The method of claim 41, wherein the cancer is recurrent cancer.

49. The method of claim 41, wherein the cancer is unresectable.

50. The method of claim 41, wherein the subject received prior treatment with standard of care therapy for the cancer and failed the prior treatment.

51. The method of claim 41, wherein the cancer is selected from the group consisting of melanoma, pancreatic cancer, mesothelioma, colorectal cancer, lung cancer, thyroid cancer, breast cancer, choliangiocarcinoma, esophageal cancer and head and neck cancer.

52. The method of claim 51, wherein the cancer is melanoma.

53. The method of claim 52, wherein the melanoma is cutaneous melanoma.

54. The method of claim 53, wherein the cutaneous melanoma is selected from the group consisting of superficial spreading melanoma, nodular melanoma, acral lentiginous melanoma, lentigo maligna melanoma, and desmoplastic melanoma.

55. The method of claim 54, wherein the acral lentiginous melanoma is subungual melanoma.

56. The method of claim 53, wherein the subject received prior therapy with an inhibitor of PD-1 or PD-L1.

57. The method of claim 56, wherein the subject received prior therapy with an inhibitor of PD-1.

58. The method of claim 52, wherein the melanoma is sub-cutaneous melanoma.

59. The method of claim 58, wherein the sub-cutaneous melanoma is ocular melanoma or mucosal melanoma.

60. The method of claim 52, wherein the melanoma is non-cutaneous melanoma.

61. The method of claim 51, wherein the cancer is mesothelioma.

62. The method of claim 61, wherein the mesothelioma is selected from the group consisting of pleural mesothelioma, peritoneal mesothelioma, pericardial mesothelioma, and testicular mesothelioma.

63. The method of claim 62, wherein the mesothelioma is pleural mesothelioma.

64. The method of claim 63, wherein the subject has received prior therapy with a platinum-based therapy.

65. The method of claim 64, wherein the platinum-based therapy is cisplatin.

66. The method of claim 63, wherein the subject received prior therapy with pemetrexed.

67. The method of claim 51, wherein the lung cancer is non-small cell lung cancer.

68. The method of claim 67, wherein the non-small cell lung cancer has a mutant form of epidermal growth factor receptor (EGFR).

69. The method of claim 67, wherein the non-small cell lung cancer has wild-type EGFR.

70. The method of claim 69, wherein the subject has received prior therapy with a platinum-based therapy.

71. The method of claim 69, wherein the subject received prior therapy with an inhibitor of PD-1 or PD-L1.

72. The method of claim 71, wherein the subject received prior therapy with an inhibitor of PD-1.

73. The method of claim 51, wherein the breast cancer is selected from the group consisting of HER2 positive, HER2 negative, Estrogen Receptor (ER) positive, ER negative, Progesterone Receptor (PR) positive, PR negative, and triple negative breast cancer.

74. The method of claim 73, wherein the breast cancer is HER2 negative breast cancer.

75. The method of claim 74, wherein the subject received one or more prior line of therapy for the HER2 negative breast cancer.

76. The method of claim 75, wherein the one or more prior line of therapy comprised treatment with a taxane.

77. The method of claim 75, wherein the subject is hormone receptor positive.

78. The method of claim 77, wherein the subject received prior therapy with an inhibitor of CDK4/6.

79. The method of claim 77, wherein the subject received prior therapy with a hormonally-directed therapy.

80. The method of claim 51, wherein the colorectal cancer is selected from the group consisting of a colorectal adenocarcinoma, a gastrointestinal stromal tumor, a primary colorectal lymphoma, a gastrointestinal carcinoid tumor, and a leiomyosarcoma.

81. The method of claim 80, wherein the subject received two or more prior lines of therapy for the colorectal cancer.

82. The method of claim 51, wherein the pancreatic cancer is an exocrine cancer or a neuroendocrine cancer.

83. The method of claim 82, wherein the exocrine cancer is selected from the group consisting of pancreatic adenocarcinoma, acinar cell carcinoma, cystadenocarcinoma, pancreatoblastoma, adenosquamous carcinoma, signet ring carcinoma, hepatoid carcinoma, colloid carcinoma, undifferentiated carcinoma, and pancreatic mucinous cystic neoplasm.

84. The method of claim 83, wherein the pancreatic adenocarcinoma is pancreatic ductal adenocarcinoma.

85. The method of claim 83, wherein the subject received one or more prior line of therapy for the pancreatic cancer.

86. The method of claim 41, wherein the antibody or antigen-binding fragment is in a pharmaceutical composition comprising the antibody or antigen-binding fragment and a pharmaceutically acceptable carrier.

87. The method of claim 41, wherein the subject is a human.

88. A kit comprising:
(a) the antibody or antigen-binding fragment of claim 1; and
(b) instructions for using the antibody or antigen-binding fragment in a method of treating cancer in a subject, the method comprising administering to the subject the antibody or antigen-binding fragment.

89. A pharmaceutical composition comprising the antibody or antigen-binding fragment of claim 1 and one or more agents selected from the group consisting of a physiologically acceptable carrier, a diluent, an excipient and an auxiliary.

90. An antibody-drug conjugate comprising the humanized anti-CD228 antibody, or antigen-binding fragment thereof of claim 2, conjugated to a cytotoxic or cytostatic agent, wherein the anti-CD228 antibody, or antigen-binding fragment thereof, comprises a heavy chain variable region comprising an amino acid sequence at least 90% identical to SEQ ID NO: 7 provided that position H27 is occupied by D, position H30 is occupied by T, position H47 is occupied by Y, position H71 is occupied by R, and position H78 is occupied by Y, and a light chain variable region comprising an amino acid sequence at least 90% identical to SEQ ID NO: 8, provided that position L2 is occupied by F, position L36 is occupied by Y and position L46 is occupied by L, wherein amino acid positions are according to Kabat.

91. The antibody-drug conjugate of claim 90, wherein the heavy chain variable region comprises an amino acid sequence having at least 95% sequence identity to the amino acid sequence of SEQ ID NO: 7 and the light chain variable region comprises an amino acid sequence having at least 95% sequence identity to the amino acid sequence of SEQ ID NO: 8.

92. The antibody-drug conjugate of claim 90, wherein the heavy chain variable region comprises an amino acid sequence having at least 98% sequence identity to the amino acid sequence of SEQ ID NO: 7 and the light chain variable region comprises an amino acid sequence having at least 98% sequence identity to the amino acid sequence of SEQ ID NO: 8.

93. The antibody-drug conjugate of claim 90, wherein the heavy chain variable region of the anti-CD228 antibody, or antigen-binding fragment thereof, comprises the amino acid sequence of SEQ ID NO: 7 and the light chain variable region of the anti-CD228 antibody, or antigen-binding fragment thereof, comprises the amino acid sequence of SEQ ID NO:8.

94. The antibody-drug conjugate of claim 90, wherein the antibody or antigen-binding fragment is an antigen-binding fragment.

95. The antibody-drug conjugate of claim 90, wherein the antibody or antigen-binding fragment is a full-length antibody.

96. The antibody-drug conjugate of claim 90, wherein the antibody or antigen-binding fragment is conjugated to the cytotoxic or cytostatic agent via a linker.

97. The antibody-drug conjugate of claim 96, wherein the linker is a MDpr-PEG(12)-gluc linker.

98. The antibody-drug conjugate of claim 90, wherein the cytotoxic or cytostatic agent is a monomethyl auristatin.

99. The antibody-drug conjugate of claim 98, wherein the monomethyl auristatin is monomethyl auristatin E (MMAE).

100. A method of treating cancer in a subject, the method comprising administering to the subject the antibody-drug conjugate of claim 18.

101. The method of claim 100, wherein the subject has been previously treated with one or more therapeutic agents and did not respond to the treatment, wherein the one or more therapeutic agents is not the antibody-drug conjugate.

102. The method of claim 100, wherein the subject has been previously treated with one or more therapeutic agents and relapsed after the treatment, wherein the one or more therapeutic agents is not the antibody-drug conjugate.

103. The method of claim 100, wherein the subject has been previously treated with one or more therapeutic agents and has experienced disease progression during treatment, wherein the one or more therapeutic agents is not the antibody-drug conjugate.

104. The method of any one of claim 100, wherein the cancer is an advanced stage cancer.

105. The method of claim 104, wherein the advanced stage cancer is a stage 3 or stage 4 cancer.

106. The method of claim 104, wherein the advanced stage cancer is metastatic cancer.

107. The method of claim 100, wherein the cancer is recurrent cancer.

108. The method of claim 100, wherein the cancer is unresectable.

109. The method of claim 100, wherein the subject received prior treatment with standard of care therapy for the cancer and failed the prior treatment.

110. The method of claim 100, wherein the cancer is selected from the group consisting of melanoma, pancreatic cancer, mesothelioma, colorectal cancer, lung cancer, thyroid cancer, breast cancer, choliangiocarcinoma, esophageal cancer and head and neck cancer.

111. The method of claim 100, wherein the antibody-drug conjugate is in a pharmaceutical composition comprising the antibody-drug conjugate and a pharmaceutically acceptable carrier.

112. The method of claim 100, wherein the subject is a human.

113. A kit comprising:
  (a) the antibody-drug conjugate of claim 18; and
  (b) instructions for using the antibody-drug conjugate in a method of treating cancer in a subject, the method comprising administering to the subject the antibody or antigen-binding fragment.

114. A pharmaceutical composition comprising the antibody-drug conjugate of claim 18 and one or more agents selected from the group consisting of a physiologically acceptable carrier, a diluent, an excipient and an auxiliary.

* * * * *